(12) United States Patent
Guan et al.

(10) Patent No.: US 11,932,890 B2
(45) Date of Patent: *Mar. 19, 2024

(54) ALPHA-1,3-GLUCAN GRAFT COPOLYMERS

(71) Applicant: NUTRITION & BIOSCIENCES USA 4, INC., Rochester, NY (US)

(72) Inventors: Rong Guan, Wilmington, DE (US); James Joshua Ohane, West Chester, PA (US); Nikita Iltchenko, Wilmington, DE (US); Yefim Brun, Wilmington, DE (US); Brian McCauley, Wayne, PA (US); Laurie A. Howe, Bear, DE (US); Yougen Li, Pennington, NJ (US)

(73) Assignee: NUTRITION & BIOSCIENCES USA 4, INC., Rochester, NY (US)

( * ) Notice: Subject to any disclaimer, the term of this patent is extended or adjusted under 35 U.S.C. 154(b) by 37 days.

This patent is subject to a terminal disclaimer.

(21) Appl. No.: 17/406,386

(22) Filed: Aug. 19, 2021

(65) Prior Publication Data

US 2022/0127654 A1 Apr. 28, 2022

Related U.S. Application Data

(63) Continuation of application No. 16/218,518, filed on Dec. 13, 2018, now Pat. No. 11,098,334.

(60) Provisional application No. 62/733,729, filed on Sep. 20, 2018, provisional application No. 62/598,685, filed on Dec. 14, 2017.

(51) Int. Cl.
| | |
|---|---|
| C08B 37/00 | (2006.01) |
| C08B 37/02 | (2006.01) |
| C08J 5/18 | (2006.01) |
| C08L 5/02 | (2006.01) |
| C11D 3/37 | (2006.01) |
| C12P 19/08 | (2006.01) |
| C12P 19/18 | (2006.01) |

(52) U.S. Cl.
CPC .......... *C12P 19/08* (2013.01); *C08B 37/0009* (2013.01); *C08B 37/0021* (2013.01); *C08J 5/18* (2013.01); *C08L 5/02* (2013.01); *C11D 3/3707* (2013.01); *C12P 19/18* (2013.01); *C08J 2305/00* (2013.01); *C08J 2305/02* (2013.01)

(58) Field of Classification Search
CPC .... C08L 5/02; C08B 37/0021; C08B 37/0009
See application file for complete search history.

(56) References Cited

U.S. PATENT DOCUMENTS 11,098,334 B2 * 8/2021 Guan .................. C08B 37/0009

FOREIGN PATENT DOCUMENTS

| WO | WO-2017079595 A1 * | 5/2017 | .............. A61P 17/02 |
| WO | WO-2019055397 A1 * | 3/2019 | .......... C08L 23/0853 |

OTHER PUBLICATIONS

Seymour, "High-Temperature Enhancement of 13C-N.M.R. Chemical Shifts of Unusual Dextrans, and Correlation With Methylation Structural Analysis" Carbohydrate Research vol. 68 pp. 123-140 (Year: 1979).*
Pasika et al., "The Viscosity Behavior of Linear and Branched Dextran Sulfates" Journal of Polymer Science vol. 57 pp. 301-310 (Year: 1962).*

* cited by examiner

*Primary Examiner* — Eric Olson

(57) ABSTRACT

Compositions are disclosed herein comprising a graft copolymer that comprises: (i) a backbone comprising dextran that has been modified with about 1%-25% alpha-1,2 branches, and (ii) one or more alpha-1,3-glucan side chains comprising at least about 50% alpha-1,3 glycosidic linkages. Further disclosed are reactions for producing such graft copolymers, as well as their use in derivatives, films and various other applications.

16 Claims, No Drawings
Specification includes a Sequence Listing.

SEQUENCE LISTING

<160> NUMBER OF SEQ ID NOS: 71

<210> SEQ ID NO 1
<211> LENGTH: 4308
<212> TYPE: DNA
<213> ORGANISM: Streptococcus sobrinus

<400> SEQUENCE: 1

```
atggttgacg gcaaatacta ctattatgat caggacggta acgtaaagaa gaatttcgcg    60
gtgagcgttg gtgacaaaat ctactacttc gatgaaactg gtgcatataa ggataccagc   120
aaagtggacg ccgacaagag cagcagcgcg gttagccaaa acgcgaccat ctttgcggcg   180
aataaccgtg cgtacagcac ctctgcaaag aattttgaag cggtggataa ctacctgacc   240
gcagacagct ggtatcgtcc gaaatccatc ctgaaggacg gcaaaacctg gaccgagagc   300
ggtaaggatg atttccgtcc actgctgatg gcatggtggc ctgacaccga aactaagcgc   360
aactacgtga actatatgaa taaagtggtc ggtattgaca agacgtacac tgcggaaacg   420
tcgcaagcgg atttgaccgc agcggcggag ctggttcaag cgcgtatcga gcagaagatt   480
accagcgaaa acaacaccaa atggctgcgc gaagcaatct ccgcgttcgt taagacgcag   540
cctcagtgga acggcgagtc cgaaaagccg tatgacgatc acttgcagaa cggtgcgctg   600
ctgtttgata accaaaccga cctgacgcca gacacccaaa gcaattaccg tttgctgaac   660 cgtacccccga ccaatcagac tggtagcctg gatagccgtt ttacgtataa tccgaatgac   720
ccgttgggcg gctacgattt cttgctggcg aacgacgttg acaatagcaa tccggtcgtc   780
caggctgaac agttgaactg gctgcattat ctgctgaact ttggctctat ttacgctaac   840
gatgccgacg ccaattttga cagcattcgc gttgatgccg tcgataatgt cgatgctgat   900
ctgctgcaaa tcagcagcga ttacctgaaa gcagcgtatg gcatcgacaa gaataacaag   960
```

-continued

```
aatgcgaaca accatgttag catcgtcgaa gcgtggagcg acaatgatac cccgtatttg    1020
cacgacgatg gcgataatct gatgaacatg acaacaaat ttcgcctgtc catgctgtgg     1080
agcctggcaa agccgctgga caaacgtagc ggtttgaacc cgctgattca caatagcctg    1140
gtggaccgcg aggtggacga tcgtgaagtg gaaaccgtgc cgtcctacag ctttgctcgt    1200
gcacatgata gcgaggtgca ggacatcatc cgtgacatta tcaaggctga gattaaccca    1260
aatagctttg gttatagctt cactcaagaa gagatcgagc aagcctttaa gatttacaac    1320
gaggatttga agaaaacgga caagaaatac acccactaca atgtgccgct gagctacacc    1380
ctgctgctga ccaacaaggg cagcatcccg cgtgtgtact atggtgatat gttcaccgat    1440
gatggccaat acatggcaaa caagaccgtc aactacgacg caatcgagag cctgctgaaa    1500
gcccgtatga aatatgtcag cggtggccaa gcaatgcaga actatcaaat tggtaatggc    1560
gagattttga ccagcgtgcg ctatggtaaa ggtgccctga agcagagcga taagggtgac    1620
gcgacgacgc gcactagcgg tgttggcgtg gttatgggta atcagccgaa cttctccctg    1680
gacggtaaag ttgtggccct gaatatgggt gcggcccatg cgaatcaaga ataccgtgca    1740
ctgatggtca gcactaaaga cggtgtggca acttacgcaa ccgatgctga cgcatccaaa    1800
gcgggcctgg tcaagcgtac cgacgagaac ggctacctgt acttcctgaa tgatgatctg    1860
aagggcgtcg cgaaccctca ggtttccggc ttcttgcaag tgtgggttcc agttggtgcc    1920
gccgatgacc aggacattcg cgtcgccgcc agcgacacgg cgagcacgga tggtaaaagc    1980
ctgcatcaag atgcggcgat ggacagccgc gtcatgtttg agggtttcag caattttcaa    2040
tccttcgcga ccaaagaaga agaatacacg aatgttgtta tcgcgaacaa tgtcgataag    2100
ttcgttagct ggggtatcac cgattttgaa atggctccgc agtatgttag cagcaccgac    2160
ggtcagttct tggacagcgt catccagaat ggctatgcgt ttactgatcg ctatgatctg    2220
ggtatgtcca aggcgaacaa gtatggcacg gcagaccaac tggttaaggc aatcaaagcc    2280
ctgcacgcta aaggcctgaa agttatggcg gactgggtcc cggatcaaat gtacaccttt    2340
ccaaaacagg aagttgtgac cgttacccgc accgacaaat tcggtaaacc gatcgccggc    2400
tctcaaatca atcacagctt gtatgtgacc gacaccaaat ccagcggcga cgactaccaa    2460
gcgaagtacg gcggtgcctt cctggatgaa ctgaaagaaa agtacccgga actgttcacg    2520
aaaaagcaaa ttagcacggg ccaagcgatt gatccgagcg tgaaaatcaa gcagtggagc    2580
gcaaaatact tcaatggttc gaatatcctg ggtcgcggtg cggactatgt gctgagcgac    2640
caggtcagca ataagtattt caacgtggcg agcgacacct tgttcctgcc gtccagcctg    2700
ctgggcaagg tcgtggagag cggcattcgt tacgacggca agggttacat ctacaacagc    2760
tccgcgaccg gcgatcaggt caaagcgtct ttcattacgg aagccggtaa cctgtattac    2820
ttcggcaaag acggttacat ggttactggt gcccagacga ttaatggcgc caactacttc    2880
ttcctggaaa acggtacggc actgcgtaat acgatttaca ccgatgctca aggtaatagc    2940
cactattacg cgaatgatgg caaacgctat gaaaatggct atcaacagtt cggtaacgat    3000
tggcgctact ttaaagatgg taacatggca gtcggcctga ccacggttga tggcaacgtg    3060
caatactttg acaagacgg cgtccaggca aaggataaga ttatcgtcac ccgtgatggc    3120
aaggtccgtt acttcgatca gcacaacggt aacgcggcga ccaacacgtt cattgctgat    3180
aaaactggcc attggtatta cctgggtaaa gatggcgtcg cggtgactgg cgcccagacc    3240
gtcggcaaac aaaaactgta cttcgaggcc aacggtcaac aagttaaagg tgactttgtt    3300
```

```
acgtccgatg agggcaaact gtatttctat gacgttgatt ctggtgacat gtggacggac  3360
accttcatcg aggataaggc gggcaactgg ttctatttgg gcaaggatgg tgcggcagtt  3420
acgggtgccc aaacgattcg cggtcagaag ctgtacttca aggccaatgg tcaacaggtc  3480
aagggtgaca ttgttaaggg caccgacggt aaaatccgct actatgatgc aaaatccggt  3540
gaacaggtgt tcaacaaaac ggtgaaagct gcggatggca aaacgtatgt tatcggtaat  3600
gatggtgtcg cggtggaccc tagcgtggtt aaaggtcaaa cctttaagga cgcttcgggc  3660
gctctgcgtt tctacaactt gaagggtcaa ctggtcactg gcagcggctg gtatgaaacc  3720
gcgaaccatg actgggttta cattcagtcc ggcaaggcac tgaccggcga acagaccatt  3780
aacggtcaac acctgtattt caaagaagat ggtcaccaag tcaagggtca gttggtcacg  3840
ggcaccgatg gtaaagtgcg ttactatgac gccaacagcg gtgaccaagc attcaacaag  3900
agcgtcactg tgaatggtaa aacctattac tttggcaacg atggtacggc gcagactgct  3960
ggcaacccga agggtcagac gttcaaggat ggctccgaca tccgttttta ctctatggaa  4020
ggccaactgg tgaccggctc gggttggtac gagaacgcgc aaggccagtg gctgtatgtg  4080
aaaaacggta aggtgctgac tggtctgcaa accgttggca gccagcgtgt ttacttcgac  4140
gagaatggta ttcaggccaa gggcaaagca gtgcgtacca gcgatggcaa aattcgttat  4200
ttcgacgaaa acagcggcag catgatcacg aatcaatgga agttcgtcta tggtcagtat  4260
tactactttg gtaacgacgg tgcacgtatt taccgtggtt ggaactaa                4308
```

<210> SEQ ID NO 2
<211> LENGTH: 1435
<212> TYPE: PRT
<213> ORGANISM: Streptococcus sobrinus

<400> SEQUENCE: 2

```
Met Val Asp Gly Lys Tyr Tyr Tyr Asp Gln Asp Gly Asn Val Lys
1               5                   10                  15

Lys Asn Phe Ala Val Ser Val Gly Asp Lys Ile Tyr Tyr Phe Asp Glu
            20                  25                  30

Thr Gly Ala Tyr Lys Asp Thr Ser Lys Val Asp Ala Asp Lys Ser Ser
        35                  40                  45

Ser Ala Val Ser Gln Asn Ala Thr Ile Phe Ala Ala Asn Asn Arg Ala
    50                  55                  60

Tyr Ser Thr Ser Ala Lys Asn Phe Glu Ala Val Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Gly Lys Asp Asp Phe Arg Pro Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Ser Glu Asn Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Leu Phe Asp Asn Gln Thr Asp Leu
```

```
                195                 200                 205
Thr Pro Asp Thr Gln Ser Asn Tyr Arg Leu Leu Asn Arg Thr Pro Thr
210                 215                 220

Asn Gln Thr Gly Ser Leu Asp Ser Arg Phe Thr Tyr Asn Pro Asn Asp
225                 230                 235                 240

Pro Leu Gly Gly Tyr Asp Phe Leu Leu Ala Asn Asp Val Asp Asn Ser
                245                 250                 255

Asn Pro Val Val Gln Ala Glu Gln Leu Asn Trp Leu His Tyr Leu Leu
                260                 265                 270

Asn Phe Gly Ser Ile Tyr Ala Asn Asp Ala Asp Ala Asn Phe Asp Ser
                275                 280                 285

Ile Arg Val Asp Ala Val Asp Asn Val Asp Ala Asp Leu Leu Gln Ile
                290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
                340                 345                 350

Lys Phe Arg Leu Ser Met Leu Trp Ser Leu Ala Lys Pro Leu Asp Lys
                355                 360                 365

Arg Ser Gly Leu Asn Pro Leu Ile His Asn Ser Leu Val Asp Arg Glu
                370                 375                 380

Val Asp Asp Arg Glu Val Glu Thr Val Pro Ser Tyr Ser Phe Ala Arg
385                 390                 395                 400

Ala His Asp Ser Glu Val Gln Asp Ile Ile Arg Asp Ile Ile Lys Ala
                405                 410                 415

Glu Ile Asn Pro Asn Ser Phe Gly Tyr Ser Phe Thr Gln Glu Glu Ile
                420                 425                 430

Glu Gln Ala Phe Lys Ile Tyr Asn Glu Asp Leu Lys Lys Thr Asp Lys
                435                 440                 445

Lys Tyr Thr His Tyr Asn Val Pro Leu Ser Tyr Thr Leu Leu Leu Thr
450                 455                 460

Asn Lys Gly Ser Ile Pro Arg Val Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gly Gln Ala Met
                500                 505                 510

Gln Asn Tyr Gln Ile Gly Asn Gly Glu Ile Leu Thr Ser Val Arg Tyr
                515                 520                 525

Gly Lys Gly Ala Leu Lys Gln Ser Asp Lys Gly Asp Ala Thr Thr Arg
                530                 535                 540

Thr Ser Gly Val Gly Val Val Met Gly Asn Gln Pro Asn Phe Ser Leu
545                 550                 555                 560

Asp Gly Lys Val Val Ala Leu Asn Met Gly Ala Ala His Ala Asn Gln
                565                 570                 575

Glu Tyr Arg Ala Leu Met Val Ser Thr Lys Asp Gly Val Ala Thr Tyr
                580                 585                 590

Ala Thr Asp Ala Asp Ala Ser Lys Ala Gly Leu Val Lys Arg Thr Asp
                595                 600                 605

Glu Asn Gly Tyr Leu Tyr Phe Leu Asn Asp Asp Leu Lys Gly Val Ala
                610                 615                 620
```

```
Asn Pro Gln Val Ser Gly Phe Leu Gln Val Trp Val Pro Gly Ala
625                 630                 635                 640

Ala Asp Asp Gln Asp Ile Arg Val Ala Ala Ser Asp Thr Ala Ser Thr
            645                 650                 655

Asp Gly Lys Ser Leu His Gln Asp Ala Ala Met Asp Ser Arg Val Met
            660                 665                 670

Phe Glu Gly Phe Ser Asn Phe Gln Ser Phe Ala Thr Lys Glu Glu Glu
            675                 680                 685

Tyr Thr Asn Val Val Ile Ala Asn Asn Val Asp Lys Phe Val Ser Trp
690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
            725                 730                 735

Arg Tyr Asp Leu Gly Met Ser Lys Ala Asn Lys Tyr Gly Thr Ala Asp
            740                 745                 750

Gln Leu Val Lys Ala Ile Lys Ala Leu His Ala Lys Gly Leu Lys Val
            755                 760                 765

Met Ala Asp Trp Val Pro Asp Gln Met Tyr Thr Phe Pro Lys Gln Glu
770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
            805                 810                 815

Asp Asp Tyr Gln Ala Lys Tyr Gly Gly Ala Phe Leu Asp Glu Leu Lys
            820                 825                 830

Glu Lys Tyr Pro Glu Leu Phe Thr Lys Lys Gln Ile Ser Thr Gly Gln
            835                 840                 845

Ala Ile Asp Pro Ser Val Lys Ile Lys Gln Trp Ser Ala Lys Tyr Phe
850                 855                 860

Asn Gly Ser Asn Ile Leu Gly Arg Gly Ala Asp Tyr Val Leu Ser Asp
865                 870                 875                 880

Gln Val Ser Asn Lys Tyr Phe Asn Val Ala Ser Asp Thr Leu Phe Leu
            885                 890                 895

Pro Ser Ser Leu Leu Gly Lys Val Val Glu Ser Gly Ile Arg Tyr Asp
            900                 905                 910

Gly Lys Gly Tyr Ile Tyr Asn Ser Ser Ala Thr Gly Asp Gln Val Lys
            915                 920                 925

Ala Ser Phe Ile Thr Glu Ala Gly Asn Leu Tyr Tyr Phe Gly Lys Asp
            930                 935                 940

Gly Tyr Met Val Thr Gly Ala Gln Thr Ile Asn Gly Ala Asn Tyr Phe
945                 950                 955                 960

Phe Leu Glu Asn Gly Thr Ala Leu Arg Asn Thr Ile Tyr Thr Asp Ala
            965                 970                 975

Gln Gly Asn Ser His Tyr Tyr Ala Asn Asp Gly Lys Arg Tyr Glu Asn
            980                 985                 990

Gly Tyr Gln Gln Phe Gly Asn Asp Trp Arg Tyr Phe Lys Asp Gly Asn
            995                 1000                1005

Met Ala Val Gly Leu Thr Thr Val Asp Gly Asn Val Gln Tyr Phe
    1010                1015                1020

Asp Lys Asp Gly Val Gln Ala Lys Asp Lys Ile Ile Val Thr Arg
    1025                1030                1035
```

-continued

Asp Gly Lys Val Arg Tyr Phe Asp Gln His Asn Gly Asn Ala Ala
    1040                1045                1050

Thr Asn Thr Phe Ile Ala Asp Lys Thr Gly His Trp Tyr Tyr Leu
    1055                1060                1065

Gly Lys Asp Gly Val Ala Val Thr Gly Ala Gln Thr Val Gly Lys
    1070                1075                1080

Gln Lys Leu Tyr Phe Glu Ala Asn Gly Gln Gln Val Lys Gly Asp
    1085                1090                1095

Phe Val Thr Ser Asp Glu Gly Lys Leu Tyr Phe Tyr Asp Val Asp
    1100                1105                1110

Ser Gly Asp Met Trp Thr Asp Thr Phe Ile Glu Asp Lys Ala Gly
    1115                1120                1125

Asn Trp Phe Tyr Leu Gly Lys Asp Gly Ala Ala Val Thr Gly Ala
    1130                1135                1140

Gln Thr Ile Arg Gly Gln Lys Leu Tyr Phe Lys Ala Asn Gly Gln
    1145                1150                1155

Gln Val Lys Gly Asp Ile Val Lys Gly Thr Asp Gly Lys Ile Arg
    1160                1165                1170

Tyr Tyr Asp Ala Lys Ser Gly Glu Gln Val Phe Asn Lys Thr Val
    1175                1180                1185

Lys Ala Ala Asp Gly Lys Thr Tyr Val Ile Gly Asn Asp Gly Val
    1190                1195                1200

Ala Val Asp Pro Ser Val Val Lys Gly Gln Thr Phe Lys Asp Ala
    1205                1210                1215

Ser Gly Ala Leu Arg Phe Tyr Asn Leu Lys Gly Gln Leu Val Thr
    1220                1225                1230

Gly Ser Gly Trp Tyr Glu Thr Ala Asn His Asp Trp Val Tyr Ile
    1235                1240                1245

Gln Ser Gly Lys Ala Leu Thr Gly Glu Gln Thr Ile Asn Gly Gln
    1250                1255                1260

His Leu Tyr Phe Lys Glu Asp Gly His Gln Val Lys Gly Gln Leu
    1265                1270                1275

Val Thr Gly Thr Asp Gly Lys Val Arg Tyr Tyr Asp Ala Asn Ser
    1280                1285                1290

Gly Asp Gln Ala Phe Asn Lys Ser Val Thr Val Asn Gly Lys Thr
    1295                1300                1305

Tyr Tyr Phe Gly Asn Asp Gly Thr Ala Gln Thr Ala Gly Asn Pro
    1310                1315                1320

Lys Gly Gln Thr Phe Lys Asp Gly Ser Asp Ile Arg Phe Tyr Ser
    1325                1330                1335

Met Glu Gly Gln Leu Val Thr Gly Ser Gly Trp Tyr Glu Asn Ala
    1340                1345                1350

Gln Gly Gln Trp Leu Tyr Val Lys Asn Gly Lys Val Leu Thr Gly
    1355                1360                1365

Leu Gln Thr Val Gly Ser Gln Arg Val Tyr Phe Asp Glu Asn Gly
    1370                1375                1380

Ile Gln Ala Lys Gly Lys Ala Val Arg Thr Ser Asp Gly Lys Ile
    1385                1390                1395

Arg Tyr Phe Asp Glu Asn Ser Gly Ser Met Ile Thr Asn Gln Trp
    1400                1405                1410

Lys Phe Val Tyr Gly Gln Tyr Tyr Phe Gly Asn Asp Gly Ala
    1415                1420                1425

Arg Ile Tyr Arg Gly Trp Asn 1430        1435

<210> SEQ ID NO 3
<211> LENGTH: 4026
<212> TYPE: DNA
<213> ORGANISM: Streptococcus salivarius SK126

<400> SEQUENCE: 3

| | | | | | |
|---|---|---|---|---|---|
| atgatcgacg | gcaaatacta | ttatgttaat | gaggacggta | gccacaaaga | aaactttgcg | 60 |
| attacggtta | atggtcaact | gctgtatttc | ggtaaggacg | gcgcactgac | ctctagcagc | 120 |
| acttacagct | ttaccccagg | tacgacgaac | atcgtggatg | gcttttctat | caacaaccgc | 180 |
| gcgtatgact | ccagcgaagc | gtcctttgaa | ctgattgatg | gctacttgac | tgccgactcc | 240 |
| tggtatcgtc | cggcttccat | catcaaggac | ggtgtcacgt | ggcaggccag | caccgcagag | 300 |
| gactttcgcc | cgctgctgat | ggcgtggtgg | ccaaacgtgg | atacccaggt | gaactatctg | 360 |
| aactacatgt | ctaaagtgtt | taacctggac | gcaaagtata | gcagcaccga | taaacaagag | 420 |
| actctgaagg | ttgcagctaa | ggatattcag | attaagatcg | agcagaaaat | tcaggcggag | 480 |
| aaaagcaccc | aatggctgcg | cgaaacgatc | agcgcttttg | tgaaaaccca | accacagtgg | 540 |
| aacaaagaga | ctgagaatta | ctcgaaaggt | ggtggtgagg | atcatctgca | aggcggtgca | 600 |
| ctgctgtacg | tgaatgatag | ccgtaccccg | tgggcaaata | gcgattatcg | ccgcctgaac | 660 |
| cgcaccgcta | ccaatcaaac | gggtacgatt | gacaagtcca | ttctggacga | gcagagcgac | 720 |
| ccaaatcaca | tgggcggttt | cgacttcctg | ctggcgaatg | atgttgacct | gtccaacccg | 780 |
| gttgtgcagg | cagagcagct | gaaccagatt | cactacttga | tgaattgggg | ctctatcgtg | 840 |
| atgggtgaca | agacgcaaa | ctttgatggt | atccgtgtcg | atgcagttga | caacgtcgat | 900 |
| gccgacatgc | tgcaactgta | taccaactac | ttccgtgaat | actacggtgt | taacaaaagc | 960 |
| gaagcgaacg | cactggcgca | cattagcgtt | ttggaagcgt | ggagcttgaa | tgataatcac | 1020 |
| tacaacgaca | aaaccgatgg | tgcagcattg | gcgatggaga | taagcagcg | tctggcgctg | 1080 |
| ctgtttagcc | tggctaaacc | gattaaagag | cgcacccccgg | cagtgagccc | gctgtataac | 1140 |
| aacaccttca | atacgaccca | acgcgatgag | aaaaccgact | ggatcaataa | agacggttct | 1200 |
| aaggcctata | cgaggatgg | tactgtgaag | cagagcacca | ttggtaagta | caatgaaaaa | 1260 |
| tatggtgatg | catcgggcaa | ttatgtgttc | atccgtgccc | atgataacaa | tgtccaagac | 1320 |
| atcattgcgg | agatcattaa | gaaagaaatc | aacccgaaaa | gcgatggttt | caccatcact | 1380 |
| gacgccgaaa | tgaaacaagc | gttcgagatt | tacaataagg | acatgctgag | cagcgacaag | 1440 |
| aagtacaccc | tgaataacat | cccggcagct | tatgccgtga | tgttgcagaa | catggaaacg | 1500 |
| attacccgtg | tctattatgg | tgacctgtac | accgacgacg | gccactacat | ggaaaccaag | 1560 |
| tccccgtatt | acgacaccat | cgttaacctg | atgaaaagcc | gtatcaagta | cgtcagcggt | 1620 |
| ggccaggccc | aacgtagcta | ctggctgccg | accgacggca | agatggacaa | tagcgacgtt | 1680 |
| gagctgtatc | gcaccaacga | agtgtatacc | agcgtccgtt | acggtaaaga | cattatgacc | 1740 |
| gcgaacgata | ccgagggtag | caagtacagc | cgcaccagcg | gccaggtcac | cctggttgca | 1800 |
| aacaacccga | agctgaccct | ggaccagagc | gcgaagctga | atgtggaaat | gggtaagatt | 1860 |
| cacgcgaatc | agaaataccg | tgccctgatt | gtgggcacgg | ctgacggtat | caagaatttc | 1920 |
| accagcgacg | cagatgctat | cgcggcaggc | tacgtgaaag | aaaccgactc | caatggcgtt | 1980 |
| ctgacttttg | gcgctaatga | catcaaaggt | tatgaaacct | tcgacatgtc | cggctttgtt | 2040 |
| gctgtttggg | tgccggtcgg | cgcgagcgat | gatcaggaca | ttcgtgtcgc | tcctagcact | 2100 |

```
gaggccaaga agagggtga attgaccctg aaagcgaccg aagcatacga ttcccagctg    2160
atctatgaag gttttagcaa ttttcaaacc atcccggatg gtagcgaccc gagcgtgtac    2220
accaatcgca agatcgcaga gaacgtggac ctgttcaagt cctggggtgt tacctcgttt    2280
gaaatggcac cgcagttcgt ttccgcagat gatggcactt ttctggactc tgtgatccaa    2340
aacggctatg cgtttgccga tcgttacgat ttggcgatga gcaagaacaa caaatacggc    2400
agcaaagagg acttgcgtga cgcgctgaaa gccctgcata agcaggcat ccaggcgatt     2460 gcagactggg tcccggacca gatttatcag ttgccgggca agaagtggt cacggcgact      2520 cgcaccgacg gcgcaggccg taaaatcgcg gacgcgatca ttgatcatag cctgtacgtt    2580
gcgaacacta agagcagcgg caaagattac caggcgaagt acggtggtga gttcttggcg    2640
gagctgaagg ccaagtaccc ggagatgttc aaagtgaaca tgatttctac cggcaaaccg    2700
attgatgaca gcgtcaaact gaaacagtgg aaagcagaat actttaacgg caccaacgtc    2760
ttggagcgcg gtgtgggtta tgtcctgagc gatgaagcca cgggtaaata ctttaccgtc    2820
acgaaggatg caacttcat tccgttgcag ctgacgggta tgagaaagt cgtgaccggc       2880 tttagcaatg atggcaaagg tatcacctac ttcggtacga gcggcactca agcgaaatct    2940
gcgttcgtta cgttcaatgg taatacttac tattttgacg ctcgtggtca catggttacg    3000
aacggcgagt attcgccgaa cggtaaggat gtttaccgtt tcctgccgaa tggtattatg    3060
ctgtctaacg ctttttacgt tgatgcaaat ggtaacacgt acctgtacaa cagcaagggc    3120
caaatgtaca aggcggtta caccaaattt gacgttaccg aaacggacaa agatggtaag     3180
gaaagcaagg tggtgaagtt tcgttacttt acgaacgaag gtgtcatggc aaaaggcgtt    3240
accgtgattg acggcttcac gcaatacttt ggtgaagatg gtttccaagc gaaagacaag    3300
ctggtcacgt tcaagggcaa gacgtactac ttcgatgcac acaccggcaa tgcgatcaag    3360
gacacctggc gtaatatcaa tggcaagtgg tatcatttcg acgcgaacgg cgttgcagcg    3420
accggcgctc aggtcatcaa tggccaaaaa ctgtatttca cgaggacgg cagccaagtg     3480 aaaggcggtg ttgtcaaaaa cgcggacggt acgtattcta atacaaaga gggttctggt      3540 gaactggtta ccaacgagtt cttcacgacg gatggcaatg tttggtacta cgcaggcgcg    3600
aatggcaaga ccgttacggg tgcccaggtg attaacggcc aacacctgta cttcaatgcg    3660
gacggttcgc aagtgaaggg cggtgtggtc aagaacgcgg atggcaccta tagcaaatat    3720
gatgcgtcta ccggcgaacg cctgaccaat gagtttttca ccacgggtga taacaactgg    3780
tactacattg gcgcaaacgg caagagcgtg acgggcgagg tcaagatcgg tgacgatacc    3840
tatttctttg ccaaagatgg caagcaagtt aagggtcaaa ctgtcagcgc gggtaacggt    3900
cgtattagct actactatgg tgatagcggt aagcgtgcgg tgagcacttg gatcgaaatc    3960
caaccgggtg tttatgtcta cttcgacaag aacggcattg cctatccgcc tcgtgtgctg    4020
aattaa                                                                4026
```

<210> SEQ ID NO 4
<211> LENGTH: 1341
<212> TYPE: PRT
<213> ORGANISM: Streptococcus salivarius SK126

<400> SEQUENCE: 4

Met Ile Asp Gly Lys Tyr Tyr Tyr Val Asn Glu Asp Gly Ser His Lys
1               5                   10                  15

Glu Asn Phe Ala Ile Thr Val Asn Gly Gln Leu Leu Tyr Phe Gly Lys

```
                     20                  25                  30
Asp Gly Ala Leu Thr Ser Ser Ser Thr Tyr Ser Phe Thr Pro Gly Thr
                 35                  40                  45
Thr Asn Ile Val Asp Gly Phe Ser Ile Asn Asn Arg Ala Tyr Asp Ser
             50                  55                  60
Ser Glu Ala Ser Phe Glu Leu Ile Asp Gly Tyr Leu Thr Ala Asp Ser
 65                  70                  75                  80
Trp Tyr Arg Pro Ala Ser Ile Ile Lys Asp Gly Val Thr Trp Gln Ala
                     85                  90                  95
Ser Thr Ala Glu Asp Phe Arg Pro Leu Leu Met Ala Trp Trp Pro Asn
                100                 105                 110
Val Asp Thr Gln Val Asn Tyr Leu Asn Tyr Met Ser Lys Val Phe Asn
            115                 120                 125
Leu Asp Ala Lys Tyr Ser Ser Thr Asp Lys Gln Glu Thr Leu Lys Val
        130                 135                 140
Ala Ala Lys Asp Ile Gln Ile Lys Ile Glu Gln Lys Ile Gln Ala Glu
145                 150                 155                 160
Lys Ser Thr Gln Trp Leu Arg Glu Thr Ile Ser Ala Phe Val Lys Thr
                165                 170                 175
Gln Pro Gln Trp Asn Lys Glu Thr Glu Asn Tyr Ser Lys Gly Gly Gly
                180                 185                 190
Glu Asp His Leu Gln Gly Gly Ala Leu Leu Tyr Val Asn Asp Ser Arg
                195                 200                 205
Thr Pro Trp Ala Asn Ser Asp Tyr Arg Arg Leu Asn Arg Thr Ala Thr
            210                 215                 220
Asn Gln Thr Gly Thr Ile Asp Lys Ser Ile Leu Asp Glu Gln Ser Asp
225                 230                 235                 240
Pro Asn His Met Gly Gly Phe Asp Phe Leu Leu Ala Asn Asp Val Asp
                245                 250                 255
Leu Ser Asn Pro Val Val Gln Ala Glu Gln Leu Asn Gln Ile His Tyr
                260                 265                 270
Leu Met Asn Trp Gly Ser Ile Val Met Gly Asp Lys Asp Ala Asn Phe
            275                 280                 285
Asp Gly Ile Arg Val Asp Ala Val Asp Asn Val Asp Ala Asp Met Leu
        290                 295                 300
Gln Leu Tyr Thr Asn Tyr Phe Arg Glu Tyr Tyr Gly Val Asn Lys Ser
305                 310                 315                 320
Glu Ala Asn Ala Leu Ala His Ile Ser Val Leu Glu Ala Trp Ser Leu
                325                 330                 335
Asn Asp Asn His Tyr Asn Asp Lys Thr Asp Gly Ala Ala Leu Ala Met
                340                 345                 350
Glu Asn Lys Gln Arg Leu Ala Leu Leu Phe Ser Leu Ala Lys Pro Ile
            355                 360                 365
Lys Glu Arg Thr Pro Ala Val Ser Pro Leu Tyr Asn Asn Thr Phe Asn
        370                 375                 380
Thr Thr Gln Arg Asp Glu Lys Thr Asp Trp Ile Asn Lys Asp Gly Ser
385                 390                 395                 400
Lys Ala Tyr Asn Glu Asp Gly Thr Val Lys Gln Ser Thr Ile Gly Lys
                405                 410                 415
Tyr Asn Glu Lys Tyr Gly Asp Ala Ser Gly Asn Tyr Val Phe Ile Arg
                420                 425                 430
Ala His Asp Asn Asn Val Gln Asp Ile Ile Ala Glu Ile Ile Lys Lys
            435                 440                 445
```

```
Glu Ile Asn Pro Lys Ser Asp Gly Phe Thr Ile Thr Asp Ala Glu Met
    450                 455                 460

Lys Gln Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr Tyr Asp Thr Ile Val
        515                 520                 525

Asn Leu Met Lys Ser Arg Ile Lys Tyr Val Ser Gly Gln Ala Gln
    530                 535                 540

Arg Ser Tyr Trp Leu Pro Thr Asp Gly Lys Met Asp Asn Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asn Asp Thr Glu Gly Ser Lys Tyr Ser Arg Thr
            580                 585                 590

Ser Gly Gln Val Thr Leu Val Ala Asn Asn Pro Lys Leu Thr Leu Asp
        595                 600                 605

Gln Ser Ala Lys Leu Asn Val Glu Met Gly Lys Ile His Ala Asn Gln
    610                 615                 620

Lys Tyr Arg Ala Leu Ile Val Gly Thr Ala Asp Gly Ile Lys Asn Phe
625                 630                 635                 640

Thr Ser Asp Ala Asp Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Pro Ser Thr Glu Ala Lys Lys
    690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
    770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ala Asp Ala Ile Ile Asp His Ser Leu Tyr Val Ala Asn Thr Lys
    850                 855                 860
```

-continued

```
Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
            885                 890                 895

Thr Gly Lys Pro Ile Asp Asp Ser Val Lys Leu Lys Gln Trp Lys Ala
        900                 905                 910

Glu Tyr Phe Asn Gly Thr Asn Val Leu Glu Arg Gly Val Gly Tyr Val
    915                 920                 925

Leu Ser Asp Glu Ala Thr Gly Lys Tyr Phe Thr Val Thr Lys Asp Gly
930                 935                 940

Asn Phe Ile Pro Leu Gln Leu Thr Gly Asn Glu Lys Val Val Thr Gly
945                 950                 955                 960

Phe Ser Asn Asp Gly Lys Gly Ile Thr Tyr Phe Gly Thr Ser Gly Thr
            965                 970                 975

Gln Ala Lys Ser Ala Phe Val Thr Phe Asn Gly Asn Thr Tyr Tyr Phe
        980                 985                 990

Asp Ala Arg Gly His Met Val Thr Asn Gly Glu Tyr Ser Pro Asn Gly
            995                 1000                1005

Lys Asp Val Tyr Arg Phe Leu Pro Asn Gly Ile Met Leu Ser Asn
    1010                1015                1020

Ala Phe Tyr Val Asp Ala Asn Gly Asn Thr Tyr Leu Tyr Asn Ser
    1025                1030                1035

Lys Gly Gln Met Tyr Lys Gly Gly Tyr Thr Lys Phe Asp Val Thr
    1040                1045                1050

Glu Thr Asp Lys Asp Gly Lys Glu Ser Lys Val Val Lys Phe Arg
    1055                1060                1065

Tyr Phe Thr Asn Glu Gly Val Met Ala Lys Gly Val Thr Val Ile
    1070                1075                1080

Asp Gly Phe Thr Gln Tyr Phe Gly Glu Asp Gly Phe Gln Ala Lys
    1085                1090                1095

Asp Lys Leu Val Thr Phe Lys Gly Lys Thr Tyr Tyr Phe Asp Ala
    1100                1105                1110

His Thr Gly Asn Ala Ile Lys Asp Thr Trp Arg Asn Ile Asn Gly
    1115                1120                1125

Lys Trp Tyr His Phe Asp Ala Asn Gly Val Ala Ala Thr Gly Ala
    1130                1135                1140

Gln Val Ile Asn Gly Gln Lys Leu Tyr Phe Asn Glu Asp Gly Ser
    1145                1150                1155

Gln Val Lys Gly Gly Val Val Lys Asn Ala Asp Gly Thr Tyr Ser
    1160                1165                1170

Lys Tyr Lys Glu Gly Ser Gly Glu Leu Val Thr Asn Glu Phe Phe
    1175                1180                1185

Thr Thr Asp Gly Asn Val Trp Tyr Tyr Ala Gly Ala Asn Gly Lys
    1190                1195                1200

Thr Val Thr Gly Ala Gln Val Ile Asn Gly Gln His Leu Tyr Phe
    1205                1210                1215

Asn Ala Asp Gly Ser Gln Val Lys Gly Gly Val Val Lys Asn Ala
    1220                1225                1230

Asp Gly Thr Tyr Ser Lys Tyr Asp Ala Ser Thr Gly Glu Arg Leu
    1235                1240                1245

Thr Asn Glu Phe Phe Thr Thr Gly Asp Asn Asn Trp Tyr Tyr Ile
    1250                1255                1260

Gly Ala Asn Gly Lys Ser Val Thr Gly Glu Val Lys Ile Gly Asp
```

```
            1265            1270            1275
Asp Thr Tyr Phe Phe Ala Lys Asp Gly Lys Gln Val Lys Gly Gln
            1280            1285            1290

Thr Val Ser Ala Gly Asn Gly Arg Ile Ser Tyr Tyr Tyr Gly Asp
            1295            1300            1305

Ser Gly Lys Arg Ala Val Ser Thr Trp Ile Glu Ile Gln Pro Gly
            1310            1315            1320

Val Tyr Val Tyr Phe Asp Lys Asn Gly Ile Ala Tyr Pro Pro Arg
            1325            1330            1335

Val Leu Asn
            1340

<210> SEQ ID NO 5
<211> LENGTH: 3744
<212> TYPE: DNA
<213> ORGANISM: Streptococcus salivarius

<400> SEQUENCE: 5
```

| | | | | | |
|---|---|---|---|---|---|
| atgccaagcc | acattaagac | catcaacggc | aaacaatact | acgtggagga | tgacggtacg   60 |
| attcgcaaga | attacgtcct | ggagcgtatc | ggtggcagcc | aatactttaa | tgcagaaacc  120 |
| ggtgaactgt | ctaatcagaa | agagtatcgt | ttcgacaaaa | atggtggtac | tggtagcagc  180 |
| gcggacagca | cgaacaccaa | cgtgactgtg | aacggtgaca | aaaacgcatt | ttacggtacc  240 |
| acggacaaag | acattgagct | ggtcgacggc | tatttcaccg | cgaacacctg | gtatcgcccg  300 |
| aaagaaatcc | tgaaagacgg | caaagaatgg | accgccagca | cggagaacga | taaacgcccg  360 |
| ctgctgaccg | tctggtggcc | tagcaaagca | atccaggcgt | cttatctgaa | ctacatgaaa  420 |
| gagcaaggcc | tgggtaccaa | ccaaacgtac | acgagcttct | ccagccaaac | ccaaatggat  480 |
| caagcagccc | tggaagtgca | aaagcgtatt | gaagagcgca | tcgcacgcga | gggcaatacc  540 |
| gactggctgc | gcacgaccat | caagaacttc | gtgaaaaccc | aaccgggttg | aacagcacc  600 |
| tctgaaaatc | tggacaataa | tgatcatctg | caaggtggcg | ccctgctgta | caataacgac  660 |
| tcccgcacga | gccacgcgaa | cagcgactat | cgcctgctga | tcgtacgcc | gaccagccag  720 |
| accggcaaac | acaatccgaa | atacaccaaa | gataccagca | atggtggttt | cgaatttctg  780 |
| ctggcgaacg | acatcgataa | ctctaatccg | gcggttcaag | cagagcaact | gaactggctg  840 |
| cattacatta | tgaacatcgg | taccatcacg | ggcggttctg | aggatgaaaa | cttcgacggc  900 |
| gttcgtgttg | acgctgtgga | taatgtgaat | gcggatctgc | tgcaaatcgc | gagcgactat  960 |
| ttcaaagcaa | aataccggtgc | tgatcaaagc | caagatcagg | cgatcaaaca | cttgagcatc 1020 |
| ctggaagcgt | ggtcccataa | cgacgcctac | tataacgaag | ataccaaagg | cgcgcagttg 1080 |
| ccgatggatg | atccgatgca | cctggctctg | gtctactcgc | tgctgcgtcc | gatcggcaat 1140 |
| cgcagcggtg | tggaaccgct | gatttccaac | agcctgaatg | accgtagcga | gtccggtaag 1200 |
| aacagcaaac | gtatggcgaa | ctacgcgttc | gtacgcgcgc | atgatagcga | ggtgcaatcg 1260 |
| attattggcc | agatcatcaa | aaacgagatc | aatccgcaaa | gcaccggtaa | tacgttcacc 1320 |
| ctggatgaga | tgaagaaagc | gtttgagatt | tacaacaagg | atatgcgtag | cgcgaataag 1380 |
| cagtatacgc | agtacaacat | cccgagcgcg | tatgcgttga | tgctgaccca | caaggatacc 1440 |
| gttccgcgtg | tgtattacgg | tgatatgtat | acggacgacg | gtcagtacat | ggcgcaaaag 1500 |
| agcccatact | atgatgcgat | cgaaacgctg | ctgaaaggtc | gcatccgcta | tgccgcaggt 1560 |
| ggtcaggaca | tgaaggtcaa | ctatattggt | tacggtaaca | ctaacggctg | ggatgctgcg 1620 |

```
ggcgtgctga ccagcgtacg ttatggcacg ggcgcaaata gcgccagcga tacgggtacc    1680
gccgaaacgc gtaatcaagg tatggcagtg attgttagca accaaccggc gctgcgtctg    1740
actagcaatt tgaccattaa catgggtgcc gcacaccgta atcaggctta ccgtccgctg    1800
ctgctgacga ccaacgatgg cgtcgcgacc tatttgaacg atagcgatgc gaatggtatc    1860
gttaagtaca ccgacggtaa tggtaatctg accttctccg caaacgagat tcgtggcatc    1920
cgtaacccgc aagttgatgg ctatctggcc gtctgggttc cggtaggtgc gtcggagaat    1980
caggatgttc gtgtggcgcc gagcaaagag aagaacagct ccggtctggt ttacgagagc    2040
aatgctgccc tggatagcca agttatctac gaaggcttca gcaacttcca ggacttcgtt    2100
cagaatccga gccagtatac caacaaaaag attgcagaga atgcaaattt gttcaaatcc    2160
tggggtatta ccagctttga atttgcgccg cagtacgtga gctcggatga tggtagcttc    2220
ctggacagcg ttattcagaa cggttatgcg tttacggacc gctacgacat tggtatgagc    2280
aaagacaaca aatatggttc gctggcggat ttgaaggcag cactgaagag cttgcatgcc    2340
gttggtatta gcgcaatcgc ggattgggtt cctgatcaga tctacaatct gccaggcgac    2400
gaggtcgtca ccgcaacccg cgttaacaac tacggcgaaa ccaaagatgg tgcaatcatt    2460
gatcactctt tgtacgcggc caaaacccgt acttttggta acgactacca gggtaagtat    2520
ggtggtgcgt tcctggacga gctgaaacgt ctgtatccgc agatcttttga ccgcgttcag    2580 atttctaccg gtaagcgcat gaccacggac gagaagatca cccaatggtc tgcaaagtat    2640
atgaacggta cgaacatctt ggaccgtggc tctgaatacg ttttgaagaa tggtctgaat    2700
ggttactatg caccaatggg tgcaaaagtt tcgctgccga agttgtggg tagcaatcaa    2760 agcacgaatg gcgacaatca aaacggcgac ggtagcggca gtttgaaaaa gcgtctgttc    2820
agcgtgcgtt accgttataa caatggccag tacgcgaaaa atgcctttat caaagataac    2880
gacggcaatg tttactattt cgacaatagc ggtcgtatgg ctgtcggtga gaaaacgatt    2940
gacggcaagc agtacttctt cctggctaat ggcgttcagc tgcgtgacgg ctaccgtcaa    3000
aatcgtcgcg gtcaggtgtt ttactacgac cagaatggtg tgctgaacgc aaacggtaaa    3060
caagacccga agcctgacaa caataacaat gcgagcggcc gtaatcaatt cgtccagatc    3120
ggtaacaacg tgtgggcgta ttatgatggc aatggtaaac gtgtcaccgg tcaccagaac    3180
atcaacggtc aggagttgtt tttcgataac aacggtgtcc aggttaaggg tcgtacggtg    3240
aatgagaacg gtgcaattcg ctactatgac gcgaatagcg gtgagatggc acgcaatcgt    3300
ttcgcggaga ttgaaccggg cgtctgggca tactttaaca atgacggcac cgcagtgaag    3360
ggttctcaga atatcaatgg tcaagacctg tacttcgacc agaacggtcg tcaggtcaag    3420
ggtgcgctgg ccaatgttga tggcaacctg cgctattacg acgttaacag cggtgagctg    3480
taccgtaatc gtttccacga aatcgacggc agctggtatt actttgatgg taacggtaat    3540
gcggtgaagg gtatggtcaa tatcaacggc caaaatctgt tgtttgacaa taacggcaaa    3600
cagattaagg gtcatctggt ccgcgtcaac ggcgtcgtgc gctattttga tccgaactct    3660
ggtgaaatgg cggttaatcg ttgggttgag gtgagcccag gttggtgggt ttactttgac    3720
ggtgaaggtc gtggtcagat ctaa                                           3744
```

<210> SEQ ID NO 6
<211> LENGTH: 1247
<212> TYPE: PRT
<213> ORGANISM: Streptococcus salivarius

<400> SEQUENCE: 6

```
Met Pro Ser His Ile Lys Thr Ile Asn Gly Lys Gln Tyr Tyr Val Glu
1               5                   10                  15

Asp Asp Gly Thr Ile Arg Lys Asn Tyr Val Leu Glu Arg Ile Gly Gly
            20                  25                  30

Ser Gln Tyr Phe Asn Ala Glu Thr Gly Glu Leu Ser Asn Gln Lys Glu
            35                  40                  45

Tyr Arg Phe Asp Lys Asn Gly Gly Thr Gly Ser Ser Ala Asp Ser Thr
50                  55                  60

Asn Thr Asn Val Thr Val Asn Gly Asp Lys Asn Ala Phe Tyr Gly Thr
65                  70                  75                  80

Thr Asp Lys Asp Ile Glu Leu Val Asp Gly Tyr Phe Thr Ala Asn Thr
            85                  90                  95

Trp Tyr Arg Pro Lys Glu Ile Leu Lys Asp Gly Lys Glu Trp Thr Ala
            100                 105                 110

Ser Thr Glu Asn Asp Lys Arg Pro Leu Leu Thr Val Trp Trp Pro Ser
            115                 120                 125

Lys Ala Ile Gln Ala Ser Tyr Leu Asn Tyr Met Lys Glu Gln Gly Leu
            130                 135                 140

Gly Thr Asn Gln Thr Tyr Thr Ser Phe Ser Ser Gln Thr Gln Met Asp
145                 150                 155                 160

Gln Ala Ala Leu Glu Val Gln Lys Arg Ile Glu Glu Arg Ile Ala Arg
            165                 170                 175

Glu Gly Asn Thr Asp Trp Leu Arg Thr Thr Ile Lys Asn Phe Val Lys
            180                 185                 190

Thr Gln Pro Gly Trp Asn Ser Thr Ser Glu Asn Leu Asp Asn Asn Asp
            195                 200                 205

His Leu Gln Gly Gly Ala Leu Leu Tyr Asn Asn Asp Ser Arg Thr Ser
            210                 215                 220

His Ala Asn Ser Asp Tyr Arg Leu Leu Asn Arg Thr Pro Thr Ser Gln
225                 230                 235                 240

Thr Gly Lys His Asn Pro Lys Tyr Thr Lys Asp Thr Ser Asn Gly Gly
            245                 250                 255

Phe Glu Phe Leu Leu Ala Asn Asp Ile Asp Asn Ser Asn Pro Ala Val
            260                 265                 270

Gln Ala Glu Gln Leu Asn Trp Leu His Tyr Ile Met Asn Ile Gly Thr
            275                 280                 285

Ile Thr Gly Gly Ser Glu Asp Glu Asn Phe Asp Gly Val Arg Val Asp
            290                 295                 300

Ala Val Asp Asn Val Asn Ala Asp Leu Leu Gln Ile Ala Ser Asp Tyr
305                 310                 315                 320

Phe Lys Ala Lys Tyr Gly Ala Asp Gln Ser Gln Asp Gln Ala Ile Lys
            325                 330                 335

His Leu Ser Ile Leu Glu Ala Trp Ser His Asn Asp Ala Tyr Tyr Asn
            340                 345                 350

Glu Asp Thr Lys Gly Ala Gln Leu Pro Met Asp Asp Pro Met His Leu
            355                 360                 365

Ala Leu Val Tyr Ser Leu Leu Arg Pro Ile Gly Asn Arg Ser Gly Val
            370                 375                 380

Glu Pro Leu Ile Ser Asn Ser Leu Asn Asp Arg Ser Glu Ser Gly Lys
385                 390                 395                 400

Asn Ser Lys Arg Met Ala Asn Tyr Ala Phe Val Arg Ala His Asp Ser
            405                 410                 415
```

Glu Val Gln Ser Ile Ile Gly Gln Ile Ile Lys Asn Glu Ile Asn Pro
        420                 425                 430

Gln Ser Thr Gly Asn Thr Phe Thr Leu Asp Glu Met Lys Lys Ala Phe
        435                 440                 445

Glu Ile Tyr Asn Lys Asp Met Arg Ser Ala Asn Lys Gln Tyr Thr Gln
450                     455                 460

Tyr Asn Ile Pro Ser Ala Tyr Ala Leu Met Leu Thr His Lys Asp Thr
465                 470                  475                 480

Val Pro Arg Val Tyr Tyr Gly Asp Met Tyr Thr Asp Asp Gly Gln Tyr
                485                 490                 495

Met Ala Gln Lys Ser Pro Tyr Tyr Asp Ala Ile Glu Thr Leu Leu Lys
            500                 505                 510

Gly Arg Ile Arg Tyr Ala Ala Gly Gly Gln Asp Met Lys Val Asn Tyr
            515                 520                 525

Ile Gly Tyr Gly Asn Thr Asn Gly Trp Asp Ala Ala Gly Val Leu Thr
        530                 535                 540

Ser Val Arg Tyr Gly Thr Gly Ala Asn Ser Ala Ser Asp Thr Gly Thr
545                 550                 555                 560

Ala Glu Thr Arg Asn Gln Gly Met Ala Val Ile Val Ser Asn Gln Pro
                565                 570                 575

Ala Leu Arg Leu Thr Ser Asn Leu Thr Ile Asn Met Gly Ala Ala His
            580                 585                 590

Arg Asn Gln Ala Tyr Arg Pro Leu Leu Thr Thr Asn Asp Gly Val
            595                 600                 605

Ala Thr Tyr Leu Asn Asp Ser Asp Ala Asn Gly Ile Val Lys Tyr Thr
        610                 615                 620

Asp Gly Asn Gly Asn Leu Thr Phe Ser Ala Asn Glu Ile Arg Gly Ile
625                 630                 635                 640

Arg Asn Pro Gln Val Asp Gly Tyr Leu Ala Val Trp Val Pro Val Gly
                645                 650                 655

Ala Ser Glu Asn Gln Asp Val Arg Val Ala Pro Ser Lys Glu Lys Asn
            660                 665                 670

Ser Ser Gly Leu Val Tyr Glu Ser Asn Ala Ala Leu Asp Ser Gln Val
        675                 680                 685

Ile Tyr Glu Gly Phe Ser Asn Phe Gln Asp Phe Val Gln Asn Pro Ser
690                 695                 700

Gln Tyr Thr Asn Lys Lys Ile Ala Glu Asn Ala Asn Leu Phe Lys Ser
705                 710                 715                 720

Trp Gly Ile Thr Ser Phe Glu Phe Ala Pro Gln Tyr Val Ser Ser Asp
                725                 730                 735

Asp Gly Ser Phe Leu Asp Ser Val Ile Gln Asn Gly Tyr Ala Phe Thr
            740                 745                 750

Asp Arg Tyr Asp Ile Gly Met Ser Lys Asp Asn Lys Tyr Gly Ser Leu
        755                 760                 765

Ala Asp Leu Lys Ala Ala Leu Lys Ser Leu His Ala Val Gly Ile Ser
        770                 775                 780

Ala Ile Ala Asp Trp Val Pro Asp Gln Ile Tyr Asn Leu Pro Gly Asp
785                 790                 795                 800

Glu Val Val Thr Ala Thr Arg Val Asn Asn Tyr Gly Glu Thr Lys Asp
                805                 810                 815

Gly Ala Ile Ile Asp His Ser Leu Tyr Ala Ala Lys Thr Arg Thr Phe
            820                 825                 830

Gly Asn Asp Tyr Gln Gly Lys Tyr Gly Gly Ala Phe Leu Asp Glu Leu

-continued

```
            835                 840                 845
Lys Arg Leu Tyr Pro Gln Ile Phe Asp Arg Val Gln Ile Ser Thr Gly
            850                 855                 860
Lys Arg Met Thr Thr Asp Glu Lys Ile Thr Gln Trp Ser Ala Lys Tyr
865                 870                 875                 880
Met Asn Gly Thr Asn Ile Leu Asp Arg Gly Ser Glu Tyr Val Leu Lys
                885                 890                 895
Asn Gly Leu Asn Gly Tyr Tyr Gly Thr Asn Gly Gly Lys Val Ser Leu
                900                 905                 910
Pro Lys Val Val Gly Ser Asn Gln Ser Thr Asn Gly Asp Asn Gln Asn
                915                 920                 925
Gly Asp Gly Ser Gly Lys Phe Glu Lys Arg Leu Phe Ser Val Arg Tyr
            930                 935                 940
Arg Tyr Asn Asn Gly Gln Tyr Ala Lys Asn Ala Phe Ile Lys Asp Asn
945                 950                 955                 960
Asp Gly Asn Val Tyr Tyr Phe Asp Asn Ser Gly Arg Met Ala Val Gly
                965                 970                 975
Glu Lys Thr Ile Asp Gly Lys Gln Tyr Phe Phe Leu Ala Asn Gly Val
            980                 985                 990
Gln Leu Arg Asp Gly Tyr Arg Gln  Asn Arg Arg Gly Gln  Val Phe Tyr
            995                 1000                1005
Tyr Asp  Gln Asn Gly Val Leu  Asn Ala Asn Gly Lys  Gln Asp Pro
        1010                1015                1020
Lys Pro  Asp Asn Asn Asn  Ala Ser Gly Arg Asn  Gln Phe Val
        1025                1030                1035
Gln Ile  Gly Asn Asn Val Trp  Ala Tyr Tyr Asp Gly  Asn Gly Lys
        1040                1045                1050
Arg Val  Thr Gly His Gln Asn  Ile Asn Gly Gln Glu  Leu Phe Phe
        1055                1060                1065
Asp Asn  Asn Gly Val Gln Val  Lys Gly Arg Thr Val  Asn Glu Asn
        1070                1075                1080
Gly Ala  Ile Arg Tyr Tyr Asp  Ala Asn Ser Gly Glu  Met Ala Arg
        1085                1090                1095
Asn Arg  Phe Ala Glu Ile Glu  Pro Gly Val Trp Ala  Tyr Phe Asn
        1100                1105                1110
Asn Asp  Gly Thr Ala Val Lys  Gly Ser Gln Asn Ile  Asn Gly Gln
        1115                1120                1125
Asp Leu  Tyr Phe Asp Gln Asn  Gly Arg Gln Val Lys  Gly Ala Leu
        1130                1135                1140
Ala Asn  Val Asp Gly Asn Leu  Arg Tyr Tyr Asp Val  Asn Ser Gly
        1145                1150                1155
Glu Leu  Tyr Arg Asn Arg Phe  His Glu Ile Asp Gly  Ser Trp Tyr
        1160                1165                1170
Tyr Phe  Asp Gly Asn Gly Asn  Ala Val Lys Gly Met  Val Asn Ile
        1175                1180                1185
Asn Gly  Gln Asn Leu Leu Phe  Asp Asn Asn Gly Lys  Gln Ile Lys
        1190                1195                1200
Gly His  Leu Val Arg Val Asn  Gly Val Arg Tyr  Phe Asp Pro
        1205                1210                1215
Asn Ser  Gly Glu Met Ala Val  Asn Arg Trp Val Glu  Val Ser Pro
        1220                1225                1230
Gly Trp  Trp Val Tyr Phe Asp  Gly Glu Gly Arg Gly  Gln Ile
        1235                1240                1245
```

<210> SEQ ID NO 7
<211> LENGTH: 4434
<212> TYPE: DNA
<213> ORGANISM: Streptococcus salivarius

<400> SEQUENCE: 7

```
atggacgaaa cgcaggataa gaccgtgacg cagagcaaca gcggcaccac cgcttccctg      60
gtcactagcc ctgaagccac gaaagaggcg gacaaacgca cgaacactaa agaggccgac     120
gttctgacgc ctgcaaaaga aacgaacgca gtcgagactg cgaccaccac taacacccag     180
gcgacggcgg aggccgccac gaccgcgacc accgcggacg tcgcggtggc tgcggtgccg     240
aacaaagaag cggtcgttac cacggatgct ccggcggtca cgaccgagaa agcggaagaa     300
cagccggcta ccgttaaagc agaagtcgtc aatacggaag tgaaagcgcc ggaagcggct     360
ctgaaagaca gcgaggttga ggcagcgctg agcctgaaga acatcaagaa cattgatggc     420
aagtattact atgttaatga ggatggcagc cacaaagaga atttcgctat taccgtgaat     480
ggccagctgc tgtactttgg taaagacggt gcgctgacgt cctctagcac gtattctttt     540
acccccaggca ctaccaatat cgtggacggt tttagcatta caaccgcgc ttacgacagc     600
agcgaggcga gctttgagct gatcgacggt tacttgaccg cagacagctg gtatcgtccg     660
gctagcatca tcaaagatgg tgttacgtgg caagcgtcca ccgccgagga ttttcgtccg     720
ctgctgatgg catggtggcc gaatgtggat acgcaggtga actatttgaa ttacatgtcc     780
aaagttttca acctggacgc gaaatactct agcaccgaca acaggaaaac cctgaaagtg     840
gcagcaaaag acattcaaat caagattgaa caaaagattc aagcggagaa gagcacgcag     900
tggctgcgtg aaactatcag cgcctttgtg aaaacccagc cgcagtggaa caaagaaacc     960
gagaattaca gcaagggtgg tggtgaggac cacctgcaag gtggcgcact gctgtatgtt    1020
aacgacagcc gtacccctg gcgaatagc gattaccgtc gtctgaatcg caccgcaacc    1080
aatcagacgg gcacgatcga taagtctatt ctggacgagc agtctgaccc aaaccacatg    1140
ggcggtttcg actttctgct ggcgaacgac gtcgacctga gcaatccggt cgtgcaggct    1200
gagcagctga atcaaatcca ctatctgatg aattggggtt ccattgtgat gggtgacaag    1260
gatgcgaact tgacggcat tcgtgtcgat gcagttgaca acgtggacgc ggacatgttg    1320
caactgtata ccaattactt ccgtgagtac tacggtgtga acaagagcga agctaacgca    1380
ctggctcaca tcagcgttct ggaggcgtgg agcctgaatg ataatcatta caatgacaag    1440
accgatggtc cggcactggc aatggagaat aagcaacgtc tggcgctgtt gttttcgttg    1500
gcgaaaccga tcaaagagcg tacccccggca gtgagcccgc tgtataacaa caccttcaat    1560
accacccagc gtgatgaaaa gaccgattgg attaacaaag acgtagcaa ggcttacaac    1620
gaagatggca cggtcaaaca atcgaccatc ggtaagtaca acgagaaata cggtgacgca    1680
tccggtaact acgttttcat ccgtgcccac gataacaacg tccaggacat catcgccgag    1740
atcatcaaga aagagatcaa cccgaaaagc gacggcttca ccatcaccga cgccgaaatg    1800
aagcaagcct ttgaaatcta taacaaagat atgctgtcga cgacaaaaa gtataccctg    1860
aataacattc cggcagcgta tgccgtgatg ttgcagaata tggaaacgat tacccgcgtc    1920
tattacggtg atctgtatac ggacgacggt cactacatgg aaaccaaatc tccgtattac    1980
gataccatcg tgaattttgat gaagagccgt atcaagtatg tttcgggtgg ccaggcgcaa    2040
cgtagctatt ggctgccgac cgacggtaag atggacaata gcgacgttga gctgtaccgc    2100
```

```
acgaatgagg tttacacgag cgtgcgctat ggtaaggata tcatgaccgc taatgatacc    2160
gaaggctcta agtattcccg caccagcggc caagtcacct tggtcgcgaa caatccgaag    2220
ctgaatctgg accaaagcgc caagttgaat gtggagatgg gcaaaatcca tgcgaatcag    2280
aagtatcgcg cactgattgt cggcactgcg gacggcatta agaactttac ttccgacgcg    2340
gacgccattg cagcgggtta tgtgaaagaa accgatagca acggcgtgct gaccttcggt    2400
gctaacgaca ttaagggcta cgaaacgttt gatatgagcg gtttcgtggc ggtgtgggtt    2460
ccggtgggtg catctgacaa tcaggacatt cgtgttgcgc cgagcaccga ggcaaagaaa    2520
gaaggtgagc tgaccttgaa ggcgacggaa gcgtatgata gccagctgat ttacgaaggc    2580
tttagcaatt ccagacgat cccagatggc agcgatccgt ccgtgtatac gaaccgcaag    2640
attgcggaga acgtggatct gttcaaaagc tggggtgtca ccagctttga gatggcaccg    2700
caatttgtct cggcggatga tggcaccttt ctggatagcg ttattcagaa tggctacgcc    2760
ttcgccgacc gttatgacct ggccatgtcc aagaacaaca agtatggtag caaagaggac    2820
ctgcgtgatg cactgaaagc actgcataag gcgggtattc aagctatcgc agactgggtt    2880
ccagaccaga tctaccagct gccgggcaaa gaagttgtca ccgccacccg tacggatggt    2940
gctggccgta agatcgcaga cgcgattatc gaccattctc tgtatgttgc aaacagcaaa    3000
agcagcggca agattatca agcaaagtac ggtggcgagt tcctggccga gctgaaagcc    3060
aaatacccgg aaatgttcaa agttaacatg attagcacgg gtaagccgat tgatgactcc    3120
gtgaaattga agcaatggaa agccgagtac ttcaatggca ccaacgtttt ggaacgtggt    3180
gtcggctatg ttctgagcga cgaggcgacc ggtaagtatt tcacggtgac caagaaggc    3240 aatttcattc cgctgcaact gacgggtaaa gagaaagtta tcacgggttt ctccagcgat    3300
ggtaagggta tcacctattt cggtacgagc ggtacgcagg cgaagtctgc gtttgttacc    3360
ttcaatggta acacctacta tttcgacgcg cgtggccaca tggttaccaa tagcgaatac    3420
agcccgaatg gcaaggacgt ctaccgtttt ctgccgaacg gtatcatgct gagcaatgcg    3480
ttttacattg atgcgaacgg taatacctac ctgtacaact ctaagggtca aatgtacaaa    3540
ggcggttaca cgaaattcga tgtttctgaa acggataagg acggtaaaga gtccaaggtc    3600
gtcaagttcc gctactttac gaacgaaggc gtcatggcca agggtgttac cgtcattgat    3660
ggttttaccc aatacttcgg tgaggacggc tttcaagcga aggataagct ggtcaccttc    3720
aagggcaaga cgtattactt cgacgcacac actggtaatg gtatcaaaga tacctggcgc    3780
aatatcaatg gtaaatggta ctatttcgac gcgaatggcg ttgctgcgac cggtgcgcag    3840
gtgattaacg gccagaaact gtacttcaac gaggatggct cccaagtcaa aggcggcgtg    3900
gttaagaacg cagacggcac ctatagcaaa tacaaagaag gtttggtga gctggttact    3960 aacgagtttt tcacgactga tggcaatgtt tggtactacg ccggtgcaaa tggtaaaacc    4020
gttaccggtg cacaagtgat caacggccaa catttgtact tcaatgcgga cggttcccag    4080
gtgaagggtg gcgttgtcaa gaacgcgat ggcacctaca gcaagtacaa tgctagcact    4140
ggtgaacgtc tgacgaacga gttctttacg accggtgata caattggta ttacattggc    4200 gcaaacggta agagcgtgac gggtgaggtc aagattggtg atgatactta ctttttcgcg    4260
aaggatggca aacaagttaa aggtcaaacc gtcagcgccg gtaatggtcg cattagctac    4320
tactacggtg acagcggcaa gcgtgcggtt agcacctgga ttgagattca gccgggtgtt    4380
tatgtgtatt tcgacaaaaa cggtttggcg taccctccgc gtgttctgaa ttaa          4434
```

<210> SEQ ID NO 8
<211> LENGTH: 1477
<212> TYPE: PRT
<213> ORGANISM: Streptococcus salivarius

<400> SEQUENCE: 8

```
Met Asp Glu Thr Gln Asp Lys Thr Val Thr Gln Ser Asn Ser Gly Thr
1               5                   10                  15

Thr Ala Ser Leu Val Thr Ser Pro Glu Ala Thr Lys Glu Ala Asp Lys
            20                  25                  30

Arg Thr Asn Thr Lys Glu Ala Asp Val Leu Thr Pro Ala Lys Glu Thr
        35                  40                  45

Asn Ala Val Glu Thr Ala Thr Thr Asn Thr Gln Ala Thr Ala Glu
    50                  55                  60

Ala Ala Thr Thr Ala Thr Thr Ala Asp Val Ala Val Ala Ala Val Pro
65                  70                  75                  80

Asn Lys Glu Ala Val Val Thr Thr Asp Ala Pro Ala Val Thr Thr Glu
                85                  90                  95

Lys Ala Glu Glu Gln Pro Ala Thr Val Lys Ala Glu Val Val Asn Thr
            100                 105                 110

Glu Val Lys Ala Pro Glu Ala Ala Leu Lys Asp Ser Glu Val Glu Ala
        115                 120                 125

Ala Leu Ser Leu Lys Asn Ile Lys Asn Ile Asp Gly Lys Tyr Tyr Tyr
    130                 135                 140

Val Asn Glu Asp Gly Ser His Lys Glu Asn Phe Ala Ile Thr Val Asn
145                 150                 155                 160

Gly Gln Leu Leu Tyr Phe Gly Lys Asp Gly Ala Leu Thr Ser Ser Ser
                165                 170                 175

Thr Tyr Ser Phe Thr Pro Gly Thr Thr Asn Ile Val Asp Gly Phe Ser
            180                 185                 190

Ile Asn Asn Arg Ala Tyr Asp Ser Ser Glu Ala Ser Phe Glu Leu Ile
        195                 200                 205

Asp Gly Tyr Leu Thr Ala Asp Ser Trp Tyr Arg Pro Ala Ser Ile Ile
    210                 215                 220

Lys Asp Gly Val Thr Trp Gln Ala Ser Thr Ala Glu Asp Phe Arg Pro
225                 230                 235                 240

Leu Leu Met Ala Trp Trp Pro Asn Val Asp Thr Gln Val Asn Tyr Leu
                245                 250                 255

Asn Tyr Met Ser Lys Val Phe Asn Leu Asp Ala Lys Tyr Ser Ser Thr
            260                 265                 270

Asp Lys Gln Glu Thr Leu Lys Val Ala Ala Lys Asp Ile Gln Ile Lys
        275                 280                 285

Ile Glu Gln Lys Ile Gln Ala Glu Lys Ser Thr Gln Trp Leu Arg Glu
    290                 295                 300

Thr Ile Ser Ala Phe Val Lys Thr Gln Pro Gln Trp Asn Lys Glu Thr
305                 310                 315                 320

Glu Asn Tyr Ser Lys Gly Gly Glu Asp His Leu Gln Gly Gly Ala
                325                 330                 335

Leu Leu Tyr Val Asn Asp Ser Arg Thr Pro Trp Ala Asn Ser Asp Tyr
            340                 345                 350

Arg Arg Leu Asn Arg Thr Ala Thr Asn Gln Thr Gly Thr Ile Asp Lys
        355                 360                 365

Ser Ile Leu Asp Glu Gln Ser Asp Pro Asn His Met Gly Gly Phe Asp
    370                 375                 380
```

-continued

```
Phe Leu Leu Ala Asn Asp Val Asp Leu Ser Asn Pro Val Val Gln Ala
385                 390                 395                 400

Glu Gln Leu Asn Gln Ile His Tyr Leu Met Asn Trp Gly Ser Ile Val
            405                 410                 415

Met Gly Asp Lys Asp Ala Asn Phe Asp Gly Ile Arg Val Asp Ala Val
        420                 425                 430

Asp Asn Val Asp Ala Asp Met Leu Gln Leu Tyr Thr Asn Tyr Phe Arg
    435                 440                 445

Glu Tyr Tyr Gly Val Asn Lys Ser Glu Ala Asn Ala Leu Ala His Ile
450                 455                 460

Ser Val Leu Glu Ala Trp Ser Leu Asn Asp Asn His Tyr Asn Asp Lys
465                 470                 475                 480

Thr Asp Gly Ala Ala Leu Ala Met Glu Asn Lys Gln Arg Leu Ala Leu
            485                 490                 495

Leu Phe Ser Leu Ala Lys Pro Ile Lys Glu Arg Thr Pro Ala Val Ser
        500                 505                 510

Pro Leu Tyr Asn Asn Thr Phe Asn Thr Thr Gln Arg Asp Glu Lys Thr
    515                 520                 525

Asp Trp Ile Asn Lys Asp Gly Ser Lys Ala Tyr Asn Glu Asp Gly Thr
530                 535                 540

Val Lys Gln Ser Thr Ile Gly Lys Tyr Asn Glu Lys Tyr Gly Asp Ala
545                 550                 555                 560

Ser Gly Asn Tyr Val Phe Ile Arg Ala His Asp Asn Asn Val Gln Asp
            565                 570                 575

Ile Ile Ala Glu Ile Ile Lys Lys Glu Ile Asn Pro Lys Ser Asp Gly
        580                 585                 590

Phe Thr Ile Thr Asp Ala Glu Met Lys Gln Ala Phe Glu Ile Tyr Asn
    595                 600                 605

Lys Asp Met Leu Ser Ser Asp Lys Lys Tyr Thr Leu Asn Asn Ile Pro
610                 615                 620

Ala Ala Tyr Ala Val Met Leu Gln Asn Met Glu Thr Ile Thr Arg Val
625                 630                 635                 640

Tyr Tyr Gly Asp Leu Tyr Thr Asp Asp Gly His Tyr Met Glu Thr Lys
            645                 650                 655

Ser Pro Tyr Tyr Asp Thr Ile Val Asn Leu Met Lys Ser Arg Ile Lys
        660                 665                 670

Tyr Val Ser Gly Gly Gln Ala Gln Arg Ser Tyr Trp Leu Pro Thr Asp
    675                 680                 685

Gly Lys Met Asp Asn Ser Asp Val Glu Leu Tyr Arg Thr Asn Glu Val
690                 695                 700

Tyr Thr Ser Val Arg Tyr Gly Lys Asp Ile Met Thr Ala Asn Asp Thr
705                 710                 715                 720

Glu Gly Ser Lys Tyr Ser Arg Thr Ser Gly Gln Val Thr Leu Val Ala
            725                 730                 735

Asn Asn Pro Lys Leu Asn Leu Asp Gln Ser Ala Lys Leu Asn Val Glu
        740                 745                 750

Met Gly Lys Ile His Ala Asn Gln Lys Tyr Arg Ala Leu Ile Val Gly
    755                 760                 765

Thr Ala Asp Gly Ile Lys Asn Phe Thr Ser Asp Ala Asp Ile Ala
770                 775                 780

Ala Gly Tyr Val Lys Glu Thr Asp Ser Asn Gly Val Leu Thr Phe Gly
785                 790                 795                 800

Ala Asn Asp Ile Lys Gly Tyr Glu Thr Phe Asp Met Ser Gly Phe Val
```

```
                805                  810                 815
Ala Val Trp Val Pro Val Gly Ala Ser Asp Asn Gln Asp Ile Arg Val
                820                 825                 830
Ala Pro Ser Thr Glu Ala Lys Lys Glu Gly Glu Leu Thr Leu Lys Ala
                835                 840                 845
Thr Glu Ala Tyr Asp Ser Gln Leu Ile Tyr Glu Gly Phe Ser Asn Phe
                850                 855                 860
Gln Thr Ile Pro Asp Gly Ser Asp Pro Ser Val Tyr Thr Asn Arg Lys
865                 870                 875                 880
Ile Ala Glu Asn Val Asp Leu Phe Lys Ser Trp Gly Val Thr Ser Phe
                885                 890                 895
Glu Met Ala Pro Gln Phe Val Ser Ala Asp Asp Gly Thr Phe Leu Asp
                900                 905                 910
Ser Val Ile Gln Asn Gly Tyr Ala Phe Ala Asp Arg Tyr Asp Leu Ala
                915                 920                 925
Met Ser Lys Asn Asn Lys Tyr Gly Ser Lys Glu Asp Leu Arg Asp Ala
                930                 935                 940
Leu Lys Ala Leu His Lys Ala Gly Ile Gln Ala Ile Ala Asp Trp Val
945                 950                 955                 960
Pro Asp Gln Ile Tyr Gln Leu Pro Gly Lys Glu Val Val Thr Ala Thr
                965                 970                 975
Arg Thr Asp Gly Ala Gly Arg Lys Ile Ala Asp Ala Ile Ile Asp His
                980                 985                 990
Ser Leu Tyr Val Ala Asn Ser Lys  Ser Ser Gly Lys Asp  Tyr Gln Ala
                995                 1000                1005
Lys Tyr Gly Gly Glu Phe Leu  Ala Glu Leu Lys Ala  Lys Tyr Pro
  1010                 1015                1020
Glu Met Phe Lys Val Asn Met  Ile Ser Thr Gly Lys  Pro Ile Asp
  1025                 1030                1035
Asp Ser Val Lys Leu Lys Gln  Trp Lys Ala Glu Tyr  Phe Asn Gly
  1040                 1045                1050
Thr Asn Val Leu Glu Arg Gly  Val Gly Tyr Val Leu  Ser Asp Glu
  1055                 1060                1065
Ala Thr Gly Lys Tyr Phe Thr  Val Thr Lys Glu Gly  Asn Phe Ile
  1070                 1075                1080
Pro Leu Gln Leu Thr Gly Lys  Glu Lys Val Ile Thr  Gly Phe Ser
  1085                 1090                1095
Ser Asp Gly Lys Gly Ile Thr  Tyr Phe Gly Thr Ser  Gly Thr Gln
  1100                 1105                1110
Ala Lys Ser Ala Phe Val Thr  Phe Asn Gly Asn Thr  Tyr Tyr Phe
  1115                 1120                1125
Asp Ala Arg Gly His Met Val  Thr Asn Ser Glu Tyr  Ser Pro Asn
  1130                 1135                1140
Gly Lys Asp Val Tyr Arg Phe  Leu Pro Asn Gly Ile  Met Leu Ser
  1145                 1150                1155
Asn Ala Phe Tyr Ile Asp Ala  Asn Gly Asn Thr Tyr  Leu Tyr Asn
  1160                 1165                1170
Ser Lys Gly Gln Met Tyr Lys  Gly Gly Tyr Thr Lys  Phe Asp Val
  1175                 1180                1185
Ser Glu Thr Asp Lys Asp Gly  Lys Glu Ser Lys Val  Val Lys Phe
  1190                 1195                1200
Arg Tyr Phe Thr Asn Glu Gly  Val Met Ala Lys Gly  Val Thr Val
  1205                 1210                1215
```

Ile Asp Gly Phe Thr Gln Tyr Phe Gly Glu Asp Gly Phe Gln Ala
1220                1225                1230

Lys Asp Lys Leu Val Thr Phe Lys Gly Lys Thr Tyr Tyr Phe Asp
1235                1240                1245

Ala His Thr Gly Asn Gly Ile Lys Asp Thr Trp Arg Asn Ile Asn
1250                1255                1260

Gly Lys Trp Tyr Tyr Phe Asp Ala Asn Gly Val Ala Ala Thr Gly
1265                1270                1275

Ala Gln Val Ile Asn Gly Gln Lys Leu Tyr Phe Asn Glu Asp Gly
1280                1285                1290

Ser Gln Val Lys Gly Val Val Lys Asn Ala Asp Gly Thr Tyr
1295                1300                1305

Ser Lys Tyr Lys Glu Gly Phe Gly Glu Leu Val Thr Asn Glu Phe
1310                1315                1320

Phe Thr Thr Asp Gly Asn Val Trp Tyr Tyr Ala Gly Ala Asn Gly
1325                1330                1335

Lys Thr Val Thr Gly Ala Gln Val Ile Asn Gly Gln His Leu Tyr
1340                1345                1350

Phe Asn Ala Asp Gly Ser Gln Val Lys Gly Gly Val Val Lys Asn
1355                1360                1365

Ala Asp Gly Thr Tyr Ser Lys Tyr Asn Ala Ser Thr Gly Glu Arg
1370                1375                1380

Leu Thr Asn Glu Phe Phe Thr Thr Gly Asp Asn Asn Trp Tyr Tyr
1385                1390                1395

Ile Gly Ala Asn Gly Lys Ser Val Thr Gly Glu Val Lys Ile Gly
1400                1405                1410

Asp Asp Thr Tyr Phe Phe Ala Lys Asp Gly Lys Gln Val Lys Gly
1415                1420                1425

Gln Thr Val Ser Ala Gly Asn Gly Arg Ile Ser Tyr Tyr Tyr Gly
1430                1435                1440

Asp Ser Gly Lys Arg Ala Val Ser Thr Trp Ile Glu Ile Gln Pro
1445                1450                1455

Gly Val Tyr Val Tyr Phe Asp Lys Asn Gly Leu Ala Tyr Pro Pro
1460                1465                1470

Arg Val Leu Asn
     1475

<210> SEQ ID NO 9
<211> LENGTH: 4311
<212> TYPE: DNA
<213> ORGANISM: Streptococcus downei

<400> SEQUENCE: 9
atggttgacg gcaaatacta ctactacgat caggacggca acgtaaagaa aaacttcgcg      60
gttagcgtgg gcgagaaaat ctattacttt gacgaaactg gcgcctacaa agacaccagc     120
aaagttgagg cggacaaaag cggcagcgac attagcaagg aagagactac cttcgcggca     180
aacaaccgcg cctacagcac cagcgcggag aattttgagg cgatcgacaa ttatctgacc     240
gcggactcct ggtatcgtcc taaatccatc ctgaaggatg caaaacgtg acggaaagc      300 agcaaagatg actttcgtcc gctgctgatg gcgtggtggc cggataccga acgaagcgc     360 aattacgtga actacatgaa caaagttgtt ggcatcgaca agacctatac cgcggaaacc     420
agccaggccg acttgaccgc tgcggcggaa ctggtgcaag cacgcattga gcagaagatc     480

-continued

```
acgaccgaac agaacacgaa atggctgcgt gaggcaatct cggcatttgt aaaacgcaa      540
ccgcagtgga acggtgaaag cgagaagccg tacgacgatc acctgcaaaa cggtgctctg     600
aaatttgata atcagagcga cctgaccccg atacgcaaa gcaactaccg tctgttgaac      660
cgtaccccga ctaatcagac gggtagcctg acagccgct tcacttataa cgcgaacgac      720
cctttgggcg gttatgagct gctgctggca aatgacgtcg ataacagcaa tccgatcgtg     780
caggcggagc agctgaactg gctgcattac ctgctgaatt ttggtacgat ctacgccaaa     840
gatgccgacg ctaacttcga tagcattcgt gtggacgcgg ttgataacgt cgatgcggat    900
ctgctgcaaa ttagcagcga ttacctgaaa gcagcctacg gcattgataa gaataacaaa    960
aacgcgaaca accacgtgag cattgtcgaa gcctggagcg ataatgatac cccgtacctg   1020
catgacgatg gtgacaacct gatgaatatg gataacaaat ttcgcctgtc catgctgtgg   1080
tcgctggcca aaccgctgga caagcgtagc ggtctgaacc cgctgattca taacagcttg   1140
gtggatcgtg aagttgatga ccgcgaggtt gaaacggttc cgagctattc ttttgcacgt   1200
gcgcatgata gcgaggtcca ggacttgatc cgtgacatca tcaaggcaga gatcaatccg   1260
aacgcattcg gttatagctt tacccaagac gagattgacc aggcctttaa gatttacaat   1320
gaggatctga agaaaacgga taagaaatac acccactata atgtgccgtt gagctacacc   1380
ctgctgctga cgaataaggg tagcatccca cgtgtctact atggtgatat gtttaccgac   1440
gatggtcagt atatggcgaa caaaaccgtc aactatgacg ccattgaatc tctgctgaaa   1500
gcgcgtatga agtatgtcgc tggcggtcaa gcaatgcaga actaccaaat cggtaatggt   1560
gagatcctga ccagcgttcg ttatggtaag ggtgccctga acagagcga caaaggtgat   1620
gcgaccacgc gcaccagcgg tgtcggtgtc gttatgggca atcagccaaa ctttagcttg   1680
gacggcaaag tggtggctct gaacatgggc gcagctcatg cgaatcagga gtatcgtgcg   1740
ctgatggtta gcacgaaaga cggtgttgcc acgtatgcga ccgatgcaga tgcgagcaaa   1800
gccggtctgt tcaaacgtac cgacgaaaac ggctacctgt atttcctgaa tgacgacctg   1860
aagggtgtgg ccaatcctca ggtgagcggt ttcttgcagg tgtgggttcc ggtgggtgcc   1920
gcggatgatc aagatatccg tgttgcagct agcgataccg catccaccga tggcaagagc   1980
ctgcaccaag acgccgcgat ggatagccgt gttatgtttg aaggcttctc taactttcag   2040
tcctttgcca cgaaagaaga ggaatatacc aacgtcgtta tcgccaacaa tgtggataag   2100
ttcgttagct ggggtatcac ggatttcgag atggccccac aatatgtttc cagcaccgac   2160
ggtcaattcc tggactctgt cattcagaac ggttatgctt ttacgaccg ttatgacttg   2220
ggcatgtcta aggcaaacaa atacggcacg gccgatcaac tggttaaggc cattaaggcc   2280
ctgcacgcga agggcctgaa ggttatggca gattgggtgc cggatcagat gtataccttc   2340
ccgaaacagg aagtcgtgac cgttacccgt accgacaaat ttggcaaacc gatcgcaggt   2400
tcccaaatca atcatagcct gtatgttacc gataccaagt ccagcggcga tgactatcag   2460
gccaaatatg gtggtgcgtt tctggacgag ctgaaggaga aatatccgga gctgttcacg   2520
aagaaacaaa tcagcacggg tcaagctatt gacccgagcg tgaaaatcaa acagtggtct   2580
gctaagtatt tcaatggctc caacatcctg ggtcgcggtg cggactacgt actgtcggat   2640
caggcgagca acaaatacct gaacgtgtct gacgataaac tgttcctgcc gaaaaccttg   2700
ctgggccaag ttgtcgagag cggtatccgc tttgacggca ctggttatgt gtacaactct   2760
agcactacgg gtgaaaaagt taccgattcc ttcattacgg aggcaggtaa tctgtactac   2820
ttcggtcaag acggctatat ggtgaccggc gcacagaaca ttaagggcag caactattac   2880
```

-continued

```
ttcctggcca atggtgcggc cctgcgtaac accgtttaca ccgatgcgca aggtcagaat    2940
cactattacg gcaacgacgg caagcgttat gagaatggtt accaacagtt cggcaacgat    3000
tcttggcgtt acttcaaaaa tggcgtgatg gcgctgggtc tgactacggt ggatggtcac    3060
gtgcagtatt tcgataaaga tggtgtccag gccaaggata gatcattgt cacccgcgat     3120
ggcaaagtcc gctatttcga ccagcacaac ggtaatgcgg ttactaacac gttcgttgcg    3180
gacaagacgg tcactggta ctatctgggc aaagacggcg tcgcggttac cggtgcgcag     3240
actgtgggta acagcattt gtactttgaa gcgaacggtc aacaagtcaa gggtgacttc     3300
gtgacggcta agacggtaa actgtacttc tatgatgtgg acagcggcga catgtggacc     3360
aataccttta tcgaggataa agcgggtaat tggttctacc tgggtaagga cggtgcggcc    3420
gtcaccggtg cacagacgat caaaggccag aaattgtatt tcaaagccaa cggtcagcaa    3480
gttaaaggtg acattgtcaa ggacgcggac ggtaagatcc gttattacga cgctcagacc    3540
ggtgaacagt tctttaacaa gtccgttagc gtcaacggta agacctacta tttcggtagc    3600
gacggcaccg cgcaaaccca ggcgaatccg aaaggccaaa cctttaagga tggtagcggc    3660
gttctgcgtt tctacaattt ggagggccag tatgtctcgg gcagcggctg gtacgaaacg    3720
gccgagcacg agtgggtata tgtgaaatcc ggtaaagttc tgaccggtgc ccagacgatt    3780
ggtaatcaac gtgtttactt caaggacaat ggtcaccagg tgaaaggcca gctggtcacg    3840
ggtaatgacg gtaaattgcg ttactacgac gcgaacagcg gtgatcaagc attcaacaaa    3900
tccgtcacgg ttaacggtaa aacctactac tttggcagcg atggtacggc gcagacgcag    3960
gctaatccta agggtcagac cttcaaagat ggtagcggcg tgctgcgttt ttacaacttg    4020
gaaggccaat acgtgtctgg cagcggttgg tacaagaatg cgcagggcca gtggctgtac    4080
gtgaaagatg gcaaggtcct gaccggtctg caaacggtcg gcaatcagaa ggtctacttc    4140
gacaaaaatg gcatccaagc aaagggtaag gccgttcgca cgtccgatgg taaagtgcgc    4200
tactttgatg agaatagcgg tagcatgatt acgaaccaat ggaagttcgt ttacggtcaa    4260
tactattact tcggttctga cggcgcagcg gtttaccgtg gttggaacta a             4311
```

<210> SEQ ID NO 10
<211> LENGTH: 1436
<212> TYPE: PRT
<213> ORGANISM: Streptococcus downei

<400> SEQUENCE: 10

```
Met Val Asp Gly Lys Tyr Tyr Tyr Asp Gln Asp Gly Asn Val Lys
1               5                  10                  15

Lys Asn Phe Ala Val Ser Val Gly Glu Lys Ile Tyr Tyr Phe Asp Glu
            20                  25                  30

Thr Gly Ala Tyr Lys Asp Thr Ser Lys Val Glu Ala Asp Lys Ser Gly
        35                  40                  45

Ser Asp Ile Ser Lys Glu Glu Thr Thr Phe Ala Ala Asn Asn Arg Ala
    50                  55                  60

Tyr Ser Thr Ser Ala Glu Asn Phe Glu Ala Ile Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Ser Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
```

-continued

```
            115                 120                 125
Val Val Gly Ile Asp Lys Thr Tyr Thr Ala Glu Thr Ser Gln Ala Asp
        130                 135                 140

Leu Thr Ala Ala Ala Glu Leu Val Gln Ala Arg Ile Glu Gln Lys Ile
145                 150                 155                 160

Thr Thr Glu Gln Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Gln Ser Asp Leu
        195                 200                 205

Thr Pro Asp Thr Gln Ser Asn Tyr Arg Leu Leu Asn Arg Thr Pro Thr
    210                 215                 220

Asn Gln Thr Gly Ser Leu Asp Ser Arg Phe Thr Tyr Asn Ala Asn Asp
225                 230                 235                 240

Pro Leu Gly Gly Tyr Glu Leu Leu Ala Asn Asp Val Asp Asn Ser
                245                 250                 255

Asn Pro Ile Val Gln Ala Glu Gln Leu Asn Trp Leu His Tyr Leu Leu
            260                 265                 270

Asn Phe Gly Thr Ile Tyr Ala Lys Asp Ala Asp Ala Asn Phe Asp Ser
        275                 280                 285

Ile Arg Val Asp Ala Val Asp Asn Val Asp Ala Asp Leu Leu Gln Ile
    290                 295                 300

Ser Ser Asp Tyr Leu Lys Ala Ala Tyr Gly Ile Asp Lys Asn Asn Lys
305                 310                 315                 320

Asn Ala Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
            340                 345                 350

Lys Phe Arg Leu Ser Met Leu Trp Ser Leu Ala Lys Pro Leu Asp Lys
        355                 360                 365

Arg Ser Gly Leu Asn Pro Leu Ile His Asn Ser Leu Val Asp Arg Glu
    370                 375                 380

Val Asp Asp Arg Glu Val Glu Thr Val Pro Ser Tyr Ser Phe Ala Arg
385                 390                 395                 400

Ala His Asp Ser Glu Val Gln Asp Leu Ile Arg Asp Ile Ile Lys Ala
                405                 410                 415

Glu Ile Asn Pro Asn Ala Phe Gly Tyr Ser Phe Thr Gln Asp Glu Ile
            420                 425                 430

Asp Gln Ala Phe Lys Ile Tyr Asn Glu Asp Leu Lys Lys Thr Asp Lys
        435                 440                 445

Lys Tyr Thr His Tyr Asn Val Pro Leu Ser Tyr Thr Leu Leu Leu Thr
    450                 455                 460

Asn Lys Gly Ser Ile Pro Arg Val Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ala Gly Gln Ala Met
            500                 505                 510

Gln Asn Tyr Gln Ile Gly Asn Gly Glu Ile Leu Thr Ser Val Arg Tyr
        515                 520                 525

Gly Lys Gly Ala Leu Lys Gln Ser Asp Lys Gly Asp Ala Thr Thr Arg
    530                 535                 540
```

-continued

```
Thr Ser Gly Val Gly Val Met Gly Asn Gln Pro Asn Phe Ser Leu
545                 550                 555                 560

Asp Gly Lys Val Val Ala Leu Asn Met Gly Ala Ala His Ala Asn Gln
                565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Leu Val Lys Arg Thr Asp
            595                 600                 605

Glu Asn Gly Tyr Leu Tyr Phe Leu Asn Asp Asp Leu Lys Gly Val Ala
        610                 615                 620

Asn Pro Gln Val Ser Gly Phe Leu Gln Val Trp Val Pro Val Gly Ala
625                 630                 635                 640

Ala Asp Asp Gln Asp Ile Arg Val Ala Ala Ser Asp Thr Ala Ser Thr
                645                 650                 655

Asp Gly Lys Ser Leu His Gln Asp Ala Ala Met Asp Ser Arg Val Met
            660                 665                 670

Phe Glu Gly Phe Ser Asn Phe Gln Ser Phe Ala Thr Lys Glu Glu
        675                 680                 685

Tyr Thr Asn Val Val Ile Ala Asn Asn Val Asp Lys Phe Val Ser Trp
690                 695                 700

Gly Ile Thr Asp Phe Glu Met Ala Pro Gln Tyr Val Ser Ser Thr Asp
705                 710                 715                 720

Gly Gln Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp
            740                 745                 750

Gln Leu Val Lys Ala Ile Lys Ala Leu His Ala Lys Gly Leu Lys Val
        755                 760                 765

Met Ala Asp Trp Val Pro Asp Gln Met Tyr Thr Phe Pro Lys Gln Glu
770                 775                 780

Val Val Thr Val Thr Arg Thr Asp Lys Phe Gly Lys Pro Ile Ala Gly
785                 790                 795                 800

Ser Gln Ile Asn His Ser Leu Tyr Val Thr Asp Thr Lys Ser Ser Gly
                805                 810                 815

Asp Asp Tyr Gln Ala Lys Tyr Gly Gly Ala Phe Leu Asp Glu Leu Lys
            820                 825                 830

Glu Lys Tyr Pro Glu Leu Phe Thr Lys Lys Gln Ile Ser Thr Gly Gln
        835                 840                 845

Ala Ile Asp Pro Ser Val Lys Ile Lys Gln Trp Ser Ala Lys Tyr Phe
850                 855                 860

Asn Gly Ser Asn Ile Leu Gly Arg Gly Ala Asp Tyr Val Leu Ser Asp
865                 870                 875                 880

Gln Ala Ser Asn Lys Tyr Leu Asn Val Ser Asp Lys Leu Phe Leu
                885                 890                 895

Pro Lys Thr Leu Leu Gly Gln Val Val Glu Ser Gly Ile Arg Phe Asp
            900                 905                 910

Gly Thr Gly Tyr Val Tyr Asn Ser Ser Thr Gly Glu Lys Val Thr
        915                 920                 925

Asp Ser Phe Ile Thr Glu Ala Gly Asn Leu Tyr Tyr Phe Gly Gln Asp
930                 935                 940

Gly Tyr Met Val Thr Gly Ala Gln Asn Ile Lys Gly Ser Asn Tyr Tyr
945                 950                 955                 960
```

-continued

Phe Leu Ala Asn Gly Ala Ala Leu Arg Asn Thr Val Tyr Thr Asp Ala
            965                 970                 975
Gln Gly Gln Asn His Tyr Tyr Gly Asn Asp Gly Lys Arg Tyr Glu Asn
        980                 985                 990
Gly Tyr Gln Gln Phe Gly Asn Asp Ser Trp Arg Tyr Phe Lys Asn Gly
    995                1000                1005
Val Met Ala Leu Gly Leu Thr Thr Val Asp Gly His Val Gln Tyr
    1010                1015                1020
Phe Asp Lys Asp Gly Val Gln Ala Lys Asp Lys Ile Ile Val Thr
    1025                1030                1035
Arg Asp Gly Lys Val Arg Tyr Phe Asp Gln His Asn Gly Asn Ala
    1040                1045                1050
Val Thr Asn Thr Phe Val Ala Asp Lys Thr Gly His Trp Tyr Tyr
    1055                1060                1065
Leu Gly Lys Asp Gly Val Ala Val Thr Gly Ala Gln Thr Val Gly
    1070                1075                1080
Lys Gln His Leu Tyr Phe Glu Ala Asn Gly Gln Gln Val Lys Gly
    1085                1090                1095
Asp Phe Val Thr Ala Lys Asp Gly Lys Leu Tyr Phe Tyr Asp Val
    1100                1105                1110
Asp Ser Gly Asp Met Trp Thr Asn Thr Phe Ile Glu Asp Lys Ala
    1115                1120                1125
Gly Asn Trp Phe Tyr Leu Gly Lys Asp Gly Ala Ala Val Thr Gly
    1130                1135                1140
Ala Gln Thr Ile Lys Gly Gln Lys Leu Tyr Phe Lys Ala Asn Gly
    1145                1150                1155
Gln Gln Val Lys Gly Asp Ile Val Lys Asp Ala Asp Gly Lys Ile
    1160                1165                1170
Arg Tyr Tyr Asp Ala Gln Thr Gly Glu Gln Val Phe Asn Lys Ser
    1175                1180                1185
Val Ser Val Asn Gly Lys Thr Tyr Tyr Phe Gly Ser Asp Gly Thr
    1190                1195                1200
Ala Gln Thr Gln Ala Asn Pro Lys Gly Gln Thr Phe Lys Asp Gly
    1205                1210                1215
Ser Gly Val Leu Arg Phe Tyr Asn Leu Glu Gly Gln Tyr Val Ser
    1220                1225                1230
Gly Ser Gly Trp Tyr Glu Thr Ala Glu His Glu Trp Val Tyr Val
    1235                1240                1245
Lys Ser Gly Lys Val Leu Thr Gly Ala Gln Thr Ile Gly Asn Gln
    1250                1255                1260
Arg Val Tyr Phe Lys Asp Asn Gly His Gln Val Lys Gly Gln Leu
    1265                1270                1275
Val Thr Gly Asn Asp Gly Lys Leu Arg Tyr Tyr Asp Ala Asn Ser
    1280                1285                1290
Gly Asp Gln Ala Phe Asn Lys Ser Val Thr Val Asn Gly Lys Thr
    1295                1300                1305
Tyr Tyr Phe Gly Ser Asp Gly Thr Ala Gln Thr Gln Ala Asn Pro
    1310                1315                1320
Lys Gly Gln Thr Phe Lys Asp Gly Ser Gly Val Leu Arg Phe Tyr
    1325                1330                1335
Asn Leu Glu Gly Gln Tyr Val Ser Gly Ser Gly Trp Tyr Lys Asn
    1340                1345                1350
Ala Gln Gly Gln Trp Leu Tyr Val Lys Asp Gly Lys Val Leu Thr

```
           1355                1360                1365
Gly Leu Gln Thr Val Gly Asn Gln Lys Val Tyr Phe Asp Lys Asn
    1370                1375                1380

Gly Ile Gln Ala Lys Gly Lys Ala Val Arg Thr Ser Asp Gly Lys
    1385                1390                1395

Val Arg Tyr Phe Asp Glu Asn Ser Gly Ser Met Ile Thr Asn Gln
    1400                1405                1410

Trp Lys Phe Val Tyr Gly Gln Tyr Tyr Tyr Phe Gly Ser Asp Gly
    1415                1420                1425

Ala Ala Val Tyr Arg Gly Trp Asn
    1430                1435

<210> SEQ ID NO 11
<211> LENGTH: 3942
<212> TYPE: DNA
<213> ORGANISM: Streptococcus mutans

<400> SEQUENCE: 11
atgattgacg gcaaatacta ctactatgac aacaacggca aagtacgcac caatttcacg      60
ttgatcgcgg acggtaaaat cctgcatttt gatgaaactg cgcgtacac cgacactagc      120 attgataccg tgaacaagga tattgtcacg acgcgtagca acctgtataa gaaatacaat      180
caagtgtatg atcgcagcgc gcagagcttc gagcatgttg atcactacct gacggcggaa      240
tcttggtacc gtccgaaata cattctgaaa gatggcaaga cctggaccca gagcaccgag      300
aaggacttcc gtcctctgct gatgacctgg tggccgagcc aggaaacgca gcgccagtat      360
gtcaacttca tgaacgccca gttgggtatc aacaaaacgt acgacgacac cagcaatcag      420
ctgcaattga acatcgctgc tgcaacgatc aagcaaaga tcgaagccaa atcacgacg       480 ctgaagaaca ccgattggct gcgtcaaacg atcagcgcgt cgtcaaaaac ccaaagcgct      540
tggaatagcg acagcgaaaa gccgtttgat gaccatctgc aaaacggtgc ggttctgtat      600
gataacgaag gtaaattgac gccgtatgcc aatagcaact atcgtattct gaaccgcacg      660
ccgaccaacc agaccggtaa gaaggacccg cgttataccg ccgacaacac gatcggcggc      720
tacgagtttc tgctggccaa cgacgtggat aatagcaacc cggtggttca ggccgagcag      780
ctgaactggc tgcacttcct gatgaacttt ggtaatatct acgcaaacga ccctgacgct      840
aacttcgact ccatccgcgt tgacgctgtc gataatgtgg acgccgatct gttacagatc      900
gcgggtgact atctgaaagc ggcaagggc atccataaga tgacaaagc ggcgaacgac      960 cacctgtcca ttctggaagc gtggagcgac aatgacactc cgtatctgca tgatgatggc      1020
gacaacatga ttaacatgga taacaaactg cgcctgagcc tgctgttctc cctggcgaaa      1080
ccgctgaatc agcgtagcgg tatgaacccg ttgattacga acagcctggt caaccgtact      1140
gatgataatg ccgaaacggc ggcagtgcca agctactctt ttatccgtgc ccacgatagc      1200
gaggtccagg atttgattcg tgatatcatt aaggctgaga ttaacccgaa cgtcgtcggt      1260
tacagcttca cgatggaaga gattaagaag gcatttgaga tctacaataa ggacctgttg      1320
gccacggaga agaagtatac ccactataac accgcattga gctacgcgtt gctgctgacg      1380
aacaagagca gcgtgccgcg tgtctactat ggtgatatgt ttacggacga tggtcaatac      1440
atggcccaca gaccattaa ctacgaggca atcgaaaccc tgctgaaagc acgtatcaag      1500
tacgtgtccg gtggtcaggc tatgcgcaac cagcaagtgg gtaattcgga gatcatcacc      1560
agcgtgcgtt acggtaaagg tgcgctgaag gcgatggata cgggtgaccg cactacccgt      1620
```

```
acctctggtg tggcggtcat tgagggcaac aacccgagct tgcgcctgaa ggcttctgat    1680
cgtgtggttg tgaatatggg tgcggcccac aaaaatcaag cctatcgccc gctgctgttg    1740
acgaccgata acggcattaa ggcctatcac agcgaccaag aagcggcagg cctggtgcgt    1800
tacaccaacg accgtggcga actgatcttt accgcagccg acattaaggg ctacgcaaat    1860
ccgcaagtta gcggctacct gggcgtctgg gtccctgttg gcgcagcagc tgatcaggac    1920
gttcgtgttg cggcgagcac cgcgccaagc acggacggca agagcgttca ccagaacgcg    1980
gctctggaca gccgtgtgat gttcgagggt ttctcgaact tccaggcatt tgctaccaag    2040
aaagaagagt ataccaatgt ggtcatcgct aagaatgtgg ataagttcgc ggagtggggt    2100
gtcaccgatt tcgagatggc tccgcaatac gtttctagca ccgacggtag cttttttggat   2160
agcgtgattc aaaacggtta tgcttttacc gaccgttacg acctgggcat cagcaagccg    2220
aacaaatatg gcaccgcgga cgatctggtt aaagcgatta aggcattgca cagcaaaggc    2280
atcaaagtta tggcggattg ggttccggac cagatgtatg ccctgccgga aaagaggtt     2340
gtgacggcaa cccgtgttga caaatacggt acgccggtag ctggcagcca gatcaaaaac    2400
acgctgtacg tggtcgatgg taaatctagc ggtaaggacc agcaggcgaa gtacggtggt    2460
gccttcctgg aagagctgca agcgaagtat ccggaactgt tcgcgcgcaa acagattagc    2520
accggtgttc cgatggaccc gagcgtcaag attaagcaat ggagcgcaaa atacttcaac    2580
ggcacgaata tcctgggtcg tggtgctggt tacgtgctga agatcaggc aaccaacacc     2640
tactttaaca tcagcgacaa taaagagatc aatttcctgc aaagacgtt gctgaaccag     2700
gattctcaag ttggctttag ctacgacggt aagggctatg tgtactacag cacctcgggc    2760
taccaggcta aaaacacgtt catcagcgag ggtgacaagt ggtattactt cgacaataac    2820
ggttatatgg ttaccggcgc acagagcatt aatggtgtga actattactt cctgccgaat    2880
ggtttacagc tgcgtgatgc gattctgaaa atgaggacg tacgtacgc gtattatggc       2940
aatgatggtc gccgctacga gaatggctat tatcagtttta tgagcggtgt ttggcgccat    3000
ttcaataatg gcgagatgtc cgttggtctg accgtcattg acggtcaagt tcaatacttt    3060
gacgagatgg gttaccaggc gaaaggcaaa ttcgttacca ccgcggatgg taagatccgt    3120
tacttcgata agcagagcgg caatatgtat cgtaatcgtt tcattgagaa cgaagagggc    3180
aaatggctgt acctgggtga ggacggcgcg gcagtcaccg gtagccagac gatcaatggt    3240
cagcacctgt attttcgtgc taacggcgtt caggttaagg gtgagttcgt gaccgatcgt    3300
catgccgcga tctcttatta cgacggcaac agcggtgatc agatccgcaa ccgtttcgtc    3360
cgcaatgcgc aaggccagtg gttttacttt gacaacaatg gctatgcagt aactggtgct    3420
cgtacgatca acgccagca cctgtatttc cgcgcgaacg tgttcaggt aaaaggtgag      3480
tttgttacgg accgccacgg ccgcattagc tattatgatg gtaatagcgg tgaccaaatt    3540
cgcaatcgtt tcgtgcgtaa tgcacagggt cagtggttct acttcgacaa taatggttat    3600
gcagtcacgg gtgcacgtac cattaacggc caacacctgt actttcgcgc aatggtgtg    3660
caagtgaaag gcgaatttgt tactgatcgt tatggtcgta tcagctacta tgatggcaat    3720
tctggcgacc aaaattcgca atgctttgtt cgtaacgccc aaggtcaatg gttctatttc    3780
gacaacaacg gttacgcggt gaccggtgcc cgcacgatta atggtcaaca cttgtacttc    3840
cgtgccaacg gtgtccaggt gaagggtgaa tttgtgaccg accgctatgg tcgcatttct    3900
tactacgacg caaattccgg tgaacgcgtc cgtatcaatt aa                        3942
```

<210> SEQ ID NO 12
<211> LENGTH: 1313
<212> TYPE: PRT
<213> ORGANISM: Streptococcus mutans

<400> SEQUENCE: 12

Met Ile Asp Gly Lys Tyr Tyr Tyr Asp Asn Asn Gly Lys Val Arg
1               5                   10                  15

Thr Asn Phe Thr Leu Ile Ala Asp Gly Lys Ile Leu His Phe Asp Glu
            20                  25                  30

Thr Gly Ala Tyr Thr Asp Thr Ser Ile Asp Thr Val Asn Lys Asp Ile
        35                  40                  45

Val Thr Thr Arg Ser Asn Leu Tyr Lys Lys Tyr Asn Gln Val Tyr Asp
50                  55                  60

Arg Ser Ala Gln Ser Phe Glu His Val Asp His Tyr Leu Thr Ala Glu
65                  70                  75                  80

Ser Trp Tyr Arg Pro Lys Tyr Ile Leu Lys Asp Gly Lys Thr Trp Thr
            85                  90                  95

Gln Ser Thr Glu Lys Asp Phe Arg Pro Leu Leu Met Thr Trp Trp Pro
        100                 105                 110

Ser Gln Glu Thr Gln Arg Gln Tyr Val Asn Phe Met Asn Ala Gln Leu
    115                 120                 125

Gly Ile Asn Lys Thr Tyr Asp Asp Thr Ser Asn Gln Leu Gln Leu Asn
130                 135                 140

Ile Ala Ala Thr Ile Gln Ala Lys Ile Glu Ala Lys Ile Thr Thr
145                 150                 155                 160

Leu Lys Asn Thr Asp Trp Leu Arg Gln Thr Ile Ser Ala Phe Val Lys
            165                 170                 175

Thr Gln Ser Ala Trp Asn Ser Asp Ser Glu Lys Pro Phe Asp Asp His
        180                 185                 190

Leu Gln Asn Gly Ala Val Leu Tyr Asp Asn Glu Gly Lys Leu Thr Pro
    195                 200                 205

Tyr Ala Asn Ser Asn Tyr Arg Ile Leu Asn Arg Thr Pro Thr Asn Gln
210                 215                 220

Thr Gly Lys Lys Asp Pro Arg Tyr Thr Ala Asp Asn Thr Ile Gly Gly
225                 230                 235                 240

Tyr Glu Phe Leu Leu Ala Asn Asp Val Asp Asn Ser Asn Pro Val Val
            245                 250                 255

Gln Ala Glu Gln Leu Asn Trp Leu His Phe Leu Met Asn Phe Gly Asn
        260                 265                 270

Ile Tyr Ala Asn Asp Pro Asp Ala Asn Phe Asp Ser Ile Arg Val Asp
    275                 280                 285

Ala Val Asp Asn Val Asp Ala Asp Leu Leu Gln Ile Ala Gly Asp Tyr
290                 295                 300

Leu Lys Ala Ala Lys Gly Ile His Lys Asn Asp Lys Ala Ala Asn Asp
305                 310                 315                 320

His Leu Ser Ile Leu Glu Ala Trp Ser Asp Asn Asp Thr Pro Tyr Leu
            325                 330                 335

His Asp Asp Gly Asp Asn Met Ile Asn Met Asp Asn Lys Leu Arg Leu
        340                 345                 350

Ser Leu Leu Phe Ser Leu Ala Lys Pro Leu Asn Gln Arg Ser Gly Met
    355                 360                 365

Asn Pro Leu Ile Thr Asn Ser Leu Val Asn Arg Thr Asp Asp Asn Ala
370                 375                 380

```
Glu Thr Ala Ala Val Pro Ser Tyr Ser Phe Ile Arg Ala His Asp Ser
385                 390                 395                 400

Glu Val Gln Asp Leu Ile Arg Asp Ile Ile Lys Ala Glu Ile Asn Pro
            405                 410                 415

Asn Val Val Gly Tyr Ser Phe Thr Met Glu Glu Ile Lys Lys Ala Phe
        420                 425                 430

Glu Ile Tyr Asn Lys Asp Leu Leu Ala Thr Glu Lys Lys Tyr Thr His
    435                 440                 445

Tyr Asn Thr Ala Leu Ser Tyr Ala Leu Leu Leu Thr Asn Lys Ser Ser
450                 455                 460

Val Pro Arg Val Tyr Tyr Gly Asp Met Phe Thr Asp Asp Gly Gln Tyr
465                 470                 475                 480

Met Ala His Lys Thr Ile Asn Tyr Glu Ala Ile Glu Thr Leu Leu Lys
                485                 490                 495

Ala Arg Ile Lys Tyr Val Ser Gly Gly Gln Ala Met Arg Asn Gln Gln
                500                 505                 510

Val Gly Asn Ser Glu Ile Ile Thr Ser Val Arg Tyr Gly Lys Gly Ala
            515                 520                 525

Leu Lys Ala Met Asp Thr Gly Asp Arg Thr Thr Arg Thr Ser Gly Val
530                 535                 540

Ala Val Ile Glu Gly Asn Asn Pro Ser Leu Arg Leu Lys Ala Ser Asp
545                 550                 555                 560

Arg Val Val Val Asn Met Gly Ala Ala His Lys Asn Gln Ala Tyr Arg
                565                 570                 575

Pro Leu Leu Leu Thr Thr Asp Asn Gly Ile Lys Ala Tyr His Ser Asp
            580                 585                 590

Gln Glu Ala Ala Gly Leu Val Arg Tyr Thr Asn Asp Arg Gly Glu Leu
        595                 600                 605

Ile Phe Thr Ala Ala Asp Ile Lys Gly Tyr Ala Asn Pro Gln Val Ser
    610                 615                 620

Gly Tyr Leu Gly Val Trp Val Pro Val Gly Ala Ala Asp Gln Asp
625                 630                 635                 640

Val Arg Val Ala Ala Ser Thr Ala Pro Ser Thr Asp Gly Lys Ser Val
                645                 650                 655

His Gln Asn Ala Ala Leu Asp Ser Arg Val Met Phe Glu Gly Phe Ser
            660                 665                 670

Asn Phe Gln Ala Phe Ala Thr Lys Lys Glu Glu Tyr Thr Asn Val Val
        675                 680                 685

Ile Ala Lys Asn Val Asp Lys Phe Ala Glu Trp Gly Val Thr Asp Phe
    690                 695                 700

Glu Met Ala Pro Gln Tyr Val Ser Ser Thr Asp Gly Ser Phe Leu Asp
705                 710                 715                 720

Ser Val Ile Gln Asn Gly Tyr Ala Phe Thr Asp Arg Tyr Asp Leu Gly
                725                 730                 735

Ile Ser Lys Pro Asn Lys Tyr Gly Thr Ala Asp Asp Leu Val Lys Ala
            740                 745                 750

Ile Lys Ala Leu His Ser Lys Gly Ile Lys Val Met Ala Asp Trp Val
        755                 760                 765

Pro Asp Gln Met Tyr Ala Leu Pro Glu Lys Glu Val Val Thr Ala Thr
    770                 775                 780

Arg Val Asp Lys Tyr Gly Thr Pro Val Ala Gly Ser Gln Ile Lys Asn
785                 790                 795                 800

Thr Leu Tyr Val Val Asp Gly Lys Ser Ser Gly Lys Asp Gln Gln Ala
```

```
                805                 810                 815
Lys Tyr Gly Gly Ala Phe Leu Glu Glu Leu Gln Ala Lys Tyr Pro Glu
                820                 825                 830
Leu Phe Ala Arg Lys Gln Ile Ser Thr Gly Val Pro Met Asp Pro Ser
                835                 840                 845
Val Lys Ile Lys Gln Trp Ser Ala Lys Tyr Phe Asn Gly Thr Asn Ile
                850                 855                 860
Leu Gly Arg Gly Ala Gly Tyr Val Leu Lys Asp Gln Ala Thr Asn Thr
865                 870                 875                 880
Tyr Phe Asn Ile Ser Asp Asn Lys Glu Ile Asn Phe Leu Pro Lys Thr
                885                 890                 895
Leu Leu Asn Gln Asp Ser Gln Val Gly Phe Ser Tyr Asp Gly Lys Gly
                900                 905                 910
Tyr Val Tyr Tyr Ser Thr Ser Gly Tyr Gln Ala Lys Asn Thr Phe Ile
                915                 920                 925
Ser Glu Gly Asp Lys Trp Tyr Tyr Phe Asp Asn Asn Gly Tyr Met Val
                930                 935                 940
Thr Gly Ala Gln Ser Ile Asn Gly Val Asn Tyr Tyr Phe Leu Pro Asn
945                 950                 955                 960
Gly Leu Gln Leu Arg Asp Ala Ile Leu Lys Asn Glu Asp Gly Thr Tyr
                965                 970                 975
Ala Tyr Tyr Gly Asn Asp Gly Arg Arg Tyr Glu Asn Gly Tyr Tyr Gln
                980                 985                 990
Phe Met Ser Gly Val Trp Arg His Phe Asn Asn Gly Glu Met Ser Val
                995                 1000                1005
Gly Leu Thr Val Ile Asp Gly Gln Val Gln Tyr Phe Asp Glu Met
                1010                1015                1020
Gly Tyr Gln Ala Lys Gly Lys Phe Val Thr Ala Asp Gly Lys
                1025                1030                1035
Ile Arg Tyr Phe Asp Lys Gln Ser Gly Asn Met Tyr Arg Asn Arg
                1040                1045                1050
Phe Ile Glu Asn Glu Glu Gly Lys Trp Leu Tyr Leu Gly Glu Asp
                1055                1060                1065
Gly Ala Ala Val Thr Gly Ser Gln Thr Ile Asn Gly Gln His Leu
                1070                1075                1080
Tyr Phe Arg Ala Asn Gly Val Gln Val Lys Gly Glu Phe Val Thr
                1085                1090                1095
Asp Arg His Gly Arg Ile Ser Tyr Tyr Asp Gly Asn Ser Gly Asp
                1100                1105                1110
Gln Ile Arg Asn Arg Phe Val Arg Asn Ala Gln Gly Gln Trp Phe
                1115                1120                1125
Tyr Phe Asp Asn Asn Gly Tyr Ala Val Thr Gly Ala Arg Thr Ile
                1130                1135                1140
Asn Gly Gln His Leu Tyr Phe Arg Ala Asn Gly Val Gln Val Lys
                1145                1150                1155
Gly Glu Phe Val Thr Asp Arg His Gly Arg Ile Ser Tyr Tyr Asp
                1160                1165                1170
Gly Asn Ser Gly Asp Gln Ile Arg Asn Arg Phe Val Arg Asn Ala
                1175                1180                1185
Gln Gly Gln Trp Phe Tyr Phe Asp Asn Asn Gly Tyr Ala Val Thr
                1190                1195                1200
Gly Ala Arg Thr Ile Asn Gly Gln His Leu Tyr Phe Arg Ala Asn
                1205                1210                1215
```

| Gly | Val | Gln | Val | Lys | Gly | Glu | Phe | Val | Thr | Asp | Arg | Tyr | Gly | Arg |
|-----|-----|-----|-----|-----|-----|-----|-----|-----|-----|-----|-----|-----|-----|-----|
| 1220 | | | | 1225 | | | | | 1230 | | | | | |

| Ile | Ser | Tyr | Tyr | Asp | Gly | Asn | Ser | Gly | Asp | Gln | Ile | Arg | Asn | Arg |
|-----|-----|-----|-----|-----|-----|-----|-----|-----|-----|-----|-----|-----|-----|-----|
| 1235 | | | | | 1240 | | | | | 1245 | | | | |

| Phe | Val | Arg | Asn | Ala | Gln | Gly | Gln | Trp | Phe | Tyr | Phe | Asp | Asn | Asn |
|-----|-----|-----|-----|-----|-----|-----|-----|-----|-----|-----|-----|-----|-----|-----|
| 1250 | | | | | 1255 | | | | | 1260 | | | | |

| Gly | Tyr | Ala | Val | Thr | Gly | Ala | Arg | Thr | Ile | Asn | Gly | Gln | His | Leu |
|-----|-----|-----|-----|-----|-----|-----|-----|-----|-----|-----|-----|-----|-----|-----|
| 1265 | | | | | 1270 | | | | | 1275 | | | | |

| Tyr | Phe | Arg | Ala | Asn | Gly | Val | Gln | Val | Lys | Gly | Glu | Phe | Val | Thr |
|-----|-----|-----|-----|-----|-----|-----|-----|-----|-----|-----|-----|-----|-----|-----|
| 1280 | | | | | 1285 | | | | | 1290 | | | | |

| Asp | Arg | Tyr | Gly | Arg | Ile | Ser | Tyr | Tyr | Asp | Ala | Asn | Ser | Gly | Glu |
|-----|-----|-----|-----|-----|-----|-----|-----|-----|-----|-----|-----|-----|-----|-----|
| 1295 | | | | | 1300 | | | | | 1305 | | | | |

| Arg | Val | Arg | Ile | Asn |
|-----|-----|-----|-----|-----|
| 1310 | | | | |

<210> SEQ ID NO 13
<211> LENGTH: 3972
<212> TYPE: DNA
<213> ORGANISM: Streptococcus dentirousetti

<400> SEQUENCE: 13

| | | | | | |
|---|---|---|---|---|---|
| atggttgacg gcaaatacta ctactacgat gcagacggca acgtaaagaa aaacttcgcg | 60 |
| gttagcgttg gcgatgccat tttctatttt gatgaaacgg gtgcctacaa agataccagc | 120 |
| aaagttgatg cggataagac cagctctagc gtcaatcaga ccacggaaac gttcgcagcg | 180 |
| aataaccgtg cgtatagcac cgcagccgag aactttgaag cgattgataa ctacctgact | 240 |
| gcggatagct ggtatcgtcc gaagtctatc ttgaaagatg gtacgacgtg gaccgaaagc | 300 |
| accaaggatg atttctcgccc gctgctgatg gcgtggtggc cggataccga aaccaaacgt | 360 |
| aactacgtga actatatgaa caaggtggtc ggtatcgaca aaacgtacac cgcggaaacg | 420 |
| tcccaagctg acctgacggc ggcagccgaa ctggtgcagg cgcgtatcga gcagaaaatc | 480 |
| actagcgaaa agaatacgaa gtggctgcgt gaggcgattt ccgcgttcgt taagactcaa | 540 |
| ccgcagtgga atggcgagag cgagaaacct tatgatgacc acctgcaaaa tggtgcgctg | 600 |
| aagttcgaca atgaaaccag cctgaccccg gatacgcaga gcggctatcg catcctgaac | 660 |
| cgtaccccga cgaatcaaac cggtagcctg gacccgcgct tcaccttaa tcagaatgac | 720 |
| ccgctgggtg gttatgagta tttgctggct aatgatgtcg ataacagcaa cccggtcgtt | 780 |
| caggccgaga gcctgaactg gctgcattac ctgctgaatt ttggtagcat ttacgcgaat | 840 |
| gatccggagg ccaatttcga cagcatccgt gtggacgcgg tggacaatgt tgacgcagac | 900 |
| ctgctgcaaa ttagctcgga ttacctgaaa tcggcgtaca aaattgacaa gaacaacaaa | 960 |
| aatgcgaacg accacgttag catcgtcgag gcgtggagcg acaatgatac cccgtacctg | 1020 |
| aatgatgatg cgacaatctc gatgaacatg gataacaagt tcgtctgag catgctgtgg | 1080 |
| agcctggcga agccaaccaa tgtccgtagc ggcttgaatc cgctgatcca aacagcgtg | 1140 |
| gttgaccgtg aggtggacga ccgtgaagtt gaggctaccc cgaattacag ctttgcacgc | 1200 |
| gcacacgaca cgaagttca agatttgatt cgcgacatca tcaaagctga gatcaaccca | 1260 |
| aacagcttcg gttatagctt taccaagag gaatcgacc aggccttcaa gatctacaat | 1320 |
| gaggatttga gaaaaccaa taagaagtat accccactaca acgtccgct gagctacacc | 1380 |
| ctgctgctga cgaacaaggg cagcattcca cgcatttact acggtgacat gtttacggat | 1440 |
| gacggtcagt atatggccaa caaaaccgtt aactatgacg ccattgagag cctgctgaaa | 1500 |

-continued

```
gcacgtatga agtatgttag cggtggccaa gcgatgcaga attacaacat cggcaacggc   1560
gagattctga ccagcgtccg ttacggtaag ggtgccctga acagagcga caaaggcgat   1620 aagactactc gtaccagcgg tattggcgtt gtgatgggta accagagcaa tttcagcctg   1680
gagggcaagg tggtggccct gaatatgggt gcaacgcata ccaaacagaa gtatcgtgca   1740
ttgatggtgt ctacggaaac cggcgtggcg atttacaata gcgatgaaga agcagaggca   1800
gcaggcctga tcaaaacgac cgatgagaat ggttatttgt actttctgaa tgacgatctg   1860
aagggcgtgg ctaacccgca ggtcagcggc ttcctgcaag tgtgggttcc ggttggtgca   1920
ccggctgacc aggacattcg tgtggcggcg accgatgcgg cttctaccga cggtaagagc   1980
ctgcatcagg acgcagctct ggattctcgc gtcatgtttg aaggtttcag caacttccag   2040
agcttcgcaa ccaaggaaga ggaatacacc aacgttgtta ttgcaaagaa cgtggataag   2100
ttcgtgagct ggggtatcac cgacttcgag atggcaccgc agtacgttag ctctaccgat   2160
ggcacctttc tggatagcgt gattcaaaat ggctatgcct ttacggaccg ttacgacctg   2220
ggtatgagca agcaaacaa gtatggtact gctgaccaac tggtggccgc gattaaagcg   2280
ctgcatgcga agggtctgcg tgtgatggcg gattgggtcc cagatcaaat gtacactttc   2340
cctaagaagg aagtggttac cgttacccgt acggacaaat ttggcaatcc agtggcaggc   2400
agccaaatca accacacctt gtacgtcact gatactaagg gtagcggtga cgactaccag   2460
gcgaagtacg gtggcgcatt cctggatgaa ctgaaagaaa gtacccgga gctgtttacc   2520 aagaagcaaa tcagcaccgg tcaggcaatc gacccgagcg tgaaaatcaa gcagtggagc   2580
gcgaagtact tcaacggtag caatatcttg ggtcgcggtg cgaactacgt gctgtccgac   2640
caggcgtcta acaagtactt taacgtggcc gaaggtaaag tctttctgcc agcggcgatg   2700
ctgggtaagg tcgtcgagag cggtatccgt ttcgacggta aaggttatat ctataacagc   2760
agcaccactg gcgaacaagt gaaggacagc ttcattaccg aagcgggtaa cttgtactat   2820
tttggcaaag atggttatat ggtcatgggt gcacagaata tccagggtgc taactactac   2880
ttcttggcga atggtgcggc cctgcgcaat agcatcctga cggatcagga tgcaaaagc   2940 cactattatg caaatgacgg caagcgttat gagaacggct actatcaatt cggtaacgac   3000
tcctggcgct attttgaaaa cggcgttatg gccgttggtt tgacgcgcgt tgcgggccac   3060
gaccaatact ttgataagga tggtatccaa gcgaagaata agatcattgt tacgcgtgac   3120
ggtaaggtcc gctacttcga cgaacacaac ggcaatgctg ccacgaatac gtttatcagc   3180
gatcaagccg gccattggta ctacctgggt aaagatggtc tcgccgtgac gggtgcgcag   3240
accgttggca agcaacacct gtacttcgag gctaacggcc aacaagtaaa aggcgatttt   3300
gttaccgcca aggacggtaa gttgtatttt ctggacggtg actctggcga catgtggacc   3360
gataccttcg tccaggataa ggctggtcat tggttctatc tgggcaaaga cggtgcggcg   3420
gtaaccggtg cccagaccgt ccgtggtcag aagctgtact caaagcgaa tggccagcag   3480 gttaagggtg acattgtgaa aggcgcggat ggtaaaatcc gttactatga tgcaaattcc   3540
ggtgaccagg tttacaatcg cacggtgaaa ggctccgacg gcaagaccta tcattggt   3600 aatgacggcg tcgcaatcac gcaaaccatc gccaaaggcc agaccatcaa ggatggcagc   3660
gttctgcgct tctatagcat ggagggtcag ctggtgaccg gcagcggctg gtattccaac   3720
gcgaaaggtc aatggttgta tgtcaagaac ggtcaagtcc tgacgggttt gcagacggtg   3780
ggcagccagc gtgtgtactt tgacgcaaat ggtattcaag cgaaaggtaa agcagtgcgt   3840
```

-continued

```
acctccgatg caaactgcg ttacttcgat gcgaacagcg gcagcatgat caccaatcag    3900
tggaaagaag ttaatggtca gtactactat ttcgacaaca acggtgttgc gatctatcgc    3960
ggttggaact aa                                                        3972
```

<210> SEQ ID NO 14
<211> LENGTH: 1323
<212> TYPE: PRT
<213> ORGANISM: Streptococcus dentirousetti

<400> SEQUENCE: 14

| Met | Val | Asp | Gly | Lys | Tyr | Tyr | Tyr | Asp | Ala | Asp | Gly | Asn | Val | Lys |
|---|---|---|---|---|---|---|---|---|---|---|---|---|---|---|
| 1 | | | | 5 | | | | | 10 | | | | | 15 |

| Lys | Asn | Phe | Ala | Val | Ser | Val | Gly | Asp | Ala | Ile | Phe | Tyr | Phe | Asp | Glu |
|---|---|---|---|---|---|---|---|---|---|---|---|---|---|---|---|
| | | | 20 | | | | | 25 | | | | | 30 | | |

Thr Gly Ala Tyr Lys Asp Thr Ser Lys Val Asp Ala Asp Lys Thr Ser
                35                  40                  45

Ser Ser Val Asn Gln Thr Thr Glu Thr Phe Ala Ala Asn Asn Arg Ala
50                  55                  60

Tyr Ser Thr Ala Ala Glu Asn Phe Glu Ala Ile Asp Asn Tyr Leu Thr
65                  70                  75                  80

Ala Asp Ser Trp Tyr Arg Pro Lys Ser Ile Leu Lys Asp Gly Thr Thr
                85                  90                  95

Trp Thr Glu Ser Thr Lys Asp Asp Phe Arg Pro Leu Leu Met Ala Trp
            100                 105                 110

Trp Pro Asp Thr Glu Thr Lys Arg Asn Tyr Val Asn Tyr Met Asn Lys
        115                 120                 125

Val Val Gly Ile Asp Lys Thr Tyr Thr Ala Glu Thr Ser Gln Ala Asp
130                 135                 140

Leu Thr Ala Ala Ala Glu Leu Val Gln Ala Arg Ile Glu Gln Lys Ile
145                 150                 155                 160

Thr Ser Glu Lys Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Glu Thr Ser Leu
        195                 200                 205

Thr Pro Asp Thr Gln Ser Gly Tyr Arg Ile Leu Asn Arg Thr Pro Thr
210                 215                 220

Asn Gln Thr Gly Ser Leu Asp Pro Arg Phe Thr Phe Asn Gln Asn Asp
225                 230                 235                 240

Pro Leu Gly Gly Tyr Glu Tyr Leu Leu Ala Asn Asp Val Asp Asn Ser
                245                 250                 255

Asn Pro Val Val Gln Ala Glu Ser Leu Asn Trp Leu His Tyr Leu Leu
            260                 265                 270

Asn Phe Gly Ser Ile Tyr Ala Asn Asp Pro Glu Ala Asn Phe Asp Ser
        275                 280                 285

Ile Arg Val Asp Ala Val Asp Asn Val Asp Ala Asp Leu Leu Gln Ile
290                 295                 300

Ser Ser Asp Tyr Leu Lys Ser Ala Tyr Lys Ile Asp Lys Asn Asn Lys
305                 310                 315                 320

Asn Ala Asn Asp His Val Ser Ile Val Glu Ala Trp Ser Asp Asn Asp
                325                 330                 335

Thr Pro Tyr Leu Asn Asp Asp Gly Asp Asn Leu Met Asn Met Asp Asn
            340                 345                 350

```
Lys Phe Arg Leu Ser Met Leu Trp Ser Leu Ala Lys Pro Thr Asn Val
            355                 360                 365

Arg Ser Gly Leu Asn Pro Leu Ile His Asn Ser Val Val Asp Arg Glu
    370                 375                 380

Val Asp Asp Arg Glu Val Glu Ala Thr Pro Asn Tyr Ser Phe Ala Arg
385                 390                 395                 400

Ala His Asp Ser Glu Val Gln Asp Leu Ile Arg Asp Ile Ile Lys Ala
                405                 410                 415

Glu Ile Asn Pro Asn Ser Phe Gly Tyr Ser Phe Thr Gln Glu Glu Ile
                420                 425                 430

Asp Gln Ala Phe Lys Ile Tyr Asn Glu Asp Leu Lys Lys Thr Asn Lys
            435                 440                 445

Lys Tyr Thr His Tyr Asn Val Pro Leu Ser Tyr Thr Leu Leu Leu Thr
        450                 455                 460

Asn Lys Gly Ser Ile Pro Arg Ile Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gly Gln Ala Met
                500                 505                 510

Gln Asn Tyr Asn Ile Gly Asn Gly Glu Ile Leu Thr Ser Val Arg Tyr
            515                 520                 525

Gly Lys Gly Ala Leu Lys Gln Ser Asp Lys Gly Asp Lys Thr Thr Arg
        530                 535                 540

Thr Ser Gly Ile Gly Val Val Met Gly Asn Gln Ser Asn Phe Ser Leu
545                 550                 555                 560

Glu Gly Lys Val Val Ala Leu Asn Met Gly Ala Thr His Thr Lys Gln
                565                 570                 575

Lys Tyr Arg Ala Leu Met Val Ser Thr Glu Thr Gly Val Ala Ile Tyr
            580                 585                 590

Asn Ser Asp Glu Glu Ala Glu Ala Ala Gly Leu Ile Lys Thr Thr Asp
        595                 600                 605

Glu Asn Gly Tyr Leu Tyr Phe Leu Asn Asp Asp Leu Lys Gly Val Ala
    610                 615                 620

Asn Pro Gln Val Ser Gly Phe Leu Gln Val Trp Val Pro Val Gly Ala
625                 630                 635                 640

Pro Ala Asp Gln Asp Ile Arg Val Ala Ala Thr Asp Ala Ala Ser Thr
                645                 650                 655

Asp Gly Lys Ser Leu His Gln Asp Ala Ala Leu Asp Ser Arg Val Met
            660                 665                 670

Phe Glu Gly Phe Ser Asn Phe Gln Ser Phe Ala Thr Lys Glu Glu Glu
        675                 680                 685

Tyr Thr Asn Val Val Ile Ala Lys Asn Val Asp Lys Phe Val Ser Trp
    690                 695                 700

Gly Ile Thr Asp Phe Glu Met Ala Pro Gln Tyr Val Ser Ser Thr Asp
705                 710                 715                 720

Gly Thr Phe Leu Asp Ser Val Ile Gln Asn Gly Tyr Ala Phe Thr Asp
                725                 730                 735

Arg Tyr Asp Leu Gly Met Ser Lys Ala Asn Lys Tyr Gly Thr Ala Asp
            740                 745                 750

Gln Leu Val Ala Ala Ile Lys Ala Leu His Ala Lys Gly Leu Arg Val
        755                 760                 765
```

-continued

Met Ala Asp Trp Val Pro Asp Gln Met Tyr Thr Phe Pro Lys Lys Glu
770                 775                 780

Val Val Thr Val Thr Arg Thr Asp Lys Phe Gly Asn Pro Val Ala Gly
785                 790                 795                 800

Ser Gln Ile Asn His Thr Leu Tyr Val Thr Asp Thr Lys Gly Ser Gly
        805                 810                 815

Asp Asp Tyr Gln Ala Lys Tyr Gly Gly Ala Phe Leu Asp Glu Leu Lys
            820                 825                 830

Glu Lys Tyr Pro Glu Leu Phe Thr Lys Lys Gln Ile Ser Thr Gly Gln
            835                 840                 845

Ala Ile Asp Pro Ser Val Lys Ile Lys Gln Trp Ser Ala Lys Tyr Phe
850                 855                 860

Asn Gly Ser Asn Ile Leu Gly Arg Gly Ala Asn Tyr Val Leu Ser Asp
865                 870                 875                 880

Gln Ala Ser Asn Lys Tyr Phe Asn Val Ala Glu Gly Lys Val Phe Leu
            885                 890                 895

Pro Ala Ala Met Leu Gly Lys Val Val Glu Ser Gly Ile Arg Phe Asp
            900                 905                 910

Gly Lys Gly Tyr Ile Tyr Asn Ser Ser Thr Thr Gly Glu Gln Val Lys
            915                 920                 925

Asp Ser Phe Ile Thr Glu Ala Gly Asn Leu Tyr Tyr Phe Gly Lys Asp
930                 935                 940

Gly Tyr Met Val Met Gly Ala Gln Asn Ile Gln Gly Ala Asn Tyr Tyr
945                 950                 955                 960

Phe Leu Ala Asn Gly Ala Ala Leu Arg Asn Ser Ile Leu Thr Asp Gln
                965                 970                 975

Asp Gly Lys Ser His Tyr Tyr Ala Asn Asp Gly Lys Arg Tyr Glu Asn
            980                 985                 990

Gly Tyr Tyr Gln Phe Gly Asn Asp Ser Trp Arg Tyr Phe Glu Asn Gly
            995                 1000                1005

Val Met Ala Val Gly Leu Thr Arg Val Ala Gly His Asp Gln Tyr
    1010                1015                1020

Phe Asp Lys Asp Gly Ile Gln Ala Lys Asn Lys Ile Ile Val Thr
    1025                1030                1035

Arg Asp Gly Lys Val Arg Tyr Phe Asp Glu His Asn Gly Asn Ala
    1040                1045                1050

Ala Thr Asn Thr Phe Ile Ser Asp Gln Ala Gly His Trp Tyr Tyr
    1055                1060                1065

Leu Gly Lys Asp Gly Val Ala Val Thr Gly Ala Gln Thr Val Gly
    1070                1075                1080

Lys Gln His Leu Tyr Phe Glu Ala Asn Gly Gln Gln Val Lys Gly
    1085                1090                1095

Asp Phe Val Thr Ala Lys Asp Gly Lys Leu Tyr Phe Leu Asp Gly
    1100                1105                1110

Asp Ser Gly Asp Met Trp Thr Asp Thr Phe Val Gln Asp Lys Ala
    1115                1120                1125

Gly His Trp Phe Tyr Leu Gly Lys Asp Gly Ala Ala Val Thr Gly
    1130                1135                1140

Ala Gln Thr Val Arg Gly Gln Lys Leu Tyr Phe Lys Ala Asn Gly
    1145                1150                1155

Gln Gln Val Lys Gly Asp Ile Val Lys Gly Ala Asp Gly Lys Ile
    1160                1165                1170

Arg Tyr Tyr Asp Ala Asn Ser Gly Asp Gln Val Tyr Asn Arg Thr

```
                1175                1180               1185
Val Lys Gly Ser Asp Gly Lys Thr Tyr Ile Ile Gly Asn Asp Gly
          1190              1195                1200

Val Ala Ile Thr Gln Thr Ile Ala Lys Gly Gln Thr Ile Lys Asp
          1205              1210                1215

Gly Ser Val Leu Arg Phe Tyr Ser Met Glu Gly Gln Leu Val Thr
          1220              1225                1230

Gly Ser Gly Trp Tyr Ser Asn Ala Lys Gly Gln Trp Leu Tyr Val
          1235              1240                1245

Lys Asn Gly Gln Val Leu Thr Gly Leu Gln Thr Val Gly Ser Gln
          1250              1255                1260

Arg Val Tyr Phe Asp Ala Asn Gly Ile Gln Ala Lys Gly Lys Ala
          1265              1270                1275

Val Arg Thr Ser Asp Gly Lys Leu Arg Tyr Phe Asp Ala Asn Ser
          1280              1285                1290

Gly Ser Met Ile Thr Asn Gln Trp Lys Glu Val Asn Gly Gln Tyr
          1295              1300                1305

Tyr Tyr Phe Asp Asn Asn Gly Val Ala Ile Tyr Arg Gly Trp Asn
          1310              1315                1320
```

<210> SEQ ID NO 15
<211> LENGTH: 4047
<212> TYPE: DNA
<213> ORGANISM: Streptococcus oralis

<400> SEQUENCE: 15

```
atgatcgacg gcaaaaacta ctacgtacag gatgatggca cggtaaagaa gaatttcgcg    60
gtagaactga atggtcgtat cctgtatttt gatgcagaaa ccggcgctct ggttgatagc   120
aacgagtatc agttccaaca gggtacgagc agcctgaaca tgaatttttc tcagaagaac   180
gcattctatg gtacgaccga taaggatatt gagactgtgg atggctacct gaccgcagat   240
agctggtatc gcccgaaatt catcctgaag gatggcaaga cgtggaccgc gagcacggaa   300
acggatctgc gtccgctgtt gatggcatgg tggcccggaca gcgtaccca aatcaactat   360 ctgaactaca tgaaccagca gggtctgggt gcgggtgcgt tgagaacaa gtggagcag   420 gccctgctga cgggtgcaag ccaacaggta caacgcaaga tcgaagagaa gattggtaaa   480
gagggtgata ccaagtggct gcgcaccctg atgggtgcgt cgtgaaaac gcaaccaaac   540 tggaatatca aaccgagtc tgaaacgacc ggcacgaaaa aggaccatct gcaaggcggt   600
gcactgctgt atacgaacaa cgagaaatcc ccgcacgcgg acagcaaatt tcgtctgctg   660
aatcgtaccc cgaccagcca aaccggcacg ccgaagtatt tcatcgacaa gtctaacggt   720
ggctacgaat ttctgctggc gaacgatttt gacaatagca tcctgcggt acaagctgag   780 cagctgaatt ggctgcacta catgatgaac tttggcagca ttgttgcgaa tgatccgacc   840
gcgaatttcg acggcgttcg tgtggatgct gttgataacg tcaatgcgga cttgttgcaa   900
attgcaagcg attactttaa gagccgttac aaagtcggtg agagcgaaga agaagcgatc   960
aagcacctgt ccatcctgga agcatggagc gataacgacc cggactacaa caaagatacc  1020
aagggtgcac agttggcgat tgataacaaa ctgcgcctga gcctgctgta ctctttcatg  1080
cgtaatctga gcatccgtag cggtgttgaa ccgacgatta ccaatagcct gaatgaccgt  1140
tccagcgaaa agaagaacgg cgagcgtatg gcaaattaca tcttcgtgcg tgcccacgat  1200
agcgaggtcc aaacggtgat cgccgacatc attcgcgaaa acatcaatcc gaacaccgac  1260
```

-continued

```
ggcctgacgt ttacgatgga cgagctgaag caggcattca agatttacaa cgaggacatg    1320
cgcaaggcgg acaaaaagta tacccagttt aacattccta ccgcacacgc gctgatgctg    1380
tctaataagg attctattac ccgcgtgtac tatggtgatc tgtatactga cgatggtcag    1440
tacatggaga agaaaagccc gtatcacgat gcgattgacg ctctgctgcg tgcacgtatt    1500
aaatacgtcg cgggtggcca ggatatgaaa gtgacctata tgggcgtgcc gcgtgaagcg    1560
gataagtgga gctataacgg cattctgacc agcgtgcgct atggcacggg cgctaacgaa    1620
gccacggatg agggcactgc ggaaacgcgc acgcaaggta tggcagtgat tgcgagcaat    1680
aatccaaatc tgaaactgaa tgaatgggac aagttgcaag tcaacatggg tgcggcgcat    1740
aagaatcaat attaccgtcc ggttctgctg accactaagg acggtatcag ccgttatctg    1800
accgatgaag aagtgcctca gagcctgtgg aaaagacgg acgcaaacgg tattctgacc    1860
ttcgacatga atgatattgc tggctacagc aacgtgcaag ttagcggtta cctggccgtc    1920
tgggtcccgg tcggtgcgaa ggcggatcaa gatgcgcgca cgaccgcatc caagaagaaa    1980
aatgcgtcgg gtcaggtgta cgaaagcagc gcggctctgg atagccagct gatttacgaa    2040
ggtttcagca actttcaaga ctttgccact cgcgatgatc agtacacgaa caaggtcatt    2100
gcgaaaaacg tgaatctgtt caaagaatgg ggtgtgacca gcttcgagct gccgccgcag    2160
tacgtgagca gccaagatgg cacctttctg gacagcatta tccaaaacgg ctatgcattt    2220
gaagaccgtt acgatatggc gatgagcaag aataacaagt atggtagcct gaaagacctg    2280
ttgaacgcgc tgcgcgcact gcacagcgtc aacattcaag caatcgccga ttgggtgccg    2340
gaccaaattt acaacttgcc gggcaaagag gtggtgaccg caactcgtgt caacaactac    2400
ggcacctacc gtgagggtgc tgaaatcaaa gaaaagctgt atgtcgccaa tagcaagacc    2460
aacgaaaccg atttccaagg taaatacggt ggtgcgttcc tggatgagct gaaggcgaag    2520
tacccggaga ttttcgagcg tgtccaaatc agcaacggcc aaaagatgac taccgatgaa    2580
aagatcacca aatggagcgc gaaatacttt aatggcacca atattctggg tcgtggcgcg    2640
tactatgtcc tgaaagattg gccagcaat gattacctga cgaaccgtaa cggcgagatt    2700
gttttgccga gcaactggt taacaagaat agctataccg gctttgtcag cgacgcgaac    2760
ggcacgaagt tctattctac ctctggctac caggcgaaga acagcttcat tcaagacgaa    2820
aacggtaatt ggtattactt tgacaaacgt ggttatctgg ttacgggcgc acacgagatt    2880
gatggcaagc atgtctactt cctgaaaaac ggtatccaac tgcgtgacag catccgtgag    2940
gatgagaacg gtaatcaata ctattacgac cagaccggcg cacaagtgct gaaccgttac    3000
tacacgacgg acggtcagaa ttggcgctat ttcgatgcga aaggtgttat ggcacgcggc    3060
ctggtaaaga ttggtgacgg ccaacagttt ttcgatgaaa acggttacca ggtcaagggc    3120
aagattgtta gcgcaaaaga cggcaagctg cgctactttg ataaagactc tggcaatgct    3180
gtcattaatc gtttcgcgca gggtgacaat ccgagcgact ggtactattt cggtgtggaa    3240
tttgctaaac tgacgggttt gcaaaagatc ggccagcaga cgctgtattt tgaccaagac    3300
ggtaagcaag tcaaaggtaa gatcgtaact ctgtcggaca aaagcattcg ttacttcgat    3360
gccaacagcg gtgaaatggc ggttggcaag ttcgcggaag gtgcaaagaa tgagtggtat    3420
tatttcgata aaaccggcaa agcggttact ggtttgcaga aaattggtaa gcagaccctg    3480
tactttgacc aggacggtaa acaggttaaa gcaaggttg tcacgctggc tgataaaagc    3540
atccgctact tcgacgcaga ctccggcgag atggcggtcg gtaagtttgc agagggtgcg    3600
aagaacgagt ggtactattt tgatcagact ggcaaggccg tgactggttt gcaaaagatt    3660
```

-continued

```
gacaagcaaa ccttgtactt cgaccaggac ggtaaacaag tcaagggtaa gattgtgacg    3720
ttgagcgaca agtcgatccg ttactttgat gctaatagcg gtgagatggc tactaacaaa    3780
ttcgtcgagg gctcgcagaa tgaatggtac tacttcgatc aagcgggtaa ggctgttacg    3840
ggcttgcaac aggtcggtca gcaaactctg tacttcaccc aggatggtaa gcaagtgaag    3900
ggtaaggtcg tggacgtgaa cggtgtttct cgttatttcg acgcaaactc cggtgacatg    3960
gctcgttcta atggattca actggaagat ggcagctgga tgtatttcga ccgtgacggt    4020
cgtggccaga attttggccg taactaa                                        4047
```

<210> SEQ ID NO 16
<211> LENGTH: 1348
<212> TYPE: PRT
<213> ORGANISM: Streptococcus oralis

<400> SEQUENCE: 16

```
Met Ile Asp Gly Lys Asn Tyr Tyr Val Gln Asp Gly Thr Val Lys
  1               5                  10                  15

Lys Asn Phe Ala Val Glu Leu Asn Gly Arg Ile Leu Tyr Phe Asp Ala
                 20                  25                  30

Glu Thr Gly Ala Leu Val Asp Ser Asn Glu Tyr Gln Phe Gln Gln Gly
             35                  40                  45

Thr Ser Ser Leu Asn Asn Glu Phe Ser Gln Lys Asn Ala Phe Tyr Gly
         50                  55                  60

Thr Thr Asp Lys Asp Ile Glu Thr Val Asp Gly Tyr Leu Thr Ala Asp
 65                  70                  75                  80

Ser Trp Tyr Arg Pro Lys Phe Ile Leu Lys Asp Gly Lys Thr Trp Thr
                 85                  90                  95

Ala Ser Thr Glu Thr Asp Leu Arg Pro Leu Leu Met Ala Trp Trp Pro
            100                 105                 110

Asp Lys Arg Thr Gln Ile Asn Tyr Leu Asn Tyr Met Asn Gln Gln Gly
            115                 120                 125

Leu Gly Ala Gly Ala Phe Glu Asn Lys Val Glu Gln Ala Leu Leu Thr
130                 135                 140

Gly Ala Ser Gln Gln Val Gln Arg Lys Ile Glu Glu Lys Ile Gly Lys
145                 150                 155                 160

Glu Gly Asp Thr Lys Trp Leu Arg Thr Leu Met Gly Ala Phe Val Lys
                165                 170                 175

Thr Gln Pro Asn Trp Asn Ile Lys Thr Glu Ser Glu Thr Thr Gly Thr
            180                 185                 190

Lys Lys Asp His Leu Gln Gly Gly Ala Leu Leu Tyr Thr Asn Asn Glu
        195                 200                 205

Lys Ser Pro His Ala Asp Ser Lys Phe Arg Leu Leu Asn Arg Thr Pro
    210                 215                 220

Thr Ser Gln Thr Gly Thr Pro Lys Tyr Phe Ile Asp Lys Ser Asn Gly
225                 230                 235                 240

Gly Tyr Glu Phe Leu Leu Ala Asn Asp Phe Asn Ser Asn Pro Ala
                245                 250                 255

Val Gln Ala Glu Gln Leu Asn Trp Leu His Tyr Met Met Asn Phe Gly
            260                 265                 270

Ser Ile Val Ala Asn Asp Pro Thr Ala Asn Phe Asp Gly Val Arg Val
        275                 280                 285

Asp Ala Val Asp Asn Val Asn Ala Asp Leu Leu Gln Ile Ala Ser Asp
    290                 295                 300
```

```
Tyr Phe Lys Ser Arg Tyr Lys Val Gly Glu Ser Glu Glu Ala Ile
305                 310                 315                 320

Lys His Leu Ser Ile Leu Glu Ala Trp Ser Asp Asn Asp Pro Asp Tyr
            325                 330                 335

Asn Lys Asp Thr Lys Gly Ala Gln Leu Ala Ile Asp Asn Lys Leu Arg
            340                 345                 350

Leu Ser Leu Leu Tyr Ser Phe Met Arg Asn Leu Ser Ile Arg Ser Gly
            355                 360                 365

Val Glu Pro Thr Ile Thr Asn Ser Leu Asn Asp Arg Ser Ser Glu Lys
370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
                405                 410                 415

Pro Asn Thr Asp Gly Leu Thr Phe Thr Met Asp Glu Leu Lys Gln Ala
            420                 425                 430

Phe Lys Ile Tyr Asn Glu Asp Met Arg Lys Ala Asp Lys Lys Tyr Thr
            435                 440                 445

Gln Phe Asn Ile Pro Thr Ala His Ala Leu Met Leu Ser Asn Lys Asp
450                 455                 460

Ser Ile Thr Arg Val Tyr Tyr Gly Asp Leu Tyr Thr Asp Asp Gly Gln
465                 470                 475                 480

Tyr Met Glu Lys Lys Ser Pro Tyr His Asp Ala Ile Asp Ala Leu Leu
                485                 490                 495

Arg Ala Arg Ile Lys Tyr Val Ala Gly Gln Asp Met Lys Val Thr
            500                 505                 510

Tyr Met Gly Val Pro Arg Glu Ala Asp Lys Trp Ser Tyr Asn Gly Ile
            515                 520                 525

Leu Thr Ser Val Arg Tyr Gly Thr Gly Ala Asn Glu Ala Thr Asp Glu
530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
                565                 570                 575

Gly Ala Ala His Lys Asn Gln Tyr Tyr Arg Pro Val Leu Leu Thr Thr
            580                 585                 590

Lys Asp Gly Ile Ser Arg Tyr Leu Thr Asp Glu Val Pro Gln Ser
            595                 600                 605

Leu Trp Lys Lys Thr Asp Ala Asn Gly Ile Leu Thr Phe Asp Met Asn
            610                 615                 620

Asp Ile Ala Gly Tyr Ser Asn Val Gln Val Ser Gly Tyr Leu Ala Val
625                 630                 635                 640

Trp Val Pro Val Gly Ala Lys Ala Asp Gln Asp Ala Arg Thr Thr Ala
                645                 650                 655

Ser Lys Lys Lys Asn Ala Ser Gly Gln Val Tyr Glu Ser Ser Ala Ala
                660                 665                 670

Leu Asp Ser Gln Leu Ile Tyr Glu Gly Phe Ser Asn Phe Gln Asp Phe
            675                 680                 685

Ala Thr Arg Asp Asp Gln Tyr Thr Asn Lys Val Ile Ala Lys Asn Val
            690                 695                 700

Asn Leu Phe Lys Glu Trp Gly Val Thr Ser Phe Glu Leu Pro Pro Gln
705                 710                 715                 720
```

```
Tyr Val Ser Ser Gln Asp Gly Thr Phe Leu Asp Ser Ile Ile Gln Asn
            725                 730                 735

Gly Tyr Ala Phe Glu Asp Arg Tyr Asp Met Ala Met Ser Lys Asn Asn
            740                 745                 750

Lys Tyr Gly Ser Leu Lys Asp Leu Leu Asn Ala Leu Arg Ala Leu His
            755                 760                 765

Ser Val Asn Ile Gln Ala Ile Ala Asp Trp Val Pro Asp Gln Ile Tyr
770                 775                 780

Asn Leu Pro Gly Lys Glu Val Val Thr Ala Thr Arg Val Asn Asn Tyr
785                 790                 795                 800

Gly Thr Tyr Arg Glu Gly Ala Glu Ile Lys Glu Lys Leu Tyr Val Ala
                805                 810                 815

Asn Ser Lys Thr Asn Glu Thr Asp Phe Gln Gly Lys Tyr Gly Gly Ala
                820                 825                 830

Phe Leu Asp Glu Leu Lys Ala Lys Tyr Pro Glu Ile Phe Glu Arg Val
            835                 840                 845

Gln Ile Ser Asn Gly Gln Lys Met Thr Thr Asp Glu Lys Ile Thr Lys
            850                 855                 860

Trp Ser Ala Lys Tyr Phe Asn Gly Thr Asn Ile Leu Gly Arg Gly Ala
865                 870                 875                 880

Tyr Tyr Val Leu Lys Asp Trp Ala Ser Asn Asp Tyr Leu Thr Asn Arg
                885                 890                 895

Asn Gly Glu Ile Val Leu Pro Lys Gln Leu Val Asn Lys Asn Ser Tyr
                900                 905                 910

Thr Gly Phe Val Ser Asp Ala Asn Gly Thr Lys Phe Tyr Ser Thr Ser
            915                 920                 925

Gly Tyr Gln Ala Lys Asn Ser Phe Ile Gln Asp Glu Asn Gly Asn Trp
            930                 935                 940

Tyr Tyr Phe Asp Lys Arg Gly Tyr Leu Val Thr Gly Ala His Glu Ile
945                 950                 955                 960

Asp Gly Lys His Val Tyr Phe Leu Lys Asn Gly Ile Gln Leu Arg Asp
                965                 970                 975

Ser Ile Arg Glu Asp Glu Asn Gly Asn Gln Tyr Tyr Tyr Asp Gln Thr
            980                 985                 990

Gly Ala Gln Val Leu Asn Arg Tyr Tyr Thr Thr Asp Gly Gln Asn Trp
            995                 1000                1005

Arg Tyr Phe Asp Ala Lys Gly Val Met Ala Arg Gly Leu Val Lys
            1010                1015                1020

Ile Gly Asp Gly Gln Gln Phe Phe Asp Glu Asn Gly Tyr Gln Val
            1025                1030                1035

Lys Gly Lys Ile Val Ser Ala Lys Asp Gly Lys Leu Arg Tyr Phe
            1040                1045                1050

Asp Lys Asp Ser Gly Asn Ala Val Ile Asn Arg Phe Ala Gln Gly
            1055                1060                1065

Asp Asn Pro Ser Asp Trp Tyr Tyr Phe Gly Val Glu Phe Ala Lys
            1070                1075                1080

Leu Thr Gly Leu Gln Lys Ile Gly Gln Gln Thr Leu Tyr Phe Asp
            1085                1090                1095

Gln Asp Gly Lys Gln Val Lys Gly Lys Ile Val Thr Leu Ser Asp
            1100                1105                1110

Lys Ser Ile Arg Tyr Phe Asp Ala Asn Ser Gly Glu Met Ala Val
            1115                1120                1125

Gly Lys Phe Ala Glu Gly Ala Lys Asn Glu Trp Tyr Tyr Phe Asp
```

|   |   |   |   |   |   |   |   |   |   |
|---|---|---|---|---|---|---|---|---|---|
| 1130 | | | | | 1135 | | | | 1140 |
| Lys | Thr | Gly | Lys | Ala | Val | Thr | Gly | Leu | Gln | Lys | Ile | Gly | Lys | Gln |
| | | | | 1145 | | | | | 1150 | | | | | 1155 |

Lys Thr Gly Lys Ala Val Thr Gly Leu Gln Lys Ile Gly Lys Gln
                1145                    1150                    1155

Thr Leu Tyr Phe Asp Gln Asp Gly Lys Gln Val Lys Gly Lys Val
                1160                    1165                    1170

Val Thr Leu Ala Asp Lys Ser Ile Arg Tyr Phe Asp Ala Asp Ser
                1175                    1180                    1185

Gly Glu Met Ala Val Gly Lys Phe Ala Glu Gly Ala Lys Asn Glu
                1190                    1195                    1200

Trp Tyr Tyr Phe Asp Gln Thr Gly Lys Ala Val Thr Gly Leu Gln
                1205                    1210                    1215

Lys Ile Asp Lys Gln Thr Leu Tyr Phe Asp Gln Asp Gly Lys Gln
                1220                    1225                    1230

Val Lys Gly Lys Ile Val Thr Leu Ser Asp Lys Ser Ile Arg Tyr
                1235                    1240                    1245

Phe Asp Ala Asn Ser Gly Glu Met Ala Thr Asn Lys Phe Val Glu
                1250                    1255                    1260

Gly Ser Gln Asn Glu Trp Tyr Tyr Phe Asp Gln Ala Gly Lys Ala
                1265                    1270                    1275

Val Thr Gly Leu Gln Gln Val Gly Gln Gln Thr Leu Tyr Phe Thr
                1280                    1285                    1290

Gln Asp Gly Lys Gln Val Lys Gly Lys Val Val Asp Val Asn Gly
                1295                    1300                    1305

Val Ser Arg Tyr Phe Asp Ala Asn Ser Gly Asp Met Ala Arg Ser
                1310                    1315                    1320

Lys Trp Ile Gln Leu Glu Asp Gly Ser Trp Met Tyr Phe Asp Arg
                1325                    1330                    1335

Asp Gly Arg Gly Gln Asn Phe Gly Arg Asn
                1340                    1345

<210> SEQ ID NO 17
<211> LENGTH: 4047
<212> TYPE: DNA
<213> ORGANISM: Streptococcus sanguinis

<400> SEQUENCE: 17

```
atgattgatg gtaaaaagta ttacgtacag gacgacggca cggttaagaa gaatttcgcg     60
gttgagctga atggcaagat cctgtacttc gatgcagaga ctggtgcgtt gattgacagc    120
gcggagtatc aattccaaca aggcaccagc agcctgaata atgagttcac tcaaaagaac    180
gccttttacg gtacgaccga taaggatgtg gaaaccattg atggttactt gaccgccgat    240
tcctggtatc gtccgaagtt cattctgaaa gatggcaaaa cctggacggc gagcacggaa    300
attgacttgc gtccgttgtt gatggcgtgg tggccggaca acagaccca ggttagctac    360
ctgaattaca tgaaccagca aggcttgggt gcaggcgcct tcgaaaacaa agtgagagcag   420
gcaattctga ccggtgcgtc ccaacaggta caacgtaaaa tcgaagaacg catcggtaaa   480
gagggtgata ccaagtggct gcgtaccctg atgggtgcat ttgtaaagac ccagccgaac   540
tggaacatta gaccgagtc cgaaaccact ggcacgaata aagatcatct gcaaggtggc    600
gcactgctgt atagcaattc cgacaagacg agccatgcca actctaagta ccgtatcctg    660
aaccgcaccc cgaccaacca aacgggcacg ccgaaatact ttattgacaa gagcaatggt    720
ggttatgaat ttctgctggc gaatgacttt gacaatagca atccggcagt gcaagcggaa    780
cagctgaact ggttgcactt tatgatgaat tttggctcca tcgttgcaaa tgatccgacg    840
```

-continued

```
gccaacttcg acggcgtccg cgttgacgct gtggataacg tgaatgcgga tctgttgcaa      900
attgcgagcg actatttcaa gagccgctat aaagtcggcg aaagcgaaga agaggccatt      960
aagcacctgt ccatcctgga agcgtggagc gacaacgacc cggactacaa caaggatact     1020
aaaggtgccc aactgccgat cgacaacaaa ctgcgtctga gcctgctgta ctccttcatg     1080
cgtaagctga gcatccgtag cggcgtcgag ccgaccatca ccaactctct gaatgatcgc     1140
agcacggaga agaagaatgg tgagcgtatg caaactata tcttcgttcg tgcacatgat      1200
agcgaggtgc aaacggtcat cgccgacatt atccgtgaga acatcaatcc gaataccgac     1260
ggcctgacgt tcacgatgga tgaactgaag caggccttta aaatttacaa tgaggatatg     1320
cgtaaagccg acaaaaagta cacgcagttc aatatcccga ccgcgcacgc gctgatgctg     1380
agcaacaaag attctatcac ccgcgtttac tacggtgacc tgtatacgga tgacggtcag     1440
tatatggaaa agaaaagccc gtatcacgac gccattgacg ctctgctgcg tgcgcgtatc     1500
aaatatgttg cgggtggtca ggacatgaag gtgacctata tgggcgtgcc gcgtgaggca     1560
gataaatgga gctataacgg catcctgacc agcgttcgtt atggtacggg tgccaacgag     1620
gcaaccgacg agggtacggc agaaacccgt acccagggca tggccgtcat tgccagcaac     1680
aatccgaacc tgaaactgaa cgagtgggac aagttgcagg tcaacatggg tgcagctcac     1740
aaaaaccaat actatcgtcc ggtgctgctg accaccaagg acggcatctc gcgctacctg     1800
accgacgaag aagtcccgca gagcctgtgg aaaaagaccg atgcgaacgg catcttgacg     1860
tttgacatga atgatattgc gggttacagc aacgtccaag tgagcggtta tctggccgtc     1920
tgggttcctg tgggtgcgaa ggcggaccag gacgctcgtg ttacggcatc taagaagaaa     1980
aatgcctctg gccaagttta cgaaagcagc gcagccctgg actcccagct gatctatgag     2040
ggcttcagca attttcagga ctttgccacc cgtgacgacc agtacactaa caaggttatc     2100
gcgaaaaacg tcaatctgtt taaagagtgg ggcgtcacca gcttcgaatt gccgccacag     2160
tatgtgagca gccaagacgg tacgttcctg gatagcatca tccagaatgg ttatgcattc     2220
gaagatcgct atgatatggc gatgagcaaa acaataagt acggtagctt gaacgacctg      2280
ttgaacgcct tgcgtgcact gcatagcgtg aatatccaag cgattgcgga ttgggtgccg     2340
gaccagattt acaatctgcc gggtaaagaa gttgtcactg caacccgtgt taacaattat     2400
ggcacgtatc gtgagggtag cgagattaaa gagaacctgt acgttgctaa caccaaaacc     2460
aatggtacgg actaccaagg taagtatggt ggtgcgttct tggacgagct gaaagccaaa     2520
taccctgaga tttttgagcg cgtccaaatc agcaacggcc agaagatgac caccgacgag     2580
aagattacga aatggtccgc caaacacttt aacggcacga acattctggg tcgtggtgcg     2640
tattatgtgc tgaaagactg ggcgagcaac gagtacctga ataacaaaaa tggcgagatg     2700
gttctgccga agcagctggt taataaaaat gcatataccg gcttcgtcag cgacgcgagc     2760
ggcaccaaat actattctac cagcggctat caggctcgta atagctttat tcaagatgaa     2820
aatggtaatt ggtactactt caataaccgt ggttatttgg tgacgggtgc acaggaaatc     2880
gacggtaagc aactgtattt cctgaaaaac ggcattcagc tgcgtgattc tctgcgtgag     2940
gacgaaaacg gcaaccagta ttactatgat aagacgggtc gcaagttct gaatcgttat       3000 tacactacgg acggccaaaa ttggcgctac ttcgacgtta aaggcgtcat ggcccgtggt     3060
ctggtcacga tgggtggtaa ccaacaattc tttgaccaaa acggttacca ggttaaaggc     3120
aaaattgcgc gtgcaaaaga cggtaaactg cgttacttcg ataaagacag cggtaatgcg     3180
```

```
gcagctaacc gtttcgccca aggcgataac cctagcgact ggtactattt cggtgcagat   3240
ggtgttgcgg ttacgggcct gcaaaaggtt ggtcagcaaa ctctgtactt tgatcaggac   3300
ggcaagcagg tgaaaggtaa agttgttacc ttggcggaca aaagcattcg ttatttcgat   3360
gcaaacagcg gcgagatggc ggtgaacaag tttgtggaag gtgctaagaa cgtgtgggtac  3420 tacttcgatc aagcaggcaa agcggtgacc ggcctgcaaa ccatcaataa acaagtgctg   3480
tatttcgacc aggatggtaa acaagtcaaa ggtaaggtgg tcacgctggc tgataagtct   3540
atccgctact tcgacgcgaa cagcggtgag atggcagtgg gcaaattcgc cgaaggcgca   3600
aagaatgagt ggtattactt tgaccaggcg ggcaaggctg ttaccggtct gcaaaagatc   3660
ggccaacaga cgctgtattt cgaccagaac ggtaaacagg ttaagggtaa agtggtcacc   3720
ctggcggata gagcatccg ctatttcgac gctaactctg gcgaaatggc aagcaataag    3780
ttcgttgagg gtgccaaaaa tgaatggtac tatttcgatc aggctggcaa ggcagtgacg   3840
ggtctgcaac aaattggcca gcagaccctg tattttgacc agaatggcaa acaggtgaag   3900
ggtaagattg tgtatgttaa tggtgcgaat cgctactttg atgccaatag cggtgaaatg   3960
gcgcgtaaca agtggattca gctggaagat ggcagctgga tgtattttga ccgcaatggt   4020
cgtggtcgtc gtttcggttg gaactaa                                       4047
```

<210> SEQ ID NO 18
<211> LENGTH: 1348
<212> TYPE: PRT
<213> ORGANISM: Streptococcus sanguinis

<400> SEQUENCE: 18

```
Met Ile Asp Gly Lys Lys Tyr Tyr Val Gln Asp Asp Gly Thr Val Lys
1               5                   10                  15

Lys Asn Phe Ala Val Glu Leu Asn Gly Lys Ile Leu Tyr Phe Asp Ala
            20                  25                  30

Glu Thr Gly Ala Leu Ile Asp Ser Ala Glu Tyr Gln Phe Gln Gln Gly
        35                  40                  45

Thr Ser Ser Leu Asn Asn Glu Phe Thr Gln Lys Asn Ala Phe Tyr Gly
    50                  55                  60

Thr Thr Asp Lys Asp Val Glu Thr Ile Asp Gly Tyr Leu Thr Ala Asp
65                  70                  75                  80

Ser Trp Tyr Arg Pro Lys Phe Ile Leu Lys Asp Gly Lys Thr Trp Thr
                85                  90                  95

Ala Ser Thr Glu Ile Asp Leu Arg Pro Leu Leu Met Ala Trp Trp Pro
            100                 105                 110

Asp Lys Gln Thr Gln Val Ser Tyr Leu Asn Tyr Met Asn Gln Gln Gly
        115                 120                 125

Leu Gly Ala Gly Ala Phe Glu Asn Lys Val Glu Gln Ala Ile Leu Thr
    130                 135                 140

Gly Ala Ser Gln Gln Val Gln Arg Lys Ile Glu Glu Arg Ile Gly Lys
145                 150                 155                 160

Glu Gly Asp Thr Lys Trp Leu Arg Thr Leu Met Gly Ala Phe Val Lys
                165                 170                 175

Thr Gln Pro Asn Trp Asn Ile Lys Thr Glu Ser Glu Thr Thr Gly Thr
            180                 185                 190

Asn Lys Asp His Leu Gln Gly Gly Ala Leu Leu Tyr Ser Asn Ser Asp
        195                 200                 205

Lys Thr Ser His Ala Asn Ser Lys Tyr Arg Ile Leu Asn Arg Thr Pro
    210                 215                 220
```

```
Thr Asn Gln Thr Gly Thr Pro Lys Tyr Phe Ile Asp Lys Ser Asn Gly
225                 230                 235                 240

Gly Tyr Glu Phe Leu Leu Ala Asn Asp Phe Asp Asn Ser Asn Pro Ala
            245                 250                 255

Val Gln Ala Glu Gln Leu Asn Trp Leu His Phe Met Met Asn Phe Gly
        260                 265                 270

Ser Ile Val Ala Asn Asp Pro Thr Ala Asn Phe Asp Gly Val Arg Val
    275                 280                 285

Asp Ala Val Asp Asn Val Asn Ala Asp Leu Leu Gln Ile Ala Ser Asp
290                 295                 300

Tyr Phe Lys Ser Arg Tyr Lys Val Gly Ser Glu Glu Glu Ala Ile
305                 310                 315                 320

Lys His Leu Ser Ile Leu Glu Ala Trp Ser Asp Asn Asp Pro Asp Tyr
                325                 330                 335

Asn Lys Asp Thr Lys Gly Ala Gln Leu Pro Ile Asp Asn Lys Leu Arg
            340                 345                 350

Leu Ser Leu Leu Tyr Ser Phe Met Arg Lys Leu Ser Ile Arg Ser Gly
        355                 360                 365

Val Glu Pro Thr Ile Thr Asn Ser Leu Asn Asp Arg Ser Thr Glu Lys
370                 375                 380

Lys Asn Gly Glu Arg Met Ala Asn Tyr Ile Phe Val Arg Ala His Asp
385                 390                 395                 400

Ser Glu Val Gln Thr Val Ile Ala Asp Ile Ile Arg Glu Asn Ile Asn
                405                 410                 415

Pro Asn Thr Asp Gly Leu Thr Phe Thr Met Asp Glu Leu Lys Gln Ala
            420                 425                 430

Phe Lys Ile Tyr Asn Glu Asp Met Arg Lys Ala Asp Lys Lys Tyr Thr
        435                 440                 445

Gln Phe Asn Ile Pro Thr Ala His Ala Leu Met Leu Ser Asn Lys Asp
450                 455                 460

Ser Ile Thr Arg Val Tyr Tyr Gly Asp Leu Tyr Thr Asp Asp Gly Gln
465                 470                 475                 480

Tyr Met Glu Lys Lys Ser Pro Tyr His Asp Ala Ile Asp Ala Leu Leu
                485                 490                 495

Arg Ala Arg Ile Lys Tyr Val Ala Gly Gly Gln Asp Met Lys Val Thr
            500                 505                 510

Tyr Met Gly Val Pro Arg Glu Ala Asp Lys Trp Ser Tyr Asn Gly Ile
        515                 520                 525

Leu Thr Ser Val Arg Tyr Gly Thr Gly Ala Asn Glu Ala Thr Asp Glu
530                 535                 540

Gly Thr Ala Glu Thr Arg Thr Gln Gly Met Ala Val Ile Ala Ser Asn
545                 550                 555                 560

Asn Pro Asn Leu Lys Leu Asn Glu Trp Asp Lys Leu Gln Val Asn Met
                565                 570                 575

Gly Ala Ala His Lys Asn Gln Tyr Tyr Arg Pro Val Leu Leu Thr Thr
            580                 585                 590

Lys Asp Gly Ile Ser Arg Tyr Leu Thr Asp Glu Glu Val Pro Gln Ser
        595                 600                 605

Leu Trp Lys Lys Thr Asp Ala Asn Gly Ile Leu Thr Phe Asp Met Asn
610                 615                 620

Asp Ile Ala Gly Tyr Ser Asn Val Gln Val Ser Gly Tyr Leu Ala Val
625                 630                 635                 640
```

-continued

Trp Val Pro Val Gly Ala Lys Ala Asp Gln Asp Ala Arg Val Thr Ala
            645                 650                 655
Ser Lys Lys Lys Asn Ala Ser Gly Gln Val Tyr Glu Ser Ser Ala Ala
            660                 665                 670
Leu Asp Ser Gln Leu Ile Tyr Glu Gly Phe Ser Asn Phe Gln Asp Phe
            675                 680                 685
Ala Thr Arg Asp Asp Gln Tyr Thr Asn Lys Val Ile Ala Lys Asn Val
            690                 695                 700
Asn Leu Phe Lys Glu Trp Gly Val Thr Ser Phe Glu Leu Pro Pro Gln
705                 710                 715                 720
Tyr Val Ser Ser Gln Asp Gly Thr Phe Leu Asp Ser Ile Ile Gln Asn
                725                 730                 735
Gly Tyr Ala Phe Glu Asp Arg Tyr Asp Met Ala Met Ser Lys Asn Asn
            740                 745                 750
Lys Tyr Gly Ser Leu Asn Asp Leu Leu Asn Ala Leu Arg Ala Leu His
            755                 760                 765
Ser Val Asn Ile Gln Ala Ile Ala Asp Trp Val Pro Asp Gln Ile Tyr
            770                 775                 780
Asn Leu Pro Gly Lys Glu Val Val Thr Ala Thr Arg Val Asn Asn Tyr
785                 790                 795                 800
Gly Thr Tyr Arg Glu Gly Ser Glu Ile Lys Glu Asn Leu Tyr Val Ala
                805                 810                 815
Asn Thr Lys Thr Asn Gly Thr Asp Tyr Gln Gly Lys Tyr Gly Gly Ala
            820                 825                 830
Phe Leu Asp Glu Leu Lys Ala Lys Tyr Pro Glu Ile Phe Glu Arg Val
            835                 840                 845
Gln Ile Ser Asn Gly Gln Lys Met Thr Thr Asp Glu Lys Ile Thr Lys
            850                 855                 860
Trp Ser Ala Lys His Phe Asn Gly Thr Asn Ile Leu Gly Arg Gly Ala
865                 870                 875                 880
Tyr Tyr Val Leu Lys Asp Trp Ala Ser Asn Glu Tyr Leu Asn Asn Lys
                885                 890                 895
Asn Gly Glu Met Val Leu Pro Lys Gln Leu Val Asn Lys Asn Ala Tyr
            900                 905                 910
Thr Gly Phe Val Ser Asp Ala Ser Gly Thr Lys Tyr Tyr Ser Thr Ser
            915                 920                 925
Gly Tyr Gln Ala Arg Asn Ser Phe Ile Gln Asp Glu Asn Gly Asn Trp
            930                 935                 940
Tyr Tyr Phe Asn Asn Arg Gly Tyr Leu Val Thr Gly Ala Gln Glu Ile
945                 950                 955                 960
Asp Gly Lys Gln Leu Tyr Phe Leu Lys Asn Gly Ile Gln Leu Arg Asp
                965                 970                 975
Ser Leu Arg Glu Asp Glu Asn Gly Asn Gln Tyr Tyr Tyr Asp Lys Thr
            980                 985                 990
Gly Ala Gln Val Leu Asn Arg Tyr Tyr Thr Asp Gly Gln Asn Trp
            995                 1000                1005
Arg Tyr Phe Asp Val Lys Gly Val Met Ala Arg Gly Leu Val Thr
        1010                1015                1020
Met Gly Gly Asn Gln Gln Phe Phe Asp Gln Asn Gly Tyr Gln Val
        1025                1030                1035
Lys Gly Lys Ile Ala Arg Ala Lys Asp Gly Lys Leu Arg Tyr Phe
        1040                1045                1050
Asp Lys Asp Ser Gly Asn Ala Ala Ala Asn Arg Phe Ala Gln Gly

```
                  1055                1060                1065
Asp Asn Pro Ser Asp Trp Tyr Tyr Phe Gly Ala Asp Gly Val Ala
                1070                1075                1080

Val Thr Gly Leu Gln Lys Val Gly Gln Gln Thr Leu Tyr Phe Asp
                1085                1090                1095

Gln Asp Gly Lys Gln Val Lys Gly Lys Val Val Thr Leu Ala Asp
                1100                1105                1110

Lys Ser Ile Arg Tyr Phe Asp Ala Asn Ser Gly Glu Met Ala Val
                1115                1120                1125

Asn Lys Phe Val Glu Gly Ala Lys Asn Val Trp Tyr Tyr Phe Asp
                1130                1135                1140

Gln Ala Gly Lys Ala Val Thr Gly Leu Gln Thr Ile Asn Lys Gln
                1145                1150                1155

Val Leu Tyr Phe Asp Gln Asp Gly Lys Gln Val Lys Gly Lys Val
                1160                1165                1170

Val Thr Leu Ala Asp Lys Ser Ile Arg Tyr Phe Asp Ala Asn Ser
                1175                1180                1185

Gly Glu Met Ala Val Gly Lys Phe Ala Glu Gly Ala Lys Asn Glu
                1190                1195                1200

Trp Tyr Tyr Phe Asp Gln Ala Gly Lys Ala Val Thr Gly Leu Gln
                1205                1210                1215

Lys Ile Gly Gln Gln Thr Leu Tyr Phe Asp Gln Asn Gly Lys Gln
                1220                1225                1230

Val Lys Gly Lys Val Val Thr Leu Ala Asp Lys Ser Ile Arg Tyr
                1235                1240                1245

Phe Asp Ala Asn Ser Gly Glu Met Ala Ser Asn Lys Phe Val Glu
                1250                1255                1260

Gly Ala Lys Asn Glu Trp Tyr Tyr Phe Asp Gln Ala Gly Lys Ala
                1265                1270                1275

Val Thr Gly Leu Gln Gln Ile Gly Gln Gln Thr Leu Tyr Phe Asp
                1280                1285                1290

Gln Asn Gly Lys Gln Val Lys Gly Lys Ile Val Tyr Val Asn Gly
                1295                1300                1305

Ala Asn Arg Tyr Phe Asp Ala Asn Ser Gly Glu Met Ala Arg Asn
                1310                1315                1320

Lys Trp Ile Gln Leu Glu Asp Gly Ser Trp Met Tyr Phe Asp Arg
                1325                1330                1335

Asn Gly Arg Gly Arg Arg Phe Gly Trp Asn
                1340                1345

<210> SEQ ID NO 19
<211> LENGTH: 4023
<212> TYPE: DNA
<213> ORGANISM: unknown
<220> FEATURE:
<223> OTHER INFORMATION: unknown Streptococcus sp. C150

<400> SEQUENCE: 19
atgatcgacg gcaaatacta ctacgtaaac gaggacggca gccacaaaga gaatttcgcg      60
atcacggtta atggtcaact gctgtatttt ggtaaggatg gcgcgctgac cagcagcagc     120
acgtacagct tcacccaagg cactaccaat attgtggacg gttttagcat taacaaccgt     180
gcgtatgact ccagcgaggc ctctttcgag ctgattgacg ttatctgac tgcggactct     240 tggtaccgtc cggcgagcat tatcaaagac ggtgtgacgt ggcaagcatc caccgccgag     300
```

```
gacttccgcc cgttgctgat ggcgtggtgg ccgaacgttg atactcaggt gaactacctg    360
aactacatgt ccaaagtctt taatctggat gctaaataca gctcgactga taaacaggaa    420
accctgaagg tggcggcgaa agatatccag atcaaaattg aacaaaagat tcaggcggaa    480
aagtccacgc aatggctgcg tgaaacgatc agcgcctttg taaaaaccca gccgcaatgg    540
aacaaagaga ctgagaacta cagcaagggc ggtggtgagg accatctgca aggtggtgcc    600
ctgctgtatg ttaatgactc tcgtaccccg tgggcgaaca gcaactatcg tttgctgaac    660
cgcacggcga ccaaccagac cggtacgatc gacaagagca tcctggacga gcagagcgat    720
ccgaatcaca tgggtggttt tgatttcttg ctggctaatg acgttgactt gagcaatccg    780
gtcgtccagg cggaacaact gaatcagatc cactacctga tgaattgggg ttctattgtc    840
atgggtgata agacgcgcaa ttttgacggt attcgtgtag acgcggtgga taatgttgat    900
gcggacatgc tgcaattgta caccaactat ttccgcgaat actatggtgt caacaaaagc    960
gaggcaaacg cgctggcgca cattagcgtc ctggaagcct ggagcctgaa tgacaaccat   1020
tacaatgata agactgatgt tgcggcgctg gcaatgagga ataagcagcg cttggcactg   1080
ttgtttagcc tggcgaaacc gattaaagaa cgcacgcctg ccgtgtctcc gctgtacaac   1140
aatacgttta acaccactca gcgtgatgaa aagacggact ggatcaataa agatggttcg   1200
aaagcctaca atgaggatgg cactgtcaag aaaagcacca tcggcaagta aacgagaag    1260 tatggtgatg ctagcggcaa ctacgttttc atccgcgctc acgacaataa cgtgcaagac   1320
atcatcgcgg agatcattaa gaaagagatt aacgagaaat ctgacggttt taccattacg   1380
gattcggaga tgaagcgtgc atttgagatc tataacaaag acatgctgtc taatgacaaa   1440
aagtacacgc tgaataacat cccggcggcg tacgcggtta tgctgcaaaa catggaaacg   1500 attcccgcg tgtattacgg cgatctgtac acggacgacg gtaattacat ggaagcgaaa   1560
agcccgtact acgatacgat tgttaacttg atgaagtctc gcatcaaata cgtgagcggt   1620
ggccaggcgc agcgcagcta ctggctgccg accgatggta agatggataa gtcggatgtt   1680
gagctgtacc gtacgaacga agtgtacacg agcgtccgtt acggcaaaga cattatgacc   1740
gccgatgaca cgcaaggtag caaatacagc cgtaccagcg gtcaggtgac cctggtcgtc   1800
aacaacccaa aactgacctt ggaccaaagc gcaaagctga acgtggttat gggcaagatt   1860
catgctaatc agaagtaccg cgcactgatt gtcggtaccc cgaacggtat taagaatttc   1920
accagcgacg cagaggctat tgccgcaggc tatgtcaaag aaaccgatgg caatggcgtg   1980
ctgaccttcg gtgcaaacga catcaagggt tatgaaactt tcgatatgag cggcttcgtc   2040 gctgttttggg ttccggtcgg tgcgagcgac gaccaagata ttcgtgtggc ggcgtctacg   2100
gcagcaaaga aagagggtga gctgacgctg aaagcgaccg aagcctatga ctcccaactg   2160
atctatgaag gctttagcaa tttccagacc atcccagatg gcagcgatcc ttctgtttat   2220
accaatcgta agatcgcgga aaatgttgat ttgttcaaga gctggggtgt cacgagcttc   2280
gaaatggctc cgcagttcgt ttctgcggac gatggcacgt ttctggacag cgtcattcaa   2340
aacggctatg cgttcgcaga ccgttatgat ctggccatga gcaaaaacaa taagtacggt   2400
agcaaagaag atctgcgtaa cgcgctgaag gcactgcaca aagcaggcat tcaggcgatt   2460
gcagattggg tgccagacca aatctaccag ctgcctggca agaagttgt tactgccacc    2520 cgcacggacg gtgctggtcg caaaatcagc gatgcaatca tcgatcattc cctgtacgtt   2580
gcgaactcca agagctccgg taaggactac caagcgaagt acggtggcga gttcttggcg   2640
gaactgaagg cgaaatacccc ggaaatgttc aaagtgaaca tgattagcac cggcaaaccg   2700
```

```
attgatgata gcgtgaaact gaagcagtgg aaagcagaat acttcaacgg caccaatgtg    2760
ctggatcgcg gtgtcggtta tgttctgagc gatgaggcaa ccggtaagta tttcaccgtt    2820
accaaagagg gtaactttat cccgttgcag ctgaagggta acaagaaggt gattaccggc    2880
ttttccagcg acggtaaggg cattacctat ttcggtacta gcggtaacca agctaaatcc    2940
gcgttcgtca cttttaacgg taacacgtac tacttcgacg cacgtggcca catggttacc    3000
aacggtgagt actcgccgaa tggtaaagat gtgtatcgtt ttctgccgaa cggcattatg    3060
ctgagcaacg cgttctatgt tgacggcaat ggcaacacct acctgtacaa ctccaaaggc    3120
caaatgtata aggtggcta tagcaaattt gacgtcacgg aaacgaagga cggtaaagag    3180
agcaaagttg tcaagttccg ctactttacg aacgagggcg tgatggcgaa aggtgtcacg    3240
gttgtggatg gcttcactca gtactttaac gaggatggca ttcaaagcaa agacgagctg    3300
gtcacttaca atggcaagac ctattacttc gaagcacaca cgggcaatgc cattaagaat    3360
acgtggcgta atatcaaggg caaatggtac cattttgatg ctaacggtgt cgcggctact    3420
ggcgcacagg ttatcaacgg tcagcacctg tacttcaatg aagatggctc tcaagtaaaa    3480
ggtagcatcg tcaaaaacgc tgatggtacg ttcagcaagt acaaggacag ctctggcgat    3540
ctggtggtga acgagttttt cacgacgggt gataacgtct ggtactatgc tggtgccaat    3600
ggcaaaacgg ttactggtgc acaggtgatt aatggccagc acttgttctt caaagaggat    3660
ggcagccagg tcaagggcga cttttgtgaag aatagcgacg gcacctactc caagtatgac    3720
gctgcgagcg cgaacgtct gaccaacgag ttcttcacta cgggcgacaa tcattggtac    3780
tatattggcg ccaacggtaa gaccgttacc ggtgaagtta agattggtga cgacacgtat    3840
ttcttcgcaa aagacggtaa gcaactgaaa ggtcaaatcg ttaccacccg tagcggtcgt    3900
atcagctact actttggtga tagcggtaag aaggctatta gcacgtgggt ggagatccag    3960
ccgggtgtgt ttgtttctt cgacaaaaac ggcctggctt acccaccgga gaatatgaac    4020
tga                                                                  4023
```

<210> SEQ ID NO 20
<211> LENGTH: 1340
<212> TYPE: PRT
<213> ORGANISM: unknown
<220> FEATURE:
<223> OTHER INFORMATION: unknown Streptococcus sp. C150

<400> SEQUENCE: 20

```
Met Ile Asp Gly Lys Tyr Tyr Tyr Val Asn Glu Asp Gly Ser His Lys
  1               5                  10                  15

Glu Asn Phe Ala Ile Thr Val Asn Gly Gln Leu Leu Tyr Phe Gly Lys
             20                  25                  30

Asp Gly Ala Leu Thr Ser Ser Thr Tyr Ser Phe Thr Gln Gly Thr
         35                  40                  45

Thr Asn Ile Val Asp Gly Phe Ser Ile Asn Asn Arg Ala Tyr Asp Ser
     50                  55                  60

Ser Glu Ala Ser Phe Glu Leu Ile Asp Gly Tyr Leu Thr Ala Asp Ser
 65                  70                  75                  80

Trp Tyr Arg Pro Ala Ser Ile Ile Lys Asp Gly Val Thr Trp Gln Ala
             85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
```

```
            115                 120                 125
Leu Asp Ala Lys Tyr Ser Ser Thr Asp Lys Gln Glu Thr Leu Lys Val
            130                 135                 140
Ala Ala Lys Asp Ile Gln Ile Lys Ile Glu Gln Lys Ile Gln Ala Glu
145                 150                 155                 160
Lys Ser Thr Gln Trp Leu Arg Glu Thr Ile Ser Ala Phe Val Lys Thr
                    165                 170                 175
Gln Pro Gln Trp Asn Lys Glu Thr Glu Asn Tyr Ser Lys Gly Gly Gly
                180                 185                 190
Glu Asp His Leu Gln Gly Gly Ala Leu Leu Tyr Val Asn Asp Ser Arg
            195                 200                 205
Thr Pro Trp Ala Asn Ser Asn Tyr Arg Leu Leu Asn Arg Thr Ala Thr
210                 215                 220
Asn Gln Thr Gly Thr Ile Asp Lys Ser Ile Leu Asp Glu Gln Ser Asp
225                 230                 235                 240
Pro Asn His Met Gly Gly Phe Asp Phe Leu Leu Ala Asn Asp Val Asp
                245                 250                 255
Leu Ser Asn Pro Val Val Gln Ala Glu Gln Leu Asn Gln Ile His Tyr
            260                 265                 270
Leu Met Asn Trp Gly Ser Ile Val Met Gly Asp Lys Asp Ala Asn Phe
            275                 280                 285
Asp Gly Ile Arg Val Asp Ala Val Asp Asn Val Asp Ala Asp Met Leu
290                 295                 300
Gln Leu Tyr Thr Asn Tyr Phe Arg Glu Tyr Tyr Gly Val Asn Lys Ser
305                 310                 315                 320
Glu Ala Asn Ala Leu Ala His Ile Ser Val Leu Glu Ala Trp Ser Leu
                325                 330                 335
Asn Asp Asn His Tyr Asn Asp Lys Thr Asp Val Ala Ala Leu Ala Met
                340                 345                 350
Glu Asn Lys Gln Arg Leu Ala Leu Leu Phe Ser Leu Ala Lys Pro Ile
            355                 360                 365
Lys Glu Arg Thr Pro Ala Val Ser Pro Leu Tyr Asn Asn Thr Phe Asn
370                 375                 380
Thr Thr Gln Arg Asp Glu Lys Thr Asp Trp Ile Asn Lys Asp Gly Ser
385                 390                 395                 400
Lys Ala Tyr Asn Glu Asp Gly Thr Val Lys Lys Ser Thr Ile Gly Lys
                405                 410                 415
Tyr Asn Glu Lys Tyr Gly Asp Ala Ser Gly Asn Tyr Val Phe Ile Arg
                420                 425                 430
Ala His Asp Asn Asn Val Gln Asp Ile Ile Ala Glu Ile Ile Lys Lys
            435                 440                 445
Glu Ile Asn Glu Lys Ser Asp Gly Phe Thr Ile Thr Asp Ser Glu Met
            450                 455                 460
Lys Arg Ala Phe Glu Ile Tyr Asn Lys Asp Met Leu Ser Asn Asp Lys
465                 470                 475                 480
Lys Tyr Thr Leu Asn Asn Ile Pro Ala Ala Tyr Ala Val Met Leu Gln
                485                 490                 495
Asn Met Glu Thr Ile Thr Arg Val Tyr Tyr Gly Asp Leu Tyr Thr Asp
                500                 505                 510
Asp Gly Asn Tyr Met Glu Ala Lys Ser Pro Tyr Tyr Asp Thr Ile Val
            515                 520                 525
Asn Leu Met Lys Ser Arg Ile Lys Tyr Val Ser Gly Gly Gln Ala Gln
530                 535                 540
```

```
Arg Ser Tyr Trp Leu Pro Thr Asp Gly Lys Met Asp Lys Ser Asp Val
545                 550                 555                 560

Glu Leu Tyr Arg Thr Asn Glu Val Tyr Thr Ser Val Arg Tyr Gly Lys
            565                 570                 575

Asp Ile Met Thr Ala Asp Thr Gln Gly Ser Lys Tyr Ser Arg Thr
                580                 585                 590

Ser Gly Gln Val Thr Leu Val Val Asn Asn Pro Lys Leu Thr Leu Asp
            595                 600                 605

Gln Ser Ala Lys Leu Asn Val Val Met Gly Lys Ile His Ala Asn Gln
610                 615                 620

Lys Tyr Arg Ala Leu Ile Val Gly Thr Pro Asn Gly Ile Lys Asn Phe
625                 630                 635                 640

Thr Ser Asp Ala Glu Ala Ile Ala Ala Gly Tyr Val Lys Glu Thr Asp
                645                 650                 655

Gly Asn Gly Val Leu Thr Phe Gly Ala Asn Asp Ile Lys Gly Tyr Glu
                660                 665                 670

Thr Phe Asp Met Ser Gly Phe Val Ala Val Trp Val Pro Val Gly Ala
            675                 680                 685

Ser Asp Asp Gln Asp Ile Arg Val Ala Ala Ser Thr Ala Ala Lys Lys
            690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
            755                 760                 765

Ala Asp Asp Gly Thr Phe Leu Asp Ser Val Ile Gln Asn Gly Tyr Ala
            770                 775                 780

Phe Ala Asp Arg Tyr Asp Leu Ala Met Ser Lys Asn Asn Lys Tyr Gly
785                 790                 795                 800

Ser Lys Glu Asp Leu Arg Asn Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
            835                 840                 845

Ile Ser Asp Ala Ile Ile Asp His Ser Leu Tyr Val Ala Asn Ser Lys
850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Asp Arg Gly Val Gly Tyr Val
            915                 920                 925

Leu Ser Asp Glu Ala Thr Gly Lys Tyr Phe Thr Val Thr Lys Glu Gly
930                 935                 940

Asn Phe Ile Pro Leu Gln Leu Lys Gly Asn Lys Lys Val Ile Thr Gly
945                 950                 955                 960
```

-continued

Phe Ser Ser Asp Gly Lys Gly Ile Thr Tyr Phe Gly Thr Ser Gly Asn
                965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Gly Glu Tyr Ser Pro Asn Gly
            995                1000                1005

Lys Asp Val Tyr Arg Phe Leu Pro Asn Gly Ile Met Leu Ser Asn
        1010                1015                1020

Ala Phe Tyr Val Asp Gly Asn Gly Asn Thr Tyr Leu Tyr Asn Ser
        1025                1030                1035

Lys Gly Gln Met Tyr Lys Gly Gly Tyr Ser Lys Phe Asp Val Thr
        1040                1045                1050

Glu Thr Lys Asp Gly Lys Glu Ser Lys Val Val Lys Phe Arg Tyr
        1055                1060                1065

Phe Thr Asn Glu Gly Val Met Ala Lys Gly Val Thr Val Val Asp
        1070                1075                1080

Gly Phe Thr Gln Tyr Phe Asn Glu Asp Gly Ile Gln Ser Lys Asp
        1085                1090                1095

Glu Leu Val Thr Tyr Asn Gly Lys Thr Tyr Tyr Phe Glu Ala His
        1100                1105                1110

Thr Gly Asn Ala Ile Lys Asn Thr Trp Arg Asn Ile Lys Gly Lys
        1115                1120                1125

Trp Tyr His Phe Asp Ala Asn Gly Val Ala Ala Thr Gly Ala Gln
        1130                1135                1140

Val Ile Asn Gly Gln His Leu Tyr Phe Asn Glu Asp Gly Ser Gln
        1145                1150                1155

Val Lys Gly Ser Ile Val Lys Asn Ala Asp Gly Thr Phe Ser Lys
        1160                1165                1170

Tyr Lys Asp Ser Ser Gly Asp Leu Val Val Asn Glu Phe Phe Thr
        1175                1180                1185

Thr Gly Asp Asn Val Trp Tyr Tyr Ala Gly Ala Asn Gly Lys Thr
        1190                1195                1200

Val Thr Gly Ala Gln Val Ile Asn Gly Gln His Leu Phe Phe Lys
        1205                1210                1215

Glu Asp Gly Ser Gln Val Lys Gly Asp Phe Val Lys Asn Ser Asp
        1220                1225                1230

Gly Thr Tyr Ser Lys Tyr Asp Ala Ala Ser Gly Glu Arg Leu Thr
        1235                1240                1245

Asn Glu Phe Phe Thr Thr Gly Asp Asn His Trp Tyr Tyr Ile Gly
        1250                1255                1260

Ala Asn Gly Lys Thr Val Thr Gly Glu Val Lys Ile Gly Asp Asp
        1265                1270                1275

Thr Tyr Phe Phe Ala Lys Asp Gly Lys Gln Leu Lys Gly Gln Ile
        1280                1285                1290

Val Thr Thr Arg Ser Gly Arg Ile Ser Tyr Tyr Phe Gly Asp Ser
        1295                1300                1305

Gly Lys Lys Ala Ile Ser Thr Trp Val Glu Ile Gln Pro Gly Val
        1310                1315                1320

Phe Val Phe Phe Asp Lys Asn Gly Leu Ala Tyr Pro Pro Glu Asn
        1325                1330                1335

Met Asn
1340

<210> SEQ ID NO 21

<400> SEQUENCE: 21

000

<210> SEQ ID NO 22

<400> SEQUENCE: 22

000

<210> SEQ ID NO 23

<400> SEQUENCE: 23

000

<210> SEQ ID NO 24

<400> SEQUENCE: 24

000

<210> SEQ ID NO 25
<211> LENGTH: 4308
<212> TYPE: DNA
<213> ORGANISM: Streptococcus sobrinus

<400> SEQUENCE: 25

| | | | | | |
|---|---|---|---|---|---|
| atggttgacg | gcaaatacta | ctattatgat | caggatggca | acgttaagaa | gaatttcgcg | 60 |
| gttagcgttg | gtgacaagat | ctactacttt | gacgagactg | gtgcctacaa | agacacctct | 120 |
| aaagtggacg | cggacaagtc | tagcagcgcc | gttagccaaa | atgcgacgat | ctttgcggct | 180 |
| aacaatcgtg | cgtatagcac | ctctgctgag | aactttgagg | ccgttgataa | ctatctgacg | 240 |
| gcagatagct | ggtatcgtcc | taaatctatt | ctgaaagatg | gcaagacgtg | gaccgagtcg | 300 |
| ggtaaggacg | acttccgtcc | gctgctgatg | gcgtggtggc | cggacacgga | gactaaacgc | 360 |
| aattacgtga | attacatgaa | cctggttgtc | ggcatcgaca | agacgtacac | cgcggaaacc | 420 |
| tctcaagcag | atttgaccgc | agcggcggag | ctggtccagg | cgcgtattga | acagaaaatc | 480 |
| accacggaac | agaatacgaa | atggctgcgc | gaggcgatct | ctgctttcgt | caagacccag | 540 |
| ccgcagtgga | atggtgaaag | cgagaagccg | tatgacgacc | acctgcaaaa | cggtgctctg | 600 |
| aaattcgata | tcagagcga | cctgaccccg | gacacccaga | gcaactatcg | cctgctgaat | 660 |
| cgcacccga | ctaaccagac | tggcagcctg | acagccgtt | tcacctataa | tgcgaacgat | 720 |
| ccgttgggtg | gctacgaatt | tctgctggct | aacgacgtgg | ataatagcaa | ccctgtggtg | 780 |
| caggcagaac | aactgaactg | gttgcattac | ctgttgaatt | tggtagcat | ttacgcgaaa | 840 |
| gatgcggatg | caaacttcga | ttccatccgt | gtggacgccg | tggacaacgt | cgatgcagat | 900 |
| ctgttgcaga | ttagcagcga | ttacctgaag | gcagcctatg | gcattgacaa | gaacaataag | 960 |
| aacgcgaaca | accatgttag | cattgttgag | gcttggagcg | ataacgatac | gccgtacctg | 1020 |
| cacgatgacg | gtgataaccct | gatgaacatg | gacaataagt | tccgcttgag | catgctgtgg | 1080 |
| agcctggcca | agccgctgga | caagcgcagc | ggtctgaatc | ctctgattca | taacagcctg | 1140 |
| gtggaccgtg | aggttgatga | ccgtgaagtg | gaaacggttc | cgagctactc | ttttgcgcgt | 1200 |
| gcgcatgatt | ccgaggtcca | agacattatc | cgcgacatta | tcaaggccga | aatcaacccg | 1260 |
| aatagctttg | gttatagctt | cacccaagaa | gagattgacc | aggcgtttaa | gatctataat | 1320 |

```
gaagatctga agaaaaccga caagaaatac acccactata atgtcccgtt gagctatact    1380
ttgctgctga cgaataaagg ttcgattccg cgtgtgtatt acggtgatat gttcaccgat    1440
gatggtcaat acatggcgaa caaaacggtt aactatgatg ccattgagtc gctgctgaaa    1500
gcgcgcatga agtacgttag cggcggtcaa gcgatgcaaa actatcaaat cggcaatggt    1560
gagattctga ccagcgttcg ttatggtaag ggtgcattga agcaatccga caagggtgac    1620
gcgaccacgc gtacgtccgg tgtgggcgtc gtgatgggca accagccgaa ctttagcctg    1680
gacggcaagg tggtggcatt gaacatgggt gccgctcatg caaatcagga gtatcgtgcg    1740
ctgatggtga gcaccaagga tggcgttgcc acgtatgcca ccgacgcgga cgcaagcaag    1800
gcaggtctgg tcaaacgcac cgatgaaaat ggttatttgt actttctgaa cgacgatctg    1860
aagggtgtgg caaacccaca agtcagcggt tccttgcagg tgtgggtccc agtgggtgcg    1920
gctgacgatc aggacattcg tgttgcagcg agcgacacgg ctagcacgga cggtaagtcc    1980
ctgcatcaag atgcggcaat ggatagccgt gttatgtttg agggttttag caacttccag    2040
agctttgcaa ccaaagaaga gagtacacc aacgtagtta ttgcgaacaa cgtggacaaa    2100
ttcgttagct ggggtattac cgactttgag atggcaccgc aatatgtcag ctccaccgat    2160
ggccagtttc tggatagcgt tatccagaat ggttacgcgt tcaccgaccg ttatgatctg    2220
ggtatgagca agccaacaa atacggtacc gcggatcagc tggttaaagc aatcaaagcg    2280
ttgcacgcga agggtctgaa ggtgatggcg gactgggttc cagaccagat gtacacgttt    2340
ccgaagcagg aagttgtcac tgtcacgcgc accgacaaat ttggtaagcc gattgcgggc    2400
agccaaatca atcacagcct gtacgtgacg gacaccaaat ccagcggtga tgattaccag    2460
gccaaatatg gtggtgcgtt cctggatgag ctgaaagaga ataccccgga gctgttcacc    2520
aaaaagcaga tctcgaccgg tcaggcgatc gacccgagcg tgaagattaa gcagtggagc    2580
gcgaaatact ttaatggtag caacattctg ggtcgtggtg ccgactacgt cctgtccgat    2640
caagttagca caagtatt caatgtggcc agcgacacgc tgtttctgcc gtctagcctg    2700
ttgggtaagg ttgtcgaaag cggtattcgt tacgatggca aaggttatat ctataacagc    2760
agcgcgactg gcgaccaagt caaggcgtct tttatcacgg aagcaggcaa tctgtactac    2820
ttcggcaaag acggttacat ggttactggt gcgcagacca ttaacggtgc gaattacttc    2880
ttcttggaaa atggtacggc cctgcgtaat accatctaca ccgatgcaca gggcaactcc    2940 cactatatg ctaatgatgg caagcgttac gagaacggtt accagcagtt cggcaacgat    3000
tggcgttact tcaaagatgg taacatggcc gtcggtctga ccacggtgga tggtaacgtt    3060
cagtatttcg acaaggacgg tgtccaagct aaagacaaga ttattgtgac ccgcgatggt    3120
aaggtgcgct actttgatca acacaatggc aacgcggtca cgaatacctt tatcgccgac    3180
aagaccggtc actggtacta cctgggcaaa gatggcgtcg cggtcaccgg cgctcaaacc    3240
gtcggtaagc aaaaactgta ttttgaggcg aacggtgagc aggtgaaagg cgactttgtg    3300
actagccatg aaggcaaact gtacttttat gatgttgaca cgggcgacat gtggaccgat    3360
accttcatcg aggataaggc cggcaactgg ttctacctgg gtaaagacgg cgcagcagtt    3420
agcggtgcac agaccattcg cggtcaaaag ctgtacttca aggcgtacgg tcaacaggtc    3480
aaaggtgaca tcgttaaagg caccgacggc aagatccgtt actacgatgc gaaatccggc    3540
gagcaggttt tcaataagac ggtcaaagcc gctgatggca aaacctatgt gatcggcaac    3600
aatggtgtgg cggtcgatcc gagcgttgtt aagggtcaga cgttcaaaga cgccagcggc    3660
gcactgcgtt tttacaatct gaaaggtcaa ctggttacgg gctccggttg gtatgaaacg    3720
```

-continued

```
gccaatcacg attgggtgta tattcagagc ggtaaagcac tgaccggtga gcaaaccatc    3780
aatggtcagc acctgtactt taaagaagat ggccaccaag ttaaaggtca gctggtcacc    3840
cgtacggacg gcaaagtgcg ttactatgac gcaaattctg gcgatcaagc gttcaacaag    3900
tccgtgacgg ttaacggcaa aacgtattac ttcggtaatg atggtaccgc gcaaaccgcg    3960
ggtaacccga aaggccaaat cttcaaggac ggcagcgttc tgcgtttcta tagcatggaa    4020
ggccagctgg taattggcag cggctggtat tccaacgcgc aaggccaatg gctgtatgtg    4080
aagaatggta aagtgttgac cggttttgcag accgtcggtt cccagcgcgt gtactttgat    4140
gagaatggca ttcaagcaaa aggcaaagcg ttcgcacga gcgacggcaa aattcgctac     4200
ttcgacgaga acagcggtag catgatcacc aatcaatgga agtttgttta cggtcaatac    4260
tattactttg gtaatgacgg tgcggcaatc taccgtggtt ggaattaa                 4308
```

<210> SEQ ID NO 26
<211> LENGTH: 1435
<212> TYPE: PRT
<213> ORGANISM: Streptococcus sobrinus

<400> SEQUENCE: 26

```
Met Val Asp Gly Lys Tyr Tyr Tyr Asp Gln Asp Gly Asn Val Lys
1               5                   10                  15

Lys Asn Phe Ala Val Ser Val Gly Asp Lys Ile Tyr Tyr Phe Asp Glu
                20                  25                  30

Thr Gly Ala Tyr Lys Asp Thr Ser Lys Val Asp Ala Asp Lys Ser Ser
            35                  40                  45

Ser Ala Val Ser Gln Asn Ala Thr Ile Phe Ala Ala Asn Asn Arg Ala
        50                  55                  60

Tyr Ser Thr Ser Ala Glu Asn Phe Glu Ala Val Asp Asn Tyr Leu Thr
65                  70                  75                  80

Ala Asp Ser Trp Tyr Arg Pro Lys Ser Ile Leu Lys Asp Gly Lys Thr
                85                  90                  95

Trp Thr Glu Ser Gly Lys Asp Asp Phe Arg Pro Leu Leu Met Ala Trp
            100                 105                 110

Trp Pro Asp Thr Glu Thr Lys Arg Asn Tyr Val Asn Tyr Met Asn Leu
        115                 120                 125

Val Val Gly Ile Asp Lys Thr Tyr Thr Ala Glu Thr Ser Gln Ala Asp
    130                 135                 140

Leu Thr Ala Ala Ala Glu Leu Val Gln Ala Arg Ile Glu Gln Lys Ile
145                 150                 155                 160

Thr Thr Glu Gln Asn Thr Lys Trp Leu Arg Glu Ala Ile Ser Ala Phe
                165                 170                 175

Val Lys Thr Gln Pro Gln Trp Asn Gly Glu Ser Glu Lys Pro Tyr Asp
            180                 185                 190

Asp His Leu Gln Asn Gly Ala Leu Lys Phe Asp Asn Gln Ser Asp Leu
        195                 200                 205

Thr Pro Asp Thr Gln Ser Asn Tyr Arg Leu Leu Asn Arg Thr Pro Thr
    210                 215                 220

Asn Gln Thr Gly Ser Leu Asp Ser Arg Phe Thr Tyr Asn Ala Asn Asp
225                 230                 235                 240

Pro Leu Gly Gly Tyr Glu Phe Leu Leu Ala Asn Asp Val Asp Asn Ser
                245                 250                 255

Asn Pro Val Val Gln Ala Glu Gln Leu Asn Trp Leu His Tyr Leu Leu
            260                 265                 270
```

```
Asn Phe Gly Ser Ile Tyr Ala Lys Asp Ala Asp Ala Asn Phe Asp Ser
            275                 280                 285

Ile Arg Val Asp Ala Val Asp Asn Val Asp Ala Asp Leu Leu Gln Ile
    290                 295                 300

Ser Ser Asp Tyr Leu Lys Ala Ala Tyr Gly Ile Asp Lys Asn Asn Lys
305                 310                 315                 320

Asn Ala Asn Asn His Val Ser Ile Val Glu Ala Trp Ser Asp Asn Asp
                325                 330                 335

Thr Pro Tyr Leu His Asp Asp Gly Asp Asn Leu Met Asn Met Asp Asn
                340                 345                 350

Lys Phe Arg Leu Ser Met Leu Trp Ser Leu Ala Lys Pro Leu Asp Lys
            355                 360                 365

Arg Ser Gly Leu Asn Pro Leu Ile His Asn Ser Leu Val Asp Arg Glu
    370                 375                 380

Val Asp Asp Arg Glu Val Glu Thr Val Pro Ser Tyr Ser Phe Ala Arg
385                 390                 395                 400

Ala His Asp Ser Glu Val Gln Asp Ile Ile Arg Asp Ile Ile Lys Ala
                405                 410                 415

Glu Ile Asn Pro Asn Ser Phe Gly Tyr Ser Phe Thr Gln Glu Glu Ile
            420                 425                 430

Asp Gln Ala Phe Lys Ile Tyr Asn Glu Asp Leu Lys Lys Thr Asp Lys
    435                 440                 445

Lys Tyr Thr His Tyr Asn Val Pro Leu Ser Tyr Thr Leu Leu Leu Thr
        450                 455                 460

Asn Lys Gly Ser Ile Pro Arg Val Tyr Tyr Gly Asp Met Phe Thr Asp
465                 470                 475                 480

Asp Gly Gln Tyr Met Ala Asn Lys Thr Val Asn Tyr Asp Ala Ile Glu
                485                 490                 495

Ser Leu Leu Lys Ala Arg Met Lys Tyr Val Ser Gly Gly Gln Ala Met
            500                 505                 510

Gln Asn Tyr Gln Ile Gly Asn Gly Glu Ile Leu Thr Ser Val Arg Tyr
    515                 520                 525

Gly Lys Gly Ala Leu Lys Gln Ser Asp Lys Gly Asp Ala Thr Thr Arg
530                 535                 540

Thr Ser Gly Val Gly Val Val Met Gly Asn Gln Pro Asn Phe Ser Leu
545                 550                 555                 560

Asp Gly Lys Val Val Ala Leu Asn Met Gly Ala Ala His Ala Asn Gln
                565                 570                 575

Glu Tyr Arg Ala Leu Met Val Ser Thr Lys Asp Gly Val Ala Thr Tyr
            580                 585                 590

Ala Thr Asp Ala Asp Ala Ser Lys Ala Gly Leu Val Lys Arg Thr Asp
    595                 600                 605

Glu Asn Gly Tyr Leu Tyr Phe Leu Asn Asp Asp Leu Lys Gly Val Ala
        610                 615                 620

Asn Pro Gln Val Ser Gly Phe Leu Gln Val Trp Val Pro Val Gly Ala
625                 630                 635                 640

Ala Asp Asp Gln Asp Ile Arg Val Ala Ala Ser Asp Thr Ala Ser Thr
                645                 650                 655

Asp Gly Lys Ser Leu His Gln Asp Ala Ala Met Asp Ser Arg Val Met
            660                 665                 670

Phe Glu Gly Phe Ser Asn Phe Gln Ser Phe Ala Thr Lys Glu Glu
    675                 680                 685
```

```
Tyr Thr Asn Val Val Ile Ala Asn Asn Val Asp Lys Phe Val Ser Trp
    690             695             700
Gly Ile Thr Asp Phe Glu Met Ala Pro Gln Tyr Val Ser Ser Thr Asp
705             710             715             720
Gly Gln Phe Leu Asp Ser Val Ile Gln Asn Gly Tyr Ala Phe Thr Asp
            725             730             735
Arg Tyr Asp Leu Gly Met Ser Lys Ala Asn Lys Tyr Gly Thr Ala Asp
        740             745             750
Gln Leu Val Lys Ala Ile Lys Ala Leu His Ala Lys Gly Leu Lys Val
            755             760             765
Met Ala Asp Trp Val Pro Asp Gln Met Tyr Thr Phe Pro Lys Gln Glu
770             775             780
Val Val Thr Val Thr Arg Thr Asp Lys Phe Gly Lys Pro Ile Ala Gly
785             790             795             800
Ser Gln Ile Asn His Ser Leu Tyr Val Thr Asp Thr Lys Ser Ser Gly
            805             810             815
Asp Asp Tyr Gln Ala Lys Tyr Gly Gly Ala Phe Leu Asp Glu Leu Lys
        820             825             830
Glu Lys Tyr Pro Glu Leu Phe Thr Lys Lys Gln Ile Ser Thr Gly Gln
            835             840             845
Ala Ile Asp Pro Ser Val Lys Ile Lys Gln Trp Ser Ala Lys Tyr Phe
850             855             860
Asn Gly Ser Asn Ile Leu Gly Arg Gly Ala Asp Tyr Val Leu Ser Asp
865             870             875             880
Gln Val Ser Asn Lys Tyr Phe Asn Val Ala Ser Asp Thr Leu Phe Leu
            885             890             895
Pro Ser Ser Leu Leu Gly Lys Val Val Glu Ser Gly Ile Arg Tyr Asp
        900             905             910
Gly Lys Gly Tyr Ile Tyr Asn Ser Ser Ala Thr Gly Asp Gln Val Lys
            915             920             925
Ala Ser Phe Ile Thr Glu Ala Gly Asn Leu Tyr Tyr Phe Gly Lys Asp
930             935             940
Gly Tyr Met Val Thr Gly Ala Gln Thr Ile Asn Gly Ala Asn Tyr Phe
945             950             955             960
Phe Leu Glu Asn Gly Thr Ala Leu Arg Asn Thr Ile Tyr Thr Asp Ala
            965             970             975
Gln Gly Asn Ser His Tyr Tyr Ala Asn Asp Gly Lys Arg Tyr Glu Asn
        980             985             990
Gly Tyr Gln Gln Phe Gly Asn Asp Trp Arg Tyr Phe Lys Asp Gly Asn
            995             1000            1005
Met Ala Val Gly Leu Thr Thr Val Asp Gly Asn Val Gln Tyr Phe
    1010            1015            1020
Asp Lys Asp Gly Val Gln Ala Lys Asp Lys Ile Ile Val Thr Arg
    1025            1030            1035
Asp Gly Lys Val Arg Tyr Phe Asp Gln His Asn Gly Asn Ala Val
    1040            1045            1050
Thr Asn Thr Phe Ile Ala Asp Lys Thr Gly His Trp Tyr Tyr Leu
    1055            1060            1065
Gly Lys Asp Gly Val Ala Val Thr Gly Ala Gln Thr Val Gly Lys
    1070            1075            1080
Gln Lys Leu Tyr Phe Glu Ala Asn Gly Glu Gln Val Lys Gly Asp
    1085            1090            1095
Phe Val Thr Ser His Glu Gly Lys Leu Tyr Phe Tyr Asp Val Asp
```

Ser Gly Asp Met Trp Thr Asp Thr Phe Ile Glu Asp Lys Ala Gly
1115                1120                1125

Asn Trp Phe Tyr Leu Gly Lys Asp Gly Ala Ala Val Ser Gly Ala
1130                1135                1140

Gln Thr Ile Arg Gly Gln Lys Leu Tyr Phe Lys Ala Tyr Gly Gln
1145                1150                1155

Gln Val Lys Gly Asp Ile Val Lys Gly Thr Asp Gly Lys Ile Arg
1160                1165                1170

Tyr Tyr Asp Ala Lys Ser Gly Glu Gln Val Phe Asn Lys Thr Val
1175                1180                1185

Lys Ala Ala Asp Gly Lys Thr Tyr Val Ile Gly Asn Asn Gly Val
1190                1195                1200

Ala Val Asp Pro Ser Val Val Lys Gly Gln Thr Phe Lys Asp Ala
1205                1210                1215

Ser Gly Ala Leu Arg Phe Tyr Asn Leu Lys Gly Gln Leu Val Thr
1220                1225                1230

Gly Ser Gly Trp Tyr Glu Thr Ala Asn His Asp Trp Val Tyr Ile
1235                1240                1245

Gln Ser Gly Lys Ala Leu Thr Gly Glu Gln Thr Ile Asn Gly Gln
1250                1255                1260

His Leu Tyr Phe Lys Glu Asp Gly His Gln Val Lys Gly Gln Leu
1265                1270                1275

Val Thr Arg Thr Asp Gly Lys Val Arg Tyr Tyr Asp Ala Asn Ser
1280                1285                1290

Gly Asp Gln Ala Phe Asn Lys Ser Val Thr Val Asn Gly Lys Thr
1295                1300                1305

Tyr Tyr Phe Gly Asn Asp Gly Thr Ala Gly Thr Ala Gly Asn Pro
1310                1315                1320

Lys Gly Gln Ile Phe Lys Asp Gly Ser Val Leu Arg Phe Tyr Ser
1325                1330                1335

Met Glu Gly Gln Leu Val Ile Gly Ser Gly Trp Tyr Ser Asn Ala
1340                1345                1350

Gln Gly Gln Trp Leu Tyr Val Lys Asn Gly Lys Val Leu Thr Gly
1355                1360                1365

Leu Gln Thr Val Gly Ser Gln Arg Val Tyr Phe Asp Glu Asn Gly
1370                1375                1380

Ile Gln Ala Lys Gly Lys Ala Val Arg Thr Ser Asp Gly Lys Ile
1385                1390                1395

Arg Tyr Phe Asp Glu Asn Ser Gly Ser Met Ile Thr Asn Gln Trp
1400                1405                1410

Lys Phe Val Tyr Gly Gln Tyr Tyr Tyr Phe Gly Asn Asp Gly Ala
1415                1420                1425

Ala Ile Tyr Arg Gly Trp Asn
1430                1435

<210> SEQ ID NO 27
<211> LENGTH: 4023
<212> TYPE: DNA
<213> ORGANISM: Streptococcus salivarius PS4

<400> SEQUENCE: 27
atgattgacg gcaaatacta ctacgtaaac aaagatggct cgcacaaaga gaatttcgca      60
attaccgtga atggtcagtt gttgtatttc ggtaaggacg gtgcattgac gtctagcagc     120

```
acctacagct ttacgcaggg caccaccaac atcgttgatg gctttagcaa aaacaaccgt    180
gcgtacgatt ccagcgaggc gagctttgaa ctgatcgacg ttatctgacc gcggactcc    240
tggtatcgtc cggtgagcat tatcaaggac ggcgttacgt ggcaagccag caccaaagag    300
gactttcgcc cgctgctgat ggcctggtgg ccgaatgttg acacccaggt caactacctg    360
aattacatgt cgaaggtgtt taacctggac gcgaagtata cgagcaccga caaacaggtt    420
gacctgaatc gcgcagccaa ggacattcag gttaagattg agcaaaagat tcaggccgag    480
aagagcactc aatggctgcg tgaagcgatt tcggccttcg tcaaaaccca gccgcagtgg    540
aataaagaaa cggagaactt ctccaagggt ggtggtgagg atcatctgca aggtggtgca    600
ctgctgtacg ttaacgaccc gcgtaccccg tgggctaact ccaactaccg cctgctgaat    660
cgtactgcga ccaaccagac cggcacgatc gacaagagcg ttctggacga acagagcgat    720
cctaaccaca tgggcggctt cgatttttctg ctggcgaatg acgtcgatac cagcaatccg    780
gtggtgcagg cggaacaact gaatcagatc cactacctga tgaattgggg ttccattgtt    840
atgggcgaca aagatgcaaa cttcgatggt atccgcgtgg acgcggtcga taacgttgac    900
gcagatatgc tgcaactgta caccaactac tttcgtgagt attatggcgt gaacaaaagc    960
gaggcaaacg ctttggcgca catctcggtg ctggaagcgt ggagcttgaa tgataatcac   1020
tataatgaca agactgacgg tgcggccctg gcgatggaga caaacagcg tttggccctg   1080
ctgtttagct tggcgaaacc gatcaaagaa cgtaccctg cggtgagcc gctgtacaac   1140
aacactttca cacgacgca gcgtgacgaa aagaccgatt ggattaacaa agacggtagc   1200
aaagcctata atgaggacgg caccgtcaag cagtccacca tcggcaagta caacgagaaa   1260
tacggcgacg cgtccggcaa ttatgtgttc attcgcgccc acgataacaa cgtccaagac   1320
attattgcag agatcattaa gaaagaaatc aatccgaaaa gcgacggttt caccattacc   1380
gacgccgaaa tgaaaaaggc attcgaaatc tacaacaaag atatgctgtc ctctgataag   1440
aaatacaccc tgaacaacat cccagcggcc tacgcggtga tgctgcaaaa catggaaacc   1500
attactcgtg tgtattacgg cgatctgtat accgacgatg ccattacat ggaaaccaag   1560
agcccgtact acgacaccat tgtgaacctg atgaagaacc gtatcaaata cgtgtccggt   1620
ggtcaagcgc aacgttccta ttggctgccg accgacggta agatggataa aagcgatgtc   1680
gaactgtatc gcaccaacga ggtgtacacc agcgtccgtt acggtaagga catcatgact   1740
gccgatgaca cccaaggtag caagtacagc cgtaccagcg gtcaggtgac cctggtggtg   1800
aacaacccga gctgtctttt ggataagagc gcgaagctgg acgtcgaaat gggcaagatc   1860
catgcaaacc agaaataccg tgctctgatc gtgggtacgc cgaacggcat caaaaacttc   1920
acgagcgacg ccgaggcaat cgcggctggc tacgtgaaag aaaccgacgg caatggtgtg   1980
ctgaccttcg gtgcaaatga catcaaaggt tacgaaacgt tgacatgag cggtttcgtt   2040
gcagtttggg ttccggtagg tgcaagcgat gatcaagaca tccgtgtcgc cgcaagcacc   2100
gcggcaaaga aagaaggtga gctgactttg aaggcaactg aggcgtatga ctctcagctg   2160
atttacgaag ttttttcgaa ttttcagacc attccggatg gtagcgatcc gagcgtttac   2220
accaatcgta agatcgcgga aaatgttgat ttgttcaaga gctggggtgt gacctctttc   2280
gaaatggcgc cacagtttgt gagcgcagac gacggtacgt ttctggacag cgttatccag   2340
aacggctatg cgtttgcgga ccgttatgat ctggcgatgt ccaaaaacaa taagtacggt   2400
tcgaaagaag atctgcgtaa cgcgttgaag gctttgcaca aggccggcat ccaagccatt   2460
```

```
gcggactggg ttccggatca gatctaccaa ctgccgggca agaagtagt gaccgccact    2520 cgtaccgatg gtgccggtcg taagattagc gatgcaatta tcgatcacag cctgtacgtc    2580
gcaaacagca agtcgtctgg caaagactat caagctaaat acggtggtga gttcctggcc    2640
gagctgaaag caaagtaccc ggaaatgttt aaagtcaaca tgattagcac gggtaaaccg    2700
atcgacgact ctgtcaaact gaagcaatgg aaggcggagt actttaacgg tacgaatgtt    2760
ctggaccgtg gtgttggtta cgtcctgagc gatgaggcga cgggcaagta ctttaccgtt    2820
acgaaagagg gtaactttat cccactgcaa ttgaaaggta acgagaaagt tatcacgggc    2880
ttcagctctg acggcaaggg cattacctat ttcggcacct cgggtaatca agcgaaaagc    2940
gcttttgtca cgttcaatgg taatacctac tattttgacg cgcgtggcca catggttacc    3000
aacggcgaat atagccctaa tggtaaggat gtgtatcgtt tcctgccgaa tggtattatg    3060
ttgagcaatg cattctacgt tgacggtaac ggcaatacct acctgtacaa ctccaagggc    3120
caaatgtaca aggtggtta tagcaaattc gacgttacgg aaaccaaaga tggtaaagag    3180
agcaaagtgg tgaaatttcg ctactttacc aatgaaggtg tgatggcaaa aggtgttacc    3240
gtggtggacg gcttcactca atacttcaac gaagatggca ttcagagcaa ggacgaactg    3300
gtgacctaca atggtaaaac ctattacttc gaagcgcata ccggtaatgc gatcaaaaac    3360
acgtggcgca atatcaaggg taagtggtat cactttgatg cgaatggcgt ggcggcaacg    3420
ggtgcacagg ttatcaatgg tcagcacctg tactttaatg aggatggttc ccaggtgaag    3480
ggtggcgtcg tgaagaatgc ggatggtacc ttcagcaagt ataaagatgg ttccggtgac    3540
ctggtggtca atgagttctt cactactggt gataacgtgt ggtactacgc tggtgccaac    3600
ggcaaaactg tgacgggtgc ccaggtcatc aatggccaac acctgttttt caaagaggac    3660
ggtagccagg ttaagggtga tttcgttaag aacagcgacg gcacctactc taagtatgat    3720
gcggccagcg gcgaacgcct gacgaatgag ttttcacga ccggtgacaa ccactggtac    3780
tatattggtg ccaatggcaa aaccgttacc ggcgaagtca gatcggtga tgatacgtac    3840 ttcttcgcaa agatggcaa gcagctgaag ggccagatcg tgacgacccg cagcggtcgt    3900
atcagctact acttcggcga ctctggtaag aaggcgatta gcacctgggt ggagattcag    3960
ccgggtgttt tcgtgttttt cgacaaaaat ggcctggcat atccgccgga aacatgaat    4020 taa                                                                  4023
```

<210> SEQ ID NO 28
<211> LENGTH: 1340
<212> TYPE: PRT
<213> ORGANISM: Streptococcus salivarius PS4

<400> SEQUENCE: 28

```
Met Ile Asp Gly Lys Tyr Tyr Val Asn Lys Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Gln Gly Thr
        35                  40                  45

Thr Asn Ile Val Asp Gly Phe Ser Lys Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Val Ser Ile Ile Lys Asp Gly Val Thr Trp Gln Ala
                85                  90                  95
```

```
Ser Thr Lys Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
            115                 120                 125

Leu Asp Ala Lys Tyr Thr Ser Thr Asp Lys Gln Val Asp Leu Asn Arg
            130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Ala Ile Ser Ala Phe Val Lys Thr
                165                 170                 175

Gln Pro Gln Trp Asn Lys Glu Thr Glu Asn Phe Ser Lys Gly Gly Gly
            180                 185                 190

Glu Asp His Leu Gln Gly Gly Ala Leu Leu Tyr Val Asn Asp Pro Arg
            195                 200                 205

Thr Pro Trp Ala Asn Ser Asn Tyr Arg Leu Leu Asn Arg Thr Ala Thr
            210                 215                 220

Asn Gln Thr Gly Thr Ile Asp Lys Ser Val Leu Asp Glu Gln Ser Asp
225                 230                 235                 240

Pro Asn His Met Gly Gly Phe Asp Phe Leu Leu Ala Asn Asp Val Asp
                245                 250                 255

Thr Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
            275                 280                 285

Asp Gly Ile Arg Val Asp Ala Val Asp Asn Val Asp Ala Asp Met Leu
            290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
            355                 360                 365

Lys Glu Arg Thr Pro Ala Val Ser Pro Leu Tyr Asn Asn Thr Phe Asn
            370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
            435                 440                 445

Glu Ile Asn Pro Lys Ser Asp Gly Phe Thr Ile Thr Asp Ala Glu Met
            450                 455                 460

Lys Lys Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510
```

```
Asp Gly His Tyr Met Glu Thr Lys Ser Pro Tyr Tyr Asp Thr Ile Val
        515                 520                 525

Asn Leu Met Lys Asn Arg Ile Lys Tyr Val Ser Gly Gly Gln Ala Gln
        530                 535                 540

Arg Ser Tyr Trp Leu Pro Thr Asp Gly Lys Met Asp Lys Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asp Asp Thr Gln Gly Ser Lys Tyr Ser Arg Thr
                580                 585                 590

Ser Gly Gln Val Thr Leu Val Val Asn Asn Pro Lys Leu Ser Leu Asp
        595                 600                 605

Lys Ser Ala Lys Leu Asp Val Glu Met Gly Lys Ile His Ala Asn Gln
        610                 615                 620

Lys Tyr Arg Ala Leu Ile Val Gly Thr Pro Asn Gly Ile Lys Asn Phe
625                 630                 635                 640

Thr Ser Asp Ala Glu Ala Ile Ala Ala Gly Tyr Val Lys Glu Thr Asp
                645                 650                 655

Gly Asn Gly Val Leu Thr Phe Gly Ala Asn Asp Ile Lys Gly Tyr Glu
                660                 665                 670

Thr Phe Asp Met Ser Gly Phe Val Ala Val Trp Val Pro Val Gly Ala
        675                 680                 685

Ser Asp Asp Gln Asp Ile Arg Val Ala Ala Ser Thr Ala Ala Lys Lys
        690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
                740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
        770                 775                 780

Phe Ala Asp Arg Tyr Asp Leu Ala Met Ser Lys Asn Asn Lys Tyr Gly
785                 790                 795                 800

Ser Lys Glu Asp Leu Arg Asn Ala Leu Lys Ala Leu His Lys Ala Gly
                805                 810                 815

Ile Gln Ala Ile Ala Asp Trp Val Pro Asp Gln Ile Tyr Gln Leu Pro
        820                 825                 830

Gly Lys Glu Val Val Thr Ala Thr Arg Thr Asp Gly Ala Gly Arg Lys
        835                 840                 845

Ile Ser Asp Ala Ile Ile Asp His Ser Leu Tyr Val Ala Asn Ser Lys
        850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
                900                 905                 910

Glu Tyr Phe Asn Gly Thr Asn Val Leu Asp Arg Gly Val Gly Tyr Val
        915                 920                 925

Leu Ser Asp Glu Ala Thr Gly Lys Tyr Phe Thr Val Thr Lys Glu Gly
```

```
                930             935             940
Asn Phe Ile Pro Leu Gln Leu Lys Gly Asn Glu Lys Val Ile Thr Gly
945                 950             955                 960

Phe Ser Ser Asp Gly Lys Gly Ile Thr Tyr Phe Gly Thr Ser Gly Asn
                965             970             975

Gln Ala Lys Ser Ala Phe Val Thr Phe Asn Gly Asn Thr Tyr Tyr Phe
            980             985             990

Asp Ala Arg Gly His Met Val Thr Asn Gly Glu Tyr Ser Pro Asn Gly
        995             1000            1005

Lys Asp Val Tyr Arg Phe Leu Pro Asn Gly Ile Met Leu Ser Asn
    1010            1015            1020

Ala Phe Tyr Val Asp Gly Asn Gly Asn Thr Tyr Leu Tyr Asn Ser
    1025            1030            1035

Lys Gly Gln Met Tyr Lys Gly Gly Tyr Ser Lys Phe Asp Val Thr
    1040            1045            1050

Glu Thr Lys Asp Gly Lys Glu Ser Lys Val Val Lys Phe Arg Tyr
    1055            1060            1065

Phe Thr Asn Glu Gly Val Met Ala Lys Gly Val Thr Val Val Asp
    1070            1075            1080

Gly Phe Thr Gln Tyr Phe Asn Glu Asp Gly Ile Gln Ser Lys Asp
    1085            1090            1095

Glu Leu Val Thr Tyr Asn Gly Lys Thr Tyr Tyr Phe Glu Ala His
    1100            1105            1110

Thr Gly Asn Ala Ile Lys Asn Thr Trp Arg Asn Ile Lys Gly Lys
    1115            1120            1125

Trp Tyr His Phe Asp Ala Asn Gly Val Ala Ala Thr Gly Ala Gln
    1130            1135            1140

Val Ile Asn Gly Gln His Leu Tyr Phe Asn Glu Asp Gly Ser Gln
    1145            1150            1155

Val Lys Gly Gly Val Val Lys Asn Ala Asp Gly Thr Phe Ser Lys
    1160            1165            1170

Tyr Lys Asp Gly Ser Gly Asp Leu Val Val Asn Glu Phe Phe Thr
    1175            1180            1185

Thr Gly Asp Asn Val Trp Tyr Tyr Ala Gly Ala Asn Gly Lys Thr
    1190            1195            1200

Val Thr Gly Ala Gln Val Ile Asn Gly Gln His Leu Phe Phe Lys
    1205            1210            1215

Glu Asp Gly Ser Gln Val Lys Gly Asp Phe Val Lys Asn Ser Asp
    1220            1225            1230

Gly Thr Tyr Ser Lys Tyr Asp Ala Ala Ser Gly Glu Arg Leu Thr
    1235            1240            1245

Asn Glu Phe Phe Thr Thr Gly Asp Asn His Trp Tyr Tyr Ile Gly
    1250            1255            1260

Ala Asn Gly Lys Thr Val Thr Gly Glu Val Lys Ile Gly Asp Asp
    1265            1270            1275

Thr Tyr Phe Phe Ala Lys Asp Gly Lys Gln Leu Lys Gly Gln Ile
    1280            1285            1290

Val Thr Thr Arg Ser Gly Arg Ile Ser Tyr Tyr Phe Gly Asp Ser
    1295            1300            1305

Gly Lys Lys Ala Ile Ser Thr Trp Val Glu Ile Gln Pro Gly Val
    1310            1315            1320

Phe Val Phe Phe Asp Lys Asn Gly Leu Ala Tyr Pro Pro Glu Asn
    1325            1330            1335
```

Met Asn
  1340

<210> SEQ ID NO 29
<211> LENGTH: 4026
<212> TYPE: DNA
<213> ORGANISM: Streptococcus salivarius K12

<400> SEQUENCE: 29

| | | | | | | |
|---|---|---|---|---|---|---|
| atgacggacg | gtaaatacta | ttatgtaaat | gaggacggca | gccacaaaga | gaatttcgca | 60 |
| attacggtaa | acggtcaact | gttgtacttt | ggcaaggacg | gcgctctgac | gagcagcagc | 120 |
| acgcacagct | tcacgccggg | tactacgaat | attgtggacg | gtttctcgat | caacaaccgt | 180 |
| gcgtacgata | gcagcgaagc | gagctttgag | ctgatcaacg | gttacctgac | ggcggattcc | 240 |
| tggtatcgcc | cggtttctat | catcaaggat | ggcgtcacgt | ggcaggcaag | cactgccgag | 300 |
| gattttcgtc | cgctgttgat | ggcctggtgg | ccgaacgttg | atacccaggt | gaactatctg | 360 |
| aactatatgt | ccaaggtctt | taacctggaa | gccaagtaca | ccagcaccga | taaacaggct | 420 |
| gatctgaacc | gtgctgcaaa | ggatatccag | gtcaagatcg | aacagaagat | ccaggcggaa | 480 |
| aagagcacgc | agtggctgcg | tgagactatc | tccgcgtttg | ttaaaaccca | gccgcaatgg | 540 |
| aacaaagaga | ctgagaatta | ctccaagggt | ggtggcgaag | atcatctgca | aggcggtgcg | 600 |
| ctgttgtacg | tgaacgacag | ccgtaccccg | tgggcgaata | gcaattaccg | cctgctgaat | 660 |
| cgcacggcaa | cgaaccagac | cggtaccatt | aacaagtcgg | tgttggacga | gcaatccgat | 720 |
| ccaaatcaca | tgggtggctt | cgacttcctg | ctggcaaacg | atgtggatct | gagcaatcct | 780 |
| gttgtgcagg | ccgagcagct | gaatcaaatc | cattatctga | tgaactgggg | cagcattgtt | 840 |
| atgggtgaca | agacgcgaa | ttttgatggt | atccgtgtgg | acgccgttga | caacgtgaac | 900 |
| gctgacatgt | tgcagctgta | cacgaactac | tttcgtgagt | attacggcgt | caacaaaagc | 960 |
| gaagcgcaag | cgctggcgca | cattagcgtt | ctggaagcgt | ggagcttgaa | cgataaccac | 1020 |
| tataacgaca | aaaccgatgg | tgcggcactg | gcgatggaga | ataagcaacg | tctggccttg | 1080 |
| ctgttctctc | tggccaagcc | gatcaaagat | cgtactccgg | cagtgagccc | actgtataac | 1140 |
| aatactttca | ataccaccca | acgtgacttc | aagacggatt | ggattaacaa | ggacggtagc | 1200 |
| accgcctaca | atgaggatgg | caccgcgaaa | caatctacca | tcggtaagta | caatgagaaa | 1260 |
| tatggtgatg | caagcggtaa | ctatgtgttt | attcgtgccc | atgacaataa | cgtccaagac | 1320 |
| attattgcgg | agatcattaa | gaaagaaatc | aataagaaga | gcgatggttt | taccatcagc | 1380 |
| gatagcgaaa | tgaaacaggc | gttcgaaatc | tacaacaaag | atatgctgag | cagcaataag | 1440 |
| aaatacactc | tgaataacat | tccggcagcg | tacgccgtga | tgctgcaaaa | catggagact | 1500 |
| atcacccgtg | tgtattatgg | tgacctgtac | accgacgacg | gtcactatat | ggaaaccaag | 1560 |
| agcccgtatc | atgacaccat | tgtgaacctg | atgaaaaacc | gtatcaagta | cgtttctggt | 1620 |
| ggccaggccc | aacgctccta | ttggctgccg | accgacggta | aaatggacaa | tagcgatgtc | 1680 |
| gaactgtacc | gtactagcga | ggtctatacc | agcgttcgct | acggtaagga | cattatgacg | 1740 |
| gcggatgaca | ccgagggtag | caagtactcc | cgcacgagcg | gtcaggttac | cctggttgtt | 1800 |
| aacaacccga | agctgactct | gcatgaaagc | gccaaactga | acgtcgagat | gggtaagatc | 1860 |
| cacgcaaacc | agaaataccg | tgcgctgatt | gtgggtaccg | ccgatggcat | caaaaacttt | 1920 |
| acgtctgatg | ccgaagcgat | cgcggcaggc | tacgtaaaag | aaacggacag | caatggtgtt | 1980 |
| ctgaccttcg | gcgcaaatga | tatcaaaggt | tacgagactt | tcgatatgag | cggtttcgtc | 2040 |

-continued

```
gcagtttggg tgccggtggg tgcgagcgat gatcaggaca tccgcgtggc gccgtcgacg    2100
gaagcgaaga aagaaggtga actgacgctg aaagccacgg aagcgtatga tagccagttg    2160
atttatgaag gcttctccaa tttccagacc attccggatg gcagcgaccc gagcgtttat    2220
accaaccgca aaattgctga gaatgttgat ctgtttaagt cctggggtgt cactagcttc    2280
gaaatggctc cgcagtttgt ttcggcggac gacggcacct tcctggatag cgttatccag    2340
aacggttacg cctttgcgga ccgttatgat ttggccatga gcaagaacaa caagtacggt    2400
tctaaagagg atctgcgcga cgcactgaaa gcgctgcaca agctggcat tcaggcaatc    2460 gcggactggg tcccagacca aatctaccaa ctgccaggca agaagtggt tacggcgacg    2520 cgcacggacg gtgcgggtcg caagatcgcg gacgccatca ttgatcatag cctgtatgtt    2580
gctaactcca gagctccgg tcgcgattac caagcgcagt atggtggcga gtttctggca    2640
gagctgaaag cgaagtaccc gaaaatgttc acggaaaaca tgattagcac gggtaagccg    2700
atcgatgaca gcgtcaaact gaagcaatgg aaagccaagt atttcaatgg tacgaatgtg    2760
ctggaccgtg gtgtcggtta cgtcctgtcc gacgaggcga ccggcaaata cttcaccgtt    2820
accaaagagg gtaacttcat tccgctgcaa ctgaccggca tgaaaaagc ggtgaccggt    2880 ttcagcaacg acggcaaggg tatcacctac tttggtacga gcggtaatca ggccaagagc    2940
gcgttcgtca cctttaacgg caatacgtac tatttcgacg cgcgtggcca catggtcacg    3000
aacggcgagt atagcccgaa cggcaaagat gtctaccgtt ttctgccaaa tggtattatg    3060
ttgtcgaacg cgttttatgt cgacgcaaac ggtaatacgt acttgtacaa ctacaagggc    3120
cagatgtaca aggtggtta tacgaaattt gatgtcaccg aaactgataa agatggtaat    3180
gagagcaagg tggtcaagtt tcgttatttc accaatgagg gcgtcatggc taagggtctg    3240
accgtcattg acggtagcac ccagtacttt ggtgaggatg gttttcaaac gaaggacaag    3300
ctggcgacct ataaaggtaa gacttattac ttcgaggcac acacgggcaa tgcgatcaaa    3360
aacacctggc gtaacatcga cggtaagtgg tatcacttcg atgagaatgg cgttgccgcg    3420
accggtgcac aagtgattaa cggtcaaaaa ctgtatttca acgaggatgg ctcgcaagtg    3480
aagggcggtg ttgttaagaa cgccgacggt acctacagca aatacaaaga gggcagcggt    3540
gagctggtta ccaacgagtt tttcacgacc gacggtaatg tgtggtacta tgctggtgcg    3600
gatggcaaga ctgtgaccgg tgctcaggtc attaatggtc agcacctgta ctttaaagaa    3660
gatggcagcc aggtgaaagg tggtgtggtg aaaaacgcgg acggtacgta cagcaagtat    3720
gacgccgcca ccggtgaacg cttgaccaat gagttcttta ccacgggcga taacaattgg    3780
tactatattg gttctaatgg taagaccgta accggtgaag tcaaaatcgg tgcggacacc    3840
tattactttg ccaaagatgg caaacaggtc aagggccaaa ccgtcaccgc aggcaatggc    3900
cgcatctcct attactacgg cgattctggt aagaaagcaa tcagcacgtg gatcgaaatt    3960
caaccgggta tctatgtcta ttttgataag acgggcatcg cgtacccacc gcgtgtgctg    4020
aattaa                                                              4026
```

<210> SEQ ID NO 30
<211> LENGTH: 1341
<212> TYPE: PRT
<213> ORGANISM: Streptococcus salivarius K12

<400> SEQUENCE: 30

```
Met Thr Asp Gly Lys Tyr Tyr Tyr Val Asn Glu Asp Gly Ser His Lys
1               5                   10                  15
```

```
Glu Asn Phe Ala Ile Thr Val Asn Gly Gln Leu Leu Tyr Phe Gly Lys
                20                  25                  30

Asp Gly Ala Leu Thr Ser Ser Thr His Ser Phe Thr Pro Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asn Gly Tyr Leu Thr Ala Asp Ser
65                  70                  75                  80

Trp Tyr Arg Pro Val Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
                100                 105                 110

Val Asp Thr Gln Val Asn Tyr Leu Asn Tyr Met Ser Lys Val Phe Asn
                115                 120                 125

Leu Glu Ala Lys Tyr Thr Ser Thr Asp Lys Gln Ala Asp Leu Asn Arg
130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
                180                 185                 190

Glu Asp His Leu Gln Gly Gly Ala Leu Leu Tyr Val Asn Asp Ser Arg
                195                 200                 205

Thr Pro Trp Ala Asn Ser Asn Tyr Arg Leu Leu Asn Arg Thr Ala Thr
    210                 215                 220

Asn Gln Thr Gly Thr Ile Asn Lys Ser Val Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Gln Ala Glu Gln Leu Asn Gln Ile His Tyr
                260                 265                 270

Leu Met Asn Trp Gly Ser Ile Val Met Gly Asp Lys Asp Ala Asn Phe
    275                 280                 285

Asp Gly Ile Arg Val Asp Ala Val Asp Asn Val Asn Ala Asp Met Leu
    290                 295                 300

Gln Leu Tyr Thr Asn Tyr Phe Arg Glu Tyr Tyr Gly Val Asn Lys Ser
305                 310                 315                 320

Glu Ala Gln Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
                340                 345                 350

Glu Asn Lys Gln Arg Leu Ala Leu Leu Phe Ser Leu Ala Lys Pro Ile
                355                 360                 365

Lys Asp Arg Thr Pro Ala Val Ser Pro Leu Tyr Asn Asn Thr Phe Asn
                370                 375                 380

Thr Thr Gln Arg Asp Phe Lys Thr Asp Trp Ile Asn Lys Asp Gly Ser
385                 390                 395                 400

Thr Ala Tyr Asn Glu Asp Gly Thr Ala Lys Gln Ser Thr Ile Gly Lys
                405                 410                 415

Tyr Asn Glu Lys Tyr Gly Asp Ala Ser Gly Asn Tyr Val Phe Ile Arg
                420                 425                 430
```

```
Ala His Asp Asn Asn Val Gln Asp Ile Ile Ala Glu Ile Lys Lys
        435                 440                 445

Glu Ile Asn Lys Lys Ser Asp Gly Phe Thr Ile Ser Asp Ser Glu Met
450                 455                 460

Lys Gln Ala Phe Glu Ile Tyr Asn Lys Asp Met Leu Ser Ser Asn Lys
465                 470                 475                 480

Lys Tyr Thr Leu Asn Asn Ile Pro Ala Ala Tyr Ala Val Met Leu Gln
            485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr His Asp Thr Ile Val
        515                 520                 525

Asn Leu Met Lys Asn Arg Ile Lys Tyr Val Ser Gly Gly Gln Ala Gln
        530                 535                 540

Arg Ser Tyr Trp Leu Pro Thr Asp Gly Lys Met Asp Asn Ser Asp Val
545                 550                 555                 560

Glu Leu Tyr Arg Thr Ser Glu Val Tyr Thr Ser Val Arg Tyr Gly Lys
                565                 570                 575

Asp Ile Met Thr Ala Asp Asp Thr Glu Gly Ser Lys Tyr Ser Arg Thr
            580                 585                 590

Ser Gly Gln Val Thr Leu Val Val Asn Asn Pro Lys Leu Thr Leu His
        595                 600                 605

Glu Ser Ala Lys Leu Asn Val Glu Met Gly Lys Ile His Ala Asn Gln
        610                 615                 620

Lys Tyr Arg Ala Leu Ile Val Gly Thr Ala Asp Gly Ile Lys Asn Phe
625                 630                 635                 640

Thr Ser Asp Ala Glu Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
            660                 665                 670

Thr Phe Asp Met Ser Gly Phe Val Ala Val Trp Val Pro Val Gly Ala
        675                 680                 685

Ser Asp Asp Gln Asp Ile Arg Val Ala Pro Ser Thr Glu Ala Lys Lys
        690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
        770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ala Asp Ala Ile Ile Asp His Ser Leu Tyr Val Ala Asn Ser Lys
```

```
                850           855           860
Ser Ser Gly Arg Asp Tyr Gln Ala Gln Tyr Gly Gly Glu Phe Leu Ala
865               870               875               880
Glu Leu Lys Ala Lys Tyr Pro Lys Met Phe Thr Glu Asn Met Ile Ser
              885               890               895
Thr Gly Lys Pro Ile Asp Asp Ser Val Lys Leu Lys Gln Trp Lys Ala
              900               905               910
Lys Tyr Phe Asn Gly Thr Asn Val Leu Asp Arg Gly Val Gly Tyr Val
              915               920               925
Leu Ser Asp Glu Ala Thr Gly Lys Tyr Phe Thr Val Thr Lys Glu Gly
          930               935               940
Asn Phe Ile Pro Leu Gln Leu Thr Gly Asn Glu Lys Ala Val Thr Gly
945               950               955               960
Phe Ser Asn Asp Gly Lys Gly Ile Thr Tyr Phe Gly Thr Ser Gly Asn
              965               970               975
Gln Ala Lys Ser Ala Phe Val Thr Phe Asn Gly Asn Thr Tyr Tyr Phe
              980               985               990
Asp Ala Arg Gly His Met Val Thr Asn Gly Glu Tyr Ser Pro Asn Gly
          995               1000              1005
Lys Asp Val Tyr Arg Phe Leu Pro Asn Gly Ile Met Leu Ser Asn
      1010              1015              1020
Ala Phe Tyr Val Asp Ala Asn Gly Asn Thr Tyr Leu Tyr Asn Tyr
      1025              1030              1035
Lys Gly Gln Met Tyr Lys Gly Gly Tyr Thr Lys Phe Asp Val Thr
      1040              1045              1050
Glu Thr Asp Lys Asp Gly Asn Glu Ser Lys Val Val Lys Phe Arg
      1055              1060              1065
Tyr Phe Thr Asn Glu Gly Val Met Ala Lys Gly Leu Thr Val Ile
      1070              1075              1080
Asp Gly Ser Thr Gln Tyr Phe Gly Glu Asp Gly Phe Gln Thr Lys
      1085              1090              1095
Asp Lys Leu Ala Thr Tyr Lys Gly Lys Thr Tyr Tyr Phe Glu Ala
      1100              1105              1110
His Thr Gly Asn Ala Ile Lys Asn Thr Trp Arg Asn Ile Asp Gly
      1115              1120              1125
Lys Trp Tyr His Phe Asp Glu Asn Gly Val Ala Ala Thr Gly Ala
      1130              1135              1140
Gln Val Ile Asn Gly Gln Lys Leu Tyr Phe Asn Glu Asp Gly Ser
      1145              1150              1155
Gln Val Lys Gly Gly Val Val Lys Asn Ala Asp Gly Thr Tyr Ser
      1160              1165              1170
Lys Tyr Lys Glu Gly Ser Gly Glu Leu Val Thr Asn Glu Phe Phe
      1175              1180              1185
Thr Thr Asp Gly Asn Val Trp Tyr Tyr Ala Gly Ala Asp Gly Lys
      1190              1195              1200
Thr Val Thr Gly Ala Gln Val Ile Asn Gly Gln His Leu Tyr Phe
      1205              1210              1215
Lys Glu Asp Gly Ser Gln Val Lys Gly Gly Val Val Lys Asn Ala
      1220              1225              1230
Asp Gly Thr Tyr Ser Lys Tyr Asp Ala Ala Thr Gly Glu Arg Leu
      1235              1240              1245
Thr Asn Glu Phe Phe Thr Thr Gly Asp Asn Asn Trp Tyr Tyr Ile
      1250              1255              1260
```

| | | | | | | | | | |
|---|---|---|---|---|---|---|---|---|---|
|Gly|Ser|Asn|Gly|Lys|Thr|Val|Thr|Gly|Glu|Val|Lys|Ile|Gly|Ala|
| |1265| | |1270| | | |1275| |

Gly Ser Asn Gly Lys Thr Val Thr Gly Glu Val Lys Ile Gly Ala
    1265              1270                1275

Asp Thr Tyr Tyr Phe Ala Lys Asp Gly Lys Gln Val Lys Gly Gln
    1280              1285                1290

Thr Val Thr Ala Gly Asn Gly Arg Ile Ser Tyr Tyr Tyr Gly Asp
    1295              1300                1305

Ser Gly Lys Lys Ala Ile Ser Thr Trp Ile Glu Ile Gln Pro Gly
    1310              1315                1320

Ile Tyr Val Tyr Phe Asp Lys Thr Gly Ile Ala Tyr Pro Pro Arg
    1325              1330                1335

Val Leu Asn
    1340

<210> SEQ ID NO 31

<400> SEQUENCE: 31

000

<210> SEQ ID NO 32

<400> SEQUENCE: 32

000

<210> SEQ ID NO 33
<211> LENGTH: 4026
<212> TYPE: DNA
<213> ORGANISM: Streptococcus salivarius JIM8777

<400> SEQUENCE: 33

| | | |
|---|---|---|
|atgatcgacg gcaaatacta ctatgtaaac gaggacggca gccacaaaga gaatttcgcg|60|
|attacggtaa acggtcagct gctgtacttt ggtaaggacg gtgctctgac gagcagctcc|120|
|acgtacagct ttaccccggg tacgaccaat attgtcgatg gcttcagcat taacaaccgt|180|
|gcgtatgaca gcagcgaggc atcctttgag ctgatcgatg gttatttgac cgcggatagc|240|
|tggtatcgtc cggcgagcat cattaaggac ggcgttacgt ggcaggcctc gaccgcagaa|300|
|gattttcgtc cgctgctgat ggcttggtgg ccgaatgttg acacccaggt gaattatctg|360|
|aattacatgt ccaaggtttt caacctggat gcaaagtaca ccagcaccga caagcaggaa|420|
|accctgaacg tggctgcgaa agatatccaa gtcaagattg agcaaaagat tcaggcagag|480|
|aaatctaccc agtggctgcg tgaaacgatt agcgcgtttg ttaaaactca gccgcaatgg|540|
|aataagaaa cggaaaacta ttccaagggt ggtggcgagg accatctgca aggcggtgcc|600|
|ctgttgtacg ttaacgattc gcgcaccccg tgggcgaact cgaactatcg cttgctgaac|660|
|cataccgcta ccaatcaaaa aggcactatt gacaaatctg tcctggacga gcagagcgac|720|
|ccgaaccaca tggcggtttt cgattttctg ctggcgaacg acgtcgacct gagcaacccg|780|
|gtggtgcagg ccgaacaact gaaccagatt cactacctga tgaattgggg tagcatcgtg|840|
|atgggtgata agatgcgaa ctttgacggc attcgtgtcg atgcggtcga taacgtggac|900|
|gccgacatgt tgcagctgta cacgaactac tttcgtgagt actacggcgt taacaagagc|960|
|gaagcaaatg ccctggcgca tatcagcgtt ctggaagcgt ggagcctgaa tgacaatcac|1020|
|tataacgata gacggacgg tgcggccctg gcaatggaga taaacaacg tctggcgctg|1080|
|ctgttcagcc tggcgaaacc gatcaaagag cgtacgccgg ctgtgagccc actgtataac|1140|

```
aacaccttca atactacgca gcgtgacgag aaaacggact ggattaacaa agacggtagc    1200
aaagcgtata acgaggatgg taccgtcaag caatcgacca ttggtaagta caatgagaag    1260
tatggcgacg caagcggtaa ttacgtgttc attcgtgccc acgacaacaa tgttcaagac    1320
atcatcgccg aaatcatcaa gaaagagatc aaccctaaga gcgacggttt caccatcacc    1380
gacgcagaga tgaagaaggc ctttgaaatc tacaacaagg acatgttgag cagcgataag    1440
aagtatactc tgaacaacat tccggctgcg tacgcggtga tgttgcagaa tatggaaacc    1500
atcacgcgtg tttactatgg tgatctgtat accgataatg gcaactacat ggaaacgaaa    1560
agcccgtact atgacaccat tgttaatctg atgaagaatc gcatcaagta tgtgtctggc    1620
ggtcaagcgc agcgttctta ctggctgccg accgatggta agatggacaa tagcgatgtg    1680
gaactgtacc gcaccaacga ggtatacgct tctgtgcgct atggtaaaga cattatgacc    1740
gccgatgata ccgagggttc caagtactcc cgtacgagcg gccaagttac cttggtggca    1800
aacaacccga aattgaccct ggaccaaagc gcgaaactga agtggagat gggtaagatc     1860 cacgcaaatc aaaagtaccg tgcactgatt gtcggtaccg ccgacggtat caagaatttc    1920
accagcgatg cggatgcgat tgcagcaggc tatgttaaag agactgatag caatggtgtg    1980
ctgacgtttg gtgcgaacga cattaaaggc tatgaaacgt ttgacatgag cggtttcgtt    2040
gcggtgtggg tgcctgtggg tgctagcgat gatcaggata tccgtgtcgc gccgagcacc    2100
gaggcaaaga agaaggtga gctgacgttg aaagcgaccg aggcctatga cagccagttg      2160
atttacgaag gtttcagcaa tttccaaacc attccagacg gttccgatcc gagcgtctac    2220
accaatcgca aaatcgcgga aaacgttgat ctgttcaaaa gctggggtgt gaccagcttc    2280
gaaatggcac cgcaattcgt tagcgcggac gatggtacgt tcttggacag cgttatccaa    2340
aatggctatg cgttcgccga tcgttatgac ttggcgatga gcaaaaacaa caaatacggc    2400
agcaaagagg atctgcgcga cgccctgaaa gcgctgcata agcgggtat tcaagccatc      2460 gctgactggg ttccggacca gatctaccag ctgccgggta agaagtcgt taccgcgacc      2520 cgcaccgatg gcgctggccg taagatcgcg gatgcaatta tcgatcatag cttgtatgtg    2580
gccaatacta aaagctccgg taaggattac caggcgaaat atggtggtga atttctggct    2640
gagctgaagg ccaaataccc ggagatgttc aaggtcaaca tgattagcac cggcaaacct    2700
attgatgact ctgtcaaatt gaaacaatgg aaggcagagt atttcaatgg cactaacgtc    2760
ctggaacgtg gtgttggtta cgtgctgagc gacgaggcga ccggtaaata cttcaccgtt    2820
acgaaggacg gcaatttcat cccgctgcaa ctgaccggta tgagaaggt tgtgacgggt      2880 ttttctaatg acggtaaggg cattacctac ttcggtacct cgggtaccca ggcaaagagc    2940
gcattcgtga cgtttaacgg taacacctac tactttgatg cacgcggcca catggtgacg    3000
aacggcgagt acagcccgaa cggcaaggat gtttatcgct tcctgccgaa tggcatcatg    3060
ctgtccaatg cgttttacgt cgatgcaaat ggtaatactt acctgtacaa cagcaagggt    3120
cagatgtata agggcggtta taccaagttc gacgttactg aaacggacaa ggacggtaaa    3180
gagagcaaag tagtgaagtt tcgttatttc acgaacgaag gcgtcatggc gaaaggtgtc    3240
accgttattg atggctttac ccagtatttc ggtgaagatg gctttcaagc gaaggacaag    3300
ctggtgacct ttaagggcaa aacctactat tttgacgcgc acacgggcaa cgccatcaag    3360
aacacctggc gtaatatcga cggtaagtgg tatcattttg atgcgaacgg tgtggcggcg    3420
accggcgcac aggtcattaa tggtcaaaaa ctgtacttta atgaggacgg tagccaagtc    3480
aaaggtggcg tcgtcaagaa tgcagatggc acctatagca aatacaaaga gggctccggt    3540
```

```
gagctggtta ccaacgagtt ctttaccacg gatggtaacg tctggtacta tgctggtgcg   3600
aatggcaaga ccgttaccgg tgcacaggtt atcaacggcc agcacctgta cttcaatgcg   3660
gatggctctc aagtgaaggg cggtgtcgtc aaaaacgcgg acggtacgta ctccaaatac   3720
gatgccgcga ccggtgaacg tctgaccaat gagttttca cgactggtga caacaattgg    3780
tactacatcg gcgccaacgg taagacggtt acgggcgaag tgaaaattgg cgacgatacg   3840
tactacttcg caaaagatgg taaacaggtg aaaggtcaga cggtttccgc tggtaatggc   3900
cgcatcagct actattacgg tgactctggt aaacgtgcgg ttagcacgtg ggttgaaatt   3960
caaccgggcg tgtatgtcta ttttgataag aatggcctgg catatccacc gcgcgttttg   4020
aattaa                                                              4026
```

```
<210> SEQ ID NO 34
<211> LENGTH: 1341
<212> TYPE: PRT
<213> ORGANISM: Streptococcus salivarius JIM8777

<400> SEQUENCE: 34

Met Ile Asp Gly Lys Tyr Tyr Val Asn Glu Asp Gly Ser His Lys
1               5                   10                  15

Glu Asn Phe Ala Ile Thr Val Asn Gly Gln Leu Leu Tyr Phe Gly Lys
            20                  25                  30

Asp Gly Ala Leu Thr Ser Ser Thr Tyr Ser Phe Thr Pro Gly Thr
        35                  40                  45

Thr Asn Ile Val Asp Gly Phe Ser Ile Asn Asn Arg Ala Tyr Asp Ser
    50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
        115                 120                 125

Leu Asp Ala Lys Tyr Thr Ser Thr Asp Lys Gln Glu Thr Leu Asn Val
    130                 135                 140

Ala Ala Lys Asp Ile Gln Val Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
            180                 185                 190

Glu Asp His Leu Gln Gly Gly Ala Leu Leu Tyr Val Asn Asp Ser Arg
        195                 200                 205

Thr Pro Trp Ala Asn Ser Asn Tyr Arg Leu Leu Asn His Thr Ala Thr
    210                 215                 220

Asn Gln Lys Gly Thr Ile Asp Lys Ser Val Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
```

```
            275                 280                 285
Asp Gly Ile Arg Val Asp Ala Val Asp Asn Val Asp Ala Asp Met Leu
    290                 295                 300
Gln Leu Tyr Thr Asn Tyr Phe Arg Glu Tyr Tyr Gly Val Asn Lys Ser
305                 310                 315                 320
Glu Ala Asn Ala Leu Ala His Ile Ser Val Leu Glu Ala Trp Ser Leu
                325                 330                 335
Asn Asp Asn His Tyr Asn Asp Lys Thr Asp Gly Ala Ala Leu Ala Met
                340                 345                 350
Glu Asn Lys Gln Arg Leu Ala Leu Leu Phe Ser Leu Ala Lys Pro Ile
            355                 360                 365
Lys Glu Arg Thr Pro Ala Val Ser Pro Leu Tyr Asn Asn Thr Phe Asn
370                 375                 380
Thr Thr Gln Arg Asp Glu Lys Thr Asp Trp Ile Asn Lys Asp Gly Ser
385                 390                 395                 400
Lys Ala Tyr Asn Glu Asp Gly Thr Val Lys Gln Ser Thr Ile Gly Lys
                405                 410                 415
Tyr Asn Glu Lys Tyr Gly Asp Ala Ser Gly Asn Tyr Val Phe Ile Arg
            420                 425                 430
Ala His Asp Asn Asn Val Gln Asp Ile Ile Ala Glu Ile Lys Lys
            435                 440                 445
Glu Ile Asn Pro Lys Ser Asp Gly Phe Thr Ile Thr Asp Ala Glu Met
            450                 455                 460
Lys Lys Ala Phe Glu Ile Tyr Asn Lys Asp Met Leu Ser Ser Asp Lys
465                 470                 475                 480
Lys Tyr Thr Leu Asn Asn Ile Pro Ala Ala Tyr Ala Val Met Leu Gln
                485                 490                 495
Asn Met Glu Thr Ile Thr Arg Val Tyr Tyr Gly Asp Leu Tyr Thr Asp
                500                 505                 510
Asn Gly Asn Tyr Met Glu Thr Lys Ser Pro Tyr Tyr Asp Thr Ile Val
            515                 520                 525
Asn Leu Met Lys Asn Arg Ile Lys Tyr Val Ser Gly Gly Gln Ala Gln
            530                 535                 540
Arg Ser Tyr Trp Leu Pro Thr Asp Gly Lys Met Asp Asn Ser Asp Val
545                 550                 555                 560
Glu Leu Tyr Arg Thr Asn Glu Val Tyr Ala Ser Val Arg Tyr Gly Lys
                565                 570                 575
Asp Ile Met Thr Ala Asp Asp Thr Glu Gly Ser Lys Tyr Ser Arg Thr
                580                 585                 590
Ser Gly Gln Val Thr Leu Val Ala Asn Asn Pro Lys Leu Thr Leu Asp
            595                 600                 605
Gln Ser Ala Lys Leu Lys Val Glu Met Gly Lys Ile His Ala Asn Gln
        610                 615                 620
Lys Tyr Arg Ala Leu Ile Val Gly Thr Ala Asp Gly Ile Lys Asn Phe
625                 630                 635                 640
Thr Ser Asp Ala Asp Ala Ile Ala Ala Gly Tyr Val Lys Glu Thr Asp
                645                 650                 655
Ser Asn Gly Val Leu Thr Phe Gly Ala Asn Asp Ile Lys Gly Tyr Glu
            660                 665                 670
Thr Phe Asp Met Ser Gly Phe Val Ala Val Trp Val Pro Val Gly Ala
            675                 680                 685
Ser Asp Asp Gln Asp Ile Arg Val Ala Pro Ser Thr Glu Ala Lys Lys
            690                 695                 700
```

```
Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
            740                 745                 750

Lys Ser Trp Gly Val Thr Ser Phe Glu Met Ala Pro Gln Phe Val Ser
        755                 760                 765

Ala Asp Asp Gly Thr Phe Leu Asp Ser Val Ile Gln Asn Gly Tyr Ala
770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
            820                 825                 830

Gly Lys Glu Val Val Thr Ala Thr Arg Thr Asp Gly Ala Gly Arg Lys
        835                 840                 845

Ile Ala Asp Ala Ile Ile Asp His Ser Leu Tyr Val Ala Asn Thr Lys
850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
            900                 905                 910

Glu Tyr Phe Asn Gly Thr Asn Val Leu Glu Arg Gly Val Gly Tyr Val
        915                 920                 925

Leu Ser Asp Glu Ala Thr Gly Lys Tyr Phe Val Thr Lys Asp Gly
930                 935                 940

Asn Phe Ile Pro Leu Gln Leu Thr Gly Asn Glu Lys Val Val Thr Gly
945                 950                 955                 960

Phe Ser Asn Asp Gly Lys Gly Ile Thr Tyr Phe Gly Thr Ser Gly Thr
                965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Gly Glu Tyr Ser Pro Asn Gly
        995                 1000                1005

Lys Asp Val Tyr Arg Phe Leu Pro Asn Gly Ile Met Leu Ser Asn
    1010                1015                1020

Ala Phe Tyr Val Asp Ala Asn Gly Asn Thr Tyr Leu Tyr Asn Ser
    1025                1030                1035

Lys Gly Gln Met Tyr Lys Gly Tyr Thr Lys Phe Asp Val Thr
    1040                1045                1050

Glu Thr Asp Lys Asp Gly Lys Glu Ser Lys Val Val Lys Phe Arg
    1055                1060                1065

Tyr Phe Thr Asn Glu Gly Val Met Ala Lys Gly Val Thr Val Ile
    1070                1075                1080

Asp Gly Phe Thr Gln Tyr Phe Gly Glu Asp Gly Phe Gln Ala Lys
    1085                1090                1095

Asp Lys Leu Val Thr Phe Lys Gly Lys Thr Tyr Tyr Phe Asp Ala
    1100                1105                1110
```

```
His Thr Gly Asn Ala Ile Lys Asn Thr Trp Arg Asn Ile Asp Gly
    1115                1120                1125

Lys Trp Tyr His Phe Asp Ala Asn Gly Val Ala Ala Thr Gly Ala
    1130                1135                1140

Gln Val Ile Asn Gly Gln Lys Leu Tyr Phe Asn Glu Asp Gly Ser
    1145                1150                1155

Gln Val Lys Gly Gly Val Val Lys Asn Ala Asp Gly Thr Tyr Ser
    1160                1165                1170

Lys Tyr Lys Glu Gly Ser Gly Glu Leu Val Thr Asn Glu Phe Phe
    1175                1180                1185

Thr Thr Asp Gly Asn Val Trp Tyr Tyr Ala Gly Ala Asn Gly Lys
    1190                1195                1200

Thr Val Thr Gly Ala Gln Val Ile Asn Gly Gln His Leu Tyr Phe
    1205                1210                1215

Asn Ala Asp Gly Ser Gln Val Lys Gly Gly Val Val Lys Asn Ala
    1220                1225                1230

Asp Gly Thr Tyr Ser Lys Tyr Asp Ala Ala Thr Gly Glu Arg Leu
    1235                1240                1245

Thr Asn Glu Phe Phe Thr Thr Gly Asp Asn Asn Trp Tyr Tyr Ile
    1250                1255                1260

Gly Ala Asn Gly Lys Thr Val Thr Gly Glu Val Lys Ile Gly Asp
    1265                1270                1275

Asp Thr Tyr Tyr Phe Ala Lys Asp Gly Lys Gln Val Lys Gly Gln
    1280                1285                1290

Thr Val Ser Ala Gly Asn Gly Arg Ile Ser Tyr Tyr Tyr Gly Asp
    1295                1300                1305

Ser Gly Lys Arg Ala Val Ser Thr Trp Val Glu Ile Gln Pro Gly
    1310                1315                1320

Val Tyr Val Tyr Phe Asp Lys Asn Gly Leu Ala Tyr Pro Pro Arg
    1325                1330                1335

Val Leu Asn
    1340

<210> SEQ ID NO 35

<400> SEQUENCE: 35

000

<210> SEQ ID NO 36

<400> SEQUENCE: 36

000

<210> SEQ ID NO 37

<400> SEQUENCE: 37

000

<210> SEQ ID NO 38

<400> SEQUENCE: 38

000

<210> SEQ ID NO 39
```

```
<400> SEQUENCE: 39
000

<210> SEQ ID NO 40
<400> SEQUENCE: 40
000

<210> SEQ ID NO 41
<400> SEQUENCE: 41
000

<210> SEQ ID NO 42
<400> SEQUENCE: 42
000

<210> SEQ ID NO 43
<400> SEQUENCE: 43
000

<210> SEQ ID NO 44
<400> SEQUENCE: 44
000

<210> SEQ ID NO 45
<400> SEQUENCE: 45
000

<210> SEQ ID NO 46
<400> SEQUENCE: 46
000

<210> SEQ ID NO 47
<400> SEQUENCE: 47
000

<210> SEQ ID NO 48
<400> SEQUENCE: 48
000

<210> SEQ ID NO 49
<400> SEQUENCE: 49
000

<210> SEQ ID NO 50
<400> SEQUENCE: 50
```

<210> SEQ ID NO 51

<400> SEQUENCE: 51

000

<210> SEQ ID NO 52

<400> SEQUENCE: 52

000

<210> SEQ ID NO 53

<400> SEQUENCE: 53

000

<210> SEQ ID NO 54

<400> SEQUENCE: 54

000

<210> SEQ ID NO 55

<400> SEQUENCE: 55

000

<210> SEQ ID NO 56

<400> SEQUENCE: 56

000

<210> SEQ ID NO 57

<400> SEQUENCE: 57

000

<210> SEQ ID NO 58

<400> SEQUENCE: 58

000

<210> SEQ ID NO 59
<211> LENGTH: 1242
<212> TYPE: PRT
<213> ORGANISM: Streptococcus sp. C150

<400> SEQUENCE: 59

```
Met Ile Asn Gly Lys Glu Tyr Tyr Val Glu Asp Asp Gly Thr Val Arg
1               5                   10                  15

Lys Asn Tyr Val Leu Glu Arg Asn Gly Gly Ser Gln Tyr Phe Asn Ala
                20                  25                  30

Glu Thr Gly Glu Leu Ser Asn Gln Lys Asp Tyr Arg Phe Asp Lys Asn
            35                  40                  45

Gly Gly Thr Gly Ser Ala Ala Asp Ser Thr Asn Thr Asn Val Thr
        50                  55                  60

Val Asn Gly Asp Lys Asn Ala Phe Tyr Gly Thr Thr Glu Lys Asp Ile
```

```
                65                  70                  75                  80
Glu Leu Val Asp Gly Tyr Phe Thr Ala Asn Thr Trp Tyr Arg Pro Lys
                    85                  90                  95
Glu Ile Leu Lys Asp Gly Lys Glu Trp Thr Ala Ser Thr Glu Asn Asp
                100                 105                 110
Lys Arg Pro Leu Leu Thr Val Trp Trp Pro Ser Lys Ala Ile Gln Ala
                115                 120                 125
Ser Tyr Leu Asn Tyr Met Arg Glu Gly Leu Gly Thr Asn Gln Thr
    130                 135                 140
Phe Thr Ser Tyr Ser Ser Gln Thr Gln Met Asp Gln Ala Ala Leu Glu
145                 150                 155                 160
Val Gln Lys Arg Ile Glu Arg Ile Ala Arg Gly Asn Thr Asp
                    165                 170                 175
Trp Leu Arg Thr Thr Ile Lys Asn Phe Val Lys Thr Gln Pro Gly Trp
                180                 185                 190
Asn Ser Thr Ser Glu Asn Leu Asp Asn Ser Asp His Leu Gln Gly Gly
                195                 200                 205
Ala Leu Leu Tyr Asn Asn Ser Asn Arg Thr Ser Tyr Ala Asn Ser Asp
    210                 215                 220
Tyr Arg Leu Leu Asn Arg Thr Pro Thr Gln Gln Asp Gly Thr Arg Arg
225                 230                 235                 240
Tyr Phe Lys Asp Asn Ser Ser Gly Gly Phe Glu Phe Leu Leu Ala Asn
                245                 250                 255
Asp Ile Asp Asn Ser Asn Pro Ala Val Gln Ala Glu Gln Leu Asn Trp
                260                 265                 270
Leu His Tyr Ile Met Asn Ile Gly Ser Leu Thr Gly Gly Ser Glu Asp
                275                 280                 285
Glu Asn Phe Asp Gly Val Arg Val Asp Ala Val Asp Asn Val Asn Ala
    290                 295                 300
Asp Leu Leu Gln Ile Ala Ser Asp Tyr Phe Lys Ala Lys Tyr Gly Val
305                 310                 315                 320
Glu Lys Ser Glu Glu Glu Ala Ile Lys His Leu Ser Ile Leu Glu Ala
                325                 330                 335
Trp Ser His Asn Asp Ala Tyr Tyr Asn Glu Asp Thr Lys Gly Ala Gln
                340                 345                 350
Leu Pro Met Asp Asp Pro Leu Arg Leu Ala Met Val Phe Ser Phe Leu
    355                 360                 365
Arg Pro Ile Gly Asn Arg Ser Gly Leu Glu Pro Leu Ile Thr Asn Ser
    370                 375                 380
Leu Asn Asp Arg Ser Glu Ser Lys Lys Asn Thr Lys Arg Met Ala Asn
385                 390                 395                 400
Tyr Thr Phe Val Arg Ala His Asp Ser Glu Val Gln Ser Val Ile Gly
                405                 410                 415
Gln Ile Ile Lys Asn Glu Ile Asn Pro Gln Ser Thr Gly Asn Thr Phe
                420                 425                 430
Thr Leu Asp Glu Met Lys Lys Ala Phe Lys Ile Tyr Asn Ala Asp Met
    435                 440                 445
Arg Ser Ala Asn Lys Arg Tyr Thr Gln Tyr Asn Ile Pro Ser Ala Tyr
    450                 455                 460
Ala Phe Met Leu Thr Asn Lys Asp Thr Val Pro Arg Val Tyr Gly
465                 470                 475                 480
Asp Leu Tyr Thr Asp Asp Gly Gln Tyr Met Ala Gln Lys Ser Pro Tyr
                485                 490                 495
```

```
His Asp Ala Ile Ser Thr Leu Leu Gln Ala Arg Ile Arg Tyr Ala Ala
            500                 505                 510

Gly Gly Gln Asp Met Lys Met Ser Tyr Val Gly Ser Gly Asn Thr Asn
            515                 520                 525

Gly Trp Asp Ala Ser Gly Val Leu Thr Ser Val Arg Tyr Gly Lys Gly
            530                 535                 540

Ala Asn Asn Ala Ser Asp Ala Gly Thr Ala Glu Thr Arg Asn Gln Gly
545                 550                 555                 560

Met Ala Val Ile Leu Ser Asn Gln Pro Ala Leu Arg Leu Asn Ser Asn
                565                 570                 575

Leu Thr Ile Asn Met Gly Ala Ala His Arg Asn Gln Ala Tyr Arg Pro
            580                 585                 590

Leu Leu Leu Thr Thr Ser Asn Gly Val Ala Ser Tyr Leu Asn Asp Gly
            595                 600                 605

Asp Ala Asn Gly Ile Val Lys Tyr Thr Asp Ala Asn Gly Tyr Leu Thr
            610                 615                 620

Phe Asn Pro Gly Glu Ile Ser Gly Val Arg Asn Ala Gln Val Asp Gly
625                 630                 635                 640

Tyr Leu Ala Val Trp Val Pro Leu Gly Ala Ser Glu Asn Gln Asp Val
                645                 650                 655

Arg Val Ala Ala Ser Lys Ser Lys Asn Ser Ser Gly Leu Val Tyr Asp
            660                 665                 670

Ser Ser Ala Ala Leu Asp Ser Gln Val Ile Tyr Glu Gly Phe Ser Asn
            675                 680                 685

Phe Gln Asp Phe Val Gln Asp Pro Ser Gln Tyr Thr Asn Lys Lys Ile
            690                 695                 700

Ala Glu Asn Ala Asn Leu Phe Lys Ser Trp Gly Ile Thr Ser Phe Glu
705                 710                 715                 720

Phe Ala Pro Gln Tyr Val Ser Asp Asp Gly Thr Phe Leu Asp Ser
                725                 730                 735

Val Ile Gln Asn Gly Tyr Ala Phe Ser Asp Arg Tyr Asp Ile Gly Met
            740                 745                 750

Ser Lys Asp Asn Lys Tyr Gly Ser Leu Ala Asp Leu Lys Ala Ala Leu
            755                 760                 765

Lys Ser Leu His Ala Val Gly Ile Ser Ala Ile Ala Asp Trp Val Pro
            770                 775                 780

Asp Gln Ile Tyr Asn Leu Pro Gly Asp Glu Val Val Thr Ala Thr Arg
785                 790                 795                 800

Val Asn Asn Tyr Gly Glu Thr Lys Asp Gly Ala Ile Ile Asp His Ser
                805                 810                 815

Leu Tyr Val Ala Lys Thr Arg Thr Phe Gly Asn Asp Tyr Gln Gly Lys
            820                 825                 830

Tyr Gly Gly Ala Tyr Leu Asp Glu Leu Lys Arg Leu Tyr Pro Gln Phe
            835                 840                 845

Phe Asp Arg Val Gln Ile Ser Thr Gly Lys Arg Leu Thr Thr Asp Glu
            850                 855                 860

Lys Ile Thr Lys Trp Ser Ala Lys Tyr Met Asn Gly Thr Asn Ile Leu
865                 870                 875                 880

Asp Arg Gly Ser Glu Tyr Val Leu Lys Asn Gly Leu Ser Gly Tyr Tyr
                885                 890                 895

Gly Thr Asn Gly Gly Lys Val Ser Leu Pro Lys Val Val Gly Ser Asn
            900                 905                 910
```

```
Gln Ser Thr Asn Asn Asn Gln Asn Gly Asp Gly Ser Gly Arg Phe
            915                 920                 925

Glu Lys Ser Trp Gly Ser Val Tyr Tyr Arg Tyr Asn Asp Gly Gln Arg
    930                 935                 940

Ala Arg Asn Ala Phe Ile Lys Asp Asn Asp Gly Asn Val Tyr Tyr Phe
945                 950                 955                 960

Asp Asn Thr Gly Arg Met Ala Ile Gly Glu Lys Thr Ile Asp Gly Lys
                965                 970                 975

Gln Tyr Phe Phe Leu Ala Asn Gly Val Gln Leu Arg Asp Gly Tyr Arg
            980                 985                 990

Gln Asn Arg Arg Gly Gln Val Phe Tyr Tyr Asp Glu Asn Gly Ile Met
        995                 1000                1005

Ser Gln Thr Gly Lys Pro Ser Pro Lys Pro Glu Pro Lys Pro Asp
    1010                1015                1020

Asn Asn Thr Phe Ser Arg Asn Gln Phe Ile Gln Ile Gly Asn Asn
    1025                1030                1035

Val Trp Ala Tyr Tyr Asp Gly Asn Gly Lys Arg Val Ile Gly Arg
    1040                1045                1050

Gln Asn Ile Asn Gly Gln Glu Leu Phe Phe Asp Asn Asn Gly Val
    1055                1060                1065

Gln Val Lys Gly Arg Thr Ala Gln Val Asp Gly Val Thr Arg Tyr
    1070                1075                1080

Phe Asp Ala Asn Ser Gly Glu Met Ala Arg Asn Arg Phe Ala Glu
    1085                1090                1095

Val Glu Pro Gly Val Trp Ala Tyr Phe Asn Asn Asp Gly Ala Ala
    1100                1105                1110

Val Thr Gly Ser Gln Asn Ile Asn Gly Gln Thr Leu Tyr Phe Asp
    1115                1120                1125

Gln Asn Gly His Gln Val Lys Gly Ala Leu Val Thr Val Asp Gly
    1130                1135                1140

Asn Leu Arg Tyr Tyr Asp Ala Asn Ser Gly Asp Leu Tyr Arg Asn
    1145                1150                1155

Arg Phe Gln Glu Val Asn Gly Ser Trp Tyr Tyr Phe Asp Gly Asn
    1160                1165                1170

Gly Asn Ala Val Lys Gly Met Val Asn Ile Asn Gly Gln Asn Leu
    1175                1180                1185

Leu Phe Asp Asn Asp Gly Lys Gln Val Lys Gly His Leu Val Arg
    1190                1195                1200

Val Asn Gly Val Ile Arg Tyr Tyr Asp Pro Asn Ser Gly Glu Met
    1205                1210                1215

Ala Val Asn Arg Trp Val Glu Ile Ser Ser Gly Trp Trp Val Tyr
    1220                1225                1230

Phe Asp Gly Glu Gly Arg Gly Gln Ile
    1235                1240

<210> SEQ ID NO 60
<211> LENGTH: 1518
<212> TYPE: PRT
<213> ORGANISM: Streptococcus salivarius

<400> SEQUENCE: 60

Met Glu Asn Lys Ile His Tyr Lys Leu His Lys Val Lys Lys Gln Trp
1               5                   10                  15

Val Thr Ile Ala Val Ala Ser Val Ala Leu Ala Thr Val Leu Gly Gly
            20                  25                  30
```

```
Leu Ser Val Thr Thr Ser Ser Val Ala Asp Glu Thr Gln Asp Lys
        35                  40                  45

Thr Val Thr Gln Ser Asn Ser Gly Thr Thr Ala Ser Leu Val Thr Ser
 50                  55                  60

Pro Glu Ala Thr Lys Glu Ala Asp Lys Arg Thr Asn Thr Lys Glu Ala
 65                  70                  75                  80

Asp Val Leu Thr Pro Ala Lys Glu Thr Asn Ala Val Glu Thr Ala Thr
                 85                  90                  95

Thr Thr Asn Thr Gln Ala Thr Ala Glu Ala Ala Thr Thr Ala Thr Thr
                100                 105                 110

Ala Asp Val Ala Val Ala Ala Val Pro Asn Lys Glu Ala Val Val Thr
                115                 120                 125

Thr Asp Ala Pro Ala Val Thr Thr Glu Lys Ala Glu Glu Gln Pro Ala
        130                 135                 140

Thr Val Lys Ala Glu Val Val Asn Thr Glu Val Lys Ala Pro Glu Ala
145                 150                 155                 160

Ala Leu Lys Asp Ser Glu Val Glu Ala Ala Leu Ser Leu Lys Asn Ile
                165                 170                 175

Lys Asn Ile Asp Gly Lys Tyr Tyr Val Asn Glu Asp Gly Ser His
                180                 185                 190

Lys Glu Asn Phe Ala Ile Thr Val Asn Gly Gln Leu Leu Tyr Phe Gly
                195                 200                 205

Lys Asp Gly Ala Leu Thr Ser Ser Ser Thr Tyr Ser Phe Thr Pro Gly
        210                 215                 220

Thr Thr Asn Ile Val Asp Gly Phe Ser Ile Asn Arg Ala Tyr Asp
225                 230                 235                 240

Ser Ser Glu Ala Ser Phe Glu Leu Ile Asp Gly Tyr Leu Thr Ala Asp
                245                 250                 255

Ser Trp Tyr Arg Pro Ala Ser Ile Ile Lys Asp Gly Val Thr Trp Gln
                260                 265                 270

Ala Ser Thr Ala Glu Asp Phe Arg Pro Leu Leu Met Ala Trp Trp Pro
        275                 280                 285

Asn Val Asp Thr Gln Val Asn Tyr Leu Asn Tyr Met Ser Lys Val Phe
290                 295                 300

Asn Leu Asp Ala Lys Tyr Ser Ser Thr Asp Lys Gln Glu Thr Leu Lys
305                 310                 315                 320

Val Ala Ala Lys Asp Ile Gln Ile Lys Ile Glu Gln Lys Ile Gln Ala
                325                 330                 335

Glu Lys Ser Thr Gln Trp Leu Arg Glu Thr Ile Ser Ala Phe Val Lys
        340                 345                 350

Thr Gln Pro Gln Trp Asn Lys Glu Thr Glu Asn Tyr Ser Lys Gly Gly
        355                 360                 365

Gly Glu Asp His Leu Gln Gly Gly Ala Leu Leu Tyr Val Asn Asp Ser
        370                 375                 380

Arg Thr Pro Trp Ala Asn Ser Asp Tyr Arg Arg Leu Asn Arg Thr Ala
385                 390                 395                 400

Thr Asn Gln Thr Gly Thr Ile Asp Lys Ser Ile Leu Asp Glu Gln Ser
                405                 410                 415

Asp Pro Asn His Met Gly Gly Phe Asp Phe Leu Leu Ala Asn Asp Val
                420                 425                 430

Asp Leu Ser Asn Pro Val Val Gln Ala Glu Gln Leu Asn Gln Ile His
        435                 440                 445
```

```
Tyr Leu Met Asn Trp Gly Ser Ile Val Met Gly Asp Lys Asp Ala Asn
    450                 455                 460
Phe Asp Gly Ile Arg Val Asp Ala Val Asp Asn Val Asp Ala Asp Met
465                 470                 475                 480
Leu Gln Leu Tyr Thr Asn Tyr Phe Arg Glu Tyr Tyr Gly Val Asn Lys
                485                 490                 495
Ser Glu Ala Asn Ala Leu Ala His Ile Ser Val Leu Glu Ala Trp Ser
                500                 505                 510
Leu Asn Asp Asn His Tyr Asn Asp Lys Thr Asp Gly Ala Ala Leu Ala
                515                 520                 525
Met Glu Asn Lys Gln Arg Leu Ala Leu Leu Phe Ser Leu Ala Lys Pro
    530                 535                 540
Ile Lys Glu Arg Thr Pro Ala Val Ser Pro Leu Tyr Asn Asn Thr Phe
545                 550                 555                 560
Asn Thr Thr Gln Arg Asp Glu Lys Thr Asp Trp Ile Asn Lys Asp Gly
                565                 570                 575
Ser Lys Ala Tyr Asn Glu Asp Gly Thr Val Lys Gln Ser Thr Ile Gly
                580                 585                 590
Lys Tyr Asn Glu Lys Tyr Gly Asp Ala Ser Gly Asn Tyr Val Phe Ile
    595                 600                 605
Arg Ala His Asp Asn Asn Val Gln Asp Ile Ile Ala Glu Ile Ile Lys
    610                 615                 620
Lys Glu Ile Asn Pro Lys Ser Asp Gly Phe Thr Ile Thr Asp Ala Glu
625                 630                 635                 640
Met Lys Gln Ala Phe Glu Ile Tyr Asn Lys Asp Met Leu Ser Ser Asp
                645                 650                 655
Lys Lys Tyr Thr Leu Asn Asn Ile Pro Ala Ala Tyr Ala Val Met Leu
                660                 665                 670
Gln Asn Met Glu Thr Ile Thr Arg Val Tyr Tyr Gly Asp Leu Tyr Thr
    675                 680                 685
Asp Asp Gly His Tyr Met Glu Thr Lys Ser Pro Tyr Tyr Asp Thr Ile
    690                 695                 700
Val Asn Leu Met Lys Ser Arg Ile Lys Tyr Val Ser Gly Gly Gln Ala
705                 710                 715                 720
Gln Arg Ser Tyr Trp Leu Pro Thr Asp Gly Lys Met Asp Asn Ser Asp
                725                 730                 735
Val Glu Leu Tyr Arg Thr Asn Glu Val Tyr Thr Ser Val Arg Tyr Gly
                740                 745                 750
Lys Asp Ile Met Thr Ala Asn Asp Thr Glu Gly Ser Lys Tyr Ser Arg
    755                 760                 765
Thr Ser Gly Gln Val Thr Leu Val Ala Asn Asn Pro Lys Leu Asn Leu
    770                 775                 780
Asp Gln Ser Ala Lys Leu Asn Val Glu Met Gly Lys Ile His Ala Asn
785                 790                 795                 800
Gln Lys Tyr Arg Ala Leu Ile Val Gly Thr Ala Asp Gly Ile Lys Asn
                805                 810                 815
Phe Thr Ser Asp Ala Asp Ala Ile Ala Ala Gly Tyr Val Lys Glu Thr
                820                 825                 830
Asp Ser Asn Gly Val Leu Thr Phe Gly Ala Asn Asp Ile Lys Gly Tyr
    835                 840                 845
Glu Thr Phe Asp Met Ser Gly Phe Val Ala Val Trp Val Pro Val Gly
    850                 855                 860
Ala Ser Asp Asn Gln Asp Ile Arg Val Ala Pro Ser Thr Glu Ala Lys
```

```
                865                 870                 875                 880
Lys Glu Gly Glu Leu Thr Leu Lys Ala Thr Glu Ala Tyr Asp Ser Gln
                    885                 890                 895
Leu Ile Tyr Glu Gly Phe Ser Asn Phe Gln Thr Ile Pro Asp Gly Ser
                900                 905                 910
Asp Pro Ser Val Tyr Thr Asn Arg Lys Ile Ala Glu Asn Val Asp Leu
            915                 920                 925
Phe Lys Ser Trp Gly Val Thr Ser Phe Glu Met Ala Pro Gln Phe Val
    930                 935                 940
Ser Ala Asp Asp Gly Thr Phe Leu Asp Ser Val Ile Gln Asn Gly Tyr
945                 950                 955                 960
Ala Phe Ala Asp Arg Tyr Asp Leu Ala Met Ser Lys Asn Asn Lys Tyr
                965                 970                 975
Gly Ser Lys Glu Asp Leu Arg Asp Ala Leu Lys Ala Leu His Lys Ala
            980                 985                 990
Gly Ile Gln Ala Ile Ala Asp Trp Val Pro Asp Gln Ile Tyr Gln Leu
        995                 1000                1005
Pro Gly Lys Glu Val Val Thr Ala Thr Arg Thr Asp Gly Ala Gly
    1010                1015                1020
Arg Lys Ile Ala Asp Ala Ile Asp His Ser Leu Tyr Val Ala
    1025                1030                1035
Asn Ser Lys Ser Ser Gly Lys Asp Tyr Gln Ala Lys Tyr Gly Gly
    1040                1045                1050
Glu Phe Leu Ala Glu Leu Lys Ala Lys Tyr Pro Glu Met Phe Lys
    1055                1060                1065
Val Asn Met Ile Ser Thr Gly Lys Pro Ile Asp Asp Ser Val Lys
    1070                1075                1080
Leu Lys Gln Trp Lys Ala Glu Tyr Phe Asn Gly Thr Asn Val Leu
    1085                1090                1095
Glu Arg Gly Val Gly Tyr Val Leu Ser Asp Glu Ala Thr Gly Lys
    1100                1105                1110
Tyr Phe Thr Val Thr Lys Glu Gly Asn Phe Ile Pro Leu Gln Leu
    1115                1120                1125
Thr Gly Lys Glu Lys Val Ile Thr Gly Phe Ser Ser Asp Gly Lys
    1130                1135                1140
Gly Ile Thr Tyr Phe Gly Thr Ser Gly Thr Gln Ala Lys Ser Ala
    1145                1150                1155
Phe Val Thr Phe Asn Gly Asn Thr Tyr Tyr Phe Asp Ala Arg Gly
    1160                1165                1170
His Met Val Thr Asn Ser Glu Tyr Ser Pro Asn Gly Lys Asp Val
    1175                1180                1185
Tyr Arg Phe Leu Pro Asn Gly Ile Met Leu Ser Asn Ala Phe Tyr
    1190                1195                1200
Ile Asp Ala Asn Gly Asn Thr Tyr Leu Tyr Asn Ser Lys Gly Gln
    1205                1210                1215
Met Tyr Lys Gly Gly Tyr Thr Lys Phe Asp Val Ser Glu Thr Asp
    1220                1225                1230
Lys Asp Gly Lys Glu Ser Lys Val Val Lys Phe Arg Tyr Phe Thr
    1235                1240                1245
Asn Glu Gly Val Met Ala Lys Gly Val Thr Val Ile Asp Gly Phe
    1250                1255                1260
Thr Gln Tyr Phe Gly Glu Asp Gly Phe Gln Ala Lys Asp Lys Leu
    1265                1270                1275
```

Val Thr Phe Lys Gly Lys Thr Tyr Tyr Phe Asp Ala His Thr Gly
1280            1285                1290

Asn Gly Ile Lys Asp Thr Trp Arg Asn Ile Asn Gly Lys Trp Tyr
    1295            1300                1305

Tyr Phe Asp Ala Asn Gly Val Ala Ala Thr Gly Ala Gln Val Ile
1310            1315                1320

Asn Gly Gln Lys Leu Tyr Phe Asn Glu Asp Gly Ser Gln Val Lys
    1325            1330                1335

Gly Gly Val Val Lys Asn Ala Asp Gly Thr Tyr Ser Lys Tyr Lys
1340            1345                1350

Glu Gly Phe Gly Glu Leu Val Thr Asn Glu Phe Phe Thr Thr Asp
    1355            1360                1365

Gly Asn Val Trp Tyr Tyr Ala Gly Ala Asn Gly Lys Thr Val Thr
1370            1375                1380

Gly Ala Gln Val Ile Asn Gly Gln His Leu Tyr Phe Asn Ala Asp
1385            1390                1395

Gly Ser Gln Val Lys Gly Gly Val Val Lys Asn Ala Asp Gly Thr
1400            1405                1410

Tyr Ser Lys Tyr Asn Ala Ser Thr Gly Glu Arg Leu Thr Asn Glu
1415            1420                1425

Phe Phe Thr Thr Gly Asp Asn Asn Trp Tyr Tyr Ile Gly Ala Asn
1430            1435                1440

Gly Lys Ser Val Thr Gly Glu Val Lys Ile Gly Asp Asp Thr Tyr
1445            1450                1455

Phe Phe Ala Lys Asp Gly Lys Gln Val Lys Gly Gln Thr Val Ser
1460            1465                1470

Ala Gly Asn Gly Arg Ile Ser Tyr Tyr Tyr Gly Asp Ser Gly Lys
1475            1480                1485

Arg Ala Val Ser Thr Trp Ile Glu Ile Gln Pro Gly Val Tyr Val
1490            1495                1500

Tyr Phe Asp Lys Asn Gly Leu Ala Tyr Pro Pro Arg Val Leu Asn
1505            1510                1515

<210> SEQ ID NO 61
<211> LENGTH: 1528
<212> TYPE: PRT
<213> ORGANISM: Streptococcus salivarius K12

<400> SEQUENCE: 61

Met Thr Asn Lys Ile Thr Gly Lys Ile Met Glu Asn Lys Val His
1               5                   10                  15

Tyr Lys Leu His Lys Val Lys Lys Gln Trp Val Thr Ile Ala Val
                20                  25                  30

Ser Ala Ala Leu Ala Thr Val Val Gly Gly Leu Ser Ala Thr Thr Ser
        35                  40                  45

Ser Val Ser Ala Asp Glu Thr Gln Asp Lys Ile Val Thr Gln Pro Asn
    50                  55                  60

Leu Asp Thr Thr Ala Asp Leu Val Ser Thr Glu Ala Thr Lys Glu
65                  70                  75                  80

Val Asp Lys Arg Thr Asn Thr Lys Glu Ala Asp Val Leu Thr Pro Ala
                85                  90                  95

Lys Glu Thr Asn Ala Val Glu Thr Ala Thr Thr Asn Thr Gln Ala
                100                 105                 110

Thr Ala Glu Ala Ala Thr Thr Ala Thr Thr Ser Asp Val Ala Val Ala

```
            115                 120                 125
Ala Val Pro Asn Lys Glu Ala Val Val Thr Thr Asp Ala Pro Ala Val
            130                 135                 140
Thr Thr Glu Lys Ala Glu Glu Gln Pro Ala Thr Val Lys Ala Glu Val
145                 150                 155                 160
Val Asn Thr Glu Val Lys Ala Pro Gln Ala Ala Leu Lys Asp Ser Glu
                        165                 170                 175
Val Glu Ala Ala Leu Ser Leu Lys Asn Ile Lys Tyr Thr Asp Gly Lys
                180                 185                 190
Tyr Tyr Tyr Val Asn Glu Asp Gly Ser His Lys Glu Asn Phe Ala Ile
            195                 200                 205
Thr Val Asn Gly Gln Leu Leu Tyr Phe Gly Lys Asp Gly Ala Leu Thr
        210                 215                 220
Ser Ser Ser Thr His Ser Phe Thr Pro Gly Thr Thr Asn Ile Val Asp
225                 230                 235                 240
Gly Phe Ser Ile Asn Asn Arg Ala Tyr Asp Ser Ser Glu Ala Ser Phe
                        245                 250                 255
Glu Leu Ile Asn Gly Tyr Leu Thr Ala Asp Ser Trp Tyr Arg Pro Val
                260                 265                 270
Ser Ile Ile Lys Asp Gly Val Thr Trp Gln Ala Ser Thr Ala Glu Asp
            275                 280                 285
Phe Arg Pro Leu Leu Met Ala Trp Trp Pro Asn Val Asp Thr Gln Val
        290                 295                 300
Asn Tyr Leu Asn Tyr Met Ser Lys Val Phe Asn Leu Glu Ala Lys Tyr
305                 310                 315                 320
Thr Ser Thr Asp Lys Gln Ala Asp Leu Asn Arg Ala Ala Lys Asp Ile
                        325                 330                 335
Gln Val Lys Ile Glu Gln Lys Ile Gln Ala Glu Lys Ser Thr Gln Trp
                340                 345                 350
Leu Arg Glu Thr Ile Ser Ala Phe Val Lys Thr Gln Pro Gln Trp Asn
            355                 360                 365
Lys Glu Thr Glu Asn Tyr Ser Lys Gly Gly Gly Glu Asp His Leu Gln
        370                 375                 380
Gly Gly Ala Leu Leu Tyr Val Asn Asp Ser Arg Thr Pro Trp Ala Asn
385                 390                 395                 400
Ser Asn Tyr Arg Leu Leu Asn Arg Thr Ala Thr Asn Gln Thr Gly Thr
                        405                 410                 415
Ile Asn Lys Ser Val Leu Asp Glu Gln Ser Asp Pro Asn His Met Gly
                420                 425                 430
Gly Phe Asp Phe Leu Leu Ala Asn Asp Val Asp Leu Ser Asn Pro Val
            435                 440                 445
Val Gln Ala Glu Gln Leu Asn Gln Ile His Tyr Leu Met Asn Trp Gly
        450                 455                 460
Ser Ile Val Met Gly Asp Lys Asp Ala Asn Phe Asp Gly Ile Arg Val
465                 470                 475                 480
Asp Ala Val Asp Asn Val Asn Ala Asp Met Leu Gln Leu Tyr Thr Asn
                        485                 490                 495
Tyr Phe Arg Glu Tyr Tyr Gly Val Asn Lys Ser Glu Ala Gln Ala Leu
                500                 505                 510
Ala His Ile Ser Val Leu Glu Ala Trp Ser Leu Asn Asp Asn His Tyr
            515                 520                 525
Asn Asp Lys Thr Asp Gly Ala Ala Leu Ala Met Glu Asn Lys Gln Arg
        530                 535                 540
```

```
Leu Ala Leu Leu Phe Ser Leu Ala Lys Pro Ile Lys Asp Arg Thr Pro
545                 550                 555                 560

Ala Val Ser Pro Leu Tyr Asn Asn Thr Phe Asn Thr Thr Gln Arg Asp
                565                 570                 575

Phe Lys Thr Asp Trp Ile Asn Lys Asp Gly Ser Thr Ala Tyr Asn Glu
            580                 585                 590

Asp Gly Thr Ala Lys Gln Ser Thr Ile Gly Lys Tyr Asn Glu Lys Tyr
        595                 600                 605

Gly Asp Ala Ser Gly Asn Tyr Val Phe Ile Arg Ala His Asp Asn Asn
    610                 615                 620

Val Gln Asp Ile Ile Ala Glu Ile Ile Lys Lys Glu Ile Asn Lys Lys
625                 630                 635                 640

Ser Asp Gly Phe Thr Ile Ser Asp Ser Glu Met Lys Gln Ala Phe Glu
                645                 650                 655

Ile Tyr Asn Lys Asp Met Leu Ser Ser Asn Lys Lys Tyr Thr Leu Asn
                660                 665                 670

Asn Ile Pro Ala Ala Tyr Ala Val Met Leu Gln Asn Met Glu Thr Ile
            675                 680                 685

Thr Arg Val Tyr Tyr Gly Asp Leu Tyr Thr Asp Gly His Tyr Met
690                 695                 700

Glu Thr Lys Ser Pro Tyr His Asp Thr Ile Val Asn Leu Met Lys Asn
705                 710                 715                 720

Arg Ile Lys Tyr Val Ser Gly Gln Ala Gln Arg Ser Tyr Trp Leu
                725                 730                 735

Pro Thr Asp Gly Lys Met Asp Asn Ser Asp Val Glu Leu Tyr Arg Thr
            740                 745                 750

Ser Glu Val Tyr Thr Ser Val Arg Tyr Gly Lys Asp Ile Met Thr Ala
        755                 760                 765

Asp Asp Thr Glu Gly Ser Lys Tyr Ser Arg Thr Ser Gly Gln Val Thr
    770                 775                 780

Leu Val Val Asn Asn Pro Lys Leu Thr Leu His Glu Ser Ala Lys Leu
785                 790                 795                 800

Asn Val Glu Met Gly Lys Ile His Ala Asn Gln Lys Tyr Arg Ala Leu
                805                 810                 815

Ile Val Gly Thr Ala Asp Gly Ile Lys Asn Phe Thr Ser Asp Ala Glu
                820                 825                 830

Ala Ile Ala Ala Gly Tyr Val Lys Glu Thr Asp Ser Asn Gly Val Leu
            835                 840                 845

Thr Phe Gly Ala Asn Asp Ile Lys Gly Tyr Glu Thr Phe Asp Met Ser
850                 855                 860

Gly Phe Val Ala Val Trp Val Pro Val Gly Ala Ser Asp Asp Gln Asp
865                 870                 875                 880

Ile Arg Val Ala Pro Ser Thr Glu Ala Lys Lys Glu Gly Glu Leu Thr
                885                 890                 895

Leu Lys Ala Thr Glu Ala Tyr Asp Ser Gln Leu Ile Tyr Glu Gly Phe
                900                 905                 910

Ser Asn Phe Gln Thr Ile Pro Asp Gly Ser Asp Pro Ser Val Tyr Thr
            915                 920                 925

Asn Arg Lys Ile Ala Glu Asn Val Asp Leu Phe Lys Ser Trp Gly Val
        930                 935                 940

Thr Ser Phe Glu Met Ala Pro Gln Phe Val Ser Ala Asp Asp Gly Thr
945                 950                 955                 960
```

-continued

```
Phe Leu Asp Ser Val Ile Gln Asn Gly Tyr Ala Phe Ala Asp Arg Tyr
                965                 970                 975

Asp Leu Ala Met Ser Lys Asn Asn Lys Tyr Gly Ser Lys Glu Asp Leu
        980                 985                 990

Arg Asp Ala Leu Lys Ala Leu His  Lys Ala Gly Ile Gln  Ala Ile Ala
        995                 1000                1005

Asp Trp Val Pro Asp Gln Ile  Tyr Gln Leu Pro Gly  Lys Glu Val
       1010                 1015                1020

Val Thr Ala Thr Arg Thr Asp  Gly Ala Gly Arg Lys  Ile Ala Asp
       1025                 1030                1035

Ala Ile Ile Asp His Ser Leu  Tyr Val Ala Asn Ser  Lys Ser Ser
       1040                 1045                1050

Gly Arg Asp Tyr Gln Ala Gln  Tyr Gly Gly Glu Phe  Leu Ala Glu
       1055                 1060                1065

Leu Lys Ala Lys Tyr Pro Lys  Met Phe Thr Glu Asn  Met Ile Ser
       1070                 1075                1080

Thr Gly Lys Pro Ile Asp Asp  Ser Val Lys Leu Lys  Gln Trp Lys
       1085                 1090                1095

Ala Lys Tyr Phe Asn Gly Thr  Asn Val Leu Asp Arg  Gly Val Gly
       1100                 1105                1110

Tyr Val Leu Ser Asp Glu Ala  Thr Gly Lys Tyr Phe  Thr Val Thr
       1115                 1120                1125

Lys Glu Gly Asn Phe Ile Pro  Leu Gln Leu Thr Gly  Asn Glu Lys
       1130                 1135                1140

Ala Val Thr Gly Phe Ser Asn  Asp Gly Lys Gly Ile  Thr Tyr Phe
       1145                 1150                1155

Gly Thr Ser Gly Asn Gln Ala  Lys Ser Ala Phe Val  Thr Phe Asn
       1160                 1165                1170

Gly Asn Thr Tyr Tyr Phe Asp  Ala Arg Gly His Met  Val Thr Asn
       1175                 1180                1185

Gly Glu Tyr Ser Pro Asn Gly  Lys Asp Val Tyr Arg  Phe Leu Pro
       1190                 1195                1200

Asn Gly Ile Met Leu Ser Asn  Ala Phe Tyr Val Asp  Ala Asn Gly
       1205                 1210                1215

Asn Thr Tyr Leu Tyr Asn Tyr  Lys Gly Gln Met Tyr  Lys Gly Gly
       1220                 1225                1230

Tyr Thr Lys Phe Asp Val Thr  Glu Thr Asp Lys Asp  Gly Asn Glu
       1235                 1240                1245

Ser Lys Val Val Lys Phe Arg  Tyr Phe Thr Asn Glu  Gly Val Met
       1250                 1255                1260

Ala Lys Gly Leu Thr Val Ile  Asp Gly Ser Thr Gln  Tyr Phe Gly
       1265                 1270                1275

Glu Asp Gly Phe Gln Thr Lys  Asp Lys Leu Ala Thr  Tyr Lys Gly
       1280                 1285                1290

Lys Thr Tyr Tyr Phe Glu Ala  His Thr Gly Asn Ala  Ile Lys Asn
       1295                 1300                1305

Thr Trp Arg Asn Ile Asp Gly  Lys Trp Tyr His Phe  Asp Glu Asn
       1310                 1315                1320

Gly Val Ala Ala Thr Gly Ala  Gln Val Ile Asn Gly  Gln Lys Leu
       1325                 1330                1335

Tyr Phe Asn Glu Asp Gly Ser  Gln Val Lys Gly Gly  Val Val Lys
       1340                 1345                1350

Asn Ala Asp Gly Thr Tyr Ser  Lys Tyr Lys Glu Gly  Ser Gly Glu
```

Leu Val Thr Asn Glu Phe Phe Thr Thr Asp Gly Asn Val Trp Tyr
1370                1375                1380

Tyr Ala Gly Ala Asp Gly Lys Thr Val Thr Gly Ala Gln Val Ile
    1385                1390                1395

Asn Gly Gln His Leu Tyr Phe Lys Glu Asp Gly Ser Gln Val Lys
1400                1405                1410

Gly Gly Val Val Lys Asn Ala Asp Gly Thr Tyr Ser Lys Tyr Asp
    1415                1420                1425

Ala Ala Thr Gly Glu Arg Leu Thr Asn Glu Phe Phe Thr Thr Gly
1430                1435                1440

Asp Asn Asn Trp Tyr Tyr Ile Gly Ser Asn Gly Lys Thr Val Thr
    1445                1450                1455

Gly Glu Val Lys Ile Gly Ala Asp Thr Tyr Tyr Phe Ala Lys Asp
1460                1465                1470

Gly Lys Gln Val Lys Gly Gln Thr Val Thr Ala Gly Asn Gly Arg
    1475                1480                1485

Ile Ser Tyr Tyr Tyr Gly Asp Ser Gly Lys Lys Ala Ile Ser Thr
1490                1495                1500

Trp Ile Glu Ile Gln Pro Gly Ile Tyr Val Tyr Phe Asp Lys Thr
    1505                1510                1515

Gly Ile Ala Tyr Pro Pro Arg Val Leu Asn
1520                1525

<210> SEQ ID NO 62
<211> LENGTH: 1518
<212> TYPE: PRT
<213> ORGANISM: Streptococcus salivarius SK126

<400> SEQUENCE: 62

Met Glu Asn Lys Ile His Tyr Lys Leu His Lys Val Lys Lys Gln Trp
1               5                   10                  15

Val Thr Ile Ala Val Ala Ser Val Ala Leu Ala Thr Val Leu Gly Gly
                20                  25                  30

Leu Ser Val Thr Thr Ser Ser Val Ser Ala Asp Glu Thr Gln Asp Lys
            35                  40                  45

Thr Val Thr Gln Ser Asn Ser Gly Thr Thr Ala Ser Leu Val Thr Ser
        50                  55                  60

Pro Glu Ala Thr Lys Glu Ala Asp Lys Arg Thr Asn Thr Lys Glu Ala
65                  70                  75                  80

Asp Val Leu Thr Pro Ala Lys Glu Thr Asn Ala Val Glu Thr Ala Thr
                85                  90                  95

Thr Thr Asn Thr Gln Ala Thr Ala Glu Ala Ala Thr Ala Thr Thr
            100                 105                 110

Ala Asp Val Ala Val Ala Val Pro Asn Lys Glu Ala Val Val Thr
        115                 120                 125

Thr Asp Ala Pro Ala Val Thr Thr Glu Lys Ala Glu Glu Gln Pro Ala
130                 135                 140

Thr Val Lys Ala Glu Val Val Asn Thr Glu Val Lys Ala Pro Glu Ala
145                 150                 155                 160

Ala Leu Lys Asp Ser Glu Val Glu Ala Ala Leu Ser Leu Lys Asn Ile
                165                 170                 175

Lys Asn Ile Asp Gly Lys Tyr Tyr Tyr Val Asn Glu Asp Gly Ser His
            180                 185                 190

```
Lys Glu Asn Phe Ala Ile Thr Val Asn Gly Gln Leu Leu Tyr Phe Gly
            195                 200                 205

Lys Asp Gly Ala Leu Thr Ser Ser Thr Tyr Ser Phe Thr Pro Gly
            210                 215                 220

Thr Thr Asn Ile Val Asp Gly Phe Ser Ile Asn Asn Arg Ala Tyr Asp
225                 230                 235                 240

Ser Ser Glu Ala Ser Phe Glu Leu Ile Asp Gly Tyr Leu Thr Ala Asp
                245                 250                 255

Ser Trp Tyr Arg Pro Ala Ser Ile Ile Lys Asp Gly Val Thr Trp Gln
                260                 265                 270

Ala Ser Thr Ala Glu Asp Phe Arg Pro Leu Leu Met Ala Trp Trp Pro
            275                 280                 285

Asn Val Asp Thr Gln Val Asn Tyr Leu Asn Tyr Met Ser Lys Val Phe
            290                 295                 300

Asn Leu Asp Ala Lys Tyr Ser Ser Thr Asp Lys Gln Glu Thr Leu Lys
305                 310                 315                 320

Val Ala Ala Lys Asp Ile Gln Ile Lys Ile Glu Gln Lys Ile Gln Ala
                325                 330                 335

Glu Lys Ser Thr Gln Trp Leu Arg Glu Thr Ile Ser Ala Phe Val Lys
            340                 345                 350

Thr Gln Pro Gln Trp Asn Lys Glu Thr Glu Asn Tyr Ser Lys Gly Gly
            355                 360                 365

Gly Glu Asp His Leu Gln Gly Gly Ala Leu Leu Tyr Val Asn Asp Ser
            370                 375                 380

Arg Thr Pro Trp Ala Asn Ser Asp Tyr Arg Arg Leu Asn Arg Thr Ala
385                 390                 395                 400

Thr Asn Gln Thr Gly Thr Ile Asp Lys Ser Ile Leu Asp Glu Gln Ser
                405                 410                 415

Asp Pro Asn His Met Gly Gly Phe Asp Phe Leu Leu Ala Asn Asp Val
                420                 425                 430

Asp Leu Ser Asn Pro Val Val Gln Ala Glu Gln Leu Asn Gln Ile His
            435                 440                 445

Tyr Leu Met Asn Trp Gly Ser Ile Val Met Gly Asp Lys Asp Ala Asn
450                 455                 460

Phe Asp Gly Ile Arg Val Asp Ala Val Asp Asn Val Asp Ala Asp Met
465                 470                 475                 480

Leu Gln Leu Tyr Thr Asn Tyr Phe Arg Glu Tyr Tyr Gly Val Asn Lys
                485                 490                 495

Ser Glu Ala Asn Ala Leu Ala His Ile Ser Val Leu Glu Ala Trp Ser
            500                 505                 510

Leu Asn Asp Asn His Tyr Asn Asp Lys Thr Asp Gly Ala Ala Leu Ala
            515                 520                 525

Met Glu Asn Lys Gln Arg Leu Ala Leu Leu Phe Ser Leu Ala Lys Pro
530                 535                 540

Ile Lys Glu Arg Thr Pro Ala Val Ser Pro Leu Tyr Asn Asn Thr Phe
545                 550                 555                 560

Asn Thr Thr Gln Arg Asp Glu Lys Thr Asp Trp Ile Asn Lys Asp Gly
                565                 570                 575

Ser Lys Ala Tyr Asn Glu Asp Gly Thr Val Lys Gln Ser Thr Ile Gly
            580                 585                 590

Lys Tyr Asn Glu Lys Tyr Gly Asp Ala Ser Gly Asn Tyr Val Phe Ile
            595                 600                 605

Arg Ala His Asp Asn Asn Val Gln Asp Ile Ile Ala Glu Ile Ile Lys
```

```
                610                 615                 620
Lys Glu Ile Asn Pro Lys Ser Asp Gly Phe Thr Ile Thr Asp Ala Glu
625                 630                 635                 640

Met Lys Gln Ala Phe Glu Ile Tyr Asn Lys Asp Met Leu Ser Ser Asp
                645                 650                 655

Lys Lys Tyr Thr Leu Asn Asn Ile Pro Ala Ala Tyr Ala Val Met Leu
                    660                 665                 670

Gln Asn Met Glu Thr Ile Thr Arg Val Tyr Tyr Gly Asp Leu Tyr Thr
                675                 680                 685

Asp Asp Gly His Tyr Met Glu Thr Lys Ser Pro Tyr Tyr Asp Thr Ile
                690                 695                 700

Val Asn Leu Met Lys Ser Arg Ile Lys Tyr Val Ser Gly Gly Gln Ala
705                 710                 715                 720

Gln Arg Ser Tyr Trp Leu Pro Thr Asp Gly Lys Met Asp Asn Ser Asp
                725                 730                 735

Val Glu Leu Tyr Arg Thr Asn Glu Val Tyr Thr Ser Val Arg Tyr Gly
                    740                 745                 750

Lys Asp Ile Met Thr Ala Asn Asp Thr Glu Gly Ser Lys Tyr Ser Arg
                755                 760                 765

Thr Ser Gly Gln Val Thr Leu Val Ala Asn Asn Pro Lys Leu Thr Leu
770                 775                 780

Asp Gln Ser Ala Lys Leu Asn Val Glu Met Gly Lys Ile His Ala Asn
785                 790                 795                 800

Gln Lys Tyr Arg Ala Leu Ile Val Gly Thr Ala Asp Gly Ile Lys Asn
                805                 810                 815

Phe Thr Ser Asp Ala Asp Ala Ile Ala Ala Gly Tyr Val Lys Glu Thr
                820                 825                 830

Asp Ser Asn Gly Val Leu Thr Phe Gly Ala Asn Asp Ile Lys Gly Tyr
                835                 840                 845

Glu Thr Phe Asp Met Ser Gly Phe Val Ala Val Trp Val Pro Val Gly
                850                 855                 860

Ala Ser Asp Asp Gln Asp Ile Arg Val Ala Pro Ser Thr Glu Ala Lys
865                 870                 875                 880

Lys Glu Gly Glu Leu Thr Leu Lys Ala Thr Glu Ala Tyr Asp Ser Gln
                    885                 890                 895

Leu Ile Tyr Glu Gly Phe Ser Asn Phe Gln Thr Ile Pro Asp Gly Ser
                900                 905                 910

Asp Pro Ser Val Tyr Thr Asn Arg Lys Ile Ala Glu Asn Val Asp Leu
                915                 920                 925

Phe Lys Ser Trp Gly Val Thr Ser Phe Glu Met Ala Pro Gln Phe Val
930                 935                 940

Ser Ala Asp Asp Gly Thr Phe Leu Asp Ser Val Ile Gln Asn Gly Tyr
945                 950                 955                 960

Ala Phe Ala Asp Arg Tyr Asp Leu Ala Met Ser Lys Asn Asn Lys Tyr
                965                 970                 975

Gly Ser Lys Glu Asp Leu Arg Asp Ala Leu Lys Ala Leu His Lys Ala
                980                 985                 990

Gly Ile Gln Ala Ile Ala Asp Trp Val Pro Asp Gln Ile Tyr Gln Leu
                995                 1000                1005

Pro Gly Lys Glu Val Val Thr Ala Thr Arg Thr Asp Gly Ala Gly
    1010                1015                1020

Arg Lys Ile Ala Asp Ala Ile Ile Asp His Ser Leu Tyr Val Ala
    1025                1030                1035
```

-continued

```
Asn Thr Lys Ser Ser Gly Lys Asp Tyr Gln Ala Lys Tyr Gly Gly
    1040            1045                1050

Glu Phe Leu Ala Glu Leu Lys Ala Lys Tyr Pro Glu Met Phe Lys
    1055            1060                1065

Val Asn Met Ile Ser Thr Gly Lys Pro Ile Asp Asp Ser Val Lys
    1070            1075                1080

Leu Lys Gln Trp Lys Ala Glu Tyr Phe Asn Gly Thr Asn Val Leu
    1085            1090                1095

Glu Arg Gly Val Gly Tyr Val Leu Ser Asp Glu Ala Thr Gly Lys
    1100            1105                1110

Tyr Phe Thr Val Thr Lys Asp Gly Asn Phe Ile Pro Leu Gln Leu
    1115            1120                1125

Thr Gly Asn Glu Lys Val Val Thr Gly Phe Ser Asn Asp Gly Lys
    1130            1135                1140

Gly Ile Thr Tyr Phe Gly Thr Ser Gly Thr Gln Ala Lys Ser Ala
    1145            1150                1155

Phe Val Thr Phe Asn Gly Asn Thr Tyr Tyr Phe Asp Ala Arg Gly
    1160            1165                1170

His Met Val Thr Asn Gly Glu Tyr Ser Pro Asn Gly Lys Asp Val
    1175            1180                1185

Tyr Arg Phe Leu Pro Asn Gly Ile Met Leu Ser Asn Ala Phe Tyr
    1190            1195                1200

Val Asp Ala Asn Gly Asn Thr Tyr Leu Tyr Asn Ser Lys Gly Gln
    1205            1210                1215

Met Tyr Lys Gly Gly Tyr Thr Lys Phe Asp Val Thr Glu Thr Asp
    1220            1225                1230

Lys Asp Gly Lys Glu Ser Lys Val Val Lys Phe Arg Tyr Phe Thr
    1235            1240                1245

Asn Glu Gly Val Met Ala Lys Gly Val Thr Val Ile Asp Gly Phe
    1250            1255                1260

Thr Gln Tyr Phe Gly Glu Asp Gly Phe Gln Ala Lys Asp Lys Leu
    1265            1270                1275

Val Thr Phe Lys Gly Lys Thr Tyr Tyr Phe Asp Ala His Thr Gly
    1280            1285                1290

Asn Ala Ile Lys Asp Thr Trp Arg Asn Ile Asn Gly Lys Trp Tyr
    1295            1300                1305

His Phe Asp Ala Asn Gly Val Ala Ala Thr Gly Ala Gln Val Ile
    1310            1315                1320

Asn Gly Gln Lys Leu Tyr Phe Asn Glu Asp Gly Ser Gln Val Lys
    1325            1330                1335

Gly Gly Val Val Lys Asn Ala Asp Gly Thr Tyr Ser Lys Tyr Lys
    1340            1345                1350

Glu Gly Ser Gly Glu Leu Val Thr Asn Glu Phe Phe Thr Thr Asp
    1355            1360                1365

Gly Asn Val Trp Tyr Tyr Ala Gly Ala Asn Gly Lys Thr Val Thr
    1370            1375                1380

Gly Ala Gln Val Ile Asn Gly Gln His Leu Tyr Phe Asn Ala Asp
    1385            1390                1395

Gly Ser Gln Val Lys Gly Gly Val Val Lys Asn Ala Asp Gly Thr
    1400            1405                1410

Tyr Ser Lys Tyr Asp Ala Ser Thr Gly Glu Arg Leu Thr Asn Glu
    1415            1420                1425
```

-continued

```
Phe Phe Thr Thr Gly Asp Asn Asn Trp Tyr Tyr Ile Gly Ala Asn
    1430                1435                1440

Gly Lys Ser Val Thr Gly Glu Val Lys Ile Gly Asp Asp Thr Tyr
    1445                1450                1455

Phe Phe Ala Lys Asp Gly Lys Gln Val Lys Gly Gln Thr Val Ser
    1460                1465                1470

Ala Gly Asn Gly Arg Ile Ser Tyr Tyr Gly Asp Ser Gly Lys
    1475                1480                1485

Arg Ala Val Ser Thr Trp Ile Glu Ile Gln Pro Gly Val Tyr Val
    1490                1495                1500

Tyr Phe Asp Lys Asn Gly Ile Ala Tyr Pro Pro Arg Val Leu Asn
    1505                1510                1515

<210> SEQ ID NO 63
<211> LENGTH: 1431
<212> TYPE: PRT
<213> ORGANISM: Streptococcus salivarius PS4

<400> SEQUENCE: 63

Met Thr Lys Glu Thr Asn Thr Val Asp Ala Thr Thr Asn Thr
1               5                   10                  15

Gln Ala Ala Asp Ala Ala Thr Lys Thr Ala Asp Ala Ala Val Thr
            20                  25                  30

Ala Leu Pro Asn Lys Glu Ala Val Val Thr Thr Asp Ala Pro Ala Val
            35                  40                  45

Thr Thr Glu Lys Ala Ala Glu Gln Pro Ala Thr Val Lys Ser Glu Val
    50                  55                  60

Val Asn Thr Glu Val Lys Ala Pro Glu Ala Ala Leu Lys Asp Ser Glu
65                  70                  75                  80

Val Glu Ala Ala Leu Ser Leu Lys Asn Ile Lys Asn Ile Asp Gly Lys
                85                  90                  95

Tyr Tyr Tyr Val Asn Lys Asp Gly Ser His Lys Glu Asn Phe Ala Ile
            100                 105                 110

Thr Val Asn Gly Gln Leu Leu Tyr Phe Gly Lys Asp Gly Ala Leu Thr
        115                 120                 125

Ser Ser Ser Thr Tyr Ser Phe Thr Gln Gly Thr Thr Asn Ile Val Asp
    130                 135                 140

Gly Phe Ser Lys Asn Asn Arg Ala Tyr Asp Ser Ser Glu Ala Ser Phe
145                 150                 155                 160

Glu Leu Ile Asp Gly Tyr Leu Thr Ala Asp Ser Trp Tyr Arg Pro Val
                165                 170                 175

Ser Ile Ile Lys Asp Gly Val Thr Trp Gln Ala Ser Thr Lys Glu Asp
            180                 185                 190

Phe Arg Pro Leu Leu Met Ala Trp Trp Pro Asn Val Asp Thr Gln Val
        195                 200                 205

Asn Tyr Leu Asn Tyr Met Ser Lys Val Phe Asn Leu Asp Ala Lys Tyr
    210                 215                 220

Thr Ser Thr Asp Lys Gln Val Asp Leu Asn Arg Ala Ala Lys Asp Ile
225                 230                 235                 240

Gln Val Lys Ile Glu Gln Lys Ile Gln Ala Gly Lys Ser Thr Gln Trp
                245                 250                 255

Leu Arg Glu Ala Ile Ser Ala Phe Val Lys Thr Gln Pro Gln Trp Asn
            260                 265                 270

Lys Glu Thr Glu Asn Phe Ser Lys Gly Gly Gly Glu Asp His Leu Gln
        275                 280                 285
```

```
Gly Gly Ala Leu Leu Tyr Val Asn Asp Pro Arg Thr Pro Trp Ala Asn
        290                 295                 300

Ser Asn Tyr Arg Leu Leu Asn Arg Thr Ala Thr Asn Gln Thr Gly Thr
305                 310                 315                 320

Ile Asp Lys Ser Val Leu Asp Glu Gln Ser Asp Pro Asn His Met Gly
                325                 330                 335

Gly Phe Asp Phe Leu Leu Ala Asn Asp Val Asp Thr Ser Asn Pro Val
            340                 345                 350

Val Gln Ala Glu Gln Leu Asn Gln Ile His Tyr Leu Met Asn Trp Gly
        355                 360                 365

Ser Ile Val Met Gly Asp Lys Asp Ala Asn Phe Asp Gly Ile Arg Val
370                 375                 380

Asp Ala Val Asp Asn Val Asp Ala Asp Met Leu Gln Leu Tyr Thr Asn
385                 390                 395                 400

Tyr Phe Arg Glu Tyr Tyr Gly Val Asn Lys Ser Glu Ala Asn Ala Leu
                405                 410                 415

Ala His Ile Ser Val Leu Glu Ala Trp Ser Leu Asn Asp Asn His Tyr
                420                 425                 430

Asn Asp Lys Thr Asp Gly Ala Ala Leu Ala Met Glu Asn Lys Gln Arg
                435                 440                 445

Leu Ala Leu Leu Phe Ser Leu Ala Lys Pro Ile Lys Glu Arg Thr Pro
450                 455                 460

Ala Val Ser Pro Leu Tyr Asn Asn Thr Phe Asn Thr Thr Gln Arg Asp
465                 470                 475                 480

Glu Lys Thr Asp Trp Ile Asn Lys Asp Gly Ser Lys Ala Tyr Asn Glu
                485                 490                 495

Asp Gly Thr Val Lys Gln Ser Thr Ile Gly Lys Tyr Asn Glu Lys Tyr
                500                 505                 510

Gly Asp Ala Ser Gly Asn Tyr Val Phe Ile Arg Ala His Asp Asn Asn
                515                 520                 525

Val Gln Asp Ile Ile Ala Glu Ile Lys Lys Glu Ile Asn Pro Lys
        530                 535                 540

Ser Asp Gly Phe Thr Ile Thr Asp Ala Glu Met Lys Lys Ala Phe Glu
545                 550                 555                 560

Ile Tyr Asn Lys Asp Met Leu Ser Ser Asp Lys Lys Tyr Thr Leu Asn
                565                 570                 575

Asn Ile Pro Ala Ala Tyr Ala Val Met Leu Gln Asn Met Glu Thr Ile
                580                 585                 590

Thr Arg Val Tyr Tyr Gly Asp Leu Tyr Thr Asp Asp Gly His Tyr Met
        595                 600                 605

Glu Thr Lys Ser Pro Tyr Tyr Asp Thr Ile Val Asn Leu Met Lys Asn
        610                 615                 620

Arg Ile Lys Tyr Val Ser Gly Gln Ala Gln Arg Ser Tyr Trp Leu
625                 630                 635                 640

Pro Thr Asp Gly Lys Met Asp Lys Ser Asp Val Glu Leu Tyr Arg Thr
                645                 650                 655

Asn Glu Val Tyr Thr Ser Val Arg Tyr Gly Lys Asp Ile Met Thr Ala
                660                 665                 670

Asp Asp Thr Gln Gly Ser Lys Tyr Ser Arg Thr Ser Gly Gln Val Thr
            675                 680                 685

Leu Val Val Asn Asn Pro Lys Leu Ser Leu Asp Lys Ser Ala Lys Leu
        690                 695                 700
```

```
Asp Val Glu Met Gly Lys Ile His Ala Asn Gln Lys Tyr Arg Ala Leu
705                 710                 715                 720

Ile Val Gly Thr Pro Asn Gly Ile Lys Asn Phe Thr Ser Asp Ala Glu
            725                 730                 735

Ala Ile Ala Ala Gly Tyr Val Lys Glu Thr Asp Gly Asn Gly Val Leu
        740                 745                 750

Thr Phe Gly Ala Asn Asp Ile Lys Gly Tyr Glu Thr Phe Asp Met Ser
    755                 760                 765

Gly Phe Val Ala Val Trp Val Pro Val Gly Ala Ser Asp Asp Gln Asp
770                 775                 780

Ile Arg Val Ala Ala Ser Thr Ala Ala Lys Lys Glu Gly Glu Leu Thr
785                 790                 795                 800

Leu Lys Ala Thr Glu Ala Tyr Asp Ser Gln Leu Ile Tyr Glu Gly Phe
                805                 810                 815

Ser Asn Phe Gln Thr Ile Pro Asp Gly Ser Asp Pro Ser Val Tyr Thr
            820                 825                 830

Asn Arg Lys Ile Ala Glu Asn Val Asp Leu Phe Lys Ser Trp Gly Val
        835                 840                 845

Thr Ser Phe Glu Met Ala Pro Gln Phe Val Ser Ala Asp Asp Gly Thr
    850                 855                 860

Phe Leu Asp Ser Val Ile Gln Asn Gly Tyr Ala Phe Ala Asp Arg Tyr
865                 870                 875                 880

Asp Leu Ala Met Ser Lys Asn Asn Lys Tyr Gly Ser Lys Glu Asp Leu
                885                 890                 895

Arg Asn Ala Leu Lys Ala Leu His Lys Ala Gly Ile Gln Ala Ile Ala
            900                 905                 910

Asp Trp Val Pro Asp Gln Ile Tyr Gln Leu Pro Gly Lys Glu Val Val
        915                 920                 925

Thr Ala Thr Arg Thr Asp Gly Ala Gly Arg Lys Ile Ser Asp Ala Ile
    930                 935                 940

Ile Asp His Ser Leu Tyr Val Ala Asn Ser Lys Ser Ser Gly Lys Asp
945                 950                 955                 960

Tyr Gln Ala Lys Tyr Gly Gly Glu Phe Leu Ala Glu Leu Lys Ala Lys
                965                 970                 975

Tyr Pro Glu Met Phe Lys Val Asn Met Ile Ser Thr Gly Lys Pro Ile
            980                 985                 990

Asp Asp Ser Val Lys Leu Lys Gln  Trp Lys Ala Glu Tyr  Phe Asn Gly
        995                 1000                 1005

Thr Asn  Val Leu Asp Arg Gly  Val Gly Tyr Val Leu  Ser Asp Glu
    1010                 1015                 1020

Ala Thr  Gly Lys Tyr Phe  Val Thr Lys Glu Gly  Asn Phe Ile
    1025                 1030                 1035

Pro Leu  Gln Leu Lys Gly Asn  Glu Lys Val Ile Thr  Gly Phe Ser
    1040                 1045                 1050

Ser Asp  Gly Lys Gly Ile Thr  Tyr Phe Gly Thr Ser  Gly Asn Gln
    1055                 1060                 1065

Ala Lys  Ser Ala Phe Val Thr  Phe Asn Gly Asn Thr  Tyr Tyr Phe
    1070                 1075                 1080

Asp Ala  Arg Gly His Met Val  Thr Asn Gly Glu Tyr  Ser Pro Asn
    1085                 1090                 1095

Gly Lys  Asp Val Tyr Arg Phe  Leu Pro Asn Gly Ile  Met Leu Ser
    1100                 1105                 1110

Asn Ala  Phe Tyr Val Asp Gly  Asn Gly Asn Thr Tyr  Leu Tyr Asn
```

```
            1115                1120               1125

Ser Lys Gly Gln Met Tyr Lys Gly Gly Tyr Ser Lys Phe Asp Val
        1130                1135               1140

Thr Glu Thr Lys Asp Gly Lys Glu Ser Lys Val Val Lys Phe Arg
        1145                1150               1155

Tyr Phe Thr Asn Glu Gly Val Met Ala Lys Gly Val Thr Val Val
        1160                1165               1170

Asp Gly Phe Thr Gln Tyr Phe Asn Glu Asp Gly Ile Gln Ser Lys
        1175                1180               1185

Asp Glu Leu Val Thr Tyr Asn Gly Lys Thr Tyr Tyr Phe Glu Ala
        1190                1195               1200

His Thr Gly Asn Ala Ile Lys Asn Thr Trp Arg Asn Ile Lys Gly
        1205                1210               1215

Lys Trp Tyr His Phe Asp Ala Asn Gly Val Ala Ala Thr Gly Ala
        1220                1225               1230

Gln Val Ile Asn Gly Gln His Leu Tyr Phe Asn Glu Asp Gly Ser
        1235                1240               1245

Gln Val Lys Gly Gly Val Val Lys Asn Ala Asp Gly Thr Phe Ser
        1250                1255               1260

Lys Tyr Lys Asp Gly Ser Gly Asp Leu Val Val Asn Glu Phe Phe
        1265                1270               1275

Thr Thr Gly Asp Asn Val Trp Tyr Tyr Ala Gly Ala Asn Gly Lys
        1280                1285               1290

Thr Val Thr Gly Ala Gln Val Ile Asn Gly Gln His Leu Phe Phe
        1295                1300               1305

Lys Glu Asp Gly Ser Gln Val Lys Gly Asp Phe Val Lys Asn Ser
        1310                1315               1320

Asp Gly Thr Tyr Ser Lys Tyr Asp Ala Ala Ser Gly Glu Arg Leu
        1325                1330               1335

Thr Asn Glu Phe Phe Thr Gly Asp Asn His Trp Tyr Tyr Ile
        1340                1345               1350

Gly Ala Asn Gly Lys Thr Val Thr Gly Glu Val Lys Ile Gly Asp
        1355                1360               1365

Asp Thr Tyr Phe Phe Ala Lys Asp Gly Lys Gln Leu Lys Gly Gln
        1370                1375               1380

Ile Val Thr Thr Arg Ser Gly Arg Ile Ser Tyr Tyr Phe Gly Asp
        1385                1390               1395

Ser Gly Lys Lys Ala Ile Ser Thr Trp Val Glu Ile Gln Pro Gly
        1400                1405               1410

Val Phe Val Phe Phe Asp Lys Asn Gly Leu Ala Tyr Pro Pro Glu
        1415                1420               1425

Asn Met Asn
        1430

<210> SEQ ID NO 64
<211> LENGTH: 1532
<212> TYPE: PRT
<213> ORGANISM: unknown
<220> FEATURE:
<223> OTHER INFORMATION: unknown Streptococcus sp. C150

<400> SEQUENCE: 64

Met Glu Asn Lys Val His Tyr Lys Leu His Lys Val Lys Lys Gln Trp
1               5                   10                  15

Val Thr Ile Ala Val Ala Ser Ala Ala Leu Ala Thr Val Val Gly Gly
```

```
                20                  25                  30
Leu Ser Ala Thr Thr Ser Ser Val Ser Ala Asp Glu Thr Gln Asp Lys
            35                  40                  45
Thr Val Thr Gln Pro Asn Ser Asp Thr Thr Ala Asp Leu Val Thr Ser
        50                  55                  60
Thr Glu Ala Thr Lys Glu Val Asp Lys Arg Thr Asn Thr Lys Glu Ala
65                  70                  75                  80
Asp Val Leu Thr Pro Ala Lys Glu Thr Asn Thr Val Glu Thr Ala Ala
                85                  90                  95
Thr Thr Asn Thr Gln Ala Thr Ala Glu Ala Lys Thr Ala Thr Thr
            100                 105                 110
Thr Asn Thr Gln Ala Thr Ala Glu Val Ala Lys Thr Ala Thr Thr Ala
        115                 120                 125
Asp Val Ala Val Ala Ala Val Pro Asn Lys Glu Ala Val Val Thr Thr
            130                 135                 140
Asp Ala Pro Ala Val Thr Thr Glu Lys Ala Glu Glu Pro Ala Thr
145                 150                 155                 160
Val Lys Ala Glu Val Val Asn Thr Glu Val Lys Ala Pro Glu Ala Ala
                165                 170                 175
Leu Lys Asp Ser Glu Val Glu Ala Ala Leu Ser Leu Lys Asn Ile Lys
            180                 185                 190
Asn Ile Asp Gly Lys Tyr Tyr Val Asn Glu Asp Gly Ser His Lys
        195                 200                 205
Glu Asn Phe Ala Ile Thr Val Asn Gly Gln Leu Leu Tyr Phe Gly Lys
    210                 215                 220
Asp Gly Ala Leu Thr Ser Ser Thr Tyr Ser Phe Thr Gln Gly Thr
225                 230                 235                 240
Thr Asn Ile Val Asp Gly Phe Ser Ile Asn Asn Arg Ala Tyr Asp Ser
                245                 250                 255
Ser Glu Ala Ser Phe Glu Leu Ile Asp Gly Tyr Leu Thr Ala Asp Ser
            260                 265                 270
Trp Tyr Arg Pro Ala Ser Ile Ile Lys Asp Gly Val Thr Trp Gln Ala
        275                 280                 285
Ser Thr Ala Glu Asp Phe Arg Pro Leu Leu Met Ala Trp Trp Pro Asn
    290                 295                 300
Val Asp Thr Gln Val Asn Tyr Leu Asn Tyr Met Ser Lys Val Phe Asn
305                 310                 315                 320
Leu Asp Ala Lys Tyr Ser Ser Thr Asp Lys Gln Glu Thr Leu Lys Val
                325                 330                 335
Ala Ala Lys Asp Ile Gln Ile Lys Ile Glu Gln Lys Ile Gln Ala Glu
            340                 345                 350
Lys Ser Thr Gln Trp Leu Arg Glu Thr Ile Ser Ala Phe Val Lys Thr
        355                 360                 365
Gln Pro Gln Trp Asn Lys Glu Thr Glu Asn Tyr Ser Lys Gly Gly Gly
    370                 375                 380
Glu Asp His Leu Gln Gly Gly Ala Leu Leu Tyr Val Asn Asp Ser Arg
385                 390                 395                 400
Thr Pro Trp Ala Asn Ser Asn Tyr Arg Leu Leu Asn Arg Thr Ala Thr
                405                 410                 415
Asn Gln Thr Gly Thr Ile Asp Lys Ser Ile Leu Asp Glu Gln Ser Asp
            420                 425                 430
Pro Asn His Met Gly Gly Phe Asp Phe Leu Leu Ala Asn Asp Val Asp
        435                 440                 445
```

```
Leu Ser Asn Pro Val Val Gln Ala Glu Gln Leu Asn Gln Ile His Tyr
    450                 455                 460
Leu Met Asn Trp Gly Ser Ile Val Met Gly Asp Lys Asp Ala Asn Phe
465                 470                 475                 480
Asp Gly Ile Arg Val Asp Ala Val Asp Asn Val Asp Ala Asp Met Leu
                485                 490                 495
Gln Leu Tyr Thr Asn Tyr Phe Arg Glu Tyr Tyr Gly Val Asn Lys Ser
                500                 505                 510
Glu Ala Asn Ala Leu Ala His Ile Ser Val Leu Glu Ala Trp Ser Leu
                515                 520                 525
Asn Asp Asn His Tyr Asn Asp Lys Thr Asp Val Ala Ala Leu Ala Met
530                 535                 540
Glu Asn Lys Gln Arg Leu Ala Leu Leu Phe Ser Leu Ala Lys Pro Ile
545                 550                 555                 560
Lys Glu Arg Thr Pro Ala Val Ser Pro Leu Tyr Asn Asn Thr Phe Asn
                565                 570                 575
Thr Thr Gln Arg Asp Glu Lys Thr Asp Trp Ile Asn Lys Asp Gly Ser
            580                 585                 590
Lys Ala Tyr Asn Glu Asp Gly Thr Val Lys Lys Ser Thr Ile Gly Lys
        595                 600                 605
Tyr Asn Glu Lys Tyr Gly Asp Ala Ser Gly Asn Tyr Val Phe Ile Arg
    610                 615                 620
Ala His Asp Asn Asn Val Gln Asp Ile Ile Ala Glu Ile Ile Lys Lys
625                 630                 635                 640
Glu Ile Asn Glu Lys Ser Asp Gly Phe Thr Ile Thr Asp Ser Glu Met
                645                 650                 655
Lys Arg Ala Phe Glu Ile Tyr Asn Lys Asp Met Leu Ser Asn Asp Lys
            660                 665                 670
Lys Tyr Thr Leu Asn Asn Ile Pro Ala Ala Tyr Ala Val Met Leu Gln
        675                 680                 685
Asn Met Glu Thr Ile Thr Arg Val Tyr Tyr Gly Asp Leu Tyr Thr Asp
    690                 695                 700
Asp Gly Asn Tyr Met Glu Ala Lys Ser Pro Tyr Tyr Asp Thr Ile Val
705                 710                 715                 720
Asn Leu Met Lys Ser Arg Ile Lys Tyr Val Ser Gly Gly Gln Ala Gln
                725                 730                 735
Arg Ser Tyr Trp Leu Pro Thr Asp Gly Lys Met Asp Lys Ser Asp Val
            740                 745                 750
Glu Leu Tyr Arg Thr Asn Glu Val Tyr Thr Ser Val Arg Tyr Gly Lys
        755                 760                 765
Asp Ile Met Thr Ala Asp Thr Gln Gly Ser Lys Tyr Ser Arg Thr
    770                 775                 780
Ser Gly Gln Val Thr Leu Val Val Asn Asn Pro Lys Leu Thr Leu Asp
785                 790                 795                 800
Gln Ser Ala Lys Leu Asn Val Val Met Gly Lys Ile His Ala Asn Gln
                805                 810                 815
Lys Tyr Arg Ala Leu Ile Val Gly Thr Pro Asn Gly Ile Lys Asn Phe
            820                 825                 830
Thr Ser Asp Ala Glu Ala Ile Ala Ala Gly Tyr Val Lys Glu Thr Asp
        835                 840                 845
Gly Asn Gly Val Leu Thr Phe Gly Ala Asn Asp Ile Lys Gly Tyr Glu
    850                 855                 860
```

-continued

Thr Phe Asp Met Ser Gly Phe Val Ala Val Trp Val Pro Val Gly Ala
865                 870                 875                 880

Ser Asp Asp Gln Asp Ile Arg Val Ala Ser Thr Ala Ala Lys Lys
            885                 890                 895

Glu Gly Glu Leu Thr Leu Lys Ala Thr Glu Ala Tyr Asp Ser Gln Leu
            900                 905                 910

Ile Tyr Glu Gly Phe Ser Asn Phe Gln Thr Ile Pro Asp Gly Ser Asp
        915                 920                 925

Pro Ser Val Tyr Thr Asn Arg Lys Ile Ala Glu Asn Val Asp Leu Phe
    930                 935                 940

Lys Ser Trp Gly Val Thr Ser Phe Glu Met Ala Pro Gln Phe Val Ser
945                 950                 955                 960

Ala Asp Asp Gly Thr Phe Leu Asp Ser Val Ile Gln Asn Gly Tyr Ala
            965                 970                 975

Phe Ala Asp Arg Tyr Asp Leu Ala Met Ser Lys Asn Asn Lys Tyr Gly
        980                 985                 990

Ser Lys Glu Asp Leu Arg Asn Ala Leu Lys Ala Leu His Lys Ala Gly
            995                1000                1005

Ile Gln Ala Ile Ala Asp Trp Val Pro Asp Gln Ile Tyr Gln Leu
   1010                1015                1020

Pro Gly Lys Glu Val Val Thr Ala Thr Arg Thr Asp Gly Ala Gly
   1025                1030                1035

Arg Lys Ile Ser Asp Ala Ile Asp His Ser Leu Tyr Val Ala
   1040                1045                1050

Asn Ser Lys Ser Ser Gly Lys Asp Tyr Gln Ala Lys Tyr Gly Gly
   1055                1060                1065

Glu Phe Leu Ala Glu Leu Lys Ala Lys Tyr Pro Glu Met Phe Lys
   1070                1075                1080

Val Asn Met Ile Ser Thr Gly Lys Pro Ile Asp Asp Ser Val Lys
   1085                1090                1095

Leu Lys Gln Trp Lys Ala Glu Tyr Phe Asn Gly Thr Asn Val Leu
   1100                1105                1110

Asp Arg Gly Val Gly Tyr Val Leu Ser Asp Glu Ala Thr Gly Lys
   1115                1120                1125

Tyr Phe Thr Val Thr Lys Glu Gly Asn Phe Ile Pro Leu Gln Leu
   1130                1135                1140

Lys Gly Asn Lys Lys Val Ile Thr Gly Phe Ser Ser Asp Gly Lys
   1145                1150                1155

Gly Ile Thr Tyr Phe Gly Thr Ser Gly Asn Gln Ala Lys Ser Ala
   1160                1165                1170

Phe Val Thr Phe Asn Gly Asn Thr Tyr Tyr Phe Asp Ala Arg Gly
   1175                1180                1185

His Met Val Thr Asn Gly Glu Tyr Ser Pro Asn Gly Lys Asp Val
   1190                1195                1200

Tyr Arg Phe Leu Pro Asn Gly Ile Met Leu Ser Asn Ala Phe Tyr
   1205                1210                1215

Val Asp Gly Asn Gly Asn Thr Tyr Leu Tyr Asn Ser Lys Gly Gln
   1220                1225                1230

Met Tyr Lys Gly Gly Tyr Ser Lys Phe Asp Val Thr Glu Thr Lys
   1235                1240                1245

Asp Gly Lys Glu Ser Lys Val Val Lys Phe Arg Tyr Phe Thr Asn
   1250                1255                1260

Glu Gly Val Met Ala Lys Gly Val Thr Val Val Asp Gly Phe Thr

```
                  1265                1270               1275

Gln Tyr Phe Asn Glu Asp Gly Ile Gln Ser Lys Asp Glu Leu Val
            1280                1285               1290

Thr Tyr Asn Gly Lys Thr Tyr Tyr Phe Glu Ala His Thr Gly Asn
            1295                1300               1305

Ala Ile Lys Asn Thr Trp Arg Asn Ile Lys Gly Lys Trp Tyr His
            1310                1315               1320

Phe Asp Ala Asn Gly Val Ala Ala Thr Gly Ala Gln Val Ile Asn
            1325                1330               1335

Gly Gln His Leu Tyr Phe Asn Glu Asp Gly Ser Gln Val Lys Gly
            1340                1345               1350

Ser Ile Val Lys Asn Ala Asp Gly Thr Phe Ser Lys Tyr Lys Asp
            1355                1360               1365

Ser Ser Gly Asp Leu Val Val Asn Glu Phe Phe Thr Thr Gly Asp
            1370                1375               1380

Asn Val Trp Tyr Tyr Ala Gly Ala Asn Gly Lys Thr Val Thr Gly
            1385                1390               1395

Ala Gln Val Ile Asn Gly Gln His Leu Phe Phe Lys Glu Asp Gly
            1400                1405               1410

Ser Gln Val Lys Gly Asp Phe Val Lys Asn Ser Asp Gly Thr Tyr
            1415                1420               1425

Ser Lys Tyr Asp Ala Ala Ser Gly Glu Arg Leu Thr Asn Glu Phe
            1430                1435               1440

Phe Thr Thr Gly Asp Asn His Trp Tyr Tyr Ile Gly Ala Asn Gly
            1445                1450               1455

Lys Thr Val Thr Gly Glu Val Lys Ile Gly Asp Asp Thr Tyr Phe
            1460                1465               1470

Phe Ala Lys Asp Gly Lys Gln Leu Lys Gly Gln Ile Val Thr Thr
            1475                1480               1485

Arg Ser Gly Arg Ile Ser Tyr Tyr Phe Gly Asp Ser Gly Lys Lys
            1490                1495               1500

Ala Ile Ser Thr Trp Val Glu Ile Gln Pro Gly Val Phe Val Phe
            1505                1510               1515

Phe Asp Lys Asn Gly Leu Ala Tyr Pro Pro Glu Asn Met Asn
            1520                1525               1530

<210> SEQ ID NO 65
<211> LENGTH: 1341
<212> TYPE: PRT
<213> ORGANISM: Streptococcus salivarius

<400> SEQUENCE: 65

Met Ile Asp Gly Lys Tyr Tyr Tyr Val Asn Glu Asp Gly Ser His Lys
1               5                  10                  15

Glu Asn Phe Ala Ile Thr Val Asn Gly Gln Leu Leu Tyr Phe Gly Lys
                20                  25                  30

Asp Gly Ala Leu Thr Ser Ser Thr Tyr Ser Phe Thr Pro Gly Thr
            35                  40                  45

Thr Asn Ile Val Asp Gly Phe Ser Ile Asn Asn Arg Ala Tyr Asp Ser
        50                  55                  60

Ser Glu Ala Ser Phe Glu Leu Ile Asp Gly Tyr Leu Thr Ala Asp Ser
65                  70                  75                  80

Trp Tyr Arg Pro Ala Ser Ile Ile Lys Asp Gly Val Thr Trp Gln Ala
                85                  90                  95
```

-continued

Ser Thr Ala Glu Asp Phe Arg Pro Leu Leu Met Ala Trp Trp Pro Asn
            100                 105                 110

Val Asp Thr Gln Val Asn Tyr Leu Asn Tyr Met Ser Lys Val Phe Asn
            115                 120                 125

Leu Asp Ala Lys Tyr Ser Ser Thr Asp Lys Gln Glu Thr Leu Lys Val
            130                 135                 140

Ala Ala Lys Asp Ile Gln Ile Lys Ile Glu Gln Lys Ile Gln Ala Glu
145                 150                 155                 160

Lys Ser Thr Gln Trp Leu Arg Glu Thr Ile Ser Ala Phe Val Lys Thr
                165                 170                 175

Gln Pro Gln Trp Asn Lys Glu Thr Glu Asn Tyr Ser Lys Gly Gly Gly
                180                 185                 190

Glu Asp His Leu Gln Gly Gly Ala Leu Leu Tyr Val Asn Asp Ser Arg
            195                 200                 205

Thr Pro Trp Ala Asn Ser Asp Tyr Arg Arg Leu Asn Arg Thr Ala Thr
            210                 215                 220

Asn Gln Thr Gly Thr Ile Asp Lys Ser Ile Leu Asp Glu Gln Ser Asp
225                 230                 235                 240

Pro Asn His Met Gly Gly Phe Asp Phe Leu Leu Ala Asn Asp Val Asp
                245                 250                 255

Leu Ser Asn Pro Val Val Gln Ala Glu Gln Leu Asn Gln Ile His Tyr
            260                 265                 270

Leu Met Asn Trp Gly Ser Ile Val Met Gly Asp Lys Asp Ala Asn Phe
            275                 280                 285

Asp Gly Ile Arg Val Asp Ala Val Asp Asn Val Asp Ala Asp Met Leu
            290                 295                 300

Gln Leu Tyr Thr Asn Tyr Phe Arg Glu Tyr Tyr Gly Val Asn Lys Ser
305                 310                 315                 320

Glu Ala Asn Ala Leu Ala His Ile Ser Val Leu Glu Ala Trp Ser Leu
                325                 330                 335

Asn Asp Asn His Tyr Asn Asp Lys Thr Asp Gly Ala Ala Leu Ala Met
            340                 345                 350

Glu Asn Lys Gln Arg Leu Ala Leu Leu Phe Ser Leu Ala Lys Pro Ile
            355                 360                 365

Lys Glu Arg Thr Pro Ala Val Ser Pro Leu Tyr Asn Asn Thr Phe Asn
            370                 375                 380

Thr Thr Gln Arg Asp Glu Lys Thr Asp Trp Ile Asn Lys Asp Gly Ser
385                 390                 395                 400

Lys Ala Tyr Asn Glu Asp Gly Thr Val Lys Gln Ser Thr Ile Gly Lys
                405                 410                 415

Tyr Asn Glu Lys Tyr Gly Asp Ala Ser Gly Asn Tyr Val Phe Ile Arg
            420                 425                 430

Ala His Asp Asn Asn Val Gln Asp Ile Ile Ala Glu Ile Ile Lys Lys
            435                 440                 445

Glu Ile Asn Pro Lys Ser Asp Gly Phe Thr Ile Thr Asp Ala Glu Met
            450                 455                 460

Lys Gln Ala Phe Glu Ile Tyr Asn Lys Asp Met Leu Ser Ser Asp Lys
465                 470                 475                 480

Lys Tyr Thr Leu Asn Asn Ile Pro Ala Ala Tyr Ala Val Met Leu Gln
                485                 490                 495

Asn Met Glu Thr Ile Thr Arg Val Tyr Tyr Gly Asp Leu Tyr Thr Asp
            500                 505                 510

Asp Gly His Tyr Met Glu Thr Lys Ser Pro Tyr Tyr Asp Thr Ile Val

```
                515                 520                 525
Asn Leu Met Lys Ser Arg Ile Lys Tyr Val Ser Gly Gly Gln Ala Gln
530                 535                 540

Arg Ser Tyr Trp Leu Pro Thr Asp Gly Lys Met Asp Asn Ser Asp Val
545                 550                 555                 560

Glu Leu Tyr Arg Thr Asn Glu Val Tyr Thr Ser Val Arg Tyr Gly Lys
                565                 570                 575

Asp Ile Met Thr Ala Asn Asp Thr Glu Gly Ser Lys Tyr Ser Arg Thr
                580                 585                 590

Ser Gly Gln Val Thr Leu Val Ala Asn Asn Pro Lys Leu Asn Leu Asp
                595                 600                 605

Gln Ser Ala Lys Leu Asn Val Glu Met Gly Lys Ile His Ala Asn Gln
610                 615                 620

Lys Tyr Arg Ala Leu Ile Val Gly Thr Ala Asp Gly Ile Lys Asn Phe
625                 630                 635                 640

Thr Ser Asp Ala Asp Ala Ile Ala Ala Gly Tyr Val Lys Glu Thr Asp
                645                 650                 655

Ser Asn Gly Val Leu Thr Phe Gly Ala Asn Asp Ile Lys Gly Tyr Glu
                660                 665                 670

Thr Phe Asp Met Ser Gly Phe Val Ala Val Trp Val Pro Val Gly Ala
                675                 680                 685

Ser Asp Asn Gln Asp Ile Arg Val Ala Pro Ser Thr Glu Ala Lys Lys
690                 695                 700

Glu Gly Glu Leu Thr Leu Lys Ala Thr Glu Ala Tyr Asp Ser Gln Leu
705                 710                 715                 720

Ile Tyr Glu Gly Phe Ser Asn Phe Gln Thr Ile Pro Asp Gly Ser Asp
                725                 730                 735

Pro Ser Val Tyr Thr Asn Arg Lys Ile Ala Glu Asn Val Asp Leu Phe
                740                 745                 750

Lys Ser Trp Gly Val Thr Ser Phe Glu Met Ala Pro Gln Phe Val Ser
                755                 760                 765

Ala Asp Asp Gly Thr Phe Leu Asp Ser Val Ile Gln Asn Gly Tyr Ala
770                 775                 780

Phe Ala Asp Arg Tyr Asp Leu Ala Met Ser Lys Asn Asn Lys Tyr Gly
785                 790                 795                 800

Ser Lys Glu Asp Leu Arg Asp Ala Leu Lys Ala Leu His Lys Ala Gly
                805                 810                 815

Ile Gln Ala Ile Ala Asp Trp Val Pro Asp Gln Ile Tyr Gln Leu Pro
                820                 825                 830

Gly Lys Glu Val Val Thr Ala Thr Arg Thr Asp Gly Ala Gly Arg Lys
                835                 840                 845

Ile Ala Asp Ala Ile Asp His Ser Leu Tyr Val Ala Asn Ser Lys
850                 855                 860

Ser Ser Gly Lys Asp Tyr Gln Ala Lys Tyr Gly Gly Glu Phe Leu Ala
865                 870                 875                 880

Glu Leu Lys Ala Lys Tyr Pro Glu Met Phe Lys Val Asn Met Ile Ser
                885                 890                 895

Thr Gly Lys Pro Ile Asp Asp Ser Val Lys Leu Lys Gln Trp Lys Ala
                900                 905                 910

Glu Tyr Phe Asn Gly Thr Asn Val Leu Glu Arg Gly Val Gly Tyr Val
                915                 920                 925

Leu Ser Asp Glu Ala Thr Gly Lys Tyr Phe Thr Val Thr Lys Glu Gly
930                 935                 940
```

```
Asn Phe Ile Pro Leu Gln Leu Thr Gly Lys Glu Lys Val Ile Thr Gly
945                 950                 955                 960

Phe Ser Ser Asp Gly Lys Gly Ile Thr Tyr Phe Gly Thr Ser Gly Thr
                965                 970                 975

Gln Ala Lys Ser Ala Phe Val Thr Phe Asn Gly Asn Thr Tyr Tyr Phe
            980                 985                 990

Asp Ala Arg Gly His Met Val Thr Asn Ser Glu Tyr Ser Pro Asn Gly
        995                 1000                1005

Lys Asp Val Tyr Arg Phe Leu Pro Asn Gly Ile Met Leu Ser Asn
    1010                1015                1020

Ala Phe Tyr Ile Asp Ala Asn Gly Asn Thr Tyr Leu Tyr Asn Ser
    1025                1030                1035

Lys Gly Gln Met Tyr Lys Gly Tyr Thr Lys Phe Asp Val Ser
    1040                1045                1050

Glu Thr Asp Lys Asp Gly Lys Glu Ser Lys Val Val Lys Phe Arg
    1055                1060                1065

Tyr Phe Thr Asn Glu Gly Val Met Ala Lys Gly Val Thr Val Ile
    1070                1075                1080

Asp Gly Phe Thr Gln Tyr Phe Gly Glu Asp Gly Phe Gln Ala Lys
    1085                1090                1095

Asp Lys Leu Val Thr Phe Lys Gly Lys Thr Tyr Tyr Phe Asp Ala
    1100                1105                1110

His Thr Gly Asn Gly Ile Lys Asp Thr Trp Arg Asn Ile Asn Gly
    1115                1120                1125

Lys Trp Tyr Tyr Phe Asp Ala Asn Gly Val Ala Ala Thr Gly Ala
    1130                1135                1140

Gln Val Ile Asn Gly Gln Lys Leu Tyr Phe Asn Glu Asp Gly Ser
    1145                1150                1155

Gln Val Lys Gly Gly Val Val Lys Asn Ala Asp Gly Thr Tyr Ser
    1160                1165                1170

Lys Tyr Lys Glu Gly Phe Gly Glu Leu Val Thr Asn Glu Phe Phe
    1175                1180                1185

Thr Thr Asp Gly Asn Val Trp Tyr Tyr Ala Gly Ala Asn Gly Lys
    1190                1195                1200

Thr Val Thr Gly Ala Gln Val Ile Asn Gly Gln His Leu Tyr Phe
    1205                1210                1215

Asn Ala Asp Gly Ser Gln Val Lys Gly Gly Val Val Lys Asn Ala
    1220                1225                1230

Asp Gly Thr Tyr Ser Lys Tyr Asn Ala Ser Thr Gly Glu Arg Leu
    1235                1240                1245

Thr Asn Glu Phe Phe Thr Thr Gly Asp Asn Asn Trp Tyr Tyr Ile
    1250                1255                1260

Gly Ala Asn Gly Lys Ser Val Thr Gly Glu Val Lys Ile Gly Asp
    1265                1270                1275

Asp Thr Tyr Phe Phe Ala Lys Asp Gly Lys Gln Val Lys Gly Gln
    1280                1285                1290

Thr Val Ser Ala Gly Asn Gly Arg Ile Ser Tyr Tyr Tyr Gly Asp
    1295                1300                1305

Ser Gly Lys Arg Ala Val Ser Thr Trp Ile Glu Ile Gln Pro Gly
    1310                1315                1320

Val Tyr Val Tyr Phe Asp Lys Asn Gly Leu Ala Tyr Pro Pro Arg
    1325                1330                1335
```

Val Leu Asn
    1340

<210> SEQ ID NO 66
<211> LENGTH: 1614
<212> TYPE: PRT
<213> ORGANISM: Lactobacillus animalis KCTC 3501

<400> SEQUENCE: 66

Asp Glu Thr Ser Ser Asn Glu Thr Gln Thr Glu Gln Thr Leu Asn
1               5                   10                  15

Thr Asp Glu Ser Thr Asp Thr Thr Asp Val Ser Asn Glu Ala Lys
            20                  25                  30

Ala Thr Glu Ala Gln Leu Thr Thr Gln Asp Ala Asp Met Ala Ser Ser
            35                  40                  45

Glu Glu Lys Thr Thr Asn Val Glu Lys Glu Val Thr Ala Glu Thr
    50                  55                  60

Asn Lys Asp Thr Thr Val Lys Asn Val Glu Ser Ser Glu Gln Asn Thr
65                  70                  75                  80

Thr Thr Val Ala Asp Lys Asn Ala Val Asp Ser Thr Ala Gln Val Asn
                85                  90                  95

Thr Ala Glu Lys Glu Asn Lys Tyr Thr Gln Glu Asn Val Asn Gly Asn
                100                 105                 110

Trp Tyr Leu Lys Asp Glu Gln Gly Asn Tyr Leu Thr Gly Phe Gln Glu
            115                 120                 125

Ile Lys Asp Gln Asn Lys Thr Val Tyr Tyr Asn Pro Asp Ser Lys Gln
        130                 135                 140

Met Val Tyr Gly Gln Gln Asn Ile Asn Gly Asn Trp Tyr Leu Phe Asp
145                 150                 155                 160

Thr Phe Asn Gly Ala Met Gln Thr Gly Leu Gln Tyr Ile Arg Asp Gln
                165                 170                 175

Lys Lys Leu Ala Tyr Tyr Asn Glu Gln Gly Gln Met Gln Tyr Gly Thr
            180                 185                 190

Val Glu Ile Asp Gly Gln Lys Tyr Gln Ala Asp Thr Phe Asn Gly Ala
        195                 200                 205

Ile Lys Gly Lys Gly Gln Thr Lys Ile Ala Asp Asn Trp Tyr Leu Phe
    210                 215                 220

Asn Asn Ala Gly Gln Val Val Asp Gly Trp Gln Trp Ile Asn Asp Gln
225                 230                 235                 240

Gly Lys Thr Val Tyr Tyr Ser Thr Lys Thr Ala Gln Met Val His Gly
                245                 250                 255

Gln Gln Asn Ile Asn Gly His Trp Tyr Leu Phe Asp Lys Thr Thr Gly
            260                 265                 270

Ala Met Gln Arg Gly Phe Gln Asn Leu Lys Ala Tyr Gly Asp Asp Lys
        275                 280                 285

Thr Val Tyr Tyr Asn Gln Asp Gly Trp Met Leu Tyr Gly Gln Gln Lys
    290                 295                 300

Ile Asp Asn Lys Trp Tyr Asn Phe Asp Thr Phe Asn Gly Ala Met Lys
305                 310                 315                 320

Thr Gly Phe Val Lys Ile Pro Glu Gln Asn Lys Thr Val Tyr Tyr Ala
                325                 330                 335

Pro Asn Gly Gln Met Gln Tyr Gly Trp Gln Trp Val Asp Asn Ala Thr
            340                 345                 350

Arg Tyr Phe Asp Thr Phe Asn Gly Ala Met Ala Thr Gly Gln Lys Leu
        355                 360                 365

-continued

Ile Thr Gly His Trp Tyr Leu Phe Asp Asn Asn Gly Ala Met Gln Arg
370                 375                 380

Gly Phe Gln Asn Leu Lys Asn Tyr Gly Asp Asn Lys Thr Val Tyr Tyr
385                 390                 395                 400

Asn Gln Asp Gly Trp Met Leu Tyr Gly Trp Gln Trp Val Asn Asn Ala
            405                 410                 415

Thr Arg Tyr Phe Asp Thr Phe Asn Gly Ala Met Thr Thr Gly Gln Lys
        420                 425                 430

Lys Ile Asn Asp His Trp Tyr Leu Phe Asp Lys Asp Gly Ala Met Gln
            435                 440                 445

Arg Gly Ile Gln Tyr Ile Pro Glu Glu Asn Lys Leu Val Tyr Tyr Asn
450                 455                 460

Gln Asp Gly Trp Met Leu Tyr Gly Lys Gln Asn Ile Asn Gly Val Asp
465                 470                 475                 480

His Asn Phe Asn Thr Phe Asn Gly Ala Leu Glu Ala Lys Gly Gln Val
            485                 490                 495

Lys Val Gly Asn Asn Trp Tyr Leu Phe Asn Asn Ser Gly Thr Ile Gln
                500                 505                 510

Thr Gly Phe Gln Asp Leu Lys Ala Tyr Gly Gln Asp Lys Val Val Tyr
        515                 520                 525

Tyr Asp Pro Lys Thr Ala Ala Met Val Tyr Gly Tyr Gln Asn Ile Asp
530                 535                 540

Gly Asn Trp Tyr Leu Phe Ser Arg Ala Asn Gly Ser Met Gln Arg Gly
545                 550                 555                 560

Leu Gln Asn Val Asn Gly Val Asp Leu Leu Phe Asp Glu Lys Thr Gly
                565                 570                 575

Ala Leu Leu Thr Gly Val Gln Asn Ile Lys Gly Asn Asn Tyr Phe Val
            580                 585                 590

Asp Lys Arg Ser Gly Asn Ile Lys Lys Asn Leu Val Val Leu Gly Ala
                595                 600                 605

Asp Asn Lys Trp Met Tyr Phe Asp Ala Lys Thr Gly Lys Gly Thr Asn
            610                 615                 620

Thr Leu Glu Asp Gln Tyr Lys Lys Gly Val Val Ser Gly Asn Val Glu
625                 630                 635                 640

Phe Ile Thr Asn Asn Ala Ala Tyr Ser Phe Asp Gly Asn Ser Phe Glu
                645                 650                 655

Asn Ile Asn Gly Phe Leu Thr Ala Asp Ser Trp Tyr Arg Pro Lys Ser
            660                 665                 670

Ile Leu Lys Asp Gly Ser Thr Trp Thr Ala Thr Thr Glu Thr Asp Leu
        675                 680                 685

Arg Pro Leu Leu Met Thr Trp Trp Pro Asn Glu Gln Ile Lys Ala Asn
690                 695                 700

Tyr Leu Asn Tyr Met Lys Asp Lys Gly Phe Ile Asn Asn Ser Gly Thr
705                 710                 715                 720

Tyr Asn Ala Glu Ser Asp Pro Asn Tyr Met Asp Phe Ala Ala Gln Glu
            725                 730                 735

Ala Gln Arg Asn Ile Glu Arg Lys Ile Thr Lys Glu Asn Asp Thr Thr
        740                 745                 750

Trp Leu Arg Asp Leu Ile Thr Asp Phe Ile Lys Thr Gln Asp Ile Trp
    755                 760                 765

Asn Glu Gln Ser Glu Gly Val Ser Thr Glu Gly Leu Gln Lys Phe Gln
770                 775                 780

```
Gly Gly Phe Leu Lys Tyr Val Asn Ser Glu Leu Thr Pro Tyr Ala Asn
785                 790                 795                 800

Ser Glu Trp Arg Lys Leu Gly Tyr Gln Pro Thr Met Leu Thr Gln Asn
            805                 810                 815

Asn Val Gly Ala Glu Phe Leu Leu Ala Asn Asp Ile Asp Asn Ser Asn
        820                 825                 830

Pro Val Gln Ala Glu Gln Leu Asn Trp Leu His Phe Leu Met Asn
        835                 840                 845

Phe Gly Thr Ile Thr Ala Asn Asp Pro Ser Ala Asn Phe Asp Gly Ile
    850                 855                 860

Arg Ile Asp Ala Val Asp Asn Val Asp Ala Ser Leu Leu Ser Ile Ala
865                 870                 875                 880

Gly Asp Tyr Phe Lys Ala Ala Tyr Lys Val Gly Gln Asn Asp Ala Thr
                885                 890                 895

Ala Asn Lys His Ile Ser Ile Leu Glu Asp Trp Asn Asp Lys Asp Pro
            900                 905                 910

Glu Tyr Val Asn Ser Ile Gly Asn Pro Gln Leu Thr Met Asp Asp Tyr
        915                 920                 925

Ile Val Gln Gln Leu Lys Phe Ser Leu Gly Gln Ala Pro Asp Lys Val
    930                 935                 940

Asp Arg Met Gln Arg Phe Lys Glu Trp Tyr Leu Val Asp Arg Ser Lys
945                 950                 955                 960

Asp Asn Thr Glu Asn Thr Ala Ile Pro Asn Tyr Ser Phe Val Arg Ala
                965                 970                 975

His Asp Ala Ser Val Gln Glu Asp Ile Leu Gln Leu Ile Gln Asp Thr
            980                 985                 990

Thr Gly Lys Pro Trp Gly Val Tyr Thr Asn Glu Glu Leu Gln Gln Gly
        995                 1000                1005

Leu Lys Asp Tyr Met Ala Asp Gln Lys Leu Thr Asn Lys Lys Tyr
    1010            1015            1020

Asn Arg Tyr Asn Ile Pro Ser Ser Tyr Ala Ile Leu Leu Thr Asn
    1025            1030            1035

Lys Asp Thr Ile Pro Arg Val Tyr Tyr Gly Asp Leu Tyr Ser Asp
    1040            1045            1050

Ala Gly Lys Tyr Met Ala Glu Lys Ser Ile Tyr Phe Asp Ala Ile
    1055            1060            1065

Asp Asn Leu Leu Lys Thr Arg Thr Lys Tyr Val Ala Gly Gly Gln
    1070            1075            1080

Thr Leu Asp Val Asp Gly His Asp Ile Leu Thr Ser Val Arg Phe
    1085            1090            1095

Gly Lys Gly Ala Leu Asn Val Thr Asp Lys Gly Thr Ser Glu Thr
    1100            1105            1110

Arg Thr Gln Gly Met Gly Leu Ile Ile Ser Asn Asn Asn Ser Leu
    1115            1120            1125

Lys Leu Asn Asp Gly Glu Lys Val Val Leu His Met Gly Ala Ala
    1130            1135            1140

His Lys Asn Gln Ala Tyr Arg Ala Val Met Leu Ser Ser Ala Asn
    1145            1150            1155

Gly Leu Ile Asn Tyr Thr Ser Asp Ala Asn Ala Pro Val Val Tyr
    1160            1165            1170

Thr Asn Asn Asp Gly Asp Leu Ile Phe Thr Asn Lys Asp Val Val
    1175            1180            1185

Thr Asn Gly Lys Val Gln Ala Asn Thr Ala Ile Lys Gly Val Met
```

```
            1190                1195                1200

Asn Pro Tyr Val Ser Gly Tyr Leu Ala Met Trp Val Pro Val Gly
    1205                1210                1215

Ala Ser Ala Thr Gln Asp Ala Arg Thr Ala Ala Ser Thr Lys Thr
    1220                1225                1230

Thr Thr Asp Gly Ser Val Phe His Ser Asn Ala Ala Leu Asp Ser
    1235                1240                1245

Asn Leu Ile Tyr Glu Gly Phe Ser Asn Phe Gln Ala Phe Pro Glu
    1250                1255                1260

Asn Ala Ser Glu Asn Ala Asn Ala Ile Ile Ala Gln Asn Val Asp
    1265                1270                1275

Leu Phe Asn Ser Trp Gly Val Thr Ser Phe Gln Leu Ala Pro Gln
    1280                1285                1290

Tyr Val Ser Ser His Asp Gly Ser Phe Leu Asp Ser Ile Ile Asp
    1295                1300                1305

Asn Gly Tyr Ala Phe Thr Asp Arg Tyr Asp Leu Ala Met Ser Lys
    1310                1315                1320

Asn Asn Lys Tyr Gly Ser Tyr Gln Asp Leu Val Asn Val Leu Lys
    1325                1330                1335

Ala Leu His Ala Gly Gly Ile Gln Val Ile Ala Asp Trp Val Pro
    1340                1345                1350

Asp Gln Ile Tyr Ser Leu Pro Gly Lys Glu Val Val Ser Val Val
    1355                1360                1365

Arg Ser Asp Glu Phe Gly Asn Lys Val Asp Gly Thr Gln Ile Asp
    1370                1375                1380

Asn Thr Leu Tyr Val Val Asn Thr Ile Gly Gly Gly Gln Tyr Gln
    1385                1390                1395

Lys Glu Tyr Gly Gly Arg Tyr Leu Glu Glu Leu Lys Gln Lys Tyr
    1400                1405                1410

Pro Glu Leu Phe Lys Thr Lys Gln Pro Ser Thr Gly Val Thr Ile
    1415                1420                1425

Asp Pro Ser Glu Lys Ile Thr Glu Trp Ser Ala Lys Tyr Leu Asn
    1430                1435                1440

Gly Thr Asn Ile Leu His Arg Gly Ala Glu Phe Val Leu Arg Asp
    1445                1450                1455

Gly Ala Thr Tyr Phe Arg Val Ala Glu Thr Ser Glu Val Phe Leu
    1460                1465                1470

Pro Ser Gln Leu Arg Gly Lys Ile Thr Lys Asn Gly Phe Trp Lys
    1475                1480                1485

Asn Asp Ala Gly Lys Val Asn Tyr Tyr Asn Ser Glu Gly Glu Ile
    1490                1495                1500

Met Lys Asn Ala Phe Val Lys Asp Gly Lys Asn Asn Trp Tyr Tyr
    1505                1510                1515

Phe Asp Asn Asp Gly Asn Met Val Thr Asn Thr Ala Leu Thr Ile
    1520                1525                1530

Asp Ser Asp Ala Gln Val Ala Asp Tyr Tyr Phe Leu Asn Asn Gly
    1535                1540                1545

Ile Ser Leu Arg Asp Gly Phe Val Gln Leu Ala Asn Gly Asp Ile
    1550                1555                1560

Tyr Tyr Tyr Asp Val Asn Gly Arg Lys Leu Lys Asn Gly Lys Val
    1565                1570                1575

Thr Val Asn Asn Val Glu Tyr Thr Thr Asp Lys Asn Gly Lys Val
    1580                1585                1590
```

```
Val Gly Glu Asn Val Leu Lys Lys Leu Asp Glu Ile Ile Thr Thr
    1595                1600                1605

Gly Lys Thr Thr Leu Ile
    1610

<210> SEQ ID NO 67
<211> LENGTH: 1557
<212> TYPE: PRT
<213> ORGANISM: Streptococcus salivarius M18

<400> SEQUENCE: 67

Glu Glu Thr Asn Asn Ser Asn Gly Ser Pro Ser Thr Thr Thr Val Gly
1               5                   10                  15

Glu Asn Thr Asn Pro Val Val Glu Lys Glu Val Gly Thr Thr Thr Glu
            20                  25                  30

Val Ala Asn Thr Ser Asn Ala Thr Thr Thr Glu Arg Ala Glu Val Thr
        35                  40                  45

Ala Asp Lys Pro Ala Glu Thr Thr Val Gln Pro Asn Ser Gly Thr Thr
    50                  55                  60

Thr Ser Asp Arg Ala Val Ala Val Glu Val Glu Ala Lys Pro Glu Thr
65                  70                  75                  80

Thr Ala Lys Pro Glu Val Ala Thr Lys Pro Glu Thr Ala Thr Thr Ser
                85                  90                  95

Glu Val Ala Ala Asn Ala Gly Val Ala Ala Pro Thr Thr Glu Lys Ser
            100                 105                 110

Lys Glu Leu Ser Glu Ala Glu Ile Lys Ala Ala Val Ser Leu Asp Asn
        115                 120                 125

Ile Lys Lys Glu Lys Asp Gly Lys Tyr Tyr Tyr Leu Leu Glu Asp Gly
    130                 135                 140

Ser His Lys Lys Asn Phe Ala Ile Thr Val Asn Gly Gln Val Leu Tyr
145                 150                 155                 160

Phe Asp Glu Asn Gly Ala Leu Ser Ser Thr Ser Thr Tyr Ser Phe Thr
                165                 170                 175

Gln Glu Thr Thr Asn Leu Val Thr Asp Phe Thr Lys Asn Asn Ala Ala
            180                 185                 190

Tyr Asp Ser Thr Lys Ala Ser Phe Glu Leu Val Asp Gly Tyr Leu Thr
        195                 200                 205

Ala Asp Ser Trp Tyr Arg Pro Lys Glu Ile Leu Glu Ala Gly Thr Thr
    210                 215                 220

Trp Lys Ala Ser Thr Glu Lys Asp Phe Arg Pro Leu Leu Met Ser Trp
225                 230                 235                 240

Trp Pro Asp Lys Asp Thr Gln Val Ala Tyr Leu Asn Tyr Met Thr Lys
                245                 250                 255

Ala Leu Ser Asn Gly Glu Glu Thr Lys Asp Val Phe Thr Ile Glu Asn
            260                 265                 270

Ser Gln Ala Ser Leu Asn Ala Ala Gln Ile Leu Gln Arg Lys Ile
        275                 280                 285

Glu Val Lys Ile Ala Ala Asn Lys Ser Thr Asp Trp Leu Arg Gln Ser
    290                 295                 300

Ile Glu Ala Phe Val Lys Asp Gln Asp Lys Trp Asn Ile Asn Ser Glu
305                 310                 315                 320

Ser Pro Gly Lys Glu His Phe Gln Lys Gly Ala Leu Leu Phe Val Asn
                325                 330                 335

Ser Asp Ser Thr Lys Trp Ala Asn Ser Asp Tyr Arg Lys Leu Asn Gln
```

-continued

```
                340             345             350
Thr Ala Thr Ser Tyr Ile Lys Asn His Lys Ile Val Asn Gly Ser Asp
            355             360             365
Gly Gly Tyr Glu Phe Leu Leu Ser Asn Asp Ile Asp Asn Ser Asn Pro
            370             375             380
Val Val Gln Ala Glu Met Leu Asn Gln Leu Tyr Tyr Phe Met Asn Trp
385             390             395             400
Gly Gln Ile Val Phe Gly Asp Lys Asp Lys Asp Ala His Phe Asp Gly
            405             410             415
Ile Arg Val Asp Ala Val Asp Asn Val Ser Val Asp Met Leu Gln Leu
            420             425             430
Val Ser Ser Tyr Met Lys Ala Ala Tyr Lys Val Asn Glu Ser Glu Ala
            435             440             445
Arg Ala Leu Ala Asn Ile Ser Ile Leu Glu Ala Trp Ser His Asn Asp
            450             455             460
Pro Tyr Tyr Val Asn Glu His Asn Thr Ala Ala Leu Ser Met Asp Asn
465             470             475             480
Gly Leu Arg Leu Ser Ile Val His Gly Leu Thr Arg Pro Val Thr Asn
            485             490             495
Lys Gly Thr Gly Ala Arg Asn Ala Ser Met Lys Asp Leu Ile Asn Gly
            500             505             510
Gly Tyr Phe Gly Leu Ser Asn Arg Ala Glu Val Thr Ser Tyr Asp Gln
            515             520             525
Leu Gly Phe Ala Thr Tyr Leu Phe Val Arg Ala His Asp Ser Glu Val
            530             535             540
Gln Thr Val Ile Ala Asp Ile Ile Ser Lys Lys Ile Asp Pro Thr Thr
545             550             555             560
Asp Gly Phe Thr Phe Thr Leu Asp Gln Leu Lys Gln Ala Phe Asp Ile
            565             570             575
Tyr Asn Ala Asp Met Leu Lys Val Asp Lys Glu Tyr Thr His Ser Asn
            580             585             590
Ile Pro Ala Ala Tyr Ala Leu Met Leu Gln Thr Met Gly Ala Ala Thr
            595             600             605
Arg Val Tyr Tyr Gly Asp Leu Tyr Thr Asp Asn Gly Gln Tyr Met Ala
            610             615             620
Lys Lys Ser Pro Tyr Phe Asp Gln Ile Thr Thr Leu Leu Lys Ala Arg
625             630             635             640
Pro Lys Tyr Val Ala Gly Gly Gln Thr Ser Tyr Ile His Asn Leu Ala
            645             650             655
Gly Asp Gly Val Ser Ser Ala Lys Asp Asn Lys Glu Val Leu Val Ser
            660             665             670
Val Arg Tyr Gly Gln Asp Leu Met Ser Lys Thr Asp Thr Glu Gly Gly
            675             680             685
Lys Tyr Gly Arg Asn Ser Gly Met Leu Thr Leu Ile Ala Asn Asn Pro
            690             695             700
Asp Leu Lys Leu Ala Asp Gly Glu Thr Ile Thr Val Asn Met Gly Ala
705             710             715             720
Ala His Lys Asn Gln Ala Tyr Arg Pro Leu Leu Leu Gly Thr Asp Lys
            725             730             735
Gly Ile Val Ser Ser Leu Asn Asp Ser Asp Thr Lys Val Val Lys Tyr
            740             745             750
Thr Asp Ala Gln Gly Asn Leu Val Phe Thr Ala Asp Glu Ile Lys Gly
            755             760             765
```

-continued

Phe Lys Thr Val Asp Met Ser Gly Tyr Leu Ser Val Trp Pro Val
770                 775                 780

Gly Ala Thr Asp Asp Gln Asn Val Leu Ala Lys Pro Ser Thr Lys Ala
785                 790                 795                 800

Tyr Lys Glu Gly Asp Lys Val Tyr Ser Ser Ala Ala Leu Glu Ala
                805                 810                 815

Gln Val Ile Tyr Glu Gly Phe Ser Asn Phe Gln Asp Phe Val Lys Glu
                820                 825                 830

Asp Ser Gln Tyr Thr Asn Lys Leu Ile Ala Ala Asn Ala Asp Leu Phe
                835                 840                 845

Lys Ser Trp Gly Ile Thr Ser Phe Glu Ile Ala Pro Gln Tyr Val Ser
850                 855                 860

Ser Lys Asp Gly Thr Phe Leu Asp Ser Ile Ile Glu Asn Gly Tyr Ala
865                 870                 875                 880

Phe Thr Asp Arg Tyr Asp Phe Ala Met Ser Lys Asn Asn Lys Tyr Gly
                885                 890                 895

Ser Lys Glu Asp Leu Arg Asp Ala Leu Lys Ala Leu His Lys Gln Gly
                900                 905                 910

Ile Gln Val Ile Ala Asp Trp Val Pro Asp Gln Leu Tyr Thr Leu Pro
                915                 920                 925

Gly Lys Glu Val Val Thr Ala Thr Arg Thr Asp Thr His Gly Lys Val
930                 935                 940

Leu Asp Asp Thr Ser Leu Val Asn Lys Leu Tyr Val Thr Asn Thr Lys
945                 950                 955                 960

Ser Ser Gly Asn Asp Phe Gln Ala Gln Tyr Gly Gly Ala Phe Leu Asp
                965                 970                 975

Lys Leu Gln Lys Leu Tyr Pro Glu Ile Phe Lys Glu Val Met Glu Ala
                980                 985                 990

Ser Gly Lys Thr Ile Asp Pro Ser Val Lys Ile Lys Gln Trp Glu Ala
                995                 1000                1005

Lys Tyr Phe Asn Gly Thr Asn Ile Gln Lys Arg Gly Ser Asp Tyr
1010                1015                1020

Val Leu Ser Asp Gly Lys Leu Tyr Phe Thr Val Asn Asp Lys Gly
1025                1030                1035

Thr Phe Leu Pro Ala Ala Leu Thr Gly Asp Thr Lys Ala Lys Thr
1040                1045                1050

Gly Phe Ala Tyr Asp Gly Thr Gly Val Thr Tyr Thr Thr Ser
1055                1060                1065

Gly Thr Gln Ala Lys Ser Gln Phe Val Thr Tyr Asn Gly Lys Gln
1070                1075                1080

Tyr Tyr Phe Asn Asp Lys Gly Tyr Leu Val Thr Gly Glu Gln Thr
1085                1090                1095

Ile Asp Gly Ser Asn Tyr Phe Phe Leu Pro Asn Gly Val Met Phe
1100                1105                1110

Thr Asp Gly Val Arg Lys Asn Ala Lys Gly Gln Ser Leu Val Tyr
1115                1120                1125

Gly Lys Ser Gly Lys Leu Thr Thr Gln Thr Gly Trp Lys Glu Val
1130                1135                1140

Thr Val Lys Asp Asp Ser Gly Lys Glu Glu Lys Phe Tyr Gln Tyr
1145                1150                1155

Phe Phe Lys Gly Gly Ile Met Ala Thr Gly Leu Thr Glu Val Glu
1160                1165                1170

```
Gly Lys Glu Lys Tyr Phe Tyr Asp Asn Gly Tyr Gln Ala Lys Gly
1175                1180                1185

Val Phe Val Pro Thr Lys Asp Gly His Leu Met Phe Phe Cys Gly
1190                1195                1200

Asp Ser Gly Glu Arg Lys Tyr Ser Gly Phe Phe Glu Gln Asp Gly
1205                1210                1215

Asn Trp Tyr Tyr Ala Asn Asp Lys Gly Tyr Val Ala Thr Gly Phe
1220                1225                1230

Thr Lys Val Gly Lys Gln Asn Leu Tyr Phe Asn Glu Lys Gly Val
1235                1240                1245

Gln Val Lys Asn Arg Phe Phe Gln Val Gly Asp Ala Thr Tyr Tyr
1250                1255                1260

Ala Asn Asn Glu Gly Asp Val Leu Arg Gly Ala Gln Thr Ile Asn
1265                1270                1275

Gly Asp Glu Leu Tyr Phe Asp Glu Ser Gly Lys Gln Val Lys Gly
1280                1285                1290

Glu Phe Val Asn Asn Pro Asp Gly Thr Thr Ser Tyr Tyr Asp Ala
1295                1300                1305

Ile Thr Gly Val Lys Leu Val Asp Thr Ser Leu Val Val Asp Gly
1310                1315                1320

Gln Thr Phe Asn Val Asp Ala Lys Gly Val Val Thr Lys Ala His
1325                1330                1335

Thr Pro Gly Phe Tyr Thr Thr Gly Asp Asn Asn Trp Phe Tyr Ala
1340                1345                1350

Asp Ser Tyr Gly Arg Asn Val Thr Gly Ala Gln Val Ile Asn Gly
1355                1360                1365

Gln His Leu Tyr Phe Asp Ala Asn Gly Arg Gln Val Lys Gly Gly
1370                1375                1380

Phe Val Thr Asn Thr Asp Gly Ser Arg Ser Phe Tyr His Trp Asn
1385                1390                1395

Thr Gly Asp Lys Leu Val Ser Thr Phe Phe Thr Thr Gly His Asp
1400                1405                1410

Arg Trp Tyr Tyr Ala Asp Asp Arg Gly Asn Val Val Thr Gly Ala
1415                1420                1425

Gln Val Ile Asn Gly Gln Lys Leu Phe Phe Asp Thr Asp Gly Lys
1430                1435                1440

Gln Val Lys Gly Ala Phe Ala Thr Asn Ala Asn Gly Ser Arg Ser
1445                1450                1455

Tyr Tyr His Trp Asn Thr Gly Asn Lys Leu Val Ser Thr Phe Phe
1460                1465                1470

Thr Ser Gly Asp Asn Asn Trp Tyr Tyr Ala Asp Ala Lys Gly Glu
1475                1480                1485

Val Val Val Gly Glu Gln Thr Ile Asn Gly Gln His Leu Tyr Phe
1490                1495                1500

Asp Gln Thr Gly Lys Gln Val Lys Gly Ala Thr Ala Thr Asn Pro
1505                1510                1515

Asp Gly Ser Ile Ser Tyr Tyr Asp Val His Thr Gly Glu Lys Ala
1520                1525                1530

Ile Asn Arg Trp Val Lys Ile Pro Ser Gly Gln Trp Val Tyr Phe
1535                1540                1545

Asn Ala Gln Gly Lys Gly Tyr Val Ser
1550                1555
```

-continued

```
<210> SEQ ID NO 68
<211> LENGTH: 1552
<212> TYPE: PRT
<213> ORGANISM: Lactobacillus animalis KCTC 3501

<400> SEQUENCE: 68
```

Glu Glu Thr Asn Asn Ser Asn Gly Ser Pro Ser Thr Thr Thr Val Gly
1               5                   10                  15

Glu Asn Thr Asn Pro Val Val Glu Lys Glu Val Gly Thr Thr Thr Glu
            20                  25                  30

Val Ala Asn Thr Ser Asn Ala Thr Thr Thr Glu Arg Ala Glu Val Thr
        35                  40                  45

Ala Asp Lys Pro Ala Glu Thr Thr Val Gln Pro Asn Ser Gly Thr Thr
    50                  55                  60

Thr Ser Asp Arg Ala Val Ala Val Glu Val Glu Ala Lys Pro Glu Thr
65                  70                  75                  80

Thr Ala Lys Pro Glu Val Ala Thr Lys Pro Glu Thr Ala Thr Thr Ser
                85                  90                  95

Glu Val Ala Ala Asn Ala Gly Val Ala Ala Pro Thr Thr Glu Lys Ser
            100                 105                 110

Lys Glu Leu Ser Glu Ala Glu Ile Lys Ala Ala Val Ser Leu Asp Asn
        115                 120                 125

Ile Lys Lys Glu Lys Asp Gly Lys Tyr Tyr Tyr Leu Leu Glu Asp Gly
    130                 135                 140

Ser His Lys Lys Asn Phe Ala Ile Thr Val Asn Gly Gln Val Leu Tyr
145                 150                 155                 160

Phe Asp Glu Asn Gly Ala Leu Ser Ser Thr Ser Thr Tyr Ser Phe Thr
                165                 170                 175

Gln Glu Thr Thr Asn Leu Val Thr Asp Phe Thr Lys Asn Asn Ala Ala
            180                 185                 190

Tyr Asp Ser Thr Lys Ala Ser Phe Glu Leu Val Asp Gly Tyr Leu Thr
        195                 200                 205

Ala Asp Ser Trp Tyr Arg Pro Lys Glu Ile Leu Glu Ala Gly Thr Thr
    210                 215                 220

Trp Lys Ala Ser Thr Glu Lys Asp Phe Arg Pro Leu Leu Met Ser Trp
225                 230                 235                 240

Trp Pro Asp Lys Asp Thr Gln Val Ala Tyr Leu Asn Tyr Met Thr Lys
                245                 250                 255

Ala Leu Ser Asn Gly Glu Glu Thr Lys Asp Val Phe Thr Ile Glu Asn
            260                 265                 270

Ser Gln Ala Ser Leu Asn Ala Ala Gln Ile Leu Gln Arg Lys Ile
        275                 280                 285

Glu Val Lys Ile Ala Ala Asn Lys Ser Thr Asp Trp Leu Arg Gln Ser
    290                 295                 300

Ile Glu Ala Phe Val Lys Asp Gln Asp Lys Trp Asn Ile Asn Ser Glu
305                 310                 315                 320

Ser Pro Gly Lys Glu His Phe Gln Lys Gly Ala Leu Leu Phe Val Asn
                325                 330                 335

Ser Asp Ser Thr Lys Trp Ala Asn Ser Asp Tyr Arg Lys Leu Asn Gln
            340                 345                 350

Thr Ala Thr Ser Tyr Ile Lys Asn His Lys Ile Val Asn Gly Ser Asp
        355                 360                 365

Gly Gly Tyr Glu Phe Leu Leu Ser Asn Asp Ile Asp Asn Ser Asn Pro
    370                 375                 380

```
Val Val Gln Ala Glu Met Leu Asn Gln Leu Tyr Tyr Phe Met Asn Trp
385                 390                 395                 400

Gly Gln Ile Val Phe Gly Asp Lys Asp Lys Asp Ala His Phe Asp Gly
            405                 410                 415

Ile Arg Val Asp Ala Val Asp Asn Val Ser Val Asp Met Leu Gln Leu
        420                 425                 430

Val Ser Ser Tyr Met Lys Ala Ala Tyr Lys Val Asn Glu Ser Glu Ala
    435                 440                 445

Arg Ala Leu Ala Asn Ile Ser Ile Leu Glu Ala Trp Ser His Asn Asp
    450                 455                 460

Pro Tyr Tyr Val Asn Glu His Asn Thr Ala Ala Leu Ser Met Asp Asn
465                 470                 475                 480

Gly Leu Arg Leu Ser Ile Val His Gly Leu Thr Arg Pro Val Thr Asn
            485                 490                 495

Lys Gly Thr Gly Ala Arg Asn Ala Ser Met Lys Asp Leu Ile Asn Gly
        500                 505                 510

Gly Tyr Phe Gly Leu Ser Asn Arg Ala Glu Val Thr Ser Tyr Asp Gln
    515                 520                 525

Leu Gly Phe Ala Thr Tyr Leu Phe Val Arg Ala His Asp Ser Glu Val
    530                 535                 540

Gln Thr Val Ile Ala Asp Ile Ile Ser Lys Lys Ile Asp Pro Thr Thr
545                 550                 555                 560

Asp Gly Phe Thr Phe Thr Leu Asp Gln Leu Lys Gln Ala Phe Asp Ile
            565                 570                 575

Tyr Asn Ala Asp Met Leu Lys Val Asp Lys Glu Tyr Thr His Ser Asn
        580                 585                 590

Ile Pro Ala Ala Tyr Ala Leu Met Leu Gln Thr Met Gly Ala Ala Thr
    595                 600                 605

Arg Val Tyr Tyr Gly Asp Leu Tyr Thr Asp Asn Gly Gln Tyr Met Ala
    610                 615                 620

Lys Lys Ser Pro Tyr Phe Asp Gln Ile Thr Thr Leu Leu Lys Ala Arg
625                 630                 635                 640

Pro Lys Tyr Val Ala Gly Gly Gln Thr Ser Tyr Ile His Asn Leu Ala
            645                 650                 655

Gly Asp Gly Val Ser Ser Ala Lys Asp Asn Lys Glu Val Leu Val Ser
        660                 665                 670

Val Arg Tyr Gly Gln Asp Leu Met Ser Lys Thr Asp Thr Glu Gly Gly
    675                 680                 685

Lys Tyr Gly Arg Asn Ser Gly Met Leu Thr Leu Ile Ala Asn Asn Pro
690                 695                 700

Asp Leu Lys Leu Ala Asp Gly Glu Thr Ile Thr Val Asn Met Gly Ala
705                 710                 715                 720

Ala His Lys Asn Gln Ala Tyr Arg Pro Leu Leu Leu Gly Thr Asp Lys
            725                 730                 735

Gly Ile Val Ser Ser Leu Asn Asp Ser Asp Thr Lys Val Val Lys Tyr
        740                 745                 750

Thr Asp Ala Gln Gly Asn Leu Val Phe Thr Ala Asp Glu Ile Lys Gly
    755                 760                 765

Phe Lys Thr Val Asp Met Ser Gly Tyr Leu Ser Val Trp Val Pro Val
    770                 775                 780

Gly Ala Thr Asp Asp Gln Asn Val Leu Ala Lys Pro Ser Thr Lys Ala
785                 790                 795                 800

Tyr Lys Glu Gly Asp Lys Val Tyr Ser Ser Ser Ala Ala Leu Glu Ala
```

```
                805                 810                 815
Gln Val Ile Tyr Glu Gly Phe Ser Asn Phe Gln Asp Phe Val Lys Glu
            820                 825                 830

Asp Ser Gln Tyr Thr Asn Lys Leu Ile Ala Ala Asn Ala Asp Leu Phe
            835                 840                 845

Lys Ser Trp Gly Ile Thr Ser Phe Glu Ile Ala Pro Gln Tyr Val Ser
        850                 855                 860

Ser Lys Asp Gly Thr Phe Leu Asp Ser Ile Ile Glu Asn Gly Tyr Ala
865                 870                 875                 880

Phe Thr Asp Arg Tyr Asp Phe Ala Met Ser Lys Asn Asn Lys Tyr Gly
                885                 890                 895

Ser Lys Glu Asp Leu Arg Asp Ala Leu Lys Ala Leu His Lys Gln Gly
            900                 905                 910

Ile Gln Val Ile Ala Asp Trp Val Pro Asp Gln Leu Tyr Thr Leu Pro
            915                 920                 925

Gly Lys Glu Val Val Thr Ala Thr Arg Thr Asp Thr His Gly Lys Val
        930                 935                 940

Leu Asp Asp Thr Ser Leu Val Asn Lys Leu Tyr Val Thr Asn Thr Lys
945                 950                 955                 960

Ser Ser Gly Asn Asp Phe Gln Ala Gln Tyr Gly Gly Ala Phe Leu Asp
                965                 970                 975

Lys Leu Gln Lys Leu Tyr Pro Glu Ile Phe Lys Glu Val Met Glu Ala
            980                 985                 990

Ser Gly Lys Thr Ile Asp Pro Ser  Val Lys Ile Lys Gln  Trp Glu Ala
            995                 1000                1005

Lys Tyr  Phe Asn Gly Thr Asn  Ile Gln Lys Arg Gly  Ser Asp Tyr
        1010                1015                1020

Val Leu  Ser Asp Gly Lys Leu  Tyr Phe Thr Val Asn  Asp Lys Gly
        1025                1030                1035

Thr Phe  Leu Pro Ala Ala Leu  Thr Gly Asp Thr Lys  Ala Lys Thr
        1040                1045                1050

Gly Phe  Ala Tyr Asp Gly Thr  Gly Val Thr Tyr Tyr  Thr Thr Ser
        1055                1060                1065

Gly Thr  Gln Ala Lys Ser Gln  Phe Val Thr Tyr Asn  Gly Lys Gln
        1070                1075                1080

Tyr Tyr  Phe Asn Asp Lys Gly  Tyr Leu Val Thr Gly  Glu Gln Thr
        1085                1090                1095

Ile Asp  Gly Ser Asn Tyr Phe  Phe Leu Pro Asn Gly  Val Met Phe
        1100                1105                1110

Thr Asp  Gly Val Arg Lys Asn  Ala Lys Gly Gln Ser  Leu Val Tyr
        1115                1120                1125

Gly Lys  Ser Gly Lys Leu Thr  Thr Gln Thr Gly Trp  Lys Glu Val
        1130                1135                1140

Thr Val  Lys Asp Asp Ser Gly  Lys Glu Glu Lys Phe  Tyr Gln Tyr
        1145                1150                1155

Phe Phe  Lys Gly Gly Ile Met  Ala Thr Gly Leu Thr  Glu Val Glu
        1160                1165                1170

Gly Lys  Glu Lys Tyr Phe Tyr  Asp Asn Gly Tyr Gln  Ala Lys Gly
        1175                1180                1185

Val Phe  Val Pro Thr Lys Asp  Gly His Leu Met Phe  Phe Cys Gly
        1190                1195                1200

Asp Ser  Gly Glu Arg Lys Tyr  Ser Gly Phe Phe Glu  Gln Asp Gly
        1205                1210                1215
```

```
Asn Trp Tyr Tyr Ala Asn Asp Lys Gly Tyr Val Ala Thr Gly Phe
1220                1225                1230

Thr Lys Val Gly Lys Gln Asn Leu Tyr Phe Asn Glu Lys Gly Val
    1235                1240                1245

Gln Val Lys Asn Arg Phe Phe Gln Val Gly Asp Ala Thr Tyr Tyr
1250                1255                1260

Ala Asn Asn Glu Gly Asp Val Leu Arg Gly Ala Gln Thr Ile Asn
1265                1270                1275

Gly Asp Glu Leu Tyr Phe Asp Glu Ser Gly Lys Gln Val Lys Gly
1280                1285                1290

Glu Phe Val Asn Asn Pro Asp Gly Thr Thr Ser Tyr Tyr Asp Ala
1295                1300                1305

Ile Thr Gly Val Lys Leu Val Asp Thr Ser Leu Val Val Asp Gly
1310                1315                1320

Gln Thr Phe Asn Val Asp Ala Lys Gly Val Val Thr Lys Ala His
1325                1330                1335

Thr Pro Gly Phe Tyr Thr Thr Gly Asp Asn Asn Trp Phe Tyr Ala
1340                1345                1350

Asp Ser Tyr Gly Arg Asn Val Thr Gly Ala Gln Val Ile Asn Gly
1355                1360                1365

Gln His Leu Tyr Phe Asp Ala Asn Gly Arg Gln Val Lys Gly Gly
1370                1375                1380

Phe Val Thr Asn Thr Asp Gly Ser Arg Ser Phe Tyr His Trp Asn
1385                1390                1395

Thr Gly Asp Lys Leu Val Ser Thr Phe Phe Thr Thr Gly His Asp
1400                1405                1410

Arg Trp Tyr Tyr Ala Asp Asp Arg Gly Asn Val Val Thr Gly Ala
1415                1420                1425

Gln Val Ile Asn Gly Gln Lys Leu Phe Phe Asp Thr Asp Gly Lys
1430                1435                1440

Gln Val Lys Gly Ala Phe Ala Thr Asn Ala Asn Gly Ser Arg Ser
1445                1450                1455

Tyr Tyr His Trp Asn Thr Gly Asn Lys Leu Val Ser Thr Phe Phe
1460                1465                1470

Thr Ser Gly Asp Asn Asn Trp Tyr Tyr Ala Asp Ala Lys Gly Glu
1475                1480                1485

Val Val Val Asn Gly Gln His Leu Tyr Phe Asp Gln Thr Gly Lys
1490                1495                1500

Gln Val Lys Gly Ala Thr Ala Thr Asn Pro Asp Gly Ser Ile Ser
1505                1510                1515

Tyr Tyr Asp Val His Thr Gly Glu Lys Ala Ile Asn Arg Trp Val
1520                1525                1530

Lys Ile Pro Ser Gly Gln Trp Val Tyr Phe Asn Ala Gln Gly Lys
1535                1540                1545

Gly Tyr Val Ser
1550

<210> SEQ ID NO 69
<211> LENGTH: 1302
<212> TYPE: PRT
<213> ORGANISM: Streptococcus criceti HS-6

<400> SEQUENCE: 69

Ala Asp Ala Thr Asp Gly Asn Gly Gly Asn Thr Gln Val Ala His Leu
```

-continued

```
1               5                   10                  15
Ile Pro Lys Glu Pro Thr Asp Tyr Lys Phe Asp Thr Pro Ser Gly Ile
                20                  25                  30

Leu Thr Gly Leu Asn Phe Ala Asn Ala Gln Thr Ser Pro Ala Gly Asp
                35                  40                  45

Asn Ala Gly Ala Asn Gln Pro Ala Gly Gly Ile Glu Pro Gln Thr Ala
50                  55                  60

Glu Asn Ala Ala Thr Asp Gly Gln Ala Val Pro Gln Thr Ser Asp Gln
65                  70                  75                  80

Pro Gly His Leu Glu Asn Val Asp Gly Lys Thr Tyr Tyr Val Asp Ala
                85                  90                  95

Asn Gly Gln Arg Leu Lys Asn Tyr Ser Thr Val Ile Asp Gly Lys Thr
                100                 105                 110

Tyr Tyr Phe Asp Ala Gln Thr Gly Gln Ala Gln Ala Glu Thr Pro Gln
                115                 120                 125

Ile Asn Gln Asn Asp Asn Gln Val Ala Pro Asp Thr Tyr Ala Ala Asn
                130                 135                 140

Asn Gln Ala Phe Thr Asn Asp Val Ser Ser Phe Glu Thr Val Asp Asn
145                 150                 155                 160

Tyr Val Thr Ala Asp Ser Trp Tyr Arg Pro Arg Lys Ile Leu Lys Asn
                165                 170                 175

Gly Glu Ser Trp Gln Ala Ser Ala Glu Ser Asp Met Arg Pro Ile Leu
                180                 185                 190

Met Thr Trp Trp Pro Asp Ala Ala Thr Lys Ala Ala Tyr Ala Asn Tyr
                195                 200                 205

Trp Val Lys Glu Gly Leu Ile Ser Gly Ser Tyr Ser Pro Asn Ser Ala
210                 215                 220

Asn Leu Glu Thr Ala Val Gln Thr Ile Gln Ala Ala Ile Glu Lys Lys
225                 230                 235                 240

Ile Ala Ser Glu Gly Ser Thr Ala Trp Leu Arg Asp Lys Met Ser Gln
                245                 250                 255

Phe Val Lys Ser Gln Asn Gln Trp Ser Leu Ala Ser Glu Asn Pro Thr
                260                 265                 270

Val Tyr Pro Asn Gln Asp His Leu Gln Gly Gly Ala Leu Leu Phe Ser
                275                 280                 285

Asn Asn Glu Ala Thr Ala His Ala Asn Ser Asp Trp Arg Leu Leu Asn
                290                 295                 300

Arg Asn Pro Thr Phe Gln Thr Gly Lys Gln Lys Tyr Phe Thr Thr Asn
305                 310                 315                 320

Tyr Ala Gly Tyr Glu Leu Leu Leu Ala Asn Asp Val Asp Asn Ser Asn
                325                 330                 335

Pro Ile Val Gln Ala Glu Gln Leu Asn His Phe His Tyr Leu Met Asn
                340                 345                 350

Trp Gly Glu Ile Val Met Gly Asp Lys Asn Ala Asn Phe Asp Gly Val
                355                 360                 365

Arg Val Asp Ala Val Asp Asn Val Asn Ala Asp Leu Leu Gln Ile Gln
370                 375                 380

Arg Asp Tyr Tyr Lys Ala Lys Tyr Gly Val Asp Gln Asn Glu Lys Asn
385                 390                 395                 400

Ala Ile Asp His Leu Ser Ile Leu Glu Ala Trp Ser Gly Asn Asp Asn
                405                 410                 415

Asp Tyr Val Lys Asp Gln Asn Asn Phe Ser Leu Ser Ile Asp Asn Ser
                420                 425                 430
```

```
Gln Arg Ser Tyr Met Leu Ala Ala Phe Ala Tyr Pro Ala Ser Gln Arg
            435                 440                 445

Gly Asn Asp Tyr Ile Ser Leu Leu Pro Lys Val Gly Leu Lys Asp Arg
    450                 455                 460

Arg Tyr Ala Lys Asn Gly Asn Pro Val Pro Asn Tyr Val Phe Ile Arg
465                 470                 475                 480

Ala His Asp Ser Glu Val Gln Thr Arg Ile Ala Lys Ile Ile Arg Glu
                485                 490                 495

Arg Leu Gly Lys Thr Asn Ala Asp Gly Leu Thr Asn Ile Thr Leu Asp
                500                 505                 510

Asp Leu Asn Lys Ala Phe Asp Ile Tyr Asn Gln Asp Met Lys Ala Val
                515                 520                 525

Asp Lys Gln Tyr Tyr Pro Asn Asn Leu Pro Met Ala Tyr Ala Trp Met
                530                 535                 540

Leu Gln Asn Lys Asp Thr Val Thr Arg Val Tyr Tyr Gly Asp Met Tyr
545                 550                 555                 560

Thr Asp Asp Gly Gln Tyr Met Glu Thr Lys Thr Pro Phe His Asp Ala
                565                 570                 575

Ile Glu Thr Leu Leu Lys Ala Arg Ile Lys Tyr Val Ala Gly Gly Gln
                580                 585                 590

Thr Ala Gly Tyr Val Gln Gly Trp Gly Ser Gly Ile Leu Thr Ser Val
                595                 600                 605

Arg Tyr Gly Lys Gly Ala Asp Thr Ala Ile Asp Ala Gly Thr Ala Glu
                610                 615                 620

Thr Arg Thr Ser Gly Met Ala Val Leu Ile Asn Lys Pro Asn Phe
625                 630                 635                 640

Gln Ser Tyr Asn Gly Leu Thr Leu Asp Met Gly Ala Ala His Lys Asn
                645                 650                 655

Gln Ala Tyr Arg Pro Leu Leu Leu Ser Thr Lys Asp Gly Ile Ala Thr
                660                 665                 670

Tyr Leu Asn Asp Ser Asp Val Ser Ser Asn Gln Tyr Lys Tyr Thr Asp
                675                 680                 685

Gly Gln Gly Arg Leu Asn Phe Ser Ala Ser Glu Leu Arg Ser Val Ala
                690                 695                 700

Asn Val Gln Val Ser Gly Met Ile Gln Val Trp Val Pro Val Gly Ala
705                 710                 715                 720

Ala Asp Asn Gln Asp Val Arg Val Ala Pro Asn Thr Asn Arg Asn Asn
                725                 730                 735

Ser Ser Asn Ile Tyr Thr Gln Ser Asp Ala Leu Asp Ser Gln Val Ile
                740                 745                 750

Tyr Glu Gly Phe Ser Asn Phe Gln Ala Phe Ala Lys Thr Pro Glu Gln
                755                 760                 765

Tyr Thr Asn Ala Val Ile Ala Lys Asn Ala Asp Leu Phe Lys Ser Trp
770                 775                 780

Gly Ile Thr Gln Phe Glu Met Ala Pro Gln Tyr Val Ser Ser Glu Asp
785                 790                 795                 800

Gly Thr Phe Leu Asp Ser Val Val Leu Asn Gly Tyr Ala Phe Ser Asp
                805                 810                 815

Arg Tyr Asp Leu Ala Met Ser Lys Asn Asn Lys Tyr Gly Ser Lys Glu
                820                 825                 830

Asp Leu Ala Asn Ala Ile Lys Gly Leu His Asn Ala Gly Ile Lys Val
                835                 840                 845
```

```
Leu Ser Asp Trp Val Pro Asp Gln Met Tyr Asn Leu Pro Gly Lys Glu
    850                 855                 860

Val Val Thr Ala Thr Arg Val Asp Gln Tyr Gly Arg Pro Lys Ala Gly
865                 870                 875                 880

Ala Thr Ile Asn Arg Thr Pro Tyr Val Asn Thr Lys Thr Tyr Gly
            885                 890                 895

Asp Tyr Gln Glu Gln Tyr Gly Gly Lys Phe Leu Asp Glu Leu Gln Lys
                900                 905                 910

Leu Tyr Pro Ser Leu Phe Thr Thr Lys Gln Ile Ser Thr Gly Lys Pro
            915                 920                 925

Ile Asp Pro Ser Val Lys Ile Thr Asn Trp Ser Ala Lys Tyr Phe Asn
930                 935                 940

Gly Ser Asn Ile Leu Gly Arg Gly Ala Lys Tyr Val Leu Ser Asp Asn
945                 950                 955                 960

Asn Lys Tyr Leu Asn Leu Gly Ala Gly Gln Phe Phe Leu Pro Thr Asn
            965                 970                 975

Leu Asn Asn Thr Tyr Gly Gln Pro Gln Ala Pro Ala Asn Gly Phe Ile
            980                 985                 990

Ser Lys Asn Gly Gly Ile His Tyr Ile Asp Asn Asn Gly Gln Glu Val
            995                 1000                1005

Lys Asn Gln Phe Lys Glu Ile Ala Gly Ser Trp Tyr Tyr Phe Asp
    1010                1015                1020

Ala Asn Gly Lys Met Ala Thr Gly Gln Thr Lys Ile Gly Asn Thr
    1025                1030                1035

Thr Tyr Leu Phe Met Pro Asn Gly Lys Gln Leu Lys Glu Gly Val
    1040                1045                1050

Trp Tyr Asp Gly Lys Lys Ala Tyr Tyr Tyr Asp Asn Gly Arg
    1055                1060                1065

Thr Trp Thr Asn Lys Gly Phe Val Glu Phe Lys Val Asn Gly Gln
    1070                1075                1080

Asp Lys Trp Arg Tyr Phe Asn Gly Asp Gly Ser Ile Ala Val Gly
    1085                1090                1095

Leu Val Ser Leu Asp Asn Arg Thr Leu Tyr Phe Asp Ala Tyr Gly
    1100                1105                1110

Tyr Gln Val Lys Gly Gln Thr Leu Thr Ile Asn Gly Lys Thr Tyr
    1115                1120                1125

Ser Phe Asp Ala Asn Glu Gly Asp Leu Ile Thr Gly Asn Thr Pro
    1130                1135                1140

Ser Pro Glu Pro Asn Asn Gln Gly Ala Trp Glu Ala Leu Gly Asp
    1145                1150                1155

Asn Gln Trp Gly Tyr Arg Lys Asp Gly Lys Leu Leu Thr Gly Ser
    1160                1165                1170

Gln Thr Ile Ala Gly Gln Lys Val Phe Phe Gln Pro Asn Gly Val
    1175                1180                1185

Gln Val Lys Gly Gly Thr Ala Lys Asp Glu Ala Gly Val Leu Arg
    1190                1195                1200

Phe Tyr Asp Arg Asp Gln Gly His Leu Ala Gly Lys Gly Trp Tyr
    1205                1210                1215

Ser Thr Ala Asp Asn Asn Trp Val Tyr Val Asp Asp Ala Gly Arg
    1220                1225                1230

Val Val Thr Gly Leu Gln Lys Ile Gly Ser Gln Thr Leu Tyr Phe
    1235                1240                1245

Asp Asp Asn Gly Ile Gln Ala Lys Gly Lys Ala Ile Trp Asp Lys
```

```
                1250                1255                1260

Asp Gly Asn Leu Arg Tyr Phe Ala Ala Gly Ser Gly Asp Met Ile
            1265                1270                1275

Thr Asn Arg Trp Tyr Asn Ile Gly Asp Asn Gln Trp Tyr Trp Phe
        1280                1285                1290

Asn Asn Gln Gly Ile Ala Ser Arg Trp
        1295                1300

<210> SEQ ID NO 70
<211> LENGTH: 1107
<212> TYPE: PRT
<213> ORGANISM: Leuconostoc mesenteroides

<400> SEQUENCE: 70

Val Lys Gly Asp Lys Arg Thr Ile Asp Gly Val Leu Tyr Thr Phe Asp
 1               5                  10                  15

Lys Glu Ser Gly Glu Arg Lys Gly Leu Asp Ser Ile Ser Val Leu Pro
                20                  25                  30

Thr Asn Gly Gln Tyr Thr Thr Asp Lys Ala Gln Asn Trp Tyr Tyr Gln
            35                  40                  45

Val Asp Gly Glu Asn Val Lys Gly Leu Tyr Thr Asn Asn Asp Gly Gln
        50                  55                  60

Leu Arg Tyr Phe Asp Leu Thr Thr Gly Val Gln Thr Lys Gly Asn Phe
 65                  70                  75                  80

Val Thr Ile Gly Asn Asp Thr Tyr Tyr Phe Thr Lys Glu Gln Gly Asp
                85                  90                  95

Gly Gln Ile Val Ser Glu Val Val Ser Gly His Tyr Gly Thr Val Gln
            100                 105                 110

Leu Ser Asp Asn Ser Ser Ala Trp Val Tyr Arg Gly Ala Asn Asp Gln
        115                 120                 125

Ile Leu Lys Gly Leu Gln Asn Ile Asn Gly Arg Leu Gln Tyr Phe Asp
    130                 135                 140

Leu Thr Thr Gly Ala Gln Leu Lys Gly Gly Ala Ala Asn Tyr Asp Gly
145                 150                 155                 160

Asn Leu Tyr Tyr Phe Glu Ser Ser Asp Gly Asn Leu Val Ser Lys Ile
                165                 170                 175

Gln Gln Ser Tyr Ser Thr Gly Asn Tyr Val Thr Asp Gly Asp Lys Val
            180                 185                 190

Thr Tyr Ala Asp Glu Gln Asn Asn Gln Val Thr Gly Leu Ala Leu Ile
        195                 200                 205

Asp Asp Gln Leu Gln Tyr Phe Asp Pro Ser Asp Gly Arg Gln Val Lys
    210                 215                 220

Asn Glu Gln Val Ile Val Asp Gly Val Thr Tyr Tyr Phe Asp Lys Asn
225                 230                 235                 240

Gly Asn Gly Gln Tyr Leu Phe Thr Asn Thr Ala Thr Met Ser Thr Asn
                245                 250                 255

Glu Phe Ala Lys His Ser Ala Ala Tyr Ser Asn Asp Ser Ser Ser Phe
            260                 265                 270

Lys Asn Thr Ile Asp Gly Phe Leu Thr Ala Asp Thr Trp Tyr Arg Pro
        275                 280                 285

Lys Asp Ile Leu Glu Asn Gly Gln Thr Trp Val Val Ser Ser Thr Asn
    290                 295                 300

Asp Val Arg Pro Leu Ile Thr Val Trp Trp Leu Asn Lys Asp Val Gln
305                 310                 315                 320
```

-continued

```
Val Asn Tyr Ser Asn Phe Met Lys Gln Asn Gly Leu Leu Asp Thr Ser
                325                 330                 335

Ser Gln Phe Asn Leu Gln Ser Asp Gln Tyr Asp Leu Asn Val Ala Ala
            340                 345                 350

Gln Lys Val Gln Val Ala Ile Glu Lys Arg Ile Ser Lys Glu Lys Ser
        355                 360                 365

Thr Asp Trp Leu Lys Asp Leu Leu Phe Glu Ala His Glu Asp Thr Pro
    370                 375                 380

Ser Phe Val Lys Gln Gln Phe Ile Trp Asn Lys Asp Ser Glu Tyr Gln
385                 390                 395                 400

Gly Gln Gly Asp Ala Trp Phe Gln Gly Gly Tyr Leu Lys Tyr Gly Asn
                405                 410                 415

Asn Glu Leu Thr Pro Thr Thr Asn Ser Asp Tyr Arg Glu Ser Gly Asn
            420                 425                 430

Thr Leu Asp Phe Leu Leu Ala Asn Asp Val Asp Asn Ser Asn Pro Ala
        435                 440                 445

Val Gln Ala Glu Asn Leu Asn Trp Leu His Tyr Leu Met Asn Phe Gly
    450                 455                 460

Thr Ile Thr Ala Asn Asp Asp Ala Asn Phe Asp Ser Ile Arg Ile
465                 470                 475                 480

Asp Ala Val Asp Phe Ile Asp Asn Asp Ala Ile Gln Arg Thr Tyr Asp
                485                 490                 495

Tyr Met Arg Asp Ala Tyr Lys Val Asp Ala Ser Glu Asp Asn Ala Asn
            500                 505                 510

Lys His Ile Ser Leu Val Glu Ala Gly Leu Asp Ala Gly Thr Ser Thr
        515                 520                 525

Ile Lys Ser Asp Ala Leu Val Glu Ser Asn Phe Arg Glu Ala Ala Thr
    530                 535                 540

Leu Ser Leu Ala Asn Gln Ser Gly Glu Asn Ser Ser Leu Thr Asn Met
545                 550                 555                 560

Leu Gln Asp Ile Asp Gly Gly Gln Ile Ile Ala Asp His Ala Asn Asn
                565                 570                 575

Ala Thr Glu Asn Glu Ser Thr Pro Asn Tyr Ser Ile Ile His Ala His
            580                 585                 590

Asp Lys Gly Ile Gln Glu Lys Val Gly Ala Ala Ile Thr Asp Val Thr
        595                 600                 605

Gly Ala Asp Trp Thr Asn Phe Thr Asp Asp Gln Leu Lys Glu Gly Leu
    610                 615                 620

Ala Ala Tyr Tyr Gln Asp Gln Arg Ser Thr Asn Lys Lys Tyr Asn Ile
625                 630                 635                 640

Tyr Asn Leu Pro Ser Ile Tyr Ala Leu Met Leu Thr Asn Lys Asp Thr
                645                 650                 655

Val Pro Arg Val Tyr Tyr Gly Asp Met Tyr Gln Asp Asp Gly Gln Tyr
            660                 665                 670

Met Glu Lys Gln Ser Ile Tyr Tyr Asp Ala Ile Val Ser Leu Met Asn
        675                 680                 685

Thr Arg Lys Ser Tyr Val Ser Gly Gly Gln Thr Met Asp Val Asp Glu
    690                 695                 700

His Gly Leu Leu Lys Ser Val Arg Phe Gly Lys Asp Ala Met Thr Ala
705                 710                 715                 720

Ser Asp Leu Gly Thr Asn Glu Thr Arg Thr Glu Gly Val Gly Val Leu
                725                 730                 735

Val Gly Asn Asp Ser Ser Leu Lys Leu Asn Asp Ser Asp Thr Val Thr
```

```
        740                 745                 750
Leu Glu Met Gly Ala His Lys Asn Gln Lys Tyr Arg Ala Ala Leu
            755                 760                 765
Leu Thr Thr Ser Asp Gly Ile Val Thr Tyr Asp Ala Asp Asn Asp Ala
            770                 775                 780
Pro Thr Ile Trp Thr Asp Arg Gly Thr Leu Thr Phe Ser Asn Lys
785                 790                 795                 800
Glu Ile Ala Gly Gln Asp Tyr Thr Ser Val Gln Gly Phe Ala Asn Ser
                    805                 810                 815
Gln Val Ser Gly Tyr Leu Ala Val Trp Val Pro Val Gly Ala Ser Asp
                    820                 825                 830
Asp Gln Asp Val Arg Thr Ala Ala Leu Thr Asp Ala Asn Leu Asp Asp
                    835                 840                 845
Lys Val Leu His Ser Asn Ala Ala Leu Asp Ser Asn Leu Ile Tyr Glu
            850                 855                 860
Gly Phe Ser Asn Phe Gln Pro Lys Ala Thr Thr Asn Asp Glu Leu Thr
865                 870                 875                 880
Asn Val Val Ile Ala Lys Asn Ala Asn Leu Phe Glu Lys Trp Gly Ile
                    885                 890                 895
Thr Ser Phe Glu Met Ala Pro Gln Tyr Arg Ser Ser Gly Asp His Thr
                    900                 905                 910
Phe Leu Asp Ser Thr Ile Asp Asn Gly Tyr Ala Phe Thr Asp Arg Tyr
                    915                 920                 925
Asp Leu Gly Phe Glu Thr Pro Thr Lys Tyr Gly Thr Asp Lys Asp Leu
            930                 935                 940
Arg Thr Ala Ile Lys Ala Leu His Gln Ser Asn Met Gln Val Met Ala
945                 950                 955                 960
Asp Val Val Asp Asn Gln Val Tyr Asn Leu Ser Gly Gln Glu Val Val
                    965                 970                 975
Ser Ala Ser Arg Ala Gly Val Tyr Gly Asn Asp Val Ser Thr Gly Phe
                    980                 985                 990
Gly Thr Gln Leu Tyr Ala Val Asn Ser Val Gly Gly Lys Tyr Gln
            995                 1000                1005
Ala Gln Tyr Gly Gly Glu Tyr Leu Asn Glu Leu Lys Gln Gln Tyr
            1010                1015                1020
Pro Asp Leu Phe Glu Ala Lys Thr Tyr Asp Tyr Trp Val Lys Asn
            1025                1030                1035
Tyr Ser Asn Asp Gly Ser Asp Pro Tyr Tyr Thr Leu Ser Gln Asn
            1040                1045                1050
Thr Arg Lys Asp Met Pro Ser Ser Glu Val Ile Lys Gln Trp Ser
            1055                1060                1065
Ala Lys Tyr Met Asn Gly Thr Asn Val Leu Gly Asn Gly Met Gly
            1070                1075                1080
Tyr Val Leu Lys Asp Trp Asn Thr Gly Glu Tyr Phe Lys Ile Gly
            1085                1090                1095
Glu Lys Asn Ala Asp Phe Ile Thr Asn
            1100                1105

<210> SEQ ID NO 71
<211> LENGTH: 1637
<212> TYPE: PRT
<213> ORGANISM: Fructobacillus tropaeoli

<400> SEQUENCE: 71
```

-continued

```
Asp Asp Ser Gln Gln Ser Ser Thr Gln Ile Gln Ser Thr Gln Val Thr
1               5                   10                  15

Thr Ala Leu Pro Ala Gly Gly Gln Tyr Ser Thr Thr Asn Gly Gly Gln
                20                  25                  30

Ser Trp Asn Tyr Leu Val Asn Gly Val Ala Ile Lys Gly Met Tyr Gln
            35                  40                  45

Asp Gly Gln Gly Gln Leu Arg Tyr Phe Asn Phe Ile Asp Gly Thr Gln
        50                  55                  60

Val Lys Gly Glu Phe Leu Ser Ile Asn Gly Thr Tyr Tyr Tyr Phe Asp
65                  70                  75                  80

Gln Asn Ser Gly Glu Gly His Leu Val Pro Thr Gln Ser Asn Gly His
                85                  90                  95

Tyr Thr Glu Ile Gly Asn Thr Gly Ala Trp Gly Tyr Gln Asn Ser Asn
            100                 105                 110

Gly Glu Leu Val Lys Gly Ile Gln Asn Ile Asp Gly Gln Leu Arg Tyr
        115                 120                 125

Phe Asp Glu Asn Thr Gly Asn Gln Val Lys Gly Ser Ala Thr Ile
    130                 135                 140

Gly Asn Lys Ser Tyr Tyr Phe Glu Pro Ser Gln Gly Thr Leu Thr Thr
145                 150                 155                 160

Thr Ile Asp Gln Val Ser Asp Ala Gln Asn Ala Asn Ile Arg Gly Leu
                165                 170                 175

Ala Thr Val Asn Gly Gln Leu Asn Tyr Phe Asp Pro Thr Thr Gly Glu
            180                 185                 190

Gln Ala Lys His Lys Gln Val Ala Thr Asn Gly Ala Thr Tyr Tyr Phe
        195                 200                 205

Asn Asp Ser Gly Val Gly Thr Tyr Leu Phe Thr Asn Val Gln Asn Thr
    210                 215                 220

Pro Ala Asn Asp Val Ser Gln His Asn Ala Val Asn Ser Thr Asp Thr
225                 230                 235                 240

Lys Asp Tyr Thr Asn Thr Val Asp Gly Phe Leu Thr Ala Asp Thr Trp
                245                 250                 255

Tyr Arg Pro Lys Tyr Ile Leu Asp Asn Gly Glu Asn Trp Arg Ala Ser
            260                 265                 270

Asn Glu Gly Glu Tyr Arg Pro Phe Ile Met Asn Trp Trp Pro Asn Lys
        275                 280                 285

Asn Val Glu Val Asn Tyr Leu Lys Leu Met Gln Asn Asn Leu Leu
    290                 295                 300

Ser Ser Thr Val Gln Tyr Asp Leu Phe Thr Asp Gln Ala Ile Leu Asn
305                 310                 315                 320

Gln Ala Ala Tyr Gln Ala Gln Ile Ala Ile Glu Lys Arg Ile Lys Ser
                325                 330                 335

Glu Gly Ser Thr Asp Trp Leu Asn Thr Leu Phe Gly Gly Asp Asp
            340                 345                 350

Ser His Pro Ser Phe Val Lys Gln Gln Phe Ile Trp Asn Ser Asp Ser
        355                 360                 365

Glu Ser Pro Trp Gln Gly Asp Ala Trp Phe Gln Gly Gly Tyr Leu Lys
    370                 375                 380

Tyr Gly Asn Ser Val Met Thr Pro Thr Ser Asn Ser Asn Tyr Arg Gln
385                 390                 395                 400

Ala Gly Asn Ala Phe Asp Phe Leu Leu Ala Asn Asp Val Asp Asn Gln
                405                 410                 415

Asn Pro Ile Val Gln Ala Glu Asp Leu Asn Trp Leu Tyr Tyr Leu Met
```

```
                420             425             430
Asn Phe Gly Ser Ile Thr Thr Asn Gly Leu Asp Asn Asp Ser Asn Phe
            435             440             445
Asp Ser Ile Arg Leu Asp Ala Val Asp Phe Ile His Asn Asp Ala Ile
450             455             460
Gln Arg Thr Tyr Asp Tyr Leu Arg Gln Ala Phe Asn Leu Thr Lys Asn
465             470             475             480
Glu Ala Thr Ala Asn Gln His Leu Ser Leu Val Glu Ala Gly Val Asp
            485             490             495
Ala Gly Thr Thr Thr Tyr Asn Ser Asp Gly Leu Ile Glu Ser Asn Ile
            500             505             510
Arg Pro Leu Ala Thr Asp Ser Leu Thr Asn Ala Pro Gly Lys Asn Ala
            515             520             525
Ser Leu Ser Asn Leu Ile Lys Asp Val Asp Ser Gly Glu Val Ile Ala
            530             535             540
Asp His Ala Asn Phe Ser Thr Asp Asp Gly Ile Pro Asn Tyr Ser Ile
545             550             555             560
Ile His Ala His Asp Lys Gly Ile Gln Glu Asn Val Gly Ala Ala Ile
            565             570             575
Thr Ala Ala Thr Gly Ala Asp Trp Thr Asn Phe Thr Thr Glu Gln Leu
            580             585             590
Glu Gln Gly Leu Asp Leu Tyr Tyr Gln Asp Gln Arg Ser Thr Asn Lys
            595             600             605
Lys Tyr Asn Ile Tyr Asn Leu Pro Ser Ile Tyr Ala Leu Met Leu Thr
610             615             620
Asn Lys Gly Thr Val Pro Arg Val Tyr Tyr Gly Asp Met Tyr Gln Asp
625             630             635             640
Asn Gly Gln Tyr Met Gln Gln Lys Ser Leu Tyr Tyr Asp Ala Ile Ser
            645             650             655
Ser Leu Met Thr Ala Arg Lys Gln Tyr Val Ala Gly Gly Gln Thr Met
            660             665             670
Ser Val Asp Glu Asn Gly Leu Leu Lys Ser Val Arg Phe Gly Lys Asn
            675             680             685
Ala Met Thr Ala Gln Asp Thr Gly Asp Ala Glu Thr Arg Thr Glu Gly
            690             695             700
Val Gly Val Ile Ile Gly Asn Asp Pro Ser Val Lys Val Ala Asp Gly
705             710             715             720
Gln Thr Val Thr Leu Asp Met Gly Ala Ala His Lys Asn Gln Ala Tyr
            725             730             735
Arg Pro Leu Ile Leu Thr Thr Ser Asp Gly Ile Gln Thr Tyr Asp Ser
            740             745             750
Asp Glu Asn Ala Pro Val Val Tyr Thr Asp Asn Gly Ile Leu Thr
            755             760             765
Phe Ser Asn Gln Asp Ile Asn Gly Gln Ala Asn Thr Lys Ile Val Gly
            770             775             780
Thr Leu Asn Pro Gln Val Ser Gly Tyr Leu Ala Val Trp Val Pro Val
785             790             795             800
Gly Ala Ser Ala Asp Gln Asp Ala Arg Thr Ala Pro Ser Thr Gln Ser
            805             810             815
Thr Asn Asp Gly Lys Val Leu His Thr Gly Ala Ala Leu Asp Ser Asn
            820             825             830
Leu Ile Phe Glu Gly Phe Ser Asn Phe Gln Pro Met Pro Thr Thr His
            835             840             845
```

-continued

```
Asp Glu Met Thr Asn Val Val Ile Ser Gln Asn Ala Ser Gln Phe Ala
        850             855                 860

Lys Trp Gly Ile Thr Ser Phe Glu Met Ala Pro Gln Tyr Arg Ser Ser
865             870                 875                 880

Glu Asp His Ser Phe Leu Asp Ser Thr Ile Asp Asn Gly Tyr Ala Phe
                885                 890                 895

Ser Asp Arg Tyr Asp Leu Gly Phe Gly Thr Pro Thr Lys Tyr Gly Thr
            900                 905                 910

Asp Glu Asp Leu Arg Asn Ala Ile Lys Ala Leu His Gln Asn Gly Met
            915                 920                 925

Gln Val Met Ala Asp Val Val Met Asn Gln Leu Tyr Ser Leu Asn Gly
        930                 935                 940

Lys Glu Val Val Ser Ala Ser Arg Ala Gly Val Tyr Gly Asn Asp Val
945                 950                 955                 960

Asp Leu Pro Phe Gly Thr Gln Leu Tyr Val Val Asn Thr Thr Gly Gly
                965                 970                 975

Gly Glu Tyr Gln Lys Lys Tyr Gly Gly Ala Phe Leu Asn Ile Ile Lys
                980                 985                 990

Glu Lys Tyr Pro Thr Leu Phe Asp Ser Glu Ser Tyr Asp Tyr Tyr Leu
            995                 1000                1005

Lys Asn Tyr Ser Asp Asn Gly His Gly Pro Ala Tyr Met Thr Thr
        1010                1015                1020

Ala Thr Ala Thr Arg Glu Ala Ile Pro Ser Asp Gln Pro Leu Lys
        1025                1030                1035

Glu Trp Ser Ala Lys Tyr Met Asn Gly Thr Asn Ile Leu Gly Leu
        1040                1045                1050

Gly Met Gly Tyr Val Leu Lys Asp Trp Asn Asn Gly Ala Tyr Phe
        1055                1060                1065

Lys Leu Ser Gly Thr Asp Thr Leu Pro Gln Ser Leu Val Ala
        1070                1075                1080

Leu Thr Gly Trp Asn Gln Asn Asp Asp Gly Thr Trp Ser Tyr Tyr
        1085                1090                1095

Ser Thr Asp Thr Asp Asp Arg Val Thr Gly Lys Gln Val Ile Asp
        1100                1105                1110

Gly Arg Thr Leu Leu Phe Asp Asn Gln Gly Asn Gln Ile Lys Gly
        1115                1120                1125

Gly Trp Gly Glu Asn Pro Asp Gly Thr Trp Ser Tyr Tyr Asn Ala
        1130                1135                1140

Asp Thr Gly Asp Arg Val Ile Gly Glu Gln Val Ile Asp Gly Arg
        1145                1150                1155

Thr Leu Phe Phe Asp Asn Gln Gly Val Gln Val Lys Gly Gly Trp
        1160                1165                1170

Gly Glu Asn Tyr Asp Gly Thr Trp Ser Tyr Tyr Asn Ala Asp Thr
        1175                1180                1185

Gly Asp Arg Val Thr Gly Lys Gln Val Ile Asp Gly Arg Thr Leu
        1190                1195                1200

Leu Phe Asp Asn Arg Gly Val Gln Val Lys Gly Gly Trp Gly Glu
        1205                1210                1215

Asn Ser Asp Gly Thr Trp Ser Tyr Tyr Asn Ala Asp Thr Gly Asp
        1220                1225                1230

Arg Val Thr Gly Asn Gln Leu Ile Gly Gly Arg Asn Leu Leu Phe
        1235                1240                1245
```

-continued

```
Asp Asn Gln Gly Asn Gln Ile Lys Gly Gly Trp Asp Glu Asn Pro
    1250                1255                1260

Asp Gly Thr Trp Ser Tyr Tyr Asn Ala Asp Thr Gly Asp Arg Val
    1265                1270                1275

Thr Gly Val Gln Val Ile Asp Gly Lys Gln Leu Leu Phe Asp Ser
    1280                1285                1290

Asn Gly Ile Gln Val Lys Asn Ser Trp Gln Lys Asn Ala Asn Gly
    1295                1300                1305

Thr Trp Ser Tyr Tyr Asp Ala Asn Asp Gly His Leu Val Pro Ala
    1310                1315                1320

Asn Ser Ser Asn Asp Gly Thr Ser Ser Ser Thr Gln Asp Ser Gly
    1325                1330                1335

Asn Lys Ser Asn Gln Asn Pro Ser Ser Ser Ser Asn Ala Val Asn
    1340                1345                1350

Lys Thr Thr Gly Trp Ile Lys Asn Ser Asp Gly Thr Trp Ser Tyr
    1355                1360                1365

Leu Ser Ala Lys Ser Gly Gln Lys Val Thr Gly Ser Gln Thr Ile
    1370                1375                1380

Asp Gly Lys Gln Leu Leu Phe Asp Asp His Gly Val Gln Ile Lys
    1385                1390                1395

Gly Gly Trp Gly Lys Asn Ala Asp Gly Thr Trp Ser Tyr Tyr Asp
    1400                1405                1410

Ala Asn Ser Gly Glu Leu Thr Ser Thr Ser Asp Met Ser Asn Val
    1415                1420                1425

Asn Pro Gln Gln Thr Thr Thr Thr Thr Asn Glu Gln Ser Thr Thr
    1430                1435                1440

Asn Gln Pro Thr Asp Ile Thr Lys Asn Ser Asp Gly Val Tyr Val
    1445                1450                1455

Tyr Lys Asn Asp Ser Asn Lys Lys Ala Gln Gly Tyr Leu Asn Asp
    1460                1465                1470

Gly Ser Ser Trp Lys Trp Phe Asn Asp Gly Gln Leu Tyr Thr Gly
    1475                1480                1485

Phe Gln Asn Tyr Met Gly Ala Tyr Tyr Tyr Phe Ile Asn Gly Ile
    1490                1495                1500

Arg Gln Gln Asn Gln Trp Glu Asn Ile Trp Gly Leu Lys Tyr Tyr
    1505                1510                1515

Val Gly Asp Asp Gly Arg Thr Val Glu Gly Ile His Ala Ile Asp
    1520                1525                1530

Gly His Ala Tyr Asp Phe Gly Thr Asp Gly Thr Phe Asn Val Lys
    1535                1540                1545

Gly Ser Ala Ser Gly Tyr Leu Asn Asp Gly Lys Ser Trp Met Trp
    1550                1555                1560

Tyr Glu Gly Gly Asn Pro Tyr Thr Gly Phe Arg Tyr Tyr Met Asp
    1565                1570                1575

Thr Tyr Tyr Trp Phe Glu Asn Gly Val Arg Gln Asp Asn Ala Trp
    1580                1585                1590

His Gln Ala Trp Gly Leu Thr Tyr Tyr Thr Gly Ala Asp Gly Arg
    1595                1600                1605

Ala Val Gln Gly Val Gln Asn Ile Asn Gly Lys Leu Tyr Tyr Phe
    1610                1615                1620

Gly Asn Asp Gly Thr Phe Phe Met Arg Thr Asn Gln Glu Val
    1625                1630                1635
```

ALPHA-1,3-GLUCAN GRAFT COPOLYMERS

This application is a continuation of application Ser. No. 16/218,518 (filed Dec. 13, 2018) (now U.S. Pat. No. 11,098,334), which claims the benefit of U.S. Provisional Application Nos. 62/598,685 (filed Dec. 14, 2017) and 62/733,729 (filed Sep. 20, 2018). All of these prior applications are incorporated herein by reference in their entirety.

FIELD

The present disclosure is in the field of polysaccharides. For example, the disclosure pertains to compositions comprising dextran/alpha-1,3-glucan graft copolymers, derivatives thereof, and various applications using these materials.

REFERENCE TO SEQUENCE LISTING SUBMITTED ELECTRONICALLY

The official copy of the sequence listing is submitted electronically via EFS-Web as an ASCII formatted sequence listing with a file named 20181205_CL6591USNP_SequenceListing.txt created on Dec. 5, 2018, and having a size of about 387 kilobytes and is filed concurrently with the specification. The sequence listing contained in this ASCII-formatted document is part of the specification and is herein incorporated by reference in its entirety.

BACKGROUND

Driven by a desire to use polysaccharides in various applications, researchers have explored for polysaccharides that are biodegradable and that can be made economically from renewably sourced feedstocks. One such polysaccharide is alpha-1,3-glucan, an insoluble glucan polymer characterized by having alpha-1,3-glycosidic linkages. This polymer has been prepared, for example, using a glucosyltransferase enzyme isolated from *Streptococcus salivarius* (Simpson et al., *Microbiology* 141:1451-1460, 1995). Also for example, U.S. Pat. No. 7,000,000 disclosed the preparation of a spun fiber from enzymatically produced alpha-1,3-glucan. Various other glucan materials have also been studied for developing new or enhanced applications. For example, U.S. Patent Appl. Publ. No. 2015/0232819 discloses enzymatic synthesis of several insoluble glucans having mixed alpha-1,3 and -1,6 linkages.

Despite this work, new forms of alpha-1,3-glucan are desired to enhance the economic value and performance characteristics of this material in various applications. Compositions comprising alpha-1,3-glucan in the form of a graft copolymer are presently disclosed to address this need.

SUMMARY

In one embodiment, the present disclosure concerns a composition comprising a graft copolymer, or an ether- or ester-derivative thereof, wherein the graft copolymer comprises: (i) a backbone comprising dextran that has been modified with about 1%-25% alpha-1,2 branches, and (ii) one or more alpha-1,3-glucan side chains comprising at least about 50% alpha-1,3 glycosidic linkages.

In another embodiment, the present disclosure concerns a method of producing a graft copolymer, the method comprising: (a) contacting at least (i) water, (ii) sucrose, (iii) dextran that has been modified with about 1%-25% alpha-1,2 branches, and (iv) a glucosyltransferase enzyme that synthesizes alpha-1,3-glucan comprising at least about 50% alpha-1,3 glycosidic linkages, whereby a graft copolymer as presently disclosed is produced; and (b) optionally, isolating the graft copolymer produced in step (a).

In another embodiment, the present disclosure concerns a method for producing a film, the method comprising: (a) dissolving an insoluble graft copolymer as presently disclosed, or ether- or ester-derivative thereof, in a solvent to provide a solution; (b) contacting the solution with a surface; and (c) removing the solvent to form a film.

In another embodiment, the present disclosure concerns a method of producing alpha-1,3-glucan, the method comprising: (a) contacting at least (i) water, (ii) sucrose, (iii) dextran that has been modified with about 1%-50% alpha-1,2 branches, and (iv) a glucosyltransferase enzyme that synthesizes alpha-1,3-glucan comprising at least about 50% alpha-1,3 glycosidic linkages, thereby providing an enzymatic reaction, whereby alpha-1,3-glucan comprising at least about 50% alpha-1,3 glycosidic linkages is produced, and (b) optionally, isolating the alpha-1,3-glucan produced in step (a).

BRIEF DESCRIPTION OF THE SEQUENCES

TABLE 1

Summary of Nucleic Acid and Protein SEQ ID Numbers[b]

| Description | Nucleic acid SEQ ID NO. | Protein SEQ ID NO. |
|---|---|---|
| GTF 0874, *Streptococcus sobrinus*. The first 156 amino acids of the protein are deleted compared to GENBANK Identification No. 450874; a start methionine is included. | 1 [a] | 2 (1435 aa) |
| GTF 6855, *Streptococcus salivarius* SK126. The first 178 amino acids of the protein are deleted compared to GENBANK Identification No. 228476855 (Acc. No. ZP_04061500.1); a start methionine is included. | 3 [a] | 4 (1341 aa) |
| GTF 2379, *Streptococcus salivarius*. The first 203 amino acids of the protein are deleted compared to GENBANK Identification No. 662379; a start methionine is included. | 5 [a] | 6 (1247 aa) |
| GTF 7527 or GTFJ, *Streptococcus salivarius*. The first 42 amino acids of the protein are deleted compared to GENBANK Identification No. 47527; a start methionine is included. | 7 [a] | 8 (1477 aa) |
| GTF 1724, *Streptococcus downei*. The first 162 amino acids of the protein are deleted compared to GENBANK Identification No. 121724; a start methionine is included. | 9 [a] | 10 (1436 aa) |

TABLE 1-continued

Summary of Nucleic Acid and Protein SEQ ID Numbers[b]

| Description | Nucleic acid SEQ ID NO. | Protein SEQ ID NO. |
|---|---|---|
| GTF 0544, *Streptococcus mutans*. The first 164 amino acids of the protein are deleted compared to GENBANK Identification No. 290580544; a start methionine is included. | 11 [a] | 12 (1313 aa) |
| GTF 5926, *Streptococcus dentirousetti*. The first 144 amino acids of the protein are deleted compared to GENBANK Identification No. 167735926; a start methionine is included. | 13 [a] | 14 (1323 aa) |
| GTF 4297, *Streptococcus oralis*. The first 228 amino acids of the protein are deleted compared to GENBANK Identification No. 7684297; a start methionine is included. | 15 [a] | 16 (1348 aa) |
| GTF 5618, *Streptococcus sanguinis*. The first 223 amino acids of the protein are deleted compared to GENBANK Identification No. 328945618; a start methionine is included. | 17 [a] | 18 (1348 aa) |
| GTF 2765, unknown *Streptococcus* sp. C150. The first 193 amino acids of the protein are deleted compared to GENBANK Identification No. 322372765; a start methionine is included. | 19 [a] | 20 (1340 aa) |
| GTF 0427, *Streptococcus sobrinus*. The first 156 amino acids of the protein are deleted compared to GENBANK Identification No. 940427; a start methionine is included. | 25 [a] | 26 (1435 aa) |
| GTF 2919, *Streptococcus salivarius* PS4. The first 92 amino acids of the protein are deleted compared to GENBANK Identification No. 383282919; a start methionine is included. | 27 [a] | 28 (1340 aa) |
| GTF 2678, *Streptococcus salivarius* K12. The first 188 amino acids of the protein are deleted compared to GENBANK Identification No. 400182678; a start methionine is included. | 29 [a] | 30 (1341 aa) |
| GTF 3929, *Streptococcus salivarius* JIM8777. The first 178 amino acids of the protein are deleted compared to GENBANK Identification No. 387783929; a start methionine is included. | 33 [a] | 34 (1341 aa) |
| GTF 3298, *Streptococcus* sp. C150. The first 209 amino acids of the protein are deleted compared to GENBANK Identification No. 322373298; a start methionine is included. | | 59 (1242 aa) |
| Wild type GTFJ, *Streptococcus salivarius*. GENBANK Identification No. 47527. | | 60 (1518 aa) |
| Wild type GTF corresponding to GTF 2678, *Streptococcus salivarius* K12. | | 61 (1528 aa) |
| Wild type GTF corresponding to GTF 6855, *Streptococcus salivarius* SK126. | | 62 (1518 aa) |
| Wild type GTF corresponding to GTF 2919, *Streptococcus salivarius* PS4. | | 63 (1431 aa) |
| Wild type GTF corresponding to GTF 2765, unknown *Streptococcus* sp. C150. | | 64 (1532 aa) |
| Shorter version of GTF 7527, *Streptococcus salivarius*, (also referred to as "7527-NT" herein. The first 178 amino acids of the protein are deleted compared to GENBANK Identification No. 47527; a start methionine is included. | | 65 (1341 aa) |

[a] This DNA coding sequence is codon-optimized for expression in *E. coli*, and is merely disclosed as an example of a suitable coding sequence.
[b] SEQ ID NOs: 21-24, 31, 32 and 35-58 are intentionally not included in this table and merely serve as placeholders.

DETAILED DESCRIPTION

The disclosures of all cited patent and non-patent literature are incorporated herein by reference in their entirety.

Unless otherwise disclosed, the terms "a" and "an" as used herein are intended to encompass one or more (i.e., at least one) of a referenced feature.

Where present, all ranges are inclusive and combinable, except as otherwise noted. For example, when a range of "1 to 5" (i.e., 1-5) is recited, the recited range should be construed as including ranges "1 to 4", "1 to 3", "1-2", "1-2 & 4-5", "1-3 & 5", and the like.

The term "copolymer" herein refers to a polymer comprising at least two different types of alpha-glucan, such as dextran and alpha-1,3-glucan.

The terms "graft copolymer", "branched copolymer" and the like herein generally refer to a copolymer comprising a "backbone" (or "main chain") and side chains branching from the backbone. The side chains are structurally distinct from the backbone. Examples of graft copolymers herein comprise a dextran backbone that has been modified with about 1%-35% alpha-1,2 branches, and at least one side chain of alpha-1,3-glucan comprising at least about 50% alpha-1,3 glycosidic linkages. In some aspects, a dextran backbone can have an alpha-1,3-glucan extension, since the non-reducing end of dextran can prime alpha-1,3-glucan synthesis by a glucosyltransferase enzyme. A backbone can be an alpha-1,3-glucan-dextran linear copolymer in some instances.

The terms "alpha-1,3-glucan side chain" and "alpha-1,3-glucan arm" and the like can be used interchangeably herein. Alpha-1,3-glucan side chains are contemplated to be (i) extensions of alpha-1,2 branches, since alpha-1,2 branches present non-reducing ends that can possibly prime alpha-1,3-glucan synthesis by a glucosyltransferase enzyme; (ii) joined via alpha-1,3 linkage directly to the dextran backbone, in which case alpha-1,3-glucan side chain synthesis occurred by a glucosyltransferase enzyme first making an alpha-1,3 branch from the dextran backbone followed by extension of this branch by the enzyme; and/or (iii) joined via other alpha-glycosidic linkages (e.g., alpha-1,4 or alpha-1,2) to the dextran backbone (in some cases, such other linkages might result from the promiscuous activity of an alpha-1,3-glucan-synthesizing glucosyltransferase enzyme).

The terms "alpha-glucan", "alpha-glucan polymer" and the like are used interchangeably herein. An alpha-glucan is a polymer comprising glucose monomeric units linked together by alpha-glycosidic linkages. In typical embodiments, an alpha-glucan herein comprises at least about 80%, 81%, 82%, 83%, 84%, 85%, 86%, 87%, 88%, 89%, 90%, 91%, 92%, 93%, 94%, 95%, 96%, 97%, 98%, 99%, or 100% alpha-glycosidic linkages. Examples of alpha-glucan polymers herein include graft copolymers as presently disclosed.

The terms "poly alpha-1,3-glucan", "alpha-1,3-glucan", "alpha-1,3-glucan polymer" and the like are used interchangeably herein. Alpha-1,3-glucan is a polymer comprising glucose monomeric units linked together by glycosidic linkages, wherein at least about 30% of the glycosidic linkages are alpha-1,3. Alpha-1,3-glucan in certain embodiments comprises at least about 90% or 95% alpha-1,3 glycosidic linkages. Most or all of the other linkages in alpha-1,3-glucan herein typically are alpha-1,6, though some linkages may also be alpha-1,2 and/or alpha-1,4. Alpha-1,3-glucan as presently defined can characterize an alpha-1,3-glucan side chain herein. In some aspects, alpha-1,3-glucan can characterize an alpha-1,3-glucan "homopolymer", which is alpha-1,3-glucan that is not part of (i) a graft copolymer or (ii) part of a dextran-alpha-1,3-glucan linear copolymer.

The terms "dextran", "dextran polymer", "dextran molecule" and the like herein refer to a water-soluble alpha-glucan comprising at least 90% alpha-1,6 glycosidic linkages (with the balance of the linkages typically being alpha-1,3). Enzymes capable of synthesizing dextran from sucrose may be described as "dextransucrases" (EC 2.4.1.5).

A "substantially linear" dextran herein has 5% or less branches, before being modified to contain 1%-25% alpha-1,2 branches. A "completely linear" dextran has no branches, before being modified to contain 1%-25% alpha-1,2 branches. Dextran branches, if present prior to modification with alpha-1,2 branches, typically are short, being one (pendant) to three glucose monomers in length, and comprise less than about 10% of all the glucose monomers of a dextran polymer. Dextran as used in a glucosyltransferase reaction herein for alpha-1,3-glucan synthesis can optionally be characterized as a "primer".

An "alpha-1,2 branch" (and like terms) as referred to herein comprises a glucose that is alpha-1,2-linked to a dextran backbone; thus, an alpha-1,2 branch herein can also be referred to as an alpha-1,2,6 linkage. An alpha-1,2 branch (before possible extension with an alpha-1,3-glucan-synthesizing glucosyltransferase) herein typically has one glucose group (can optionally be referred to as a pendant glucose).

An "alpha-1,3 branch" (and like terms) as referred to herein comprises a glucose that is alpha-1,3-linked to a dextran backbone; thus, an alpha-1,3 branch herein can also be referred to as an alpha-1,3,6 linkage. An alpha-1,3 branch herein is contemplated to possibly result from a glucosyltransferase enzyme first making an alpha-1,3 branch from the dextran backbone followed by extension of this branch by the enzyme.

The percent branching in an alpha-glucan herein refers to that percentage of all the linkages in the alpha-glucan that represent branch points. For example, the percent of alpha-1,2 branching in an alpha-glucan herein refers to that percentage of all the linkages in the glucan that represent alpha-1,2 branch points.

The terms "linkage", "glycosidic linkage", "glycosidic bond" and the like refer to the covalent bonds connecting the sugar monomers within a saccharide compound (oligosaccharides and/or polysaccharides). Examples of glycosidic linkages include alpha-linked glucose oligomers with 1,6-alpha-D-glycosidic linkages (herein also referred to as "alpha-1,6" linkages); 1,3-alpha-D-glycosidic linkages (herein also referred to as "alpha-1,3" linkages); 1,4-alpha-D-glycosidic linkages (herein also referred to as "alpha-1,4" linkages); and 1,2-alpha-D-glycosidic linkages (herein also referred to as "alpha-1,2" linkages); and combinations of such linkages typically associated with branched saccharide oligomers. The glycosidic linkages of a glucan polymer herein can also be referred to as "glucosidic linkages". Herein, "alpha-D-glucose" is referred to as "glucose". Alpha-1,2 linkages typically only occur at branch points, and do not occur in tandem (i.e., two or more consecutive glucose monomers are not joined by consecutive alpha-1,2 linkages).

The glycosidic linkage profile of an alpha-glucan herein can be determined using any method known in the art. For example, a linkage profile can be determined using methods using nuclear magnetic resonance (NMR) spectroscopy (e.g., $^{13}$C NMR or $^1$H NMR). These and other methods that can be used are disclosed in, for example, *Food Carbohydrates: Chemistry, Physical Properties, and Applications* (S. W. Cui, Ed., Chapter 3, S. W. Cui, Structural Analysis of Polysaccharides, Taylor & Francis Group LLC, Boca Raton, FL, 2005), which is incorporated herein by reference.

The "molecular weight" of large alpha-glucan polymers herein can be represented as weight-average molecular weight (Mw) or number-average molecular weight (Mn), the units of which are in Daltons or grams/mole. Alternatively, the molecular weight of large alpha-glucan polymers can be represented as DPw (weight average degree of polymerization) or DPn (number average degree of polymerization). The molecular weight of smaller alpha-glucan polymers such as oligosaccharides typically can be provided as "DP" (degree of polymerization), which simply refers to the number of glucoses comprised within the alpha-glucan; "DP" can also characterize the molecular weight of a polymer on an individual molecule basis. Various means are known in the art for calculating these various molecular weight measurements such as with high-pressure liquid chromatography (HPLC), size exclusion chromatography (SEC), or gel permeation chromatography (GPC).

The term "sucrose" herein refers to a non-reducing disaccharide composed of an alpha-D-glucose molecule and a beta-D-fructose molecule linked by an alpha-1,2-glycosidic bond. Sucrose is known commonly as table sugar. Sucrose can alternatively be referred to as "alpha-D-glucopyranosyl-(1→2)-beta-D-fructofuranoside". "Alpha-D-glucopyranosyl" and "glucosyl" are used interchangeably herein.

The terms "glucosyltransferase", "glucosyltransferase enzyme", "GTF", "glucansucrase" and the like are used interchangeably herein. The activity of a glucosyltransferase herein catalyzes the reaction of the substrate sucrose to make the products alpha-glucan and fructose. Other products (by-products) of a GTF reaction can include glucose, various soluble gluco-oligosaccharides, and leucrose. Wild type forms of glucosyltransferase enzymes generally contain (in the N-terminal to C-terminal direction) a signal peptide (which is typically removed by cleavage processes), a variable domain, a catalytic domain, and a glucan-binding domain. A glucosyltransferase herein is classified under the glycoside hydrolase family 70 (GH70) according to the CAZy (Carbohydrate-Active EnZymes) database (Cantarel et al., *Nucleic Acids Res.* 37:D233-238, 2009). The term "dextransucrase" (and like terms) can optionally be used to characterize a glucosyltransferase enzyme that produces dextran. The term "alpha-1,2-branching enzyme" (and like terms) can optionally be used to characterize a glucosyltransferase enzyme that introduces one or more alpha-1,2 branches to a dextran backbone.

The term "glucosyltransferase catalytic domain" herein refers to the domain of a glucosyltransferase enzyme that provides alpha-glucan-synthesizing activity to a glucosyltransferase enzyme. A glucosyltransferase catalytic domain typically does not require the presence of any other domains to have this activity.

The terms "enzymatic reaction", "glucosyltransferase reaction", "glucan synthesis reaction", "reaction composition", "reaction formulation" and the like are used interchangeably herein and generally refer to a reaction that initially comprises water, sucrose, at least one active glucosyltransferase enzyme, and optionally other components such as dextran herein. Components that can be further present in a glucosyltransferase reaction typically after it has commenced include fructose, glucose, leucrose, soluble gluco-oligosaccharides (e.g., DP2-DP7) (such may be considered as products or by-products, depending on the glucosyltransferase used), and/or insoluble alpha-glucan product(s) of DP8 or higher. It would be understood that certain glucans products, such as alpha-1,3-glucan with a degree of polymerization (DP) of at least 8 or 9, are water-insoluble and thus not dissolved in a glucan synthesis reaction, but rather may be present out of solution (e.g., by virtue of having precipitated from the reaction). It is in a glucan synthesis reaction where the step of contacting water, sucrose and a glucosyltransferase enzyme is performed. The term "under suitable reaction conditions" as used herein refers to reaction conditions that support conversion of sucrose to alpha-glucan product(s) via glucosyltransferase enzyme activity. It is during such a reaction that glucosyl groups originally derived from the input sucrose are enzymatically transferred and used in alpha-glucan polymer synthesis; glucosyl groups as involved in this process can thus optionally be referred to as the glucosyl component or moiety (or like terms) of a glucosyltransferase reaction.

The "yield" of insoluble alpha-glucan product in a glucosyltransferase reaction in some aspects herein represents the molar yield based on the converted sucrose. The molar yield of an alpha-glucan product can be calculated based on the moles of insoluble alpha-glucan product divided by the moles of the sucrose converted. Moles of converted sucrose can be calculated as follows: (mass of initial sucrose−mass of final sucrose)/molecular weight of sucrose [342 g/mol]. This molar yield calculation can be considered as a measure of selectivity of the reaction toward the alpha-glucan. In some aspects, the "yield" of insoluble alpha-glucan product in a glucosyltransferase reaction can be based on the glucosyl component of the reaction. Such a yield (yield based on glucosyl) can be measured using the following formula:

$$\text{Insoluble Alpha-Glucan Yield} = ((IS/2 - (FS/2 + LE/2 + GL + SO))/(IS/2 - FS/2)) \times 100\%.$$

The fructose balance of a glucosyltransferase reaction can be measured to ensure that HPLC data, if applicable, are not out of range (90-110% is considered acceptable). Fructose balance can be measured using the following formula:

$$\text{Fructose Balance} = ((180/342 \times (FS + LE) + FR)/(180/342 \times IS)) \times 100\%.$$

In the above two formulae, IS is [Initial Sucrose], FS is [Final Sucrose], LE is [Leucrose], GL is [Glucose], SO is [Soluble Oligomers] (gluco-oligosaccharides), and FR is [Fructose]; the concentrations of each foregoing substrate/product provided in double brackets are in units of grams/L and as measured by HPLC, for example.

The terms "percent by volume", "volume percent", "vol %", "v/v %" and the like are used interchangeably herein. The percent by volume of a solute in a solution can be determined using the formula: [(volume of solute)/(volume of solution)]×100%.

The terms "percent by weight", "weight percentage (wt %)", "weight-weight percentage (% w/w)" and the like are used interchangeably herein. Percent by weight refers to the percentage of a material on a mass basis as it is comprised in a composition, mixture, or solution.

The terms "aqueous liquid", "aqueous fluid" and the like as used herein can refer to water or an aqueous solution. An "aqueous solution" herein can comprise one or more dissolved salts, where the maximal total salt concentration can be about 3.5 wt % in some embodiments. Although aqueous liquids herein typically comprise water as the only solvent in the liquid, an aqueous liquid can optionally comprise one or more other solvents (e.g., polar organic solvent) that are miscible in water. Thus, an aqueous solution can comprise a solvent having at least about 10 wt % water.

An "aqueous composition" herein has a liquid component that comprises at least about 10 wt % water, for example. Examples of aqueous compositions include mixtures, solutions, dispersions (e.g., colloidal dispersions), suspensions and emulsions, for example. An aqueous composition in certain embodiments can comprise an insoluble form of graft copolymer as disclosed herein, in which case the aqueous composition can optionally be characterized as a solid-in-liquid composition, given the insolubility of the graft copolymer.

As used herein, the term "colloidal dispersion" refers to a heterogeneous system having a dispersed phase and a dispersion medium, i.e., microscopically dispersed insoluble particles are suspended throughout another substance (e.g., an aqueous composition such as water or aqueous solution). An example of a colloidal dispersion herein is a hydrocolloid. All, or a portion of, the particles of a colloidal dispersion such as a hydrocolloid can comprise a graft copolymer herein. The terms "dispersant" and "dispersion agent" are used interchangeably herein to refer to a material that promotes the formation and/or stabilization of a dispersion.

A glucan (or ether- or ester-derivative thereof) that is "insoluble", "aqueous-insoluble", "water-insoluble" (and like terms) (e.g., alpha-1,3-glucan with a DP of 8 or higher) does not dissolve (or does not appreciably dissolve) in water or other aqueous conditions, optionally where the aqueous conditions are further characterized to have a pH of 4-9 (e.g., pH 6-8) and/or temperature of about 1 to 85° C. (e.g., 20-25° C.). In contrast, glucans (or ether- or ester-derivative thereof) such as certain oligosaccharides herein that are "soluble", "aqueous-soluble", "water-soluble" and the like (e.g., alpha-1,3-glucan with a DP less than 8) appreciably dissolve under these conditions.

The terms "film", "sheet" and like terms herein refer to a thin, visually continuous material. A film can be comprised as a thin layer or coating on a material, or can be alone (e.g., not attached to a material surface; free-standing). A "coating" as used herein refers to a thin layer covering a surface of a material.

The term "uniform thickness" as used to characterize a film or coating herein can refer to a contiguous area that (i) is at least 20% of the total film/coating area, and (ii) has a standard deviation of thickness of less than about 50 nm, for example.

The terms "elongation at break", "elongation", "rupture elongation" and the like herein refer to the percent change in length of a film under stress, measured from the start of application of stress to the film to when the film breaks.

The term "viscosity" as used herein refers to the measure of the extent to which a fluid (aqueous or non-aqueous) resists a force tending to cause it to flow. Various units of viscosity that can be used herein include centipoise (cP, cps) and Pascal-second (Pa·s), for example. A centipoise is one one-hundredth of a poise; one poise is equal to 0.100 kg·m$^{-1}$·s$^{-1}$.

The term "household care product" and like terms typically refer to products, goods and services relating to the treatment, cleaning, caring and/or conditioning of a home and its contents. The foregoing include, for example, chemicals, compositions, products, or combinations thereof having application in such care.

The terms "fabric", "textile", "cloth" and the like are used interchangeably herein to refer to a woven material having a network of natural and/or artificial fibers. Such fibers can be in the form of thread or yarn, for example.

A "fabric care composition" and like terms refer to any composition suitable for treating fabric in some manner. Examples of such a composition include laundry detergents and fabric softeners, which are examples of laundry care compositions.

The terms "heavy duty detergent", "all-purpose detergent" and the like are used interchangeably herein to refer to a detergent useful for regular washing of white and/or colored textiles at any temperature. The terms "low duty detergent", "fine fabric detergent" and the like are used interchangeably herein to refer to a detergent useful for the care of delicate fabrics such as viscose, wool, silk, microfiber or other fabric requiring special care. "Special care" can include conditions of using excess water, low agitation, and/or no bleach, for example.

A "detergent composition" herein typically comprises at least a surfactant (detergent compound) and/or a builder. A "surfactant" herein refers to a substance that tends to reduce the surface tension of a liquid in which the substance is dissolved. A surfactant may act as a detergent, wetting agent, emulsifier, foaming agent, and/or dispersant, for example.

The term "personal care product" and like terms typically refer to products, goods and services relating to the treatment, cleaning, cleansing, caring or conditioning of a person. The foregoing include, for example, chemicals, compositions, products, or combinations thereof having application in such care.

An "oral care composition" herein is any composition suitable for treating a soft or hard surface in the oral cavity such as dental (teeth) and/or gum surfaces.

Terms used herein regarding "ethers" (e.g., graft copolymer ether-derivative) are defined as in U.S. Patent Appl. Publ. Nos. 2014/179913, 2016/0304629, 2016/0311935, 2015/0239995, 2018/0230241 and/or 2018/0237816, which are incorporated herein by reference.

Terms used herein regarding "esters" (e.g., graft copolymer ester-derivative) are defined as in U.S. Patent Appl. Publ. Nos. 2014/0187767 and/or 2018/0155455, and/or Int. Patent Appl. Publ. No. WO2018/098065, which are incorporated herein by reference.

The term "degree of substitution" (DoS) as used herein refers to the average number of hydroxyl groups that are substituted (with organic groups via ether linkage, or with acyl groups via ester linkage) in each monomeric unit (glucose) of a graft copolymer ether- or ester-derivative herein.

The terms "sequence identity", "identity" and the like as used herein with respect to a polypeptide amino acid sequence are as defined and determined in U.S. Patent Appl. Publ. No. 2017/0002336, which is incorporated herein by reference.

Various polypeptide amino acid sequences and polynucleotide sequences are disclosed herein as features of certain embodiments. Variants of these sequences that are at least about 70-85%, 85-90%, or 90%-95% identical to the sequences disclosed herein can be used or referenced. Alternatively, a variant amino acid sequence or polynucleotide sequence can have at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identity with a sequence disclosed herein. The variant amino acid sequence or polynucleotide sequence has the same function/activity of the disclosed sequence, or at least about 80%, 81%, 82%, 83%, 84%, 85%, 86%, 87%, 88%, 89%, 90%, 91%, 92%, 93%, 94%, 95%, 96%, 97%, 98%, or 99% of the function/activity of the disclosed sequence. Any polypeptide amino acid sequence disclosed herein not beginning with a methionine can typically further comprise at least a start-methionine at the N-terminus of the amino acid sequence. In contrast, any polypeptide amino acid sequence disclosed herein beginning with a methionine can optionally lack such a methionine residue.

The terms "aligns with", "corresponds with", and the like can be used interchangeably herein. Some embodiments herein relate to a glucosyltransferase comprising at least one amino acid substitution at a position corresponding with at least one particular amino acid residue of SEQ ID NO:62. An amino acid position of a glucosyltransferase or subsequence thereof (e.g., catalytic domain or catalytic domain plus glucan-binding domains) (can refer to such an amino add position or sequence as a "query" position or sequence) can be characterized to correspond with a particular amino acid residue of SEQ ID NO:62 (can refer to such an amino acid position or sequence as a "subject" position or sequence) if (1) the query sequence can be aligned with the subject sequence (e.g., where an alignment indicates that the query sequence and the subject sequence [or a subsequence of the subject sequence] are at least about 30%, 40%, 50%, 60%, 70%, 80%, or 90% identical), and (2) if the query amino acid position directly aligns with (directly lines up against) the subject amino acid position in the alignment of (1). In general, one can align a query amino acid sequence with a subject sequence (SEQ ID NO:62 or a subsequence of SEQ ID NO:62) using any alignment algorithm, tool and/or software described disclosed herein (e.g., BLASTP, ClustalW, ClustalV, Clustal-Omega, EMBOSS) to determine percent identity. Just for further example, one can align a query sequence with a subject sequence herein using the Needleman-Wunsch algorithm (Needleman and Wunsch, *J. Mol. Biol.* 48:443-453, 1970) as implemented in the Needle program of the European Molecular Biology Open Software Suite (EMBOSS [e.g., version 5.0.0 or later], Rice et al., *Trends Genet.* 16:276-277, 2000). The parameters of such an EMBOSS alignment can comprise, for example: gap open penalty of 10, gap extension penalty of 0.5, EBLOSUM62 (EMBOSS version of BLOSUM62) substitution matrix.

The numbering of particular amino acid residues of SEQ ID NO:62 herein is with respect to the full-length amino acid sequence of SEQ ID NO:62. The first amino acid (i.e., position 1, Met-1) of SEQ ID NO:62 is at the start of the signal peptide. Unless otherwise disclosed, substitutions herein are with respect to the full-length amino acid sequence of SEQ ID NO:62.

A "non-native glucosyltransferase" herein ("mutant", "variant", "modified" and like terms can likewise be used to describe such a glucosyltransferase) has at least one amino acid substitution at a position corresponding with a particular amino acid residue of SEQ ID NO:62. Such at least one amino acid substitution typically is in place of the amino acid residue(s) that normally (natively) occurs at the same position in the native counterpart (parent) of the non-native glucosyltransferase (i.e., although SEQ ID NO:62 is used as a reference for position, an amino acid substitution herein is with respect to the native counterpart of a non-native glucosyltransferase) (considered another way, when aligning the sequence of a non-native glucosyltransferase with SEQ ID NO:62, determining whether a substitution exists at a particular position does not depend in-and-of-itself on the respective amino acid residue in SEQ ID NO:62, but rather depends on what amino acid exists at the subject position within the native counterpart of the non-native glucosyltransferase). The amino acid normally occurring at the relevant site in the native counterpart glucosyltransferase often (but not always) is the same as (or conserved with) the particular amino acid residue of SEQ ID NO:62 for which the alignment is made. A non-native glucosyltransferase optionally can have other amino acid changes (mutations, deletions, and/or insertions) relative to its native counterpart sequence.

It may be instructive to illustrate a substitution/alignment herein. SEQ ID NO:12 (GTF 0544) is a truncated form of a *Streptococcus sobrinus* glucosyltransferase. It is noted that Leu-193 of SEQ ID NO:12 corresponds with Leu-373 of SEQ ID NO:62 (alignment not shown). If SEQ ID NO:12 is mutated at position 193 to substitute the Leu residue with a different residue (e.g., Gln), then it can be stated that the position 193-mutated version of SEQ ID NO:12 represents a non-native glucosyltransferase having an amino acid substitution at a position corresponding with Leu-373 of SEQ ID NO:62, for example.

The term "isolated" means a substance (or process) in a form or environment that does not occur in nature. A non-limiting example of an isolated substance includes any non-naturally occurring substance such as a graft copolymer herein (as well as the enzymatic reactions and other processes used in preparation thereof). It is believed that the embodiments disclosed herein are synthetic/man-made (could not have been made except for human intervention/involvement), and/or have properties that are not naturally occurring.

The term "increased" as used herein can refer to a quantity or activity that is at least about 1%, 2%, 3%, 4%, 5%, 6%, 7%, 8%, 9%, 10%, 11%, 12%, 13%, 14%, 15%, 16%, 17%, 18%, 19%, 20%, 50%, 100%, or 200% more than the quantity or activity for which the increased quantity or activity is being compared. The terms "increased", "elevated", "enhanced", "greater than", "improved" and the like are used interchangeably herein.

New forms of alpha-1,3-glucan are desired to enhance the economic value and performance characteristics of this material in various applications. Compositions comprising alpha-1,3-glucan in the form of a graft copolymer are presently disclosed to address this need.

Certain embodiments of the present disclosure concern a composition comprising a graft copolymer, or an ether- or ester-derivative thereof, wherein said graft copolymer comprises:
(i) a backbone comprising dextran that has been modified with about 1%-25% alpha-1,2 branches, and
(ii) one or more alpha-1,3-glucan side chains comprising at least about 50% alpha-1,3 glycosidic linkages.

A dextran that forms the backbone of a graft copolymer herein can comprise about 100% alpha-1,6-glycosidic linkages (i.e., completely linear dextran backbone), or about, or at least about, 95%, 96%, 97%, 98%, 99%, or 99.5% alpha-1,6-glycosidic linkages (i.e., substantially linear dextran backbone), for example. Such a percent alpha-1,6 linkage profile is that taking account of the total of all linkages in the dextran (combination of main chain and, if present, branch portions). In some aspects, a substantially linear dextran backbone can comprise 5%, 4%, 3%, 2%, 1%, 0.5% or less branches (as present before modification with alpha-1,2 branches). If present, dextran backbone branches typically are short, being one (pendant) to three glucose monomers in length, and comprise less than about 10%, 9%, 8%, 7%, 6%, 5%, 4%, 3%, 2%, or 1% of all the glucose monomers of the dextran backbone. All the foregoing dextran backbone linkage information pertains to a dextran backbone prior to its modification with alpha-1,2 branches.

A backbone of a graft copolymer in certain embodiments can be comprised entirely of a dextran as presently disclosed. However, in some aspects, a backbone can comprise other elements. For example, a graft copolymer backbone can comprise alpha-1,3-glucan originating from the non-reducing side of a dextran main chain, by virtue of the main chain (at its non-reducing end) serving to prime alpha-1,3-glucan synthesis during synthesis of the graft copolymer.

In some aspects, a dextran backbone, prior to alpha-1,2 branch modification, can have a DP or DPw of about, or at least about, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, 50, 85, 90, 95, 100, 105, 110, 150, 200, 250, 300, 400, or 500. This DP or DPw can optionally be expressed as a range between any two of these values. Merely as examples, the DP or DPw can be about 8-20, 8-30, 8-100, or 8-500, 3-4, 3-5, 3-6, 3-7, 3-8, 4-5, 4-6, 4-7, 4-8, 5-6, 5-7, 5-8, 6-7, 6-8, or 7-8. Merely as other examples, this DP or DPw can be 90-120, 95-120, 100-120, 105-120, 110-120, 115-120, 90-115, 95-115, 100-115, 105-115, 110-115, 90-110, 95-110, 100-110, 105-110, 90-105, 95-105, 100-105, 90-100, 95-100, 90-95, 85-95, or 85-90. Yet, in some aspects, a dextran backbone, prior to alpha-1,2 branch modification, can be any as disclosed in U.S. Patent Appl. Publ. Nos. 2016/0122445, 2017/0218093, or 2018/0282385, or International Patent Appl. Publ. Nos. WO2017/079595, WO2015/183714, or WO2017/091533, for example, which are all incorporated herein by reference.

Dextran herein can be produced enzymatically, for example, prior to being modified with alpha-1,2-branches. In certain embodiments, dextran can be synthesized using a dextransucrase and/or methodology as disclosed in International Patent Appl. Publ. Nos. WO2015/183714 or WO2017/091533, or U.S. Patent Appl. Publ. No. 2018/0282385, which are all incorporated herein by reference. The dextransucrase identified as GTF8117 (SEQ ID NO:66 herein), GTF6831 (SEQ ID NO:67 or 68 herein), or GTF5604 (SEQ ID NO:69 herein) in these references can be used, if desired (or any dextransucrase comprising an amino acid sequence that is at least about 90%, 91%, 92%, 93%, 94%, 95%, 96%, 97%, 98%, or 99% identical to any of these particular dextransucrases). Such enzymatically produced dextran is linear (i.e., 100% alpha-1,6 linkages) and aqueous soluble.

A dextran that forms the backbone of a graft copolymer herein has been modified with about 1%-25% alpha-1,2 branches. These alpha-1,2 branches are distinct from any branches that may have been present in dextran prior to modification with alpha-1,2 branches. In embodiments employing a linear dextran as a substrate for alpha-1,2 branching, the backbone of a graft copolymer can simply be characterized to comprise about 1%-25% alpha-1,2 branches (or any alpha-1,2 branching percentage disclosed herein). Such a backbone thus comprises only alpha-1,6 and -1,2 linkages (alpha-1,2,6) (i.e., an alpha-1,6-linked backbone decorated with alpha-1,2-linked pendant glucoses), with no other linkage types present.

The percent alpha-1,2 branching of a backbone of a graft copolymer herein can be about, at least about, or less than about, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, or 25%, for example. This alpha-1,2 branching profile can optionally be expressed as having a range between any two of these values. Merely as examples, the percentage of alpha-1,2 branches can be about 2-25%, 2-20%, 2-15%, 2-10%, 5-25%, 5-20%, 5-15%, 5-10%, 7-13%, 8-12%, 9-11%, 10-25%, 10-20%, or 10-15%.

One or more alpha-1,2 branches of a backbone herein are typically a single glucose monomer in length (i.e., they are pendant glucoses). All of, or at least 80% or 90% of, the alpha-1,2 branches are a single glucose monomer in length, for instance.

In certain aspects, the DP or DPw of a backbone of a graft copolymer modified with about 1%-25% alpha-1,2 branches is about 10 to 500. This DP or DPw can be about, or at least about, 10, 20, 30, 40, 50, 60, 70, 80, 85, 90, 95, 100, 105, 110, 115, 120, 125, 130, 140, 150, 160, 170, 180, 190, 200, 300, 400, or 500, for example, and can optionally be expressed as a range between any two of these values. Merely as examples, the DPw of a backbone herein can be about 85-130, 85-125, 85-120, 85-115, 85-110, 85-105, 85-100, 85-95, 85-90, 90-130, 90-125, 90-120, 90-115, 90-110, 90-105, 90-100, 90-95, 95-130, 95-125, 95-120, 95-115, 95-110, 95-105, 95-100, 100-130, 100-125, 100-120, 100-115, 100-110, 100-105, 105-130, 105-125, 105-120, 105-115, 105-110, 110-130, 110-125, 110-120, 110-115, 115-130, 115-125, 115-120, 120-130, or 120-125.

The modification/addition of alpha-1,2 branches to dextran herein is typically done enzymatically. In certain embodiments, alpha-1,2 branches can be synthesized off of dextran using an alpha-1,2 branching enzyme and/or methodology as disclosed in International Patent Appl. Publ. Nos. WO2015/183714 or WO2017/091533, or U.S. Patent Appl. Publ. No. 2018/0282385, which are all incorporated herein by reference. The branching enzyme identified as GTFJ18T1 (SEQ ID NO:70 herein) or GTF9905 (SEQ ID NO:71 herein) in these references can be used, if desired (or any alpha-1,2 branching enzyme comprising an amino acid sequence that is at least about 90%, 91%, 92%, 93%, 94%, 95%, 96%, 97%, 98%, or 99% identical to any of these particular branching enzymes). Such an enzymatically produced alpha-1,2-branched dextran is aqueous soluble.

A graft copolymer as presently disclosed comprises one or more alpha-1,3-glucan side chains comprising at least about 50% alpha-1,3 glycosidic linkages. These side chains typically result via reacting an alpha-1,2-branched dextran herein with a glucosyltransferase that can synthesize alpha-1,3-glucan. For clarity purposes, these side chains ought not be considered dextran branches per se.

An alpha-1,3-glucan side chain in certain aspects can comprise about, or at least about, 50%, 60%, 70%, 80%, 85%, 90%, 95%, 96%, 97%, 98%, 99%, 99.5%, or 100% alpha-1,3 glycosidic linkages. In some aspects, accordingly, an alpha-1,3-glucan side chain has less than about 50%, 40%, 30%, 20%, 15%, 10%, 9%, 8%, 7%, 6%, 5%, 4%, 3%, 2%, 1%, 0.5%, or 0% glycosidic linkages that are not alpha-1,3. Typically, the glycosidic linkages that are not alpha-1,3 are mostly or entirely alpha-1,6. It should be understood that the higher the percentage of alpha-1,3 linkages present in a side chain, the greater the probability that the side chain is linear, since there are lower occurrences of certain linkages that might be part of branch points in the side chain. In certain embodiments, an alpha-1,3-glucan side chain has no branch points or less than about 5%, 4%, 3%, 2%, or 1% branch points as a percent of the glycosidic linkages in the side chain. Glucosyltransferases contemplated to be useful for producing alpha-1,3-glucan side chains comprising at least about 50% alpha-1,3 linkages as above are disclosed in U.S. Pat. Nos. 7,000,000 and 8,871,474, and Int. Patent Appl. Publ. No. WO2017/079595, all of which are incorporated herein by reference. In aspects in which a backbone comprises 50% alpha-1,3 glycosidic linkages, such a backbone typically does not comprise alternan (alternating alpha-1,3 and -1,6 linkages).

The DP of one or more alpha-1,3-glucan side chains in certain aspects can individually be about, or at least about, 100, 200, 300, 400, 500, 600, 700, 800, 900, 1000, 1100, or 1200. DP can optionally be expressed as a range between any two of these values. Merely as examples, the DP of one or more alpha-1,3-glucan side chains can individually be about 400-1200, 500-1200, 600-1200, 700-1200, 400-1100, 500-1100, 600-1100, 700-1100, 400-1000, 500-1000, 600-1000, 700-1000, 400-900, 500-900, 600-900, or 700-900. As more examples, the DP of one or more alpha-1,3-glucan side chains can individually (i) be about, or less than about, 300, 290, 280, 270, 260, 250, 240, 230, 220, 210, 200, 190, 180, 170, 160, 150, 140, 130, 120, 110, 100, 95, 90, 85, 80, 75, 70, 65, 60, 55, 50, 45, 40, 35, 30, 29, 28, 27, 26, 25, 24, 23, 22, 21, 20, 19, 18, 17, 16, 15, 14, 13, 12, or 11, or (ii) range from 11-25, 12-25, 11-22, 12-22, 11-20, 12-20, 20-300, 20-200, 20-150, 20-100, 20-75, 30-300, 30-200, 30-150, 30-100, 30-75, 50-300, 50-200, 50-150, 50-100, 50-75, 75-300, 75-200, 75-150, 75-100, 100-300, 100-200, 100-150, 150-300, 150-200, or 200-300. The DPw of a plurality of alpha-1,3-glucan side chains of a graft copolymer can be referred to, if desired; any of the foregoing DP values, which characterize side chains on an individual basis, can optionally be considered a DPw of all the side chains of a copolymer. In some aspects in which a graft copolymer has a plurality of alpha-1,3-glucan side chains, the individual DP values of the side chains are similar to each other (e.g., the DP values vary by less than about 2.5%, 5%, 10%, 15%, or 20%).

In some embodiments, an alpha-1,3-glucan side chain can comprise at least about 30% alpha-1,3 linkages and a percentage of alpha-1,6 linkages that brings the total of both the alpha-1,3 and -1,6 linkages in the side chain to 100%. For example, the percentage of alpha-1,3 and -1,6 linkages can be about 30-40% and 60-70%, respectively. Glucosyltransferases contemplated to be useful for producing alpha-1,3-glucan side chains comprising at least about 30% alpha-1,3 linkages are disclosed in U.S. Patent Appl. Publ. No. 2015/0232819, which is incorporated herein by reference.

One or more alpha-1,3-glucan side chains in some aspects are contemplated to be (A) extensions of alpha-1,2 branches, since alpha-1,2 branches present non-reducing ends that can possibly prime alpha-1,3-glucan synthesis by a glucosyltransferase enzyme, and/or (B) joined via alpha-1,3 linkage directly to the dextran backbone, in which case alpha-1,3-glucan side chain synthesis occurred by a glucosyltransferase enzyme first making an alpha-1,3 branch from the dextran backbone followed by extension of this branch by the enzyme. In some aspects, alpha-1,3-glucan side chains are all linked to the dextran backbone via the linkage type of (A) or (B), or via a combination of both (A) and (B) linkage types. Regarding the latter, a combination of both linkage types can comprise about 5%, 10%, 15%, 20%, 25%, 30%, 35%, 40%, 45%, 50%, 55%, 60%, 65%, 70%, 75%, 80%, 85%, 90%, or 95% of linkage type (A), with the balance of the other linkage types being of type (B).

The number of alpha-1,3-glucan side chains of a graft copolymer herein can be about, or at least about, 1, 2, 3, 4, 5, 6, 7, 8, 9, 10, 11, 12, 13, 14, 15, 16, 17, 18, 19, or 20, for example, or a range between any two of these values. Merely as examples, the number of alpha-1,3-glucan side chains can be 1-20, 1-15, 1-10, 1-5, 1-6, 2-5, 2-6, 3-5, 3-6, 4-5, 4-6, or 5-6. In some aspects, the number of alpha-1,3-glucan side chains can be up to about 10%, 20%, 30%, 40%, 50%, 60%, 70%, 80%, or 90% of the number of glucose monomers of the dextran portion of the graft copolymer.

A graft copolymer as presently disclosed typically is aqueous insoluble. Such insolubility can be in non-caustic aqueous conditions, such as the conditions of a glucosyltransferase reaction herein (e.g., pH 4-8, see below). In some aspects, a graft copolymer is insoluble in aqueous conditions at a temperature up to about 50, 60, 70, 80, 90, 100, 110, or 120° C. However, a graft copolymer can be aqueous soluble in some aspects. An aqueous composition herein such as an aqueous solution can comprise a solvent having about, or at least about, 10, 20, 30, 40, 50, 60, 70, 80, 90, or 100 wt % water, for example.

The DPw of a graft copolymer herein can be the sum of the DPw of any alpha-1,2-branched dextran backbone herein plus the DPw of any alpha-1,3-glucan side chain herein (taking into account the number of chains), for example. Merely as examples, the DPw of a graft copolymer herein can be about 1000-3000, 1500-3000, 2000-3000, 2500-3000, 1000-2500, 1500-2500, 2000-2500, 1000-2000, 1500-2000, 1000-1500, 200-1400, 200-1200, 200-1000, 200-800, 200-600, 200-400, 400-1400, 400-1200, 400-1000, 400-800, 400-600, 600-1400, 600-1200, 600-1000, or 600-800.

A graft copolymer herein can comprise about, or at least about, 1%, 2%, 3%, 4%, 5%, 6%, 7%, 8%, 9%, 10%, 11% or 12% (e.g., by weight) (or a range between any two of these values) of alpha-1,2-branched dextran backbone, for example. Merely as examples, a graft copolymer can comprise about 1-12%, 1-10%, 1-8%, 1-6%, 2-12%, 2-10%, 2-8%, 2-6%, 4-12%, 4-10%, 4-8%, or 4-6% (e.g., by weight) of alpha-1,2-branched dextran backbone, for example, or a percent (±0.5%) as reported in the below Examples ("% primer")

A graft copolymer as presently disclosed can be a product of any of the enzymatic reaction processes disclosed below, for example.

Certain embodiments of the present disclosure concern a method of producing (preparing) a graft copolymer as described herein. Such a graft polymer production method can comprise: (a) contacting at least (i) water, (ii) sucrose, (iii) dextran that has been modified with about 1%-25% alpha-1,2 branches, and (iv) a glucosyltransferase enzyme that synthesizes alpha-1,3-glucan comprising at least about 50% alpha-1,3 glycosidic linkages, thereby producing a graft copolymer as presently disclosed; and (b) optionally, isolating the graft copolymer produced in step (a). Step (a) can optionally be characterized as performing a reaction (or preparing/providing a reaction composition) comprising at least water, sucrose, dextran that has been modified with about 1%-25% alpha-1,2 branches, and a glucosyltransferase enzyme that synthesizes alpha-1,3-glucan with at least about 50% alpha-1,3 glycosidic linkages. A graft polymer production method herein can optionally further comprise, prior to step (a), modifying dextran with alpha-1,2 branches (i.e., adding alpha-1,2 branches to dextran) to provide dextran with about 1%-25% alpha-1,2 branches (for use in step [a]). Any of the foregoing features of a graft polymer production method herein (e.g., alpha-1,2-branched dextran, alpha-1,3-glucan, graft copolymer) can be as described elsewhere herein, such as above or in the below Examples. For example, the dextran used can be substantially linear dextran or completely linear dextran (prior to modification with about 1-25% alpha-1,2 branches). A method herein of producing a graft copolymer can also be characterized as a method of producing alpha-1,3-glucan, if desired.

A glucosyltransferase enzyme for producing alpha-1,3-glucan side chains of a graft copolymer herein can be derived from any microbial source, such as bacteria. Examples of bacterial glucosyltransferase enzymes are those derived from a *Streptococcus* species, *Leuconostoc* species or *Lactobacillus* species. Examples of *Streptococcus* species include *S. salivarius, S. sobrinus, S. dentirousetti, S. downei, S. mutans, S. oralis, S. gallolyticus* and *S. sanguinis*. Examples of *Leuconostoc* species include *L. mesenteroides, L. amelibiosum, L. argentinum, L. carnosum, L. citreum, L. cremoris, L. dextranicum* and *L. fructosum*. Examples of *Lactobacillus* species include *L. acidophilus, L. delbrueckii, L. helveticus, L. salivarius, L. casei, L. curvatus, L. plantarum, L. sakei, L. brevis, L. buchneri, L. fermentum* and *L. reuteri*.

A glucosyltransferase enzyme for producing alpha-1,3-glucan side chains of a graft copolymer herein can in some aspects comprise an amino acid sequence as disclosed in any of U.S. Patent Appl. Publ. Nos. 2014/0087431, 2017/0166938, 2017/0002335 and 2018/0072998 (corresponds to patent application Ser. No. 15/702,893), and U.S. patent application Ser. No. 16/127,288, all of which are incorporated herein by reference. In some aspects, a glucosyltransferase enzyme herein can comprise an amino acid sequence that is 100% identical to, or at least 90%, 91%, 92%, 93%, 94%, 95%, 96%, 97%, 98%, 98.5%, 99%, or 99.5% identical to, SEQ ID NO:2, 4, 6, 8, 10, 12, 14, 16, 18, 20, 26, 28, 30, 34, or 59 (Table 1), and have glucosyltransferase activity. It is noted that a glucosyltransferase enzyme with SEQ ID NO:2, 4, 8, 10, 14, 20, 26, 28, 30, or 34 can synthesize alpha-1,3-glucan side chains comprising at least about 90% (~100%) alpha-1,3 linkages.

The amino acid sequence of a glucosyltransferase enzyme in certain aspects has been modified such that the enzyme produces more products (alpha-1,3-glucan and fructose), and less by-products (e.g., glucose, oligosaccharides such as leucrose), from a given amount of sucrose substrate. For example, one, two, three, four, or more amino acid residues of the catalytic domain of a glucosyltransferase herein can be modified/substituted to obtain an enzyme that produces more products (insoluble alpha-glucan and fructose). Examples of a suitable modified glucosyltransferase enzyme are disclosed in the below Examples (Tables A and B). A modified glucosyltransferase enzyme, for example, can comprise one or more amino acid substitutions corresponding with those in Tables A and/or B (or in Table 3 of U.S. Patent Appl. Publ. No. 2018/0072998 [incorporated herein by reference, corresponding to patent application Ser. No. 15/702,893]) that is/are associated with an alpha-1,3-glucan yield of at least 40% (the position numbering of such at least one substitution corresponds with the position numbering of SEQ ID NO:62). A set of amino acid modifications as listed in Tables A or B can be used, for example.

The amino acid sequence of a glucosyltransferase enzyme in certain aspects has been modified such that the enzyme produces alpha-1,3-glucan with a molecular weight (DPw) that is lower than the molecular weight of alpha-1,3-glucan produced by its corresponding parent glucosyltransferase. Examples of a suitable modified glucosyltransferase enzyme are disclosed in the below Examples (Tables C and D). A modified glucosyltransferase enzyme, for example, can comprise one or more amino acid substitutions corresponding with those in Tables C and/or D that is/are associated with an alpha-1,3-glucan product molecular weight that is at least 5% less than the molecular weight of alpha-1,3-glucan produced by parent enzyme (the position numbering of such at least one substitution corresponds with the position numbering of SEQ ID NO:62). A set of amino acid modifications as listed in Table D can be used, for example.

The amino acid sequence of a glucosyltransferase enzyme in certain aspects has been modified such that the enzyme produces alpha-1,3-glucan with a molecular weight (DPw) that is higher than the molecular weight of alpha-1,3-glucan produced by its corresponding parent glucosyltransferase. Examples of a suitable modified glucosyltransferase enzyme are disclosed in the below Examples (Tables E and F). A modified glucosyltransferase enzyme, for example, can comprise one or more amino acid substitutions corresponding with those in Tables E and/or F that is/are associated with an alpha-1,3-glucan product molecular weight that is at least 5% higher than the molecular weight of alpha-1,3-glucan produced by parent enzyme (the position numbering of such at least one substitution corresponds with the position numbering of SEQ ID NO:62). A set of amino acid modifications as listed in Table 5 of U.S. patent application Ser. No. 16/127,288 can be used, for example.

In some aspects, a modified glucosyltransferase (i) comprises at least one amino acid substitution or a set of amino acid substitutions (as described above regarding yield or molecular weight), and (ii) comprises or consists of a glucosyltransferase catalytic domain that is at least about 90%, 91%, 92%, 93%, 94%, 95%, 96%, 97%, 98%, 99%, or 99.5% identical to amino acid residues 55-960 of SEQ ID NO:4, residues 54-957 of SEQ ID NO:65, residues 55-960 of SEQ ID NO:30, residues 55-960 of SEQ ID NO:28, or residues 55-960 of SEQ ID NO:20. Each of these subsequences are the approximate catalytic domains of each respective reference sequence, and are believed to be able to produce alpha-1,3-glucan comprising at least about 50% (e.g., ≥90% or ≥95%) alpha-1,3 linkages, and optionally further have a DPw of at least 100. In some aspects, a modified glucosyltransferase (i) comprises at least one amino acid substitution or a set of amino acid substitutions (as described above), and (ii) comprises or consists of an amino acid sequence that is at least about 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 69%, 70%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 99.5% identical to SEQ ID NO:62 or a subsequence thereof such as SEQ ID NO:4 (without start methionine thereof) or positions 55-960 of SEQ ID NO:4 (approximate catalytic domain).

The temperature of a reaction composition herein can be controlled, if desired, and can be about 5-50° C., 20-40° C., 30-40° C., 20-30° C., 20-25° C., 20° C., 25° C., 30° C., 35° C., or 40° C., for example.

The initial concentration of sucrose in a reaction composition herein can be about, or at least about, 10, 20, 30, 40, 45, 50, 55, 60, 80, 90, 95, 100, 105, 110, 125, 150, 200, 300, 400, 500, or 600 g/L, or a range between any two of these values. Merely as examples, the initial sucrose concentration can be about 10-150, 40-60, 45-55, 90-110, or 95-105 g/L, for example. "Initial concentration of sucrose" refers to the sucrose concentration in a reaction composition just after all the reaction components have been added/combined (e.g., at least water, sucrose, dextran with about 1%-35% alpha-1,2 branches, glucosyltransferase enzyme).

The initial concentration of an alpha-1,2-branched dextran as presently disclosed in a reaction composition can be about, or at least about, 0.1, 0.5, 1, 2, 2.5, 3, 4, 5, 6, 7, 8, 9, 10, 11, 12, 13, 14, 15, 16, 17, 18, 19, or 20 g/L, or a range between any two of these values. Merely as examples, the initial concentration of an alpha-1,2-branched dextran can be about 0.5-12, 1-12, 2-12, 4-12, 0.5-10, 1-10, 2-10, 4-10, 0.5-8, 1-8, 2-8, 4-8, 0.5-6, 1-6, 2-6, or 4-6 g/L.

In some aspects, the ratio, by weight, of alpha-1,2-branched dextran to sucrose is about 1:100 to about 1:5, or about 1:50 to about 1:5. Such a ratio is with respect to a reaction composition upon its initial setup.

The pH of a reaction composition in certain embodiments can be about 4.0-9.0, 4.0-8.5, 4.0-8.0, 5.0-8.0, 5.5-7.5, or 5.5-6.5. In some aspects, the pH can be about 4.0, 4.5, 5.0, 5.5, 6.0, 6.5, 7.0, 7.5, or 8.0. The pH can be adjusted or controlled by the addition or incorporation of a suitable buffer, including but not limited to: phosphate, tris, citrate, or a combination thereof. The buffer concentration in a reaction composition herein can be about 0.1-300 mM, 0.1-100 mM, 10-100 mM, 5 mM, 10 mM, 20 mM, or 50 mM, for example.

A reaction composition can be contained within any vessel (e.g., an inert vessel/container) suitable for applying one or more of the reaction conditions disclosed herein. An inert vessel in some aspects can be of stainless steel, plastic, or glass (or comprise two or more of these components) and be of a size suitable to contain a particular reaction. For example, the volume/capacity of an inert vessel (and/or the volume of a reaction composition herein), can be about, or at least about, 1, 10, 50, 100, 500, 1000, 2500, 5000, 10000, 12500, 15000, or 20000 liters. An inert vessel can optionally be equipped with a stirring device. Any of the foregoing features, for example, can be used to characterize an isolated reaction herein.

A reaction composition herein can contain one, two, or more different glucosyltransferase enzymes that produce alpha-1,3-glucan side chains, for example. In some embodiments, only one or two glucosyltransferase enzymes is/are comprised in a reaction composition. A reaction composition herein can be, and typically is, cell-free (e.g., no whole cells present).

Completion of a reaction in certain aspects can be determined visually (e.g., no more accumulation of insoluble graft copolymer product), and/or by measuring the amount of sucrose left in the solution (residual sucrose), where a percent sucrose consumption of at least about 90%, 95%, or 99% can indicate reaction completion. In some aspects, a reaction can be considered complete when its sucrose content is at or below about 2-5 g/L. A reaction of the disclosed process can be conducted for about 1 hour to about, or at least about, 2, 4, 6, 8, 10, 12, 14, 16, 18, 20, 22, 24, 36, 48, 60, 72, 96, 120, 144, or 168 hours, for example. A reaction can optionally be terminated and/or otherwise treated to stop glucosyltransferase activity by heating it to at least about 65° C. for at least about 30-60 minutes.

Examples of other conditions and/or components suitable for synthesizing alpha-1,3-glucan side chains in graft copolymer production herein are disclosed in U.S. Patent Appl. Publ. Nos. 2014/0087431, 2017/0166938 and 2017/0002335, which are incorporated herein by reference.

Graft copolymer produced in a reaction composition herein can optionally be isolated. In certain embodiments, isolating graft copolymer can include at least conducting a step of centrifugation, filtration, fractionation, chromatographic separation, dialysis, evaporation, or dilution. Isolation of insoluble graft copolymer can include at least conducting a step of preparing a cake of graft copolymer. Cake preparation can include at least conducting a step of centrifugation (cake is pelleted graft copolymer) and/or filtration (cake is filtered graft copolymer). Isolation can optionally further comprise washing the centrifuged and/or filtered graft copolymer one, two, or more times with water or other aqueous liquid. A wash volume can optionally be at least about 10-100% of the volume of the reaction composition used to produce the graft copolymer, for example. Washing can be done by various modes, as desired, such as by displacement or re-slurry washing. In some aspects, the aqueous portion of the resulting cake has no (detectable) dissolved sugars, or about 0.1-1.5, 0.1-1.25, 0.1-1.0, 0.1-0.75, 0.1-0.5, 0.2-0.6, 0.3-0.5, 0.2, 0.3, 0.4, 0.5, or 0.6 wt % dissolved sugars. Such dissolved sugars can include sucrose, fructose, leucrose, and/or soluble gluco-oligosaccharides, for example. Isolation herein can optionally further comprise drying graft copolymer, and/or preparing a dispersion of graft copolymer.

Preparing a dispersion of graft copolymer in some aspects can comprise: preparing a wet cake of insoluble graft copolymer (above), and dispersing the wet cake in water or an aqueous solution. Suitable means for dispersing wet cake herein include, for example, using a suitable dispersal tool such as a disperser, sonicator (e.g., ultrasonicator), homomixer, homogenizer (e.g., rotary or piston, rotar-stator), microfluidizer, planetary mixer, colloid mill, jet mill, vortex, and/or any methodology as described in International Patent Appl. Publ. Nos. WO2016/126685 or WO2016/030234, U.S. Pat. Nos. 5,767,176, 6,139,875, or 8,722,092, or U.S. Patent Appl. Publ. Nos. 2017/0055540, 2018/0021238, or 2017/0281780, all of which publications are incorporated herein by reference.

An isolated graft copolymer herein (or derivative thereof) as provided in a dry form, can comprise no more than 2.0, 1.5, 1.0, 0.5, 0.25, 0.10, 0.05, or 0.01 wt % water, for example. In some aspects, a graft copolymer product (or derivative thereof) is provided in an amount of at least 1 gram (e.g., at least about 2.5, 5, 10, 25, 50, 100, 250, 500, 750, 1000, 2500, 5000, 7500, 10000, 25000, 50000, or 100000 g); such an amount can be a dry amount, for example.

In some aspects, a graft copolymer (or derivative thereof) that has been isolated (optionally characterized as "purified") can be present in a composition at a wt % (dry weight basis) of at least about 50%, 60%, 70%, 80%, 85%, 90%, 91%, 92%, 93%, 94%, 95%, 96%, 97%, 98%, 98.5%, 99%, 99.5%, 99.8%, or 99.9%. Such isolated graft copolymer (or derivative thereof) can be used as an ingredient/component in a product/application, for example.

In some aspects, the yield of alpha-1,3-glucan as comprised in a graft copolymer product (i.e., alpha-1,3-glucan primed with alpha-1,2-branched dextran herein) of a reaction composition herein can be about, or at least about, 3%, 4%, 5%, 6%, 7%, 8%, 9%, 10%, 3-10%, 3-9%, 3-8%, 4-10%, 4-9%, or 4-8% higher than the yield of alpha-1,3-glucan synthesized in a reaction lacking a dextran primer. This is notable, since the yield of alpha-1,3-glucan in a reaction composition comprising a dextran primer lacking alpha-1,2 branches was observed in the below Examples to be at most about 2.5% higher than the yield of alpha-1,3-glucan synthesized in a reaction lacking a dextran primer (e.g., consider Tables 5 and 11). Typically, such a yield comparison can be made under otherwise identical or similar reaction conditions (e.g., initial sucrose conc., temperature, pH, and/or reaction time), and using any suitable measurement technique (e.g., HPLC or NIR spectroscopy). In some aspects, such a yield comparison can be made with respect to alpha-1,3-glucan primed with dextran having about 5-15%, 8-12%, or 9-10% alpha-1,2 branches, and/or with respect to reactions comprising an 80-120, 90-120, or 100-110 g/L initial sucrose concentration. Alpha-1,3-glucan yield in some aspects can be measured based on the glucosyl component of the reaction.

A composition of the present disclosure can be a film or coating, for example. A film or coating can be a dried film or coating in some aspects, comprising less than about 3, 2, 1, 0.5, or 0.1 wt % water, for example. The amount of graft copolymer (or derivative thereof, such as a graft copolymer ester) comprised in a film or coating herein can be about, or at least about, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.5, or 99.9 wt %, for example.

A film or coating herein can have a thickness of about, or at least about, 0.5, 0.6, 0.7, 0.8, 0.9, 1.0, 1.1, 1.2, 1.3, 1.4, 1.5, 0.5-1.5, 0.8-1.5, 1.0-1.5, 0.5-1.4, 0.8-1.4, or 1.0-1.4 mil (0.001 inch), for instance. In some aspects, such thickness is uniform, which can be characterized by having a contiguous area that (i) is at least 20%, 30%, 40%, or 50% of the total film/coating area, and (ii) has a standard deviation of thickness of less than about 0.06, 0.05, or 0.04 mil. A film or coating herein can be characterized as thin in some aspects. A film herein is typically a cast film.

A film or coating herein can exhibit various degrees of transparency as desired. For example, a film/coating can be highly transparent (e.g., high optical transparency, and/or low haze). Optical transparency as used herein can refer to a film or coating allowing at least about 10-99% light transmission, or at least about 50%, 60%, 70%, 80%, 90%, 95%, 96%, 97%, 98%, or 99% light transparency, for example. High transparency can optionally refer to a film/coating having at least about 90% optical transmittance. Transparency of a film/coating herein can be measured following test ASTM D 1746 (2009, *Standard Test Method for Transparency of Plastic Sheeting,* ASTM International, West Conshohocken, PA), for example, which is incorporated herein by reference.

A film or coating herein can optionally further comprise a plasticizer such as glycerol, propylene glycol, ethylene glycol, and/or polyethylene glycol. In certain embodiments, other film components (in addition to a graft copolymer herein) can be as disclosed in U.S. Patent. Appl. Publ. No. 2011/0151224 or 2015/0191550, or U.S. Pat. Nos. 9,688,035 or 3,345,200, all of which are incorporated herein by reference.

A film in certain aspects can exhibit a percent elongation at break of about, or at least about, 20%, 22%, 24%, 26%, 28%, 30%, 32%, 34%, 36%, 20-36%, 24-36%, or 28-36%. A film in certain aspects can exhibit a toughness of about, or at least about, 250, 300, 350, 400, 450, 500, 550, 600, 250-600, 300-600, 350-600, or 400-600 in-lb./in$^3$. A film in certain aspects can exhibit a WTM ("work-to-max", maximum amount of work applied to film before its breakage) of about, or at least about, 0.15, 0.16, 0.17, 0.18, 0.19, 0.20, 0.22, 0.24, 0.26, 0.28, 0.30, or 0.32 in-lb./in. In some aspects, a film herein can have one or more features (value±5-10% of value) of the graft copolymer-containing films tested in Table 14 (below), and/or of a film as disclosed in U.S. Pat. No. 9,688,035 or 5,750,204, which are incorporated herein by reference. Any of the foregoing film features, or any other applicable film features, can be measured optionally following methodology disclosed in Example 7, and/or as disclosed in U.S. Pat. No. 9,688,035 or U.S. Patent. Appl. Publ. No. 2015/0191550, which are both incorporated herein by reference.

The present disclosure also regards a method of producing a film, which method comprises: (a) dissolving an aqueous-insoluble graft copolymer herein, or ether- or ester-derivative thereof, in a solvent to provide a solution; (b) contacting the solution with a surface; and (c) coagulating the solution to form a film. This method can be practiced, for example, following methodology described below in Example 7 and/or as disclosed in U.S. Patent. Appl. Publ. No. 2015/0191550, which is incorporated herein by reference. In some aspects, a film production method can comprise a step (c) of removing the solvent, which removal can be done for example by drying and/or coagulation.

For the preparation of a film herein, a solution of graft copolymer in a solvent is prepared. A solvent can comprise, for example, aqueous NaOH (e.g., 4-15 wt % or 10 wt % NaOH), aqueous KOH (e.g., 4-15 wt % KOH), aqueous tetraethyl ammonium hydroxide (e.g., 20 wt %), or a mixture of DMSO (dimethyl sulfoxide) and LiCl (3-5 wt % LiCl). A solution can comprise about, or at least about, 3, 4, 5, 6, 7, 8, 9, 10, 11, 12, 13, 14, 15, 16, 17, 18, 19, 20, 21, 22, 23, 8-13, 9-13, 10-13, 8-12, 9-12, or 10-12 wt % graft copolymer, for example. In some aspects, a solution comprises less than 15, 14 or 13 wt %, graft copolymer. In some aspects of dissolving graft copolymer in a solvent, a slurry of graft copolymer in water can first be made, followed by addition of concentrated aqueous base.

A solution (for preparing a film) comprising a graft copolymer herein can further comprise additives such as a solubility additive or a rheology modifier, if desired. Examples of additives include urea and glycerol; the amount of either of these additives can be up to the wt % the graft copolymer in the solution, for example. Other additives can optionally be mixed into a graft copolymer solution, such as other polymers (e.g., in cases where a polymer blend is desired).

A graft copolymer solution is contacted with a surface/substrate during a film production process as presently disclosed. For film casting or extrusion, the viscosity of a graft copolymer solution typically is low enough to be flowable, but high enough to form a continuous film without breaking up. In some aspects, a solution concentration of less than 15 wt % (e.g., 3-15 wt %) graft copolymer is suitable for casting a film herein, whereas higher graft copolymer concentrations (e.g., 15-23 wt %) can be more suitable for extruding a film. A film can be produced by casting the graft copolymer solution onto a surface/substrate using a rod coater or a draw-down coater, for example. A suitable surface/substrate herein can be glass (optionally coated with a surfactant) or a polyester film. In some aspects, a film can be produced by extrusion through a slot die.

Solvent is removed from a graft copolymer solution (thereby forming a film) following its being contacted with a surface/substrate. In some aspects, solvent can be removed by drying and/or coagulating the graft copolymer solution. A film can be formed by directly immersing a graft copolymer solution (e.g., as cast onto a surface) in a coagulation media (thereby removing the solvent), or by first subjecting the solution to a drying step to remove a portion of the solvent, followed by coagulation to remove any remaining solvent. Solvent removal can be performed at room temperature (~20-25° C.) or any suitable temperature between 20-80° C., for example. Coagulation media can comprise a non-solvent for the graft copolymer, such as water, alcohol (e.g., methanol), acid (e.g., sulfuric acid or acetic acid), or a mixture of two or more thereof; one or more salts can also be included, if desired. In some aspects, a coagulation medium can comprise water and about 10-20 wt % (e.g., ~14 wt %) sulfuric acid and about 20-30 wt % (e.g., ~25 wt %) sodium sulfate.

A film can optionally be washed following coagulation; water or alcohol (e.g., methanol) can be used for washing, for example. If desired, washing can be done until a neutral pH (e.g., pH 6-8, or ~7) (of the wash) is achieved. Washing, or a post-washing step, can optionally further include bathing the film in a 1-10 wt % (e.g., ~5 wt %) plasticizer (e.g., glycerol or ethylene glycol) solution (e.g., water- or alcohol-based) for a suitable period of time (e.g., at least 2, 3, or 4 minutes). A film herein is typically dried, such as by exposing it at a temperature of about 70-85° C. (e.g., ~80° C.) for a suitable period of time (e.g., 10-20, or ~15 minutes).

A composition in some aspects of the present disclosure can comprise an ether derivative of a graft copolymer herein (i.e., a graft copolymer can be derivatized to be ether-linked to one or more different organic groups). The degree of substitution (DoS) of a graft copolymer with one or more etherified organic groups can be about 0.001 to about 3.0, for example. The DoS in some aspects can be about, or at least about, or up to about, 0.001, 0.0025, 0.005, 0.01, 0.025, 0.05, 0.075, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 (DoS can optionally be expressed as a range between any two of these values). An ether group can be anionic, uncharged, or cationic; the charge of an ether group can be as it exists when the graft copolymer ether derivative is in an aqueous composition herein, further taking into account the pH of the aqueous composition and whether any salts are present.

An organic group etherified to a graft copolymer herein can comprise an alkyl group such as a methyl, ethyl, propyl, butyl, pentyl, hexyl, heptyl, octyl, nonyl, or decyl group, for example. In some aspects, an organic group etherified to a graft copolymer can be a substituted alkyl group in which there is a substitution on one or more carbons of the alkyl group. The substitution(s) may be one or more hydroxyl, aldehyde, ketone, and/or carboxyl groups. For example, a substituted alkyl group can be a hydroxy alkyl group, dihydroxy alkyl group, or carboxy alkyl group. Examples of suitable hydroxy alkyl groups include hydroxymethyl, hydroxyethyl, hydroxypropyl, hydroxybutyl and hydroxypentyl groups. Other examples include dihydroxy alkyl groups (diols) such as dihydroxymethyl, dihydroxyethyl, dihydroxypropyl, dihydroxybutyl and dihydroxypentyl groups. Examples of suitable carboxy alkyl groups include carboxymethyl (—CH$_2$COOH), carboxyethyl, carboxypropyl, carboxybutyl and carboxypentyl groups. An organic group in some aspects can comprise an aryl group such as a benzyl group.

An organic group etherified to a graft copolymer herein can be a positively charged (cationic) organic group in some aspects. A positively charged group can be, for example, any of those as disclosed in U.S. Patent Appl. Publ. No. 2016/0311935, which is incorporated herein by reference. A positively charged group can comprise a substituted ammonium group, for example. Examples of substituted ammonium groups are primary, secondary, tertiary and quaternary ammonium groups. An ammonium group can be substituted with one, two, or three alkyl groups (e.g., methyl, ethyl, propyl, butyl, pentyl, hexyl, heptyl, octyl, nonyl, decyl), for example. One of the groups of a substituted ammonium group comprises one carbon, or a chain of carbons, in ether linkage to a graft copolymer; such a carbon or carbon chain can be —CH$_2$—, —CH$_2$CH—, —CH$_2$CH$_2$CH$_2$—, —CH$_2$CH$_2$CH$_2$CH$_2$—, or —CH$_2$CH$_2$CH$_2$CH$_2$CH$_2$—, for example. A carbon or carbon chain in this context can optionally have at least one substitution with an oxygen atom (e.g., alcohol group) and/or alkyl group (e.g., methyl, ethyl, propyl, butyl). One or more positively charged organic groups in some aspects can be trimethylammonium hydroxypropyl groups (structure I, when each of R$_2$, R$_3$ and R$_4$ is a methyl group).

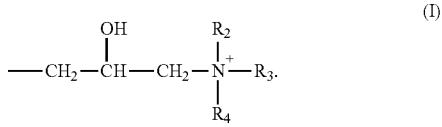

(I)

A graft copolymer ether in certain embodiments can contain one type of organic group. A non-limiting example of such a compound is carboxymethyl graft copolymer or benzyl graft copolymer. Alternatively, a graft copolymer ether compound can contain two or more different types of organic groups (e.g., both carboxymethyl and benzyl groups). In some aspects, a graft copolymer ether can comprise at least one nonionic organic group and at least one anionic group as ether groups. In some aspects, a graft copolymer ether can comprise at least one nonionic organic group and at least one positively charged organic group as ether groups. Thus, a graft copolymer ether herein can optionally be amphiphilic.

Any graft copolymer as presently disclosed is suitable for preparing an ether compound. Any suitable process for ether-derivatizing polysaccharides can be employed, such as disclosed in U.S. Pat. Nos. 2,961,439, 2,344,179, 2,203,703, 2,203,704, 2,380,879 and 2,974,134, U.S. Patent Appl. Publ. Nos. 2014/179913, 2016/0304629, 2016/0311935, 2015/0232785, 2015/0239995, 2018/0230241 and 2018/0237816, all of which are incorporated herein by reference.

A composition in some aspects of the present disclosure can comprise an ester derivative of a graft copolymer herein (i.e., a graft copolymer can be derivatized to be ester-linked to one or more different acyl groups). The DoS of a graft copolymer with one or more acyl groups can be about 0.001 to about 3.0, for example. The DoS in some aspects can be about, or at least about, or up to about, 0.001, 0.0025, 0.005, 0.01, 0.025, 0.05, 0.075, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, or 3.0 (DoS optionally be expressed as a range between any two of these values).

An acyl group can be, for example, any of those as disclosed in U.S. Patent Appl. Publ. Nos. 2014/0187767 and 2018/0155455, and Int. Patent Appl. Publ. No. WO2018/098065, which are incorporated herein by reference. Examples of acyl groups herein include methanoyl (formyl), ethanoyl (acetyl), propanoyl (propionyl), butanoyl (butyryl), pentanoyl (valeryl), hexanoyl (caproyl), heptanoyl (enanthyl), octanoyl (caprylyl), nonanoyl (pelargonyl), decanoyl (capryl), undecanoyl, dodecanoyl (lauroyl), tridecanoyl, tetradecanoyl (myristyl), pentadecanoyl, hexadecanoyl (palmityl), heptadecanoyl, octadecanoyl (stearyl), nonadecanoyl, eicosanoyl (arachidyl), uneicosanoyl, docosanoyl (behenyl), tricosanoyl, tetracosanoyl (lignoceryl), pentacosanoyl and hexacosanoyl (cerotyl) groups, for example. Additional examples of acyl groups herein include branched acyl groups (e.g., 2-methylpropanoyl, 2-methylbutanoyl, 2,2-dimethylpropanoyl, 3-methylbutanoyl, 2-methylpentanoyl, 3-methylpentanoyl group, 4-methylpentanoyl, 2,2-dimethylbutanoyl, 2,3-dimethylbutanoyl, 3,3-dimethylbutanoyl group, 2-ethylbutanoyl group, 2-ethylhexanoyl), cyclic acyl groups (e.g., cyclopropanoyl, cyclobutanoyl, cyclopentanoyl, cyclohexanoyl, cycloheptanoyl) and aryl acyl groups (e.g., benzoyl). Additional examples of acyl groups herein include —CO—CH$_2$—CH$_2$—COOH, —CO—CH$_2$—CH$_2$—CH$_2$—COOH, —CO—CH$_2$—CH$_2$—CH$_2$—CH$_2$—COOH, —CO—CH$_2$—CH$_2$—CH$_2$—CH$_2$—CH$_2$—COOH, —CO—CH$_2$—CH$_2$—CH$_2$—CH$_2$—CH$_2$—CH$_2$—COOH, —CO—CH=CH—COOH, —CO—CH=CH—CH$_2$—COOH, —CO—CH=CH—CH$_2$—CH$_2$—COOH, —CO—CH=CH—CH$_2$—CH$_2$—CH$_2$—COOH, —CO—CH=CH—CH$_2$—CH$_2$—CH$_2$—CH$_2$—COOH, —CO—CH=CH—CH$_2$—CH$_2$—CH$_2$—CH$_2$—CH$_2$—COOH, —CO—CH$_2$—CH=CH—CH$_2$—CH$_2$—COOH, —CO—CH$_2$—CH=CH—CH$_2$—CH$_2$—CH$_2$—COOH, —CO—CH$_2$—CH$_2$—CH=CH—CH$_2$—COOH, —CO—CH$_2$—CH$_2$—CH=CH—CH$_2$—CH$_2$—COOH, —CO—CH$_2$—CH$_2$—CH$_2$—CH=CH—COOH, —CO—CH$_2$—CH$_2$—CH$_2$—CH=CH—CH$_2$—COOH, —CO—CH$_2$—CH$_2$—CH$_2$—CH$_2$—CH=CH—COOH,

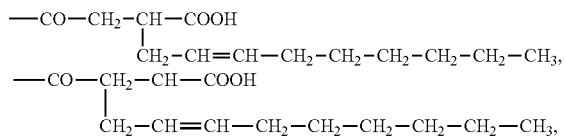

and any other acyl group that can be formed using a cyclic organic anhydride as an ester-derivatization agent.

A graft copolymer ester in certain embodiments can contain one type of acyl group (e.g., acetyl group or benzoyl group). Alternatively, a graft copolymer ester compound can contain two or more different types of acyl groups.

Any graft copolymer as presently disclosed is suitable for preparing an ester compound. Any suitable process for ester-derivatizing polysaccharides can be employed, such as disclosed in U.S. Patent Appl. Publ. Nos. 2014/0187767 and 2018/0155455, and Int. Patent Appl. Publ. No. WO2018/098065, which are incorporated herein by reference.

A graft copolymer herein, or ether- or ester-derivative thereof (non-derivatized and derivatized graft copolymers are collectively referred to herein as "graft copolymer compounds") can be present in a composition, such as an aqueous composition (e.g., colloidal dispersion, solution) or dry composition, at about, at least about, or less than about, 0.01, 0.05, 0.1, 0.2, 0.3, 0.4, 0.5, 0.6, 0.7, 0.8, 0.9, 1.0, 1.2, 1.4, 1.6, 1.8, 2.0, 2.5, 3.0, 3.5, 4.0, 4.5, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 wt %, for example. The liquid component of an aqueous composition can be water or an aqueous solution, for instance. The solvent of an aqueous solution typically is water, or can comprise about, or at least about, 10, 20, 30, 40, 50, 60, 70, 80, 90, 95, or 98 wt % water, for example.

An aqueous solution in some aspects has no (detectable) dissolved sugars, or about 0.1-1.5, 0.1-1.25, 0.1-1.0, 0.1-0.75, 0.1-0.5, 0.2-0.6, 0.3-0.5, 0.2, 0.3, 0.4, 0.5, or 0.6 wt % dissolved sugars. Such dissolved sugars can include sucrose, fructose, leucrose, and/or soluble gluco-oligosaccharides, for example. An aqueous solution in some aspects can have one or more salts/buffers (e.g., $Na^+$, $Cl^-$, NaCl, phosphate, tris, citrate) (e.g., ≤0.1, 0.5, 1.0, 2.0, or 3.0 wt %) and/or a pH of about 4.0, 4.5, 5.0, 5.5, 6.0, 6.5, 7.0, 7.5, 8.0, 8.5, 9.0, 4.0-9.0, 4.0-8.5, 4.0-8.0, 5.0-9.0, 5.0-8.5, 5.0-8.0, 6.0-9.0, 6.0-8.5, or 6.0-8.0, for example.

A composition comprising a graft copolymer compound of the present disclosure can, in some aspects, have a viscosity of about, or at least about, 10, 25, 50, 100, 250, 500, 750, 1000, 2000, 3000, 4000, 5000, 6000, 7000, 8000, 9000, 10000, 11000, 12000, 13000, 14000, 15000, 20000, 30000, 40000, 50000, 60000, 70000, 80000, 90000, 100000, 250000, 500000, or 1000000 centipoise (cP). Viscosity can be measured using a viscometer or rheometer, or using any other means known in the art. A rotational shear rate of about, or at least about, 10, 60, 150, 250, 600, 800, 1000, or 10-1000 rpm (revolutions per minute), for example, can be applied when measuring the viscosity of a composition herein. Viscosity can be measured at any suitable temperature (e.g., between 4-30, 20-30, 20-25, or 3-110° C.), and/or at any suitable pressure (e.g., atmospheric pressure, about 760 torr).

A composition comprising a graft copolymer compound of the present disclosure can, in some aspects, be non-aqueous (e.g., a dry composition). Examples of such embodiments include powders, granules, microcapsules, flakes, or any other form of particulate matter. Other examples include larger compositions such as pellets, bars, kernels, beads, tablets, sticks, or other agglomerates. A non-aqueous or dry composition typically has less than 3, 2, 1, 0.5, or 0.1 wt % water comprised therein.

A composition comprising a graft copolymer compound of the present disclosure can, in some aspects, comprise one or more salts such as a sodium salt (e.g., NaCl, $Na_2SO_4$). Other non-limiting examples of salts include those having (i) an aluminum, ammonium, barium, calcium, chromium (II or III), copper (I or II), iron (II or III), hydrogen, lead (II), lithium, magnesium, manganese (II or III), mercury (I or II), potassium, silver, sodium strontium, tin (II or IV), or zinc cation, and (ii) an acetate, borate, bromate, bromide, carbonate, chlorate, chloride, chlorite, chromate, cyanamide, cyanide, dichromate, dihydrogen phosphate, ferricyanide, ferrocyanide, fluoride, hydrogen carbonate, hydrogen phosphate, hydrogen sulfate, hydrogen sulfide, hydrogen sulfite, hydride, hydroxide, hypochlorite, iodate, iodide, nitrate, nitride, nitrite, oxalate, oxide, perchlorate, permanganate, peroxide, phosphate, phosphide, phosphite, silicate, stannate, stannite, sulfate, sulfide, sulfite, tartrate, or thiocyanate anion. Thus, any salt having a cation from (i) above and an anion from (ii) above can be in a composition, for example. A salt can be present in an aqueous composition herein at a wt % of about, or at least about, 0.01, 0.025, 0.05, 0.075, 0.1, 0.25, 0.5, 0.75, 1.0, 1.25, 1.5, 1.75, 2.0, 2.5, 3.0, 3.5, 0.01-3.5, 0.5-3.5, 0.5-2.5, or 0.5-1.5 wt % (such wt % values typically refer to the total concentration of one or more salts), for example.

A composition herein comprising a graft copolymer compound may optionally contain one or more active enzymes. Non-limiting examples of suitable enzymes include proteases, cellulases, hemicellulases, peroxidases, lipolytic enzymes (e.g., metallolipolytic enzymes), xylanases, lipases, phospholipases, esterases (e.g., arylesterase, polyesterase), perhydrolases, cutinases, pectinases, pectate lyases, mannanases, keratinases, reductases, oxidases (e.g., choline oxidase), phenoloxidases, lipoxygenases, ligninases, pullulanases, tannases, pentosanases, malanases, beta-glucanases, arabinosidases, hyaluronidases, chondroitinases, laccases, metalloproteinases, amadoriases, glucoamylases, arabinofuranosidases, phytases, isomerases, transferases and amylases. If an enzyme(s) is included, it may be comprised in a composition herein at about 0.0001-0.1 wt % (e.g., 0.01-0.03 wt %) active enzyme (e.g., calculated as pure enzyme protein), for example. In fabric care applications, cellulase can be present in an aqueous composition in which a fabric is treated (e.g., wash liquor) at a concentration that is minimally about 0.01-0.1 ppm total cellulase protein, or about 0.1-10 ppb total cellulase protein (e.g., less than 1 ppm), to maximally about 100, 200, 500, 1000, 2000, 3000, 4000, or 5000 ppm total cellulase protein, for example.

A composition comprising a graft copolymer compound herein, such as an aqueous composition or a non-aqueous composition (above), can be in the form of a household care product, personal care product, industrial product, pharmaceutical product, or food product, for example, such as described in any of U.S. Patent Appl. Publ. Nos. 2018/0022834, 2018/0237816, 2018/0230241, 20180079832, 2016/0311935, 2016/0304629, 2015/0232785, 2015/0368594, 2015/0368595, or 2016/0122445, or International Patent Appl. Publ. Nos. WO2016/160737, WO2016/160738, WO2016/133734, or WO2016/160740, which are all incorporated herein by reference. In some aspects, a composition comprising a graft copolymer compound can comprise at least one component/ingredient of a household care product, personal care product, industrial product, pharmaceutical product, or food product as disclosed in any of the foregoing publications and/or as presently disclosed.

Graft copolymer compounds disclosed herein are believed to be useful for providing one or more of the following physical properties to a personal care product, pharmaceutical product, household product, industrial product, or food product: thickening, freeze/thaw stability, lubricity, moisture retention and release, texture, consistency, shape retention, emulsification, binding, suspension, dispersion, gelation, reduced mineral hardness, for example. Examples of a concentration or amount of a graft copolymer compound in a product can be any of the weight percentages provided herein, for example.

Personal care products herein are not particularly limited and include, for example, skin care compositions, cosmetic compositions, antifungal compositions, and antibacterial compositions. Personal care products herein may be in the form of, for example, lotions, creams, pastes, balms, ointments, pomades, gels, liquids, combinations of these and the like. The personal care products disclosed herein can include at least one active ingredient, if desired. An active ingredient is generally recognized as an ingredient that causes an intended pharmacological effect.

In certain embodiments, a skin care product can be applied to skin for addressing skin damage related to a lack of moisture. A skin care product may also be used to address the visual appearance of skin (e.g., reduce the appearance of flaky, cracked, and/or red skin) and/or the tactile feel of the skin (e.g., reduce roughness and/or dryness of the skin while improved the softness and subtleness of the skin). A skin care product typically may include at least one active ingredient for the treatment or prevention of skin ailments, providing a cosmetic effect, or for providing a moisturizing benefit to skin, such as zinc oxide, petrolatum, white petrolatum, mineral oil, cod liver oil, lanolin, dimethicone, hard fat, vitamin A, allantoin, calamine, kaolin, glycerin, or colloidal oatmeal, and combinations of these. A skin care product may include one or more natural moisturizing factors such as ceramides, hyaluronic acid, glycerin, squalane, amino acids, cholesterol, fatty acids, triglycerides, phospholipids, glycosphingolipids, urea, linoleic acid, glycosaminoglycans, mucopolysaccharide, sodium lactate, or sodium pyrrolidone carboxylate, for example. Other ingredients that may be included in a skin care product include, without limitation, glycerides, apricot kernel oil, canola oil, squalane, squalene, coconut oil, corn oil, jojoba oil, jojoba wax, lecithin, olive oil, safflower oil, sesame oil, shea butter, soybean oil, sweet almond oil, sunflower oil, tea tree oil, shea butter, palm oil, cholesterol, cholesterol esters, wax esters, fatty acids, and orange oil.

A personal care product herein can also be in the form of makeup, lipstick, mascara, rouge, foundation, blush, eyeliner, lip liner, lip gloss, other cosmetics, sunscreen, sun block, nail polish, nail conditioner, bath gel, shower gel, body wash, face wash, lip balm, skin conditioner, cold cream, moisturizer, body spray, soap, body scrub, exfoliant, astringent, scruffing lotion, depilatory, permanent waving solution, antidandruff formulation, antiperspirant composition, deodorant, shaving product, pre-shaving product, aftershaving product, cleanser, skin gel, rinse, dentifrice composition, toothpaste, or mouthwash, for example. An example of a personal care product (e.g., a cleanser, soap, scrub, cosmetic) comprises a carrier or exfoliation agent (e.g., jojoba beads [jojoba ester beads]) (e.g., about 1-10, 3-7, 4-6, or 5 wt %); such an agent may optionally be dispersed within the product.

A personal care product in some aspects can be a hair care product. Examples of hair care products herein include shampoo, hair conditioner (leave-in or rinse-out), cream rinse, hair dye, hair coloring product, hair shine product, hair serum, hair anti-frizz product, hair split-end repair product, mousse, hair spray, and styling gel. A hair care product can be in the form of a liquid, paste, gel, solid, or powder in some embodiments. A hair care product as presently disclosed typically comprises one or more of the following ingredients, which are generally used to formulate hair care products: anionic surfactants such as polyoxyethylenelauryl ether sodium sulfate; cationic surfactants such as stearyltrimethylammonium chloride and/or distearyltrimethylammonium chloride; nonionic surfactants such as glyceryl monostearate, sorbitan monopalmitate and/or polyoxyethylenecetyl ether; wetting agents such as propylene glycol, 1,3-butylene glycol, glycerin, sorbitol, pyroglutamic acid salts, amino acids and/or trimethylglycine; hydrocarbons such as liquid paraffins, petrolatum, solid paraffins, squalane and/or olefin oligomers; higher alcohols such as stearyl alcohol and/or cetyl alcohol; superfatting agents; antidandruff agents; disinfectants; anti-inflammatory agents; crude drugs; water-soluble polymers such as methyl cellulose, hydroxycellulose and/or partially deacetylated chitin; antiseptics such as paraben; ultra-violet light absorbers; pearling agents; pH adjustors; perfumes; and pigments.

A pharmaceutical product herein can be in the form of an emulsion, liquid, elixir, gel, suspension, solution, cream, or ointment, for example. Also, a pharmaceutical product herein can be in the form of any of the personal care products disclosed herein, such as an antibacterial or antifungal composition. A pharmaceutical product can further comprise one or more pharmaceutically acceptable carriers, diluents, and/or pharmaceutically acceptable salts. A graft copolymer compound disclosed herein can also be used in capsules, encapsulants, tablet coatings, and as an excipients for medicaments and drugs.

A household and/or industrial product herein can be in the form of drywall tape-joint compounds; mortars; grouts; cement plasters; spray plasters; cement stucco; adhesives; pastes; wall/ceiling texturizers; binders and processing aids for tape casting, extrusion forming, injection molding and ceramics; spray adherents and suspending/dispersing aids for pesticides, herbicides, and fertilizers; fabric care products such as fabric softeners and laundry detergents; hard surface cleaners; air fresheners; polymer emulsions; gels such as water-based gels; surfactant solutions; paints such as water-based paints; protective coatings; adhesives; sealants and caulks; inks such as water-based ink; metal-working fluids; films or coatings; or emulsion-based metal cleaning fluids used in electroplating, phosphatizing, galvanizing and/or general metal cleaning operations, for example.

A graft copolymer compound disclosed herein can be comprised in a personal care product, pharmaceutical product, household product, or industrial product in an amount that provides a desired degree of thickening and/or dispersion, for example. Examples of a concentration or amount of a graft copolymer compound in a product can be any of the weight percentages provided above, for example.

Compositions disclosed herein can be in the form of a fabric care composition. A fabric care composition herein can be used for hand wash, machine wash and/or other purposes such as soaking and/or pretreatment of fabrics, for example. A fabric care composition may take the form of, for example, a laundry detergent; fabric conditioner; any wash-, rinse-, or dryer-added product; unit dose or spray. Fabric care compositions in a liquid form may be in the form of an aqueous composition as disclosed herein. In other aspects, a fabric care composition can be in a dry form such as a granular detergent or dryer-added fabric softener sheet. Other non-limiting examples of fabric care compositions herein include: granular or powder-form all-purpose or heavy-duty washing agents; liquid, gel or paste-form all-purpose or heavy-duty washing agents; liquid or dry fine-fabric (e.g. delicates) detergents; cleaning auxiliaries such as bleach additives, "stain-stick", or pre-treatments; substrate-laden products such as dry and wetted wipes, pads, or sponges; sprays and mists.

A detergent composition herein may be in any useful form, e.g., as powders, granules, pastes, bars, unit dose, or liquid. A liquid detergent may be aqueous, typically containing up to about 70 wt % of water and 0 wt % to about 30 wt % of organic solvent. It may also be in the form of a compact gel type containing only about 30 wt % water.

A detergent composition herein typically comprises one or more surfactants, wherein the surfactant is selected from nonionic surfactants, anionic surfactants, cationic surfactants, ampholytic surfactants, zwitterionic surfactants, semipolar nonionic surfactants and mixtures thereof. In some embodiments, the surfactant is present at a level of from about 0.1% to about 60%, while in alternative embodiments the level is from about 1% to about 50%, while in still further embodiments the level is from about 5% to about 40%, by weight of the detergent composition. A detergent will usually contain 0 wt % to about 50 wt % of an anionic surfactant such as linear alkylbenzenesulfonate (LAS), alpha-olefinsulfonate (AOS), alkyl sulfate (fatty alcohol sulfate) (AS), alcohol ethoxysulfate (AEOS or AES), secondary alkanesulfonates (SAS), alpha-sulfo fatty acid methyl esters, alkyl- or alkenylsuccinic acid, or soap. In addition, a detergent composition may optionally contain 0 wt % to about 40 wt % of a nonionic surfactant such as alcohol ethoxylate (AEO or AE), carboxylated alcohol ethoxylates, nonylphenol ethoxylate, alkylpolyglycoside, alkyldimethylamineoxide, ethoxylated fatty acid monoethanolamide, fatty acid monoethanolamide, or polyhydroxy alkyl fatty acid amide (as described for example in WO92/06154, which is incorporated herein by reference).

A detergent composition herein typically comprises one or more detergent builders or builder systems. In some aspects, oxidized poly alpha-1,3-glucan can be included as a co-builder, in which it is used together with one or more additional builders such as any disclosed herein. Oxidized poly alpha-1,3-glucan compounds for use herein are disclosed in U.S. Patent Appl. Publ. No. 2015/0259439. In some embodiments incorporating at least one builder, the cleaning compositions comprise at least about 1%, from about 3% to about 60%, or even from about 5% to about 40%, builder by weight of the composition. Builders (in addition to oxidized poly alpha-1,3-glucan) include, but are not limited to, alkali metal, ammonium and alkanolammonium salts of polyphosphates, alkali metal silicates, alkaline earth and alkali metal carbonates, aluminosilicates, polycarboxylate compounds, ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, various alkali metal, ammonium and substituted ammonium salts of polyacetic acids such as ethylenediamine tetraacetic acid and nitrilotriacetic acid, as well as polycarboxylates such as mellitic acid, succinic acid, citric acid, oxydisuccinic acid, polymaleic acid, benzene 1,3,5-tricarboxylic acid, carboxymethyloxysuccinic acid, and soluble salts thereof. Indeed, it is contemplated that any suitable builder will find use in various embodiments of the present disclosure. Additional examples of a detergent builder or complexing agent include zeolite, diphosphate, triphosphate, phosphonate, citrate, nitrilotriacetic acid (NTA), ethylenediaminetetraacetic acid (EDTA), diethylenetriaminepentaacetic acid (DTMPA), alkyl- or alkenylsuccinic acid, soluble silicates or layered silicates (e.g., SKS-6 from Hoechst).

In some embodiments, builders form water-soluble hardness ion complexes (e.g., sequestering builders), such as citrates and polyphosphates (e.g., sodium tripolyphosphate and sodium tripolyphospate hexahydrate, potassium tripolyphosphate, and mixed sodium and potassium tripolyphosphate, etc.). It is contemplated that any suitable builder will find use in the present disclosure, including those known in the art (See, e.g., EP2100949).

In some embodiments, suitable builders can include phosphate builders and non-phosphate builders. In some embodiments, a builder is a phosphate builder. In some embodiments, a builder is a non-phosphate builder. A builder can be used in a level of from 0.1% to 80%, or from 5% to 60%, or from 10% to 50%, by weight of the composition. In some embodiments, the product comprises a mixture of phosphate and non-phosphate builders. Suitable phosphate builders include mono-phosphates, di-phosphates, tri-polyphosphates or oligomeric-polyphosphates, including the alkali metal salts of these compounds, including the sodium salts. In some embodiments, a builder can be sodium tripolyphosphate (STPP). Additionally, the composition can comprise carbonate and/or citrate, preferably citrate that helps to achieve a neutral pH composition. Other suitable non-phosphate builders include homopolymers and copolymers of polycarboxylic acids and their partially or completely neutralized salts, monomeric polycarboxylic acids and hydroxycarboxylic acids and their salts. In some embodiments, salts of the above mentioned compounds include ammonium and/or alkali metal salts, i.e., lithium, sodium, and potassium salts, including sodium salts. Suitable polycarboxylic acids include acyclic, alicyclic, hetero-cyclic and aromatic carboxylic acids, wherein in some embodiments, they can contain at least two carboxyl groups which are in each case separated from one another by, in some instances, no more than two carbon atoms.

A detergent composition herein can comprise at least one chelating agent. Suitable chelating agents include, but are not limited to copper, iron and/or manganese chelating agents and mixtures thereof. In embodiments in which at least one chelating agent is used, the composition comprises from about 0.1% to about 15%, or even from about 3.0% to about 10%, chelating agent by weight of the composition.

A detergent composition herein can comprise at least one deposition aid. Suitable deposition aids include, but are not limited to, polyethylene glycol, polypropylene glycol, polycarboxylate, soil release polymers such as polytelephthalic acid, clays such as kaolinite, montmorillonite, atapulgite, illite, bentonite, halloysite, and mixtures thereof.

A detergent composition herein can comprise one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. Additional dye transfer inhibiting agents include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents examples of which include ethylene-diamine-tetraacetic acid (EDTA); diethylene triamine penta methylene phosphonic acid (DTPMP), hydroxy-ethane diphosphonic acid (HEDP); ethylenediamine N,N'-disuccinic acid (EDDS); methyl glycine diacetic acid (MGDA); diethylene triamine penta acetic acid (DTPA); propylene diamine tetraacetic acid (PDT A); 2-hydroxypyridine-N-oxide (HPNO); or methyl glycine diacetic acid (MGDA); glutamic acid N,N-diacetic acid (N,N-dicarboxymethyl glutamic acid tetrasodium salt (GLDA); nitrilotriacetic acid (NTA); 4,5-dihydroxy-m-benzenedisulfonic acid; citric acid and any salts thereof; N-hydroxyethyl ethylenediaminetriacetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP) and derivatives thereof, which can be used alone or in combination with any of the above. In embodiments in which at least one dye transfer inhibiting agent is used, a composition herein may comprise from about 0.0001% to about 10%, from about 0.01% to about 5%, or even from about 0.1% to about 3%, by weight of the composition.

A detergent composition herein can comprise silicates. In some of these embodiments, sodium silicates (e.g., sodium disilicate, sodium metasilicate, and/or crystalline phyllosilicates) find use. In some embodiments, silicates are present at a level of from about 1% to about 20% by weight of the composition. In some embodiments, silicates are present at a level of from about 5% to about 15% by weight of the composition.

A detergent composition herein can comprise dispersants. Suitable water-soluble organic materials include, but are not limited to the homo- or co-polymeric acids or their salts, in which the polycarboxylic acid comprises at least two carboxyl radicals separated from each other by not more than two carbon atoms.

A detergent composition herein may additionally comprise one or more enzymes. Examples of enzymes include proteases, cellulases, hemicellulases, peroxidases, lipolytic enzymes (e.g., metallolipolytic enzymes), xylanases, lipases, phospholipases, esterases (e.g., arylesterase, polyesterase), perhydrolases, cutinases, pectinases, pectate lyases, mannanases, keratinases, reductases, oxidases (e.g., choline oxidase, phenoloxidase), phenoloxidases, lipoxygenases, ligninases, pullulanases, tannases, pentosanases, malanases, beta-glucanases, arabinosidases, hyaluronidases, chondroitinases, laccases, metalloproteinases, amadoriases, glucoamylases, alpha-amylases, beta-amylases, galactosidases, galactanases, catalases, carageenases, hyaluronidases, keratinases, lactases, ligninases, peroxidases, phosphatases, polygalacturonases, pullulanases, rhamnogalactouronases, tannases, transglutaminases, xyloglucanases, xylosidases, metalloproteases, arabinofuranosidases, phytases, isomerases, transferases and/or amylases in any combination.

In some embodiments, a detergent composition can comprise one or more enzymes (e.g., any disclosed herein), each at a level from about 0.00001% to about 10% by weight of the composition and the balance of cleaning adjunct materials by weight of composition. In some other embodiments, a detergent composition can also comprise each enzyme at a level of about 0.0001% to about 10%, about 0.001% to about 5%, about 0.001% to about 2%, or about 0.005% to about 0.5%, by weight of the composition.

Enzymes that may be comprised in a detergent composition herein may be stabilized using conventional stabilizing agents, e.g., a polyol such as propylene glycol or glycerol; a sugar or sugar alcohol; lactic acid; boric acid or a boric acid derivative (e.g., an aromatic borate ester).

A detergent composition in certain embodiments may comprise one or more other types of polymers in addition to a graft copolymer compound as disclosed herein. Examples of other types of polymers useful herein include carboxymethyl cellulose (CMC), dextran, poly(vinylpyrrolidone) (PVP), polyethylene glycol (PEG), poly(vinyl alcohol) (PVA), polycarboxylates such as polyacrylates, maleic/acrylic acid copolymers and lauryl methacrylate/acrylic acid copolymers.

A detergent composition herein may contain a bleaching system. For example, a bleaching system can comprise an $H_2O_2$ source such as perborate or percarbonate, which may be combined with a peracid-forming bleach activator such as tetraacetylethylenediamine (TAED) or nonanoyloxybenzenesulfonate (NOBS). Alternatively, a bleaching system may comprise peroxyacids (e.g., amide, imide, or sulfone type peroxyacids). Alternatively still, a bleaching system can be an enzymatic bleaching system comprising perhydrolase, for example, such as the system described in WO2005/056783.

A detergent composition herein may also contain conventional detergent ingredients such as fabric conditioners, clays, foam boosters, suds suppressors, anti-corrosion agents, soil-suspending agents, anti-soil redeposition agents, dyes, bactericides, tarnish inhibiters, optical brighteners, or perfumes. The pH of a detergent composition herein (measured in aqueous solution at use concentration) is usually neutral or alkaline (e.g., pH of about 7.0 to about 11.0).

It is believed that a graft copolymer herein can be included as an anti-redeposition agent and/or clay soil removal agent in a detergent composition such as a fabric care composition, if desired (such agents can optionally be characterized as whiteness maintenance agents in certain aspects). Examples of other suitable anti-redeposition and/or clay soil removal agents herein include polyethoxy zwitterionic surfactants, water-soluble copolymers of acrylic or methacrylic acid with acrylic or methacrylic acid-ethylene oxide condensates (e.g., U.S. Pat. No. 3,719,647), cellulose derivatives such as carboxymethylcellulose and hydroxypropylcellulose (e.g., U.S. Pat. Nos. 3,597,416 and 3,523,088), and mixtures comprising nonionic alkyl polyethoxy surfactant, polyethoxy alkyl quaternary cationic surfactant and fatty amide surfactant (e.g., U.S. Pat. No. 4,228,044). Non-limiting examples of other suitable anti-redeposition and clay soil removal agents are disclosed in U.S. Pat. Nos. 4,597,898 and 4,891,160, and Int. Patent Appl. Publ. No. WO95/32272, all of which are incorporated herein by reference.

Particular forms of detergent compositions that can be adapted for purposes disclosed herein are disclosed in, for example, US20090209445A1, US20100081598A1, U.S. Pat. No. 7,001,878B2, EP 1504994B1, WO2001085888A2, WO2003089562A1, WO2009098659A1, WO2009098660A1, WO2009112992A1, WO2009124160A1, WO2009152031A1, WO2010059483A1, WO2010088112A1, WO2010090915A1, WO2010135238A1, WO2011094687A1, WO2011094690A1, WO2011127102A1, WO2011163428A1, WO2008000567A1, WO2006045391A1, WO2006007911A1, WO2012027404A1, EP1740690B1, WO2012059336A1, U.S. Pat. No. 6,730,646B1, WO2008087426A1, WO2010116139A1, and WO2012104613A1, all of which are incorporated herein by reference.

Laundry detergent compositions herein can optionally be heavy duty (all purpose) laundry detergent compositions. Exemplary heavy duty laundry detergent compositions comprise a detersive surfactant (10%-40% wt/wt), including an anionic detersive surfactant (selected from a group of linear or branched or random chain, substituted or unsubstituted alkyl sulphates, alkyl sulphonates, alkyl alkoxylated sulphate, alkyl phosphates, alkyl phosphonates, alkyl carboxylates, and/or mixtures thereof), and optionally non-ionic surfactant (selected from a group of linear or branched or random chain, substituted or unsubstituted alkyl alkoxylated alcohol, e.g., C8-C18 alkyl ethoxylated alcohols and/or C6-C12 alkyl phenol alkoxylates), where the weight ratio of anionic detersive surfactant (with a hydrophilic index (HIc) of from 6.0 to 9) to non-ionic detersive surfactant is greater than 1:1. Suitable detersive surfactants also include cationic detersive surfactants (selected from a group of alkyl pyridinium compounds, alkyl quaternary ammonium compounds, alkyl quaternary phosphonium compounds, alkyl ternary sulphonium compounds, and/or mixtures thereof);

zwitterionic and/or amphoteric detersive surfactants (selected from a group of alkanolamine sulpho-betaines); ampholytic surfactants; semi-polar non-ionic surfactants and mixtures thereof.

A detergent herein such as a heavy duty laundry detergent composition may optionally include, a surfactancy boosting polymer consisting of amphiphilic alkoxylated grease cleaning polymers (selected from a group of alkoxylated polymers having branched hydrophilic and hydrophobic properties, such as alkoxylated polyalkylenimines in the range of 0.05 wt %-10 wt %) and/or random graft polymers (typically comprising of hydrophilic backbone comprising monomers selected from the group consisting of: unsaturated C1-C6 carboxylic acids, ethers, alcohols, aldehydes, ketones, esters, sugar units, alkoxy units, maleic anhydride, saturated polyalcohols such as glycerol, and mixtures thereof; and hydrophobic side chain(s) selected from the group consisting of: C4-C25 alkyl group, polypropylene, polybutylene, vinyl ester of a saturated C1-C6 mono-carboxylic acid, C1-C6 alkyl ester of acrylic or methacrylic acid, and mixtures thereof.

A detergent herein such as a heavy duty laundry detergent composition may optionally include additional polymers such as soil release polymers (include anionically end-capped polyesters, for example SRP1, polymers comprising at least one monomer unit selected from saccharide, dicarboxylic acid, polyol and combinations thereof, in random or block configuration, ethylene terephthalate-based polymers and co-polymers thereof in random or block configuration, for example REPEL-O-TEX SF, SF-2 AND SRP6, TEXCARE SRA100, SRA300, SRN100, SRN170, SRN240, SRN300 AND SRN325, MARLOQUEST SL), anti-redeposition agent(s) herein (0.1 wt % to 10 wt %), include carboxylate polymers, such as polymers comprising at least one monomer selected from acrylic acid, maleic acid (or maleic anhydride), fumaric acid, itaconic acid, aconitic acid, mesaconic acid, citraconic acid, methylenemalonic acid, and any mixture thereof, vinylpyrrolidone homopolymer, and/or polyethylene glycol, molecular weight in the range of from 500 to 100,000 Da); and polymeric carboxylate (such as maleate/acrylate random copolymer or polyacrylate homopolymer).

A detergent herein such as a heavy duty laundry detergent composition may optionally further include saturated or unsaturated fatty acids, preferably saturated or unsaturated C12-C24 fatty acids (0 wt % to 10 wt %); deposition aids (examples for which include polysaccharides, cellulosic polymers, poly diallyl dimethyl ammonium halides (DADMAC), and co-polymers of DAD MAC with vinyl pyrrolidone, acrylamides, imidazoles, imidazolinium halides, and mixtures thereof, in random or block configuration, cationic guar gum, cationic starch, cationic polyacrylamides, and mixtures thereof.

A detergent herein such as a heavy duty laundry detergent composition may optionally further include dye transfer inhibiting agents, examples of which include manganese phthalocyanine, peroxidases, polyvinylpyrrolidone polymers, polyamine N-oxide polymers, copolymers of N-vinylpyrrolidone and N-vinylimidazole, polyvinyloxazolidones and polyvinylimidazoles and/or mixtures thereof; chelating agents, examples of which include ethylene-diamine-tetraacetic acid (EDTA), diethylene triamine penta methylene phosphonic acid (DTPMP), hydroxy-ethane diphosphonic acid (HEDP), ethylenediamine N,N'-disuccinic acid (EDDS), methyl glycine diacetic acid (MGDA), diethylene triamine penta acetic acid (DTPA), propylene diamine tetraacetic acid (PDTA), 2-hydroxypyridine-N-oxide (HPNO), or methyl glycine diacetic acid (MGDA), glutamic acid N,N-diacetic acid (N,N-dicarboxymethyl glutamic acid tetrasodium salt (GLDA), nitrilotriacetic acid (NTA), 4,5-dihydroxy-m-benzenedisulfonic acid, citric acid and any salts thereof, N-hydroxyethylethylenediaminetriacetic acid (HEDTA), triethylenetetraaminehexaacetic acid (TTHA), N-hydroxyethyliminodiacetic acid (HEIDA), dihydroxyethylglycine (DHEG), ethylenediaminetetrapropionic acid (EDTP), and derivatives thereof.

A detergent herein such as a heavy duty laundry detergent composition may optionally include silicone or fatty-acid based suds suppressors; hueing dyes, calcium and magnesium cations, visual signaling ingredients, anti-foam (0.001 wt % to about 4.0 wt %), and/or a structurant/thickener (0.01 wt % to 5 wt %) selected from the group consisting of diglycerides and triglycerides, ethylene glycol distearate, microcrystalline cellulose, microfiber cellulose, biopolymers, xanthan gum, gellan gum, and mixtures thereof). Such structurant/thickener would be, in certain embodiments, in addition to the one or more graft copolymers compounds comprised in the detergent. A structurant can also be referred to as a structural agent.

A detergent herein can be in the form of a heavy duty dry/solid laundry detergent composition, for example. Such a detergent may include: (i) a detersive surfactant, such as any anionic detersive surfactant disclosed herein, any nonionic detersive surfactant disclosed herein, any cationic detersive surfactant disclosed herein, any zwitterionic and/or amphoteric detersive surfactant disclosed herein, any ampholytic surfactant, any semi-polar non-ionic surfactant, and mixtures thereof; (ii) a builder, such as any phosphate-free builder (e.g., zeolite builders in the range of 0 wt % to less than 10 wt %), any phosphate builder (e.g., sodium tri-polyphosphate in the range of 0 wt % to less than 10 wt %), citric acid, citrate salts and nitrilotriacetic acid, any silicate salt (e.g., sodium or potassium silicate or sodium meta-silicate in the range of 0 wt % to less than 10 wt %); any carbonate salt (e.g., sodium carbonate and/or sodium bicarbonate in the range of 0 wt % to less than 80 wt %), and mixtures thereof; (iii) a bleaching agent, such as any photobleach (e.g., sulfonated zinc phthalocyanines, sulfonated aluminum phthalocyanines, xanthenes dyes, and mixtures thereof), any hydrophobic or hydrophilic bleach activator (e.g., dodecanoyl oxybenzene sulfonate, decanoyl oxybenzene sulfonate, decanoyl oxybenzoic acid or salts thereof, 3,5,5-trimethy hexanoyl oxybenzene sulfonate, tetraacetyl ethylene diamine-TAED, nonanoyloxybenzene sulfonate-NOBS, nitrile quats, and mixtures thereof), any source of hydrogen peroxide (e.g., inorganic perhydrate salts, examples of which include mono or tetra hydrate sodium salt of perborate, percarbonate, persulfate, perphosphate, or persilicate), any preformed hydrophilic and/or hydrophobic peracids (e.g., percarboxylic acids and salts, percarbonic acids and salts, perimidic acids and salts, peroxymonosulfuric acids and salts, and mixtures thereof); and/or (iv) any other components such as a bleach catalyst (e.g., imine bleach boosters examples of which include iminium cations and polyions, iminium zwitterions, modified amines, modified amine oxides, N-sulphonyl imines, N-phosphonyl imines, N-acyl imines, thiadiazole dioxides, perfluoroimines, cyclic sugar ketones, and mixtures thereof), and a metal-containing bleach catalyst (e.g., copper, iron, titanium, ruthenium, tungsten, molybdenum, or manganese cations along with an auxiliary metal cations such as zinc or aluminum and a sequestrate such as EDTA, ethylenediaminetetra(methylenephosphonic acid).

Compositions disclosed herein can be in the form of a dishwashing detergent composition, for example. Examples of dishwashing detergents include automatic dishwashing detergents (typically used in dishwasher machines) and hand-washing dish detergents. A dishwashing detergent composition can be in any dry or liquid/aqueous form as disclosed herein, for example. Components that may be included in certain embodiments of a dishwashing detergent composition include, for example, one or more of a phosphate; oxygen- or chlorine-based bleaching agent; non-ionic surfactant; alkaline salt (e.g., metasilicates, alkali metal hydroxides, sodium carbonate); any active enzyme disclosed herein; anti-corrosion agent (e.g., sodium silicate); anti-foaming agent; additives to slow down the removal of glaze and patterns from ceramics; perfume; anti-caking agent (in granular detergent); starch (in tablet-based detergents); gelling agent (in liquid/gel based detergents); and/or sand (powdered detergents).

Dishwashing detergents such as an automatic dishwasher detergent or liquid dishwashing detergent can comprise (i) a non-ionic surfactant, including any ethoxylated non-ionic surfactant, alcohol alkoxylated surfactant, epoxy-capped poly(oxyalkylated) alcohol, or amine oxide surfactant present in an amount from 0 to 10 wt %; (ii) a builder, in the range of about 5-60 wt %, including any phosphate builder (e.g., mono-phosphates, di-phosphates, tri-polyphosphates, other oligomeric-polyphosphates, sodium tripolyphosphate-STPP), any phosphate-free builder (e.g., amino acid-based compounds including methyl-glycine-diacetic acid [MGDA] and salts or derivatives thereof, glutamic-N,N-diacetic acid [GLDA] and salts or derivatives thereof, iminodisuccinic acid (IDS) and salts or derivatives thereof, carboxy methyl inulin and salts or derivatives thereof, nitrilotriacetic acid [NTA], diethylene triamine penta acetic acid [DTPA], B-alaninediacetic acid [B-ADA] and salts thereof), homopolymers and copolymers of poly-carboxylic acids and partially or completely neutralized salts thereof, monomeric polycarboxylic acids and hydroxycarboxylic acids and salts thereof in the range of 0.5 wt % to 50 wt %, or sulfonated/carboxylated polymers in the range of about 0.1 wt % to about 50 wt %; (iii) a drying aid in the range of about 0.1 wt % to about 10 wt % (e.g., polyesters, especially anionic polyesters, optionally together with further monomers with 3 to 6 functionalities—typically acid, alcohol or ester functionalities which are conducive to polycondensation, polycarbonate-, polyurethane- and/or polyurea-polyorganosiloxane compounds or precursor compounds thereof, particularly of the reactive cyclic carbonate and urea type); (iv) a silicate in the range from about 1 wt % to about 20 wt % (e.g., sodium or potassium silicates such as sodium disilicate, sodium meta-silicate and crystalline phyllosilicates); (v) an inorganic bleach (e.g., perhydrate salts such as perborate, percarbonate, perphosphate, persulfate and persilicate salts) and/or an organic bleach (e.g., organic peroxyacids such as diacyl- and tetraacylperoxides, especially diperoxydodecanedioic acid, diperoxytetradecanedioic acid, and diperoxyhexadecanedioic acid); (vi) a bleach activator (e.g., organic peracid precursors in the range from about 0.1 wt % to about 10 wt %) and/or bleach catalyst (e.g., manganese triazacyclononane and related complexes; Co, Cu, Mn, and Fe bispyridylamine and related complexes; and pentamine acetate cobalt(III) and related complexes); (vii) a metal care agent in the range from about 0.1 wt % to 5 wt % (e.g., benzatriazoles, metal salts and complexes, and/or silicates); and/or (viii) any active enzyme disclosed herein in the range from about 0.01 to 5.0 mg of active enzyme per gram of automatic dishwashing detergent composition, and an enzyme stabilizer component (e.g., oligosaccharides, polysaccharides, and inorganic divalent metal salts).

Compositions disclosed herein can be in the form of an oral care composition, for example. Examples of oral care compositions include dentifrices, toothpaste, mouth wash, mouth rinse, chewing gum, and edible strips that provide some form of oral care (e.g., treatment or prevention of cavities [dental caries], gingivitis, plaque, tartar, and/or periodontal disease). An oral care composition can also be for treating an "oral surface", which encompasses any soft or hard surface within the oral cavity including surfaces of the tongue, hard and soft palate, buccal mucosa, gums and dental surfaces. A "dental surface" herein is a surface of a natural tooth or a hard surface of artificial dentition including a crown, cap, filling, bridge, denture, or dental implant, for example.

An oral care composition herein can comprise about 0.01-15.0 wt % (e.g., ~0.1-10 wt % or ~0.1-5.0 wt %, ~0.1-2.0 wt %) of one or more graft copolymer compounds as disclosed herein, for example. One or more graft copolymer compounds comprised in an oral care composition can sometimes be provided therein as a thickening agent and/or dispersion agent, which may be useful to impart a desired consistency and/or mouth feel to the composition. One or more other thickening or dispersion agents can also be provided in an oral care composition herein, such as a carboxyvinyl polymer, carrageenan (e.g., L-carrageenan), natural gum (e.g., karaya, xanthan, gum arabic, tragacanth), colloidal magnesium aluminum silicate, or colloidal silica, for example.

An oral care composition herein may be a toothpaste or other dentifrice, for example. Such compositions, as well as any other oral care composition herein, can additionally comprise, without limitation, one or more of an anticaries agent, antimicrobial or antibacterial agent, anticalculus or tartar control agent, surfactant, abrasive, pH-modifying agent, foam modulator, humectant, flavorant, sweetener, pigment/colorant, whitening agent, and/or other suitable components. Examples of oral care compositions to which one or more graft copolymer compounds can be added are disclosed in U.S. Patent Appl. Publ. Nos. 2006/0134025, 2002/0022006 and 2008/0057007, which are incorporated herein by reference.

An anticaries agent herein can be an orally acceptable source of fluoride ions. Suitable sources of fluoride ions include fluoride, monofluorophosphate and fluorosilicate salts as well as amine fluorides, including olaflur (N'-octadecyltrimethylendiamine-N,N,N'-tris(2-ethanol)-dihydrofluoride), for example. An anticaries agent can be present in an amount providing a total of about 100-20000 ppm, about 200-5000 ppm, or about 500-2500 ppm, fluoride ions to the composition, for example. In oral care compositions in which sodium fluoride is the sole source of fluoride ions, an amount of about 0.01-5.0 wt %, about 0.05-1.0 wt %, or about 0.1-0.5 wt %, sodium fluoride can be present in the composition, for example.

An antimicrobial or antibacterial agent suitable for use in an oral care composition herein includes, for example, phenolic compounds (e.g., 4-allylcatechol; p-hydroxybenzoic acid esters such as benzylparaben, butylparaben, ethylparaben, methylparaben and propylparaben; 2-benzylphenol; butylated hydroxyanisole; butylated hydroxytoluene; capsaicin; carvacrol; creosol; eugenol; guaiacol; halogenated bisphenolics such as hexachlorophene and bromochlorophene; 4-hexylresorcinol; 8-hydroxyquinoline and salts thereof; salicylic acid esters such as menthyl salicylate, methyl salicylate and phenyl salicylate; phenol; pyrocatechol; salicylanilide; thymol; halogenated diphenylether compounds such as triclosan and triclosan monophosphate), copper (II) compounds (e.g., copper (II) chloride, fluoride, sulfate and hydroxide), zinc ion sources (e.g., zinc acetate, citrate, gluconate, glycinate, oxide, and sulfate), phthalic acid and salts thereof (e.g., magnesium monopotassium phthalate), hexetidine, octenidine, sanguinarine, benzalkonium chloride, domiphen bromide, alkylpyridinium chlorides (e.g. cetylpyridinium chloride, tetradecylpyridinium chloride, N-tetradecyl-4-ethylpyridinium chloride), iodine, sulfonamides, bisbiguanides (e.g., alexidine, chlorhexidine, chlorhexidine digluconate), piperidino derivatives (e.g., delmopinol, octapinol), magnolia extract, grapeseed extract, rosemary extract, menthol, geraniol, citral, eucalyptol, antibiotics (e.g., augmentin, amoxicillin, tetracycline, doxycycline, minocycline, metronidazole, neomycin, kanamycin, clindamycin), and/or any antibacterial agents disclosed in U.S. Pat. No. 5,776,435, which is incorporated herein by reference. One or more antimicrobial agents can optionally be present at about 0.01-10 wt % (e.g., 0.1-3 wt %), for example, in the disclosed oral care composition.

An anticalculus or tartar control agent suitable for use in an oral care composition herein includes, for example, phosphates and polyphosphates (e.g., pyrophosphates), polyaminopropanesulfonic acid (AMPS), zinc citrate trihydrate, polypeptides (e.g., polyaspartic and polyglutamic acids), polyolefin sulfonates, polyolefin phosphates, diphosphonates (e.g., azacycloalkane-2,2-diphosphonates such as azacycloheptane-2,2-diphosphonic acid), N-methyl azacyclopentane-2,3-diphosphonic acid, ethane-1-hydroxy-1,1-diphosphonic acid (EHDP), ethane-1-amino-1,1-diphosphonate, and/or phosphonoalkane carboxylic acids and salts thereof (e.g., their alkali metal and ammonium salts). Useful inorganic phosphate and polyphosphate salts include, for example, monobasic, dibasic and tribasic sodium phosphates, sodium tripolyphosphate, tetrapolyphosphate, mono-, di-, tri- and tetra-sodium pyrophosphates, disodium dihydrogen pyrophosphate, sodium trimetaphosphate, sodium hexametaphosphate, or any of these in which sodium is replaced by potassium or ammonium. Other useful anticalculus agents in certain embodiments include anionic polycarboxylate polymers (e.g., polymers or copolymers of acrylic acid, methacrylic, and maleic anhydride such as polyvinyl methyl ether/maleic anhydride copolymers). Still other useful anticalculus agents include sequestering agents such as hydroxycarboxylic acids (e.g., citric, fumaric, malic, glutaric and oxalic acids and salts thereof) and aminopolycarboxylic acids (e.g., EDTA). One or more anticalculus or tartar control agents can optionally be present at about 0.01-50 wt % (e.g., about 0.05-25 wt % or about 0.1-15 wt %), for example, in the disclosed oral care composition.

A surfactant suitable for use in an oral care composition herein may be anionic, non-ionic, or amphoteric, for example. Suitable anionic surfactants include, without limitation, water-soluble salts of $C_{8-20}$ alkyl sulfates, sulfonated monoglycerides of $C_{8-20}$ fatty acids, sarcosinates, and taurates. Examples of anionic surfactants include sodium lauryl sulfate, sodium coconut monoglyceride sulfonate, sodium lauryl sarcosinate, sodium lauryl isoethionate, sodium laureth carboxylate and sodium dodecyl benzenesulfonate. Suitable non-ionic surfactants include, without limitation, poloxamers, polyoxyethylene sorbitan esters, fatty alcohol ethoxylates, alkylphenol ethoxylates, tertiary amine oxides, tertiary phosphine oxides, and dialkyl sulfoxides. Suitable amphoteric surfactants include, without limitation, derivatives of $C_{8-20}$ aliphatic secondary and tertiary amines having an anionic group such as a carboxylate, sulfate, sulfonate, phosphate or phosphonate. An example of a suitable amphoteric surfactant is cocoamidopropyl betaine. One or more surfactants are optionally present in a total amount of about 0.01-10 wt % (e.g., about 0.05-5.0 wt % or about 0.1-2.0 wt %), for example, in the disclosed oral care composition.

An abrasive suitable for use in an oral care composition herein may include, for example, silica (e.g., silica gel, hydrated silica, precipitated silica), alumina, insoluble phosphates, calcium carbonate, and resinous abrasives (e.g., a urea-formaldehyde condensation product). Examples of insoluble phosphates useful as abrasives herein are orthophosphates, polymetaphosphates and pyrophosphates, and include dicalcium orthophosphate dihydrate, calcium pyrophosphate, beta-calcium pyrophosphate, tricalcium phosphate, calcium polymetaphosphate and insoluble sodium polymetaphosphate. One or more abrasives are optionally present in a total amount of about 5-70 wt % (e.g., about 10-56 wt % or about 15-30 wt %), for example, in the disclosed oral care composition. The average particle size of an abrasive in certain embodiments is about 0.1-30 microns (e.g., about 1-20 microns or about 5-15 microns).

An oral care composition in certain embodiments may comprise at least one pH-modifying agent. Such agents may be selected to acidify, make more basic, or buffer the pH of a composition to a pH range of about 2-10 (e.g., pH ranging from about 2-8, 3-9, 4-8, 5-7, 6-10, or 7-9). Examples of pH-modifying agents useful herein include, without limitation, carboxylic, phosphoric and sulfonic acids; acid salts (e.g., monosodium citrate, disodium citrate, monosodium malate); alkali metal hydroxides (e.g. sodium hydroxide, carbonates such as sodium carbonate, bicarbonates, sesquicarbonates); borates; silicates; phosphates (e.g., monosodium phosphate, trisodium phosphate, pyrophosphate salts); and imidazole.

A foam modulator suitable for use in an oral care composition herein may be a polyethylene glycol (PEG), for example. High molecular weight PEGs are suitable, including those having an average molecular weight of about 200000-7000000 (e.g., about 500000-5000000 or about 1000000-2500000), for example. One or more PEGs are optionally present in a total amount of about 0.1-10 wt % (e.g. about 0.2-5.0 wt % or about 0.25-2.0 wt %), for example, in the disclosed oral care composition.

An oral care composition in certain embodiments may comprise at least one humectant. A humectant in certain embodiments may be a polyhydric alcohol such as glycerin, sorbitol, xylitol, or a low molecular weight PEG. Most suitable humectants also may function as a sweetener herein. One or more humectants are optionally present in a total amount of about 1.0-70 wt % (e.g., about 1.0-50 wt %, about 2-25 wt %, or about 5-15 wt %), for example, in the disclosed oral care composition.

A natural or artificial sweetener may optionally be comprised in an oral care composition herein. Examples of suitable sweeteners include dextrose, sucrose, maltose, dextrin, invert sugar, mannose, xylose, ribose, fructose, levulose, galactose, corn syrup (e.g., high fructose corn syrup or corn syrup solids), partially hydrolyzed starch, hydrogenated starch hydrolysate, sorbitol, mannitol, xylitol, maltitol, isomalt, aspartame, neotame, saccharin and salts thereof, dipeptide-based intense sweeteners, and cyclamates. One or more sweeteners are optionally present in a total amount of about 0.005-5.0 wt %, for example, in the disclosed oral care composition.

A natural or artificial flavorant may optionally be comprised in an oral care composition herein. Examples of suitable flavorants include vanillin; sage; marjoram; parsley oil; spearmint oil; cinnamon oil; oil of wintergreen (methylsalicylate); peppermint oil; clove oil; bay oil; anise oil; eucalyptus oil; citrus oils; fruit oils; essences such as those derived from lemon, orange, lime, grapefruit, apricot, banana, grape, apple, strawberry, cherry, or pineapple; bean- and nut-derived flavors such as coffee, cocoa, cola, peanut, or almond; and adsorbed and encapsulated flavorants. Also encompassed within flavorants herein are ingredients that provide fragrance and/or other sensory effect in the mouth, including cooling or warming effects. Such ingredients include, without limitation, menthol, menthyl acetate, menthyl lactate, camphor, eucalyptus oil, eucalyptol, anethole, eugenol, cassia, oxanone, Irisone®, propenyl guaiethol, thymol, linalool, benzaldehyde, cinnamaldehyde, N-ethyl-p-menthan-3-carboxamine, N,2,3-trimethyl-2-isopropylbutanamide, 3-(1-menthoxy)-propane-1,2-diol, cinnamaldehyde glycerol acetal (CGA), and menthone glycerol acetal (MGA). One or more flavorants are optionally present in a total amount of about 0.01-5.0 wt % (e.g., about 0.1-2.5 wt %), for example, in the disclosed oral care composition.

An oral care composition in certain embodiments may comprise at least one bicarbonate salt. Any orally acceptable bicarbonate can be used, including alkali metal bicarbonates such as sodium or potassium bicarbonate, and ammonium bicarbonate, for example. One or more bicarbonate salts are optionally present in a total amount of about 0.1-50 wt % (e.g., about 1-20 wt %), for example, in the disclosed oral care composition.

An oral care composition in certain embodiments may comprise at least one whitening agent and/or colorant. A suitable whitening agent is a peroxide compound such as any of those disclosed in U.S. Pat. No. 8,540,971, which is incorporated herein by reference. Suitable colorants herein include pigments, dyes, lakes and agents imparting a particular luster or reflectivity such as pearling agents, for example. Specific examples of colorants useful herein include talc; mica; magnesium carbonate; calcium carbonate; magnesium silicate; magnesium aluminum silicate; silica; titanium dioxide; zinc oxide; red, yellow, brown and black iron oxides; ferric ammonium ferrocyanide; manganese violet; ultramarine; titaniated mica; and bismuth oxychloride. One or more colorants are optionally present in a total amount of about 0.001-20 wt % (e.g., about 0.01-10 wt % or about 0.1-5.0 wt %), for example, in the disclosed oral care composition.

Additional components that can optionally be included in an oral composition herein include one or more enzymes (above), vitamins, and anti-adhesion agents, for example. Examples of vitamins useful herein include vitamin C, vitamin E, vitamin B5, and folic acid. Examples of suitable anti-adhesion agents include solbrol, ficin, and quorum-sensing inhibitors.

The present disclosure also concerns a method of treating a material. This method comprises contacting a material with an aqueous composition comprising at least one graft copolymer compound as disclosed herein.

A material contacted with an aqueous composition in a contacting method herein can comprise a fabric in certain embodiments. A fabric herein can comprise natural fibers, synthetic fibers, semi-synthetic fibers, or any combination thereof. A semi-synthetic fiber herein is produced using naturally occurring material that has been chemically derivatized, an example of which is rayon. Non-limiting examples of fabric types herein include fabrics made of (i) cellulosic fibers such as cotton (e.g., broadcloth, canvas, chambray, chenille, chintz, corduroy, cretonne, damask, denim, flannel, gingham, jacquard, knit, matelassé, oxford, percale, poplin, plissé, sateen, seersucker, sheers, terry cloth, twill, velvet), rayon (e.g., viscose, modal, lyocell), linen, and Tencel®; (ii) proteinaceous fibers such as silk, wool and related mammalian fibers; (iii) synthetic fibers such as polyester, acrylic, nylon, and the like; (iv) long vegetable fibers from jute, flax, ramie, coir, kapok, sisal, henequen, abaca, hemp and sunn; and (v) any combination of a fabric of (i)-(iv). Fabric comprising a combination of fiber types (e.g., natural and synthetic) include those with both a cotton fiber and polyester, for example. Materials/articles containing one or more fabrics herein include, for example, clothing, curtains, drapes, upholstery, carpeting, bed linens, bath linens, tablecloths, sleeping bags, tents, car interiors, etc. Other materials comprising natural and/or synthetic fibers include, for example, non-woven fabrics, paddings, paper, and foams.

An aqueous composition that is contacted with a fabric can be, for example, a fabric care composition (e.g., laundry detergent, fabric softener). Thus, a treatment method in certain embodiments can be considered a fabric care method or laundry method if employing a fabric care composition therein. A fabric care composition herein is contemplated to effect one or more of the following fabric care benefits (i.e., surface substantive effects): wrinkle removal, wrinkle reduction, wrinkle resistance, fabric wear reduction, fabric wear resistance, fabric pilling reduction, extended fabric life, fabric color maintenance, fabric color fading reduction, reduced dye transfer, fabric color restoration, fabric soiling reduction, fabric soil release, fabric shape retention, fabric smoothness enhancement, anti-redeposition of soil on fabric, anti-greying of laundry, improved fabric hand/handle, and/or fabric shrinkage reduction.

Examples of conditions (e.g., time, temperature, wash/rinse volumes) for conducting a fabric care method or laundry method herein are disclosed in WO1997/003161 and U.S. Pat. Nos. 4,794,661, 4,580,421 and 5,945,394, which are incorporated herein by reference. In other examples, a material comprising fabric can be contacted with an aqueous composition herein: (i) for at least about 5, 10, 20, 30, 40, 50, 60, 70, 80, 90, 100, 110, or 120 minutes; (ii) at a temperature of at least about 10, 15, 20, 25, 30, 35, 40, 45, 50, 55, 60, 65, 70, 75, 80, 85, 90, or 95° C. (e.g., for laundry wash or rinse: a "cold" temperature of about 15-30° C., a "warm" temperature of about 30-50° C., a "hot" temperature of about 50-95° C.); (iii) at a pH of about 2, 3, 4, 5, 6, 7, 8, 9, 10, 11, or 12 (e.g., pH range of about 2-12, or about 3-11); (iv) at a salt (e.g., NaCl) concentration of at least about 0.5, 1.0, 1.5, 2.0, 2.5, 3.0, 3.5, or 4.0 wt %; or any combination of (i)-(iv).

The contacting step in a fabric care method or laundry method can comprise any of washing, soaking, and/or rinsing steps, for example. Contacting a material or fabric in still further embodiments can be performed by any means known in the art, such as dissolving, mixing, shaking, spraying, treating, immersing, flushing, pouring on or in, combining, painting, coating, applying, affixing to, and/or communicating an effective amount of a graft copolymer compound herein with the fabric or material. In still further embodiments, contacting may be used to treat a fabric to provide a surface substantive effect. As used herein, the term "fabric hand" or "handle" refers to a person's tactile sensory response towards fabric which may be physical, physiological, psychological, social or any combination thereof. In one embodiment, the fabric hand may be measured using a PhabrOmeter® System for measuring relative hand value (available from Nu Cybertek, Inc. Davis, CA) (American Association of Textile Chemists and Colorists [AATCC test method "202-2012, Relative Hand Value of Textiles: Instrumental Method"]).

In certain embodiments of treating a material comprising fabric, a graft copolymer compound component(s) of the aqueous composition adsorbs to the fabric. This feature is believed to render graft copolymer compounds herein useful as anti-redeposition agents and/or anti-greying agents in fabric care compositions disclosed (in addition to their viscosity-modifying effect). An anti-redeposition agent or anti-greying agent herein helps keep soil from redepositing onto clothing in wash water after the soil has been removed. It is further contemplated that adsorption of one or more graft copolymer compounds herein to a fabric enhances mechanical properties of the fabric.

Adsorption of a graft copolymer compound to a fabric herein can be measured using a colorimetric technique (e.g., Dubois et al., 1956, *Anal. Chem.* 28:350-356; Zemljič et al., 2006, *Lenzinger Berichte* 85:68-76; both incorporated herein by reference), for example, or any other method known in the art.

Other materials that can be contacted in the above treatment method include surfaces that can be treated with a dish detergent (e.g., automatic dishwashing detergent or hand dish detergent). Examples of such materials include surfaces of dishes, glasses, pots, pans, baking dishes, utensils and flatware made from ceramic material, china, metal, glass, plastic (e.g., polyethylene, polypropylene, polystyrene, etc.) and wood (collectively referred to herein as "tableware"). Thus, the treatment method in certain embodiments can be considered a dishwashing method or tableware washing method, for example. Examples of conditions (e.g., time, temperature, wash volume) for conducting a dishwashing or tableware washing method herein are disclosed in U.S. Pat. No. 8,575,083, which is incorporated herein by reference. In other examples, a tableware article can be contacted with an aqueous composition herein under a suitable set of conditions such as any of those disclosed above with regard to contacting a fabric-comprising material.

Other materials that can be contacted in the above treatment method include oral surfaces such as any soft or hard surface within the oral cavity including surfaces of the tongue, hard and soft palate, buccal mucosa, gums and dental surfaces (e.g., natural tooth or a hard surface of artificial dentition such as a crown, cap, filling, bridge, denture, or dental implant). Thus, a treatment method in certain embodiments can be considered an oral care method or dental care method, for example. Conditions (e.g., time, temperature) for contacting an oral surface with an aqueous composition herein should be suitable for the intended purpose of making such contact. Other surfaces that can be contacted in a treatment method also include a surface of the integumentary system such as skin, hair or nails.

Thus, certain embodiments of the present disclosure concern material (e.g., fabric) that comprises a graft copolymer compound herein. Such material can be produced following a material treatment method as disclosed herein, for example. A material may comprise a graft copolymer compound in certain embodiments if the compound is adsorbed to, or otherwise in contact with, the surface of the material.

Certain embodiments of a method of treating a material herein further comprise a drying step, in which a material is dried after being contacted with the aqueous composition. A drying step can be performed directly after the contacting step, or following one or more additional steps that might follow the contacting step (e.g., drying of a fabric after being rinsed, in water for example, following a wash in an aqueous composition herein). Drying can be performed by any of several means known in the art, such as air drying (e.g., ~20-25° C.), or at a temperature of at least about 30, 40, 50, 60, 70, 80, 90, 100, 120, 140, 160, 170, 175, 180, or 200° C., for example. A material that has been dried herein typically has less than 3, 2, 1, 0.5, or 0.1 wt % water comprised therein. Fabric is a preferred material for conducting an optional drying step.

An aqueous composition used in a treatment method herein can be any aqueous composition disclosed herein, such as in the above embodiments or in the below Examples. Thus, the graft copolymer component(s) of an aqueous composition can be any as disclosed herein. Examples of aqueous compositions include detergents (e.g., laundry detergent or dish detergent) and water-containing dentifrices such as toothpaste.

Certain embodiments of the present disclosure concern a method of producing alpha-1,3-glucan, which method comprises: (a) contacting at least (i) water, (ii) sucrose, (iii) dextran that has been modified with about 1%-50% alpha-1,2 branches, and (iv) a glucosyltransferase enzyme that synthesizes alpha-1,3-glucan comprising at least about 50% alpha-1,3 glycosidic linkages, thereby providing an enzymatic reaction, whereby alpha-1,3-glucan comprising at least about 50% alpha-1,3 glycosidic linkages is produced, and (b) optionally, isolating the alpha-1,3-glucan produced in step (a). This method is in addition to a method of producing a graft copolymer herein, which also represents a way of producing alpha-1,3-glucan. Significantly, step (a) of this a method can be used to modulate the molecular weight of the alpha-1,3-glucan product of the enzymatic reaction. In particular, using dextran with a lower percent alpha-1,2 branching results in production of alpha-1,3-glucan of higher/increased molecular weight compared to when using dextran with a higher percent alpha-1,2 branching (all other reaction conditions being identical or similar). For example, it is noted from the below Examples that reactions (~100-110 g/L sucrose) comprising dextran with about 29.2%, 18.6%, 9.2%, or 0% alpha-1,2 branches produced, respectively, alpha-1,3-glucan graft copolymer with a DPw of about, on average, 1499 (Table 12), 1577 (Table 2), 2115 (Table 4), or 2790 (Table 10). In some aspects, the percent alpha-1,2 branching of dextran selected for use is decreased from about 30%, 25%, 20%, 15%, or 10% to about 20%, 15%, 10%, 5%, or 2.5%, as appropriate, to achieve an increase in molecular weight of graft copolymer product. In some aspects, an increase in molecular weight can be by about, or at least about, 5%, 10%, 20%, 30%, 40%, 50%, 60%, 70%, 80%, 90%, or 100%.

In some aspects, increasing the concentration of a dextran modified with alpha-1,2 branches results in production of alpha-1,3-glucan graft copolymer of lower molecular weight compared to when using dextran at a lower concentration (all other reaction conditions being identical or similar). This feature can be observed in the below Examples (e.g., see Tables 2, 4, 10, 15 and 16), for instance. In some aspects, a decrease in molecular weight can be by about, or at least about, 5%, 10%, 20%, 30%, 40%, 50%, 60%, or 70%.

Any of the foregoing features of a method herein for modulating (up or down) alpha-1,3-glucan product molecular weight can be as described elsewhere herein, such as above or in the below Examples. For example, the dextran used can be substantially linear dextran or completely linear dextran (prior to modification with about 1-50% alpha-1,2 branches). In some aspects, dextran with about 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 1-31%, 1-30%, 9-31%, 9-30%, 10-31%, or 10-30% alpha-1,2 branches can be employed. In some aspects (e.g., lowering graft copolymer product molecular weight), the concentration of dextran used in a reaction herein can be increased from about 0.05, 0.1, 0.2, 0.5, 1.0, 2.0, or 2.5 g/L to about 0.5, 1.0, 2.0, 2.5, 5.0, or 10.0 g/L, as appropriate.

Non-limiting examples of compositions and methods disclosed herein include:

1. A composition comprising a graft copolymer, or an ether- or ester-derivative thereof, wherein the graft copolymer comprises: (i) a backbone comprising dextran that has been modified with about 1%-25% alpha-1,2 branches, and (ii) one or more alpha-1,3-glucan side chains comprising at least about 50% alpha-1,3 glycosidic linkages.
2. The composition of embodiment 1, wherein the dextran is substantially linear dextran (e.g., completely linear dextran) that has been modified with about 1%-25% alpha-1,2 branches.
3. The composition of embodiment 1 or 2, wherein the dextran has been modified with about 5%-20% alpha-1,2 branches.
4. The composition of embodiment 1, 2, or 3, wherein one or more of the alpha-1,2 branches are a single glucose monomer in length.
5. The composition of embodiment 1, 2, 3, or 4, wherein the weight-average degree of polymerization (DPw) of the backbone is about 10 to 500.
6. The composition of embodiment 1, 2, 3, 4, or 5, wherein the alpha-1,3-glucan side chains comprise at least about 90% alpha-1,3 glycosidic linkages.
7. The composition of embodiment 1, 2, 3, 4, 5, or 6, wherein the DP or DPw of the one or more alpha-1,3-glucan side chains is at least about 10 or 100.
8. The composition of embodiment 1, 2, 3, 4, 5, 6, or 7, wherein the graft copolymer or ether- or ester-derivative thereof is insoluble under aqueous conditions, or wherein the graft copolymer or ether- or ester-derivative thereof is soluble under aqueous conditions.
9. The composition of embodiment 1, 2, 3, 4, 5, 6, 7, or 8, wherein the graft copolymer is produced in a reaction composition comprising at least water, sucrose, the dextran, and a glucosyltransferase enzyme that synthesizes alpha-1,3-glucan with at least about 50% alpha-1,3 glycosidic linkages.
10. The composition of embodiment 1, 2, 3, 4, 5, 6, 7, 8, or 9, wherein the composition is a household care product, personal care product, industrial product, pharmaceutical product, or food product.
11. The composition of embodiment 1, 2, 3, 4, 5, 6, 7, 8, 9, or 10, wherein the composition is: (a) a film or coating, optionally wherein the percent elongation at break of the film is at least about 20%, or (b) a detergent composition that optionally is a fabric care composition.
12. A method of producing a graft copolymer, the method comprising: (a) contacting at least (i) water, (ii) sucrose, (iii) dextran that has been modified with about 1%-25% alpha-1,2 branches, and (iv) a glucosyltransferase enzyme that synthesizes alpha-1,3-glucan comprising at least about 50% alpha-1,3 glycosidic linkages, whereby a graft copolymer according to the composition of any one of embodiments 1-8 is produced; and (b) optionally, isolating the graft copolymer produced in step (a).
13. The method of embodiment 12, wherein the dextran is substantially linear dextran (e.g., completely linear dextran) that has been modified with about 1%-25% alpha-1,2 branches.
14. The method of embodiment 12 or 13, wherein the dextran has been modified with about 5%-20% alpha-1,2 branches.
15. The method of embodiment 12, 13, or 14, wherein the ratio, by weight, of the dextran to the sucrose is about 1:100 to about 1:5.
16. A method for producing a film, the method comprising: (a) dissolving the graft copolymer, or ether- or ester-derivative thereof, of any one of embodiments 1-8 (or an insoluble graft copolymer produced in a reaction composition according to embodiment 9) in a solvent to provide a solution; (b) contacting the solution with a surface; and (c) removing the solvent (e.g., by drying and/or coagulating the solution) to form a film.
17. The method of embodiment 16, wherein the solution of (a) comprises less than 15 wt % of the graft copolymer or ether- or ester-derivative thereof.
18. A method of producing alpha-1,3-glucan, the method comprising: (a) contacting at least (i) water, (ii) sucrose, (iii) dextran that has been modified with about 1%-50% alpha-1,2 branches (e.g., substantially linear dextran, or completely linear dextran, that has been modified with about 1%-50% alpha-1,2 branches), and (iv) a glucosyltransferase enzyme that synthesizes alpha-1,3-glucan comprising at least about 50% alpha-1,3 glycosidic linkages, thereby providing an enzymatic reaction, whereby alpha-1,3-glucan comprising at least about 50% alpha-1,3 glycosidic linkages is produced, and (b) optionally, isolating the alpha-1,3-glucan produced in step (a).

EXAMPLES

The present disclosure is further exemplified in the following Examples. It should be understood that these Examples, while indicating certain aspects herein, are given by way of illustration only. From the above discussion and these Examples, one skilled in the art can ascertain the essential characteristics of the disclosed embodiments, and without departing from the spirit and scope thereof, can make various changes and modifications to adapt the disclosed embodiments to various uses and conditions.

General Methods

Analysis of Reaction Profiles

High-performance liquid chromatography (HPLC) samples were analyzed using an Agilent 1200 series instrument equipped with a refractive index (RI) detector. Analysis was performed on two separate columns: Bio-Rad AMINEX 87C (column 1) for separation of <DP3 sugars and Bio-Rad AMINEX 42A (column 2) for separation of DP2-DP7 and higher DP oligosaccharides (DP8+). Linear calibration curves were constructed for sucrose (0.1-50 g/L), fructose (0.1-100 g/L), leucrose (0.1-100 g/L), and glucose (0.1-100 g/L) for quantitation on column 1. Linear calibration curves were constructed for DP2 (0.04-10 g/L), DP3 (0.04-10 g/L), DP4 (0.04-10 g/L), DP5 (0.04-10 g/L), DP6 (0.04-10 g/L), DP7 (0.04-10 g/L), and DP8+ (0.25-10 g/L) oligosaccharides for quantitation on column 2. DP8+ oligosaccharide calibration was performed using P1 primer (described in Example 1 below). The yield of alpha-1,3-glucan, as synthesized in unprimed or primed reactions, was measured based on the glucosyl component of the reaction.

Analysis of Glucan Molecular Weight

Insoluble glucan polymer wet cake isolated from glucosyltransferase reactions was treated with N,N-dimethylacetamide (DMAc) with 5% lithium chloride (LiCl) at 100° C. for 16 hours to form a glucan polymer solution. This solution (100 µL) was then injected into an Alliance™ 2695 HPLC (Waters Corporation, Milford, MA) equipped with a differential refractometer detector and multiangle light-scattering photometer from Wyatt Technologies (Santa Barbara, CA), both operating at 50° C. The mobile phase (DMAc containing 0.11 wt % LiCl) passed at a flow rate of 0.5 mL/min through four styrene-divinyl benzene columns in series; specifically, one KD-802, one KD-801, and two linear KD-806M columns (Shodex, Japan). The molecular weight distribution of the glucan polymer sample, as well as its average molar masses (Mn, Mw and Mz) were determined using Astra™ SEC-LS data reduction software package from Wyatt. Values of average degree of polymerization, e.g., DPw, were calculated by dividing a corresponding average molar mass by 162.

Determination of Glycosidic Linkages

Glycosidic linkages in glucan products synthesized by a glucosyltransferase were determined by $^1$H NMR (nuclear magnetic resonance) spectroscopy. Dry glucan polymer (6 to 8 mg) was dissolved in 0.75 mL of 3 wt % lithium chloride (LiCl) in deuterated dimethyl sulfoxide (DMSO-d6) by stirring overnight at ambient temperature. Deuterated water ($D_2O$) was then added (0.05 mL), and the sample was heated at 80° C. for about one hour to exchange protonated hydroxyls on the glucan polymer and ensure complete dissolution. 600 µL of the resulting clear homogeneous solution was transferred to a 5-mm NMR tube. $^1$H NMR spectra was used to quantify glycosidic linkage and a 2D $^1$H,$^{13}$C homo/hetero-nuclear suite of experiments was used to identify glucan linkages. The data were collected at 80° C. and processed on a Bruker Avance III NMR spectrometer, operating at either 500 MHz or 600 MHz. The systems are equipped with a proton-optimized cryoprobe.

Percent Primer Incorporation

The percent incorporation of dextran primer herein was calculated using the following formula: (g/L of primer consumed)/(g/L of starting primer)×100%.

High Yielding Alpha-1,3-Glucan-Producing Glucosyltransferase Enzymes

The amino acid sequence of the glucosyltransferase used to prepare amino acid substitutions was SEQ ID NO:4 (GTF 6855), which essentially is an N-terminally truncated (signal peptide and variable region removed) version of the full-length wild type glucosyltransferase (represented by SEQ ID NO:62) from Streptococcus salivarius SK126 (see Table 1). Substitutions made in SEQ ID NO:4 can be characterized as substituting for native amino acid residues, as each amino acid residue/position of SEQ ID NO:4 (apart from the Met-1 residue of SEQ ID NO:4) corresponds accordingly with an amino acid residue/position within SEQ ID NO:62. In reactions comprising at least sucrose and water, the glucosyltransferase of SEQ ID NO:4 typically produces alpha-glucan having about 100% alpha-1,3 linkages and a DPw of 400 or greater (e.g., refer to U.S. Pat. Nos. 8,871,474 and 9,169,506, and U.S. Patent Appl. Publ. Nos. 2017/0002336 and 2017/0002335, which are incorporated herein by reference). This alpha-glucan product, which is insoluble, can be isolated following enzymatic synthesis via filtration, for example.

Briefly, certain combinations of amino acid substitutions were made to SEQ ID NO:4 (GTF 6855). These substitutions are listed in Tables A and B below. Each variant enzyme listed in Table A was entered into a glucan synthesis reaction with parameters that were the same as, or similar to, the following: vessel, 250-mL indented shake flask agitated at 120 rpm; initial pH, 5.7; reaction volume, 50 mL; sucrose, 75 g/L; GTF, 1.5 mL lysate of E. coli cells heterologously expressing enzyme; $KH_2PO_4$, 20 mM; temperature, 30° C., time, about 20-24 hours. The alpha-1,3-glucan yields of these reactions (measured by HPLC analysis) are provided in Table A.

TABLE A

Alpha-1,3-Glucan Yields of GTF 6855 (SEQ ID NO: 4) Variants with Multiple Amino Acid Substitutions

| GTF[a] | Alpha-1,3-Glucan[b] Yield[c] |
|---|---|
| A510D/F607Y/R741S | 72.6% |
| A510D/F607Y/N743S | 79.2% |
| A510D/F607Y/D948G | 88.2% |
| A510D/R741S/D948G | 74.5% |
| A510D/F607Y/R741S/D948G | 82.8% |
| A510E/F607Y/R741S/R1172C | 78.2% |
| A510D/F607Y/D820G/D948G | 87.8% |
| A510D/F607Y/D948G/R1172C | 88.6% |
| A510D/F607Y/N743S/D948G/R1172C | 89.4% |
| A510D/F607Y/R741S/L784Q/F929L/R1172C | 79.3% |

[a]Each listed GTF is a version of GTF 6855 (SEQ ID NO: 4) comprising substitutions at respective positions, where each position number is in correspondence with the residue numbering of SEQ ID NO: 62. The wild type residue is listed first (before residue position number) and the substituting residue is listed second (after the residue position number).
[b]Insoluble alpha-1,3-glucan product with 100% alpha-1,3 linkages.
[c]Alpha-1,3-glucan yield based on glucosyl. The average yield of unmodified GTF 6855 (SEQ ID NO: 4, no substitutions) was about 29%.

Each variant enzyme listed in Table B was entered into a glucan synthesis reaction with parameters that were the same as, or similar to, the following: vessel, 500-mL jacketed reactor with Teflon®-pitched blade turbine (45-degree angle) on a glass stir rod and agitated at 50-200 rpm; initial pH, 5.5; reaction volume, 500 mL; sucrose, 108 g/L; $KH_2PO_4$, 1 mM; temperature, 39° C., time, about 18-24 hours; filtrate from a previous alpha-1,3-glucan synthesis reaction, 50 vol %. The alpha-1,3-glucan yields of these reactions (measured by HPLC analysis) are provided in Table B.

TABLE B

Alpha-1,3 Glucan Yields of GTF 6855 (SEQ ID NO: 4) Variants with Multiple Amino Acid-Substitutions

| GTF[a] | | | | | | | | | | Alpha-1,3-Glucan[b] Yield[c] |
|---|---|---|---|---|---|---|---|---|---|---|
| A510D | Q588L | F607Y | R741S | D948G | R722H | T877K | | M1253I | K1277N | 88% |
| A510D | Q588L | F607Y | R741S | D948G | R722H | T877K | V1188E | M1253I | Q957P | 92% |
| A510D | Q588L | F607Y | R741S | D948G | | T877K | V1188E | M1253I | Q957P | 91% |
| A510D | Q588L | F607Y | R741S | D948G | | | | M1253I | | 89% |
| A510D | Q588L | F607W | R741S | D948G | | | | | | 91% |

TABLE B-continued

Alpha-1,3 Glucan Yields of GTF 6855 (SEQ ID NO: 4) Variants with Multiple Amino Acid-Substitutions

| GTF[a] | | | | | | | | | | | | Alpha-1,3-Glucan[b] Yield[c] |
|---|---|---|---|---|---|---|---|---|---|---|---|---|
| | Q588L | F607Y | R741S | D948G | | | | | | | | 91% |
| A510D | Q588L | F607Y | R741S | D948G | N628D | T635A | | T877K | | M1253I | F929L | R1172C | 92% |
| A510D | Q588L | F607W | R741S | D948G | S631T | S710G | R722H | T877K | V1188E | M1253I | | | 94% |
| A510D | Q588L | F607W | R741S | D948G | S631T | S710G | R722H | T877K | V1188E | | | | 93% |
| A510D | Q588L | F607Y | R741S | D948G | S631T | S710G | | T877K | V1188E | M1253I | | | 96% |
| A510D | Q588L | F607Y | R741S | D948G | | | | | | | | | 89% |
| A510D | Q588L | F607W | R741S | D948G | | | | | V1188E | | | | 88% |
| A510D | Q588L | F607W | R741S | D948G | S631T | S710G | | | V1188E | | | | 96% |
| A510D | Q588L | F607W | R741S | D948G | | S710G | R722H | T877K | | M1253I | | | 96% |
| A510D | Q588L | F607W | R741S | D948G | S631T | | R722H | T877K | V1188E | M1253I | | | 96% |
| A510D | Q588L | F607W | R741S | D948G | S631T | | | T877K | V1188E | M1253I | | | 94% |
| A510D | Q588L | F607W | R741S | D948G | S631T | | | | V1188E | | | | 98% |
| A510D | Q588L | F607W | R741S | D948G | S631T | | R722H | T877K | V1188E | M1253I | | | 95% |
| A510D | Q588L | F607W | R741S | D948G | | | R722H | T877K | V1188E | M1253I | | | 93% |

[a]Each listed GTF is a version of GTF 6855 (SEQ ID NO: 4) comprising substitutions at respective positions, where each position number is in correspondence with the residue numbering of SEQ ID NO: 62.
[b]Insoluble alpha-1,3 glucan product.
[c]Alpha-1,3-glucan yield based on glucosyl.

Glucosyltransferase Enzymes That Produce Lower Molecular Weight Alpha-1,3-Glucan As discussed above, SEQ ID NO:4 (GTF 6855) is an amino acid sequence of a glucosyltransferase that can be used to prepare amino acid substitutions. Briefly, certain combinations of amino acid substitutions can be made to SEQ ID NO:4 to provide a glucosyltransferase that produces alpha-1,3-glucan of lower molecular weight (as compared to alpha-1,3-glucan product of non-modified GTF 6855). These substitutions are listed in Tables C and D below. For collecting the data in these tables, each variant enzyme was entered into a glucan synthesis reaction with parameters that were the same as, or similar to, the following: vessel, 50-mL indented shake flask agitated at 75 rpm; initial pH, 5.7; reaction volume, 10 mL; sucrose, 400 g/L; GTF, 0.3 mL of culture supernatant (prepared from lysate of E. coli cells heterologously expressing enzyme); $KH_2PO_4$, 5 mM; temperature, 35° C., time, about two days; de-activation, heated at 80° C. for 30 minutes. Insoluble glucan polymers produced in the reactions were individually harvested, water-washed, and analyzed for molecular size (DPw) via a standard SEC approach (see Tables C and D for DPw data). Glucosyltransferases with any of the amino acid substitution(s) listed in Tables C and D should be useful in practicing the presently disclosed subject matter.

TABLE C

DPw of Insoluble Alpha-1,3-Glucan Produced by GTF 6855 (SEQ ID NO: 4) and Single Amino Acid-Substituted Variants thereof

| GTF | DPw | GTF | DPw | GTF | DPw |
|---|---|---|---|---|---|
| 6855[a] | 350 | S553A | 127 | N573A | 123 |
| L513A[b] | 194 | S553C | 125 | N573A | 125 |
| L513C | 119 | S553C | 126 | N573D | 108 |
| L513C | 159 | S553E | 105 | N573D | 134 |
| L513D | 147 | S553E | 122 | N573G | 126 |
| L513D | 640 | S553F[c] | | N573G | 120 |
| L513E | 129 | S553F[c] | | N573H | 148 |
| L513E | 130 | S553H[c] | | N573I[c] | |
| L513F | 171 | S553H[c] | | N573K | 145 |
| L513G | 138 | S553I | 79 | N573K | 148 |
| L513H | 153 | S553I | 97 | N573L[c] | |
| L513H | 175 | S553M | 129 | N573M[c] | |
| L513I | 186 | S553M | 140 | N573N | 222 |
| L513K | 143 | S553N | 77 | N573P | 100 |
| L513K | 160 | S553N | 69 | N573T | 102 |

TABLE C-continued

DPw of Insoluble Alpha-1,3-Glucan Produced by GTF 6855 (SEQ ID NO: 4) and Single Amino Acid-Substituted Variants thereof

| | | | | | |
|---|---|---|---|---|---|
| L513M | 183 | S553R | 63 | N573T | 109 |
| L513M | 210 | S553T | 226 | N573V | 91 |
| L513N[c] | | S553T | 124 | N573W | 249 |
| L513N | 372 | S553V | 86 | N573W | 237 |
| L513P | 173 | S553Y | 110 | | |
| L513Q | 138 | S553Y | 52 | | |
| L513Q | 152 | | | | |
| L513R | 134 | | | | |
| L513R | 141 | | | | |
| L513S | 138 | | | | |
| L513S | 152 | | | | |
| L513T | 146 | | | | |
| L513V | 175 | | | | |
| L513V[c] | | | | | |
| L513W | 146 | | | | |
| L513W | 171 | | | | |
| L513Y | 156 | | | | |

| GTF | DPw | GTF | DPw | GTF | DPw |
|---|---|---|---|---|---|
| 6855[a] | 350 | K578A | 110 | Q616A | 175 |
| D575A[b] | 74 | K578A | 113 | Q616A | 440 |
| D575C | 199 | K578C | 132 | Q616C | 81 |
| D575C | 97 | K578D | 156 | Q616D | 115 |
| D575C[c] | | K578E | 95 | Q616E | 50 |
| D575C | 94 | K578E[c] | | Q616G | 66 |
| D575E | 90 | K578F | 103 | Q616G[c] | |
| D575E | 88 | K578G | 113 | Q616H | 61 |
| D575F | 74 | K578G | 103 | Q616I | 82 |
| D575G | 90 | K578H | 212 | Q616K | 58 |
| D575G | 89 | K578H | 187 | Q616K | 59 |
| D575H | 70 | K578I | 179 | Q616L | 61 |
| D575H | 134 | K578L | 177 | Q616L | 62 |
| D575I | 76 | K578M | 135 | Q616M | 164 |
| D575I | 98 | K578M | 141 | Q616N | 269 |
| D575K | 52 | K578N | 185 | Q616N | 211 |
| D575K | 95 | K578P | 126 | Q616P | 75 |
| D575L | 74 | K578P | 128 | Q616P | 78 |
| D575L[c] | | K578Q | 111 | Q616R | 103 |
| D575M | 66 | K578R | 214 | Q616R | 167 |
| D575M | 72 | K578R | 294 | Q616S | 72 |
| D575N | 90 | K578S | 105 | Q616T | 79 |
| D575N | 191 | K578S | 105 | Q616V | 88 |
| D575N[c] | | K578T | 131 | Q616V | 97 |
| D575P | 50 | K578T | 157 | Q616W | 60 |
| D575R | 65 | K578V | 146 | Q616W | 101 |
| D575R | 71 | K578V | 145 | Q616Y | 65 |
| D575S | 104 | K578W | 106 | | |
| D575S | 96 | K578W | 122 | | |

TABLE C-continued

DPw of Insoluble Alpha-1,3-Glucan Produced by GTF 6855 (SEQ ID NO: 4) and Single Amino Acid-Substituted Variants thereof

| D575V | 54 | K578Y | 145 |
|---|---|---|---|
| D575W | 69 | | |
| D575W | 167 | | |
| D575Y | 124 | | |
| D575Y | 69 | | |

[a]GTF 6855, SEQ ID NO: 4. The DPw of insoluble alpha-1,3-glucan produced by GTF 6855 averaged to be about 350.
[b]Each listed GTF with a substitution is a version of GTF 6855 comprising a substitution at a respective position, where the position number is in correspondence with the residue numbering of SEQ ID NO: 62.
[c]Insoluble alpha-1,3-glucan not produced or detected.

TABLE D

DPw of Insoluble Alpha-1,3-Glucan Produced by Multiple Amino Acid-Substituted Variants of GTF 6855 (SEQ ID NO: 4)

| GTF[a] | | | | | | DPw |
|---|---|---|---|---|---|---|
| P550L | N557I | N581P | | | | 12 |
| L535P | S553C | N558D | D575V | T585P | K697R | 12 |
| P550V | S553R | N581P | T585P | | | 12 |
| P550L | S553F | N581P | | | | 12 |
| P550V | N557E | T585P | | | | 12 |
| P550L | N557E | D575V | T585P | | | 13 |
| L538P | P550L | S553Y | | | | 13 |
| P544L | P550V | S553C | N573I | T585P | S589G | 13 |
| P550V | G576D | T585P | | | | 13 |
| P550L | N558D | T585P | T679I | | | 13 |
| P550L | N557E | T585P | S589G | | | 14 |
| P550L | N557E | T569L | N581P | | | 14 |
| P550L | N557E | T569L | T585P | | | 14 |
| P550V | S553T | N558D | T585P | G730D | | 14 |
| E577G | P550L | N557I | T569L | N573I | | 14 |
| P550L | S553C | D575A | T585P | S589G | | 14 |
| S553R | N573V | K578N | S631G | T660A | | 14 |
| P550V | S553R | W571V | G576D | | | 14 |
| P550V | N557E | K578D | T585P | | | 14 |
| P550V | N558D | N573P | T585P | | | 14 |
| P550L | N558D | W571V | N581P | K593E | | 14 |
| P550V | S553E | N581P | | | | 15 |
| P550L | N573I | T585P | W725R | | | 15 |
| P550L | N557I | N573P | | | | 15 |
| N557E | N573V | N581P | | | | 15 |
| P550L | N557I | G576D | Q643L | | | 15 |
| P550V | S553N | T585P | V586G | S710G | | 15 |
| P550V | S553C | D575A | T585P | | | 15 |
| S553R | N573V | K578N | S631G | T660A | | 15 |
| P550L | S553K | D575A | Y580H | | | 16 |
| P550V | D575A | T585P | S589G | K713E | | 16 |
| P550V | S553N | N573I | Y693C | | | 16 |
| P544L | P550L | N557E | N573I | T585P | | 16 |
| P550L | N558D | W571V | N581P | T585P | | 16 |
| S504G | P550V | N557Q | N581P | | | 16 |
| P550L | S553R | D575A | | | | 16 |
| P550V | N558D | W571D | D575A | T585P | | 16 |
| P544L | P550V | N557Q | N581P | | | 17 |
| P550V | S553K | T585P | | | | 17 |
| P550V | S553N | T585P | | | | 17 |
| P550L | T569L | N573I | | | | 17 |
| P550L | N558D | D575V | | | | 17 |
| L537P | P550L | N558D | N573I | | | 17 |
| P550L | S553C | W571C | G576D | T585P | | 17 |
| P550L | N557Q | W571C | G576D | T585P | | 17 |
| P550L | N558D | W571V | N581P | | | 17 |
| A542V | P550V | N558D | W571V | T585P | | 17 |
| P550V | N558D | W571V | G576D | | | 18 |
| P550V | S553N | N573I | | | | 18 |
| P550V | N557Q | D575V | A669T | | | 18 |
| P550V | N581P | I636T | | | | 18 |
| P550V | N557E | N581P | | | | 18 |
| P550V | N573I | T585P | | | | 18 |
| P550L | S553K | N558D | K578R | Y700N | | 19 |
| P550V | S553T | N558D | W571V | | | 19 |
| P514L | P550V | N557Q | T585P | D602N | | 20 |
| P550L | N557I | T569A | G576D | | | 20 |

TABLE D-continued

DPw of Insoluble Alpha-1,3-Glucan Produced by Multiple Amino Acid-Substituted Variants of GTF 6855 (SEQ ID NO: 4)

| GTF[a] | | | | | DPw |
|---|---|---|---|---|---|
| P550V | N557T | N558D | W571D | | 21 |
| P550L | N557E | D575A | T585P | | 21 |
| I545V | P550V | N557Q | T585P | D638N | 21 |
| P544L | P550V | N557I | T585P | | 22 |
| Y518C | P550V | N581P | T585P | | 22 |
| P550L | N557E | D575A | | | 22 |

[a]Each listed GTF is a version of GTF 6855 (SEQ ID NO: 4) comprising substitutions at respective positions, where each position number is in correspondence with the residue numbering of SEQ ID NO: 62.

Glucosyltransferase Enzymes That Produce Higher Molecular Weight Alpha-1,3-Glucan As discussed above, SEQ ID NO:4 (GTF 6855) is an amino acid sequence of a glucosyltransferase that can be used to prepare amino acid substitutions. Briefly, certain amino acid substitutions can be made to SEQ ID NO:4 to provide a glucosyltransferase that produces alpha-1,3-glucan of higher molecular weight (as compared to alpha-1,3-glucan product of non-modified GTF 6855). Some of these substitutions are listed in Tables E and F below, along with mutations that did not have a substantial effect on molecular weight. For collecting the data in these tables, each variant enzyme was entered into a glucan synthesis reaction with parameters as disclosed in U.S. patent application Ser. No. 16/127,288, which is incorporated herein by reference. A glucosyltransferase with any of the amino acid substitution(s) listed in Tables E and F is contemplated to be useful in practicing the presently disclosed subject matter.

TABLE E

DPw of Insoluble Alpha-1,3-Glucan Produced by GTF 6855 (SEQ ID NO: 4) and Single Amino Acid-Substituted Variants thereof

| GTF | DPw | GTF | DPw | GTF | DPw | GTF | DPw |
|---|---|---|---|---|---|---|---|
| 6855[a] | 626 | T635H | 539 | P1499Y | 587 | A510E | 625 |
| V186A[b] | 589 | T635W | 528 | Y219C | 591 | N904C | 554 |
| V186M | 580 | I636H | 521 | E243H | 618 | K930G | 637 |
| E194C | 580 | Y848E | 843 | A377I | 514 | K930V | 582 |
| L434N | 613 | D947G | 408 | I411F | 586 | D947F | 619 |
| A472C | 530 | F951Y | 325 | I411S | 591 | D947I | 610 |
| A472S | 374 | E849M | 610 | D425Q | 681 | D947K | 559 |
| A510E | 654 | Q1007A | 394 | L428V | 577 | D947N | 635 |
| A510I | 621 | D1003G | 486 | M529N | 560 | D947Q | 635 |
| A510V | 655 | A1022M | 303 | N531G | 977 | D947S | 603 |
| M529N | 558 | D1028L | 416 | G576R | 416 | D947V | 621 |
| R534G | 711 | D1028Q | 537 | Y580H | 554 | D947Y | 624 |
| R534I | 789 | A1057H | 624 | K593M | 792 | Q1007S | 578 |
| R534L | 763 | N1096A | 562 | I608Y | 708 | D1003N | 570 |
| R534M | 776 | Y1104M | 611 | N613G | 644 | I1026H | 621 |
| G576H | 436 | N1122K | 614 | N613L | 618 | D1028A | 568 |
| Q588L | 817 | E1132A | 589 | D617E | 419 | D1028M | 535 |
| I591K | 816 | E1132H | 611 | E621T | 603 | V1037A | 591 |
| I591R | 832 | E1132K | 610 | I627W | 506 | K1041A | 583 |
| Y605W | 524 | E1132R | 622 | S631D | 521 | K1041M | 648 |
| F607N | 561 | V1135K | 612 | S631E | 545 | D1080M | 554 |
| F607W | 624 | V1188E | 641 | S631R | 521 | F1244P | 589 |
| A610C | 799 | L1212N | 630 | G633W | 493 | F1244Q | 534 |
| N613I | 555 | E1250R | 606 | F634A | 523 | E1250H | 553 |
| N613M | 587 | T1381E | 612 | T635E | 561 | E1250K | 591 |
| N613T | 526 | T1431M | 625 | T635I | 648 | T1431Q | 663 |
| N613V | 578 | A1442R | 609 | T635Y | 518 | E1450D | 585 |
| K625A | 638 | E1450F | 611 | R722H | 793 | G1484P | 627 |

TABLE E-continued

DPw of Insoluble Alpha-1,3-Glucan Produced by GTF 6855 (SEQ ID NO: 4) and Single Amino Acid-Substituted Variants thereof

| GTF | DPw | GTF | DPw | GTF | DPw | GTF | DPw |
|---|---|---|---|---|---|---|---|
| K625M | 623 | E1450W | 618 | T728S | 769 | I1453G | 881 |
| A510E | 622 | I1453M | 635 | M732L | 791 | W1437N | 654 |
| S631T | 532 | V1491F | 604 | A777N | 755 | R722N | 766 |

[a]GTF 6855, SEQ ID NO: 4. The DPw of insoluble alpha-1,3-glucan produced by GTF 6855 averaged to be about 626.
[b]Each listed GTF with a substitution is a version of GTF 6855 comprising a substitution at a respective position, where the position number is in correspondence with the residue numbering of SEQ ID NO: 62.

TABLE F

DPw of Insoluble Alpha-1,3-Glucan Produced by GTF 6855 (SEQ ID NO: 4) and Single Amino Acid-Substituted Variants thereof

| GTF | DPw |
|---|---|
| 6855[a] | 558 |
| E567Q[b] | 1001 |
| I591V | 859 |
| L661P | 842 |
| N743D | 700 |
| N743S | 937 |
| N743T | 874 |
| R741A | 831 |
| R741P | 871 |
| R741Q | 886 |
| R741S | 887 |
| R741T | 693 |
| T563A | 910 |
| V586T | 874 |

[a]GTF 6855, SEQ ID NO: 4.
[b]Each listed GTF with a substitution is a version of GTF 6855 comprising a substitution at a respective position, where the position number is in correspondence with the residue numbering of SEQ ID NO: 62.

Example 1

Producing Alpha-1,3-Glucan in Glucosyltransferase Reactions Containing Dextran with 18.6% Alpha-1,2 Branches This Example describes priming alpha-1,3-glucan synthesis reactions with dextran that was previously modified to have 18.6% alpha-1,2 branches. Graft copolymers were synthesized comprising a dextran backbone and alpha-1,3-glucan arms.

Alpha-1,2-branched dextran was produced to prime glucosyltransferase reactions for alpha-1,3-glucan synthesis. Preparation of this primer was performed essentially as described in International Patent. Appl. Publ. No. WO2017/091533 and U.S. Patent Appl. Publ. No. 2018/0282385, which are both incorporated herein by reference. Briefly, linear dextran (i.e., polysaccharide with 100% alpha-1,6 glycosidic linkages) of molecular weight ~14 kDa (DPw of ~89) was produced using glucosyltransferase GTF8117 (SEQ ID NO:66). This dextran was then modified to have 18.6% alpha-1,2-branches using alpha-1,2-branching enzyme GTFJ18T1 (SEQ ID NO:70). The resulting alpha-1,2-branched dextran, which had a DPw of about 110 (~17 kDa), is referred to herein as P1 primer.

P1 primer was then included in alpha-1,3-glucan synthesis reactions comprising a glucosyltransferase to produce graft copolymers comprising a dextran backbone and alpha-1,3-glucan arms. The glucosyltransferase used in these reactions, which produces alpha-1,3-glucan with about 100% alpha-1,3 linkages, was a *Streptococcus salivarius* glucosyltransferase modified in its catalytic domain such that the enzyme could produce more products (alpha-1,3-glucan and fructose), and less by-products (e.g., glucose, oligosaccharides such as leucrose and DP2-7 gluco-oligosaccharides), from sucrose substrate, as compared to the enzyme's unmodified counterpart. The General Methods section describes preparation of this non-native glucosyltransferase (Table A).

Eight separate 100-mL alpha-1,3-glucan synthesis reactions were performed in plastic 250-mL shake flasks. Each reaction comprised water, sucrose (roughly 50 or 100 g/L), phosphate buffer (5 mM), P1 primer (roughly 0-10 g/L), and a glucosyltransferase (above). The reactions were prepared by mixing 10 or 20 mL of a 500 g/L sucrose stock solution with 5 mL of a 100 mM sodium phosphate buffer stock (adjusted to pH 5.5 with a few drops of NaOH or phosphoric acid solution). A 25 g/L P1 primer stock was used to achieve a final concentration of 0, 1, 2.5, or 10 g/L by adding 0, 4, 10 or 40 mL to each preparation containing 50 or 100 g/L sucrose to yield a total of eight separate reaction preparations. Deionized, sub-micron filtered water was added to bring the final volume to 100 mL. A 0.5-mL aliquot was withdrawn from each preparation, after which 0.2256 mL of glucosyltransferase enzyme stock was added (for final enzyme concentration of 100 U/L) to initiate each reaction for alpha-1,3-glucan synthesis. The reactions were carried out at 30° C.

At 1, 2, 3 and 24 hours after commencing the reactions, 1 mL of each reaction was withdrawn to a micro-centrifuge tube. Samples were heated to 80° C. for ~10 minutes in a dry heat block to deactivate the glucosyltransferase to stop the reaction. Deactivated samples were then spun in a table centrifuge for 10 minutes at 12,000 RPM to pellet the water-insoluble polymer products. The supernatant was withdrawn and filtered through a 0.45-μm WHATMAN syringeless filter for HPLC analysis. After 24 hours, all the reactions were placed into an 80° C. water bath for ~30 minutes to deactivate the glucosyltransferase to stop the reaction. The deactivated reactions were charged on a ~10-μm CHEMRUS fritted filter and vacuum-filtered until near-dry before washing twice with ~100 mL of cold deionized water to form a polymer wet cake. Approximately 300-500 mg of each wet cake was reserved for size-exclusion chromatography (SEC) analysis, while the remainder of each wet cake was dried in a vacuum oven at 40° C., −40 cmHg.

SEC analysis was performed to determine the molecular weight and degree of polymerization (DP) of the insoluble polymer product. PDI (polydispersity index) values were calculated using these data. The glycosidic linkage profile of each insoluble polymer product was determined by $^1$H NMR analysis using dried polymer dissolved in 3% LiCl/DMSO-$d_6$ containing a small amount of $D_2O$. Table 2 provides the results of these analyses.

TABLE 2

Structural Analysis of Alpha-1,3-Glucan Produced in Glucosyltransferase Reactions (24-hour) Containing P1 Primer

| Reaction | | Alpha-1,3-Glucan Product Profile | | | | | | |
|---|---|---|---|---|---|---|---|---|
| | | | | | Linkages | | | |
| Sucrose | Primer | | | % | (% of total residues) | | | |
| (g/L) | (g/L) | DPw | PDI | primer | 1,3 | 1,2,6 | 1,2 | 1,6 |
| 53 | 0.0 | 860.0 | 1.66 | 0.0 | 100.0 | 0.0 | 0.0 | 0.0 |
| | 1.1 | 2434.7 | 1.9 | 2.8 | 97.2 | 0.3 | 0.4 | 2.2 |
| | 2.6 | 1987.4 | 1.6 | 4.4 | 95.6 | 0.6 | 0.6 | 3.2 |
| | 10.5 | 2081.1 | 2.0 | 6.2 | 93.8 | 0.7 | 0.8 | 4.6 |

TABLE 2-continued

Structural Analysis of Alpha-1,3-Glucan Produced in Glucosyltransferase Reactions (24-hour) Containing P1 Primer

| Reaction | | Alpha-1,3-Glucan Product Profile | | | | | | |
|---|---|---|---|---|---|---|---|---|
| | | | | | Linkages | | | |
| Sucrose | Primer | | | % | (% of total residues) | | | |
| (g/L) | (g/L) | DPw | PDI | primer | 1,3 | 1,2,6 | 1,2 | 1,6 |
| 105 | 0.0 | 792.0 | 1.7 | 0.0 | 100.0 | 0.0 | 0.0 | 0.0 |
| | 1.0 | 1666.6 | 2.0 | 1.6 | 98.4 | 0.2 | 0.2 | 1.2 |
| | 2.6 | 1495.2 | 1.8 | 2.7 | 97.3 | 0.3 | 0.3 | 2.0 |
| | 10.4 | 1572.6 | 2.0 | 3.7 | 96.3 | 0.4 | 0.5 | 2.8 |

HPLC data were used to estimate the rates of the glucosyltransferase reactions based on sucrose consumption, glucan polymer yield (based on glucosyl [throughout the Examples]), and primer consumption. Monitoring the consumption of primer allowed for estimating primer incorporation into glucan polymer products. The size of individual alpha-1,3-glucan arms grafted on primer in each reaction was expected to be very similar to the size of alpha-1,3-glucan produced in control reactions that did not contain added primer; the control reaction products comprised alpha-1,3-glucan homopolymer. A glucan-to-primer molar ratio (M ratio) was calculated at 3-hour and 24-hour reaction times using this control DPw value (860 or 792) and the DPw of the P1 primer (~110). The data from these analyses are provided in Table 3. Differences in the glucan-to-primer molar ratios between the 3- and 24-hour timepoints indicated the consistency of the priming reactions.

TABLE 3

Profiles of Glucosyltransferase Reactions (24-hour) Containing P1 Primer

| Sucrose (g/L) | Primer (g/L) | Alpha-1,3-Glucan Yield (Glucosyl) | Sucrose Rate (g/L/h) | Glucan/Primer 3 hour (M ratio)$^a$ | Glucan/Primer 24 hour (M ratio)$^a$ |
|---|---|---|---|---|---|
| 53 | 0.0 | 79% | 7.5 | NA | NA |
| | 1.1 | 77% | 7.3 | 2.2 | 3.5 |
| | 2.6 | 78% | 8.2 | 2.2 | 2.6 |
| | 10.5 | 82% | 9.2 | 3.2 | 2.2 |
| 105 | 0.0 | 82% | 10.8 | NA | NA |
| | 1.0 | 79% | 10.1 | 3.2 | 7.3 |
| | 2.6 | 81% | 11.0 | 2.5 | 4.5 |
| | 10.4 | 82% | 12.5 | 2.6 | 5.5 |

$^a$Glucan/primer molar ratio was calculated using DPw (estimated) of glucan arm (860) for 53 g/L sucrose reactions, 792 for 105 g/L sucrose reactions) and DPw of primer (110).

Thus, by providing an alpha-1,2-branched dextran primer to alpha-1,3-glucan synthesis reactions, graft copolymers were synthesized comprising a dextran backbone and alpha-1,3-glucan arms. While primer was demonstrably consumed and incorporated into graft copolymer products (based on HPLC and NMR results), changes in reaction rate seemed minimal. It seemed that a higher primer concentration resulted in higher primer incorporation and higher glucan yield. Molecular weight increases were observed when primer was present (especially at 1 g/L); this was a sign of generating primed glucan product. The effect of priming on DPw and primer consumption was less in reactions with 100 g/L sucrose than those with 50 g/L sucrose, possibly indicating that less priming occurs as more sucrose is consumed. The graft copolymer products likely had an average of one to two alpha-1,3-glucan arms per dextran backbone.

Example 2

Producing Alpha-1,3-Glucan in Glucosyltransferase Reactions Containing Dextran with 9.2% Alpha-1,2 Branches This Example describes priming alpha-1,3-glucan synthesis reactions with dextran that was previously modified to have 9.2% alpha-1,2 branches. Graft copolymers were synthesized comprising a dextran backbone and alpha-1,3-glucan arms. In view of the results provided in Example 1, this Example indicates that alpha-1,3-glucan priming efficacy can be controlled by varying the alpha-1,2 branching frequency of a dextran primer.

Alpha-1,2-branched dextran was produced to prime glucosyltransferase reactions for alpha-1,3-glucan synthesis. Preparation of this primer was performed as described in Example 1 following the procedures disclosed in International Patent. Appl. Publ. No. WO2017/091533 and U.S. Patent Appl. Publ. No. 2018/0282385, with the exception that alpha-1,2-branching enzyme GTF9905 (SEQ ID NO:71) was used (instead of GTFJ18T1) with a different amount of sucrose, and the level of alpha-1,2 branches in the primer was 9.2% (instead of 18.6%). This primer, which had a molecular weight of ~15 kDa (DPw~90), is referred to herein as P2 primer. Thus, the only apparent difference between the P1 and P2 primers is their respective levels of alpha-1,2 branching.

P2 primer was then included in alpha-1,3-glucan synthesis reactions comprising a glucosyltransferase (the same enzyme as used in Example 1) to produce graft copolymers comprising a dextran backbone and alpha-1,3-glucan arms. Briefly, eight plastic shake flasks were charged with 10 or 20 mL of a 500 g/L sterile-filtered sucrose stock solution, 5 mL of a 100 mM sodium phosphate buffer stock (adjusted to pH 5.5 with a few drops of NaOH or phosphoric acid solution), and 0, 0.48, 1.20, or 4.81 mL of a 208.1 g/L P2 primer stock. Deionized, sub-micron filtered water was added to bring the final volume to 100 mL. Thus, eight preparations were made containing roughly 50 or 100 g/L sucrose, 5 mM phosphate buffer, and roughly 0, 1, 2.5, or 10 g/L P2 primer. A 0.5-mL aliquot was withdrawn from each preparation for HPLC analysis prior to adding the glucosyltransferase enzyme (t=0). Each reaction was initiated by adding 0.226 mL of glucosyltransferase enzyme stock (for final enzyme concentration of 100 U/L). The reactions were carried out at 30° C.

At 1, 2, 3, 5 and 24 hours after commencing the reactions, 1 mL of each reaction was withdrawn to a micro-centrifuge tube. Samples were heated to 80° C. for ~10 minutes in a dry heat block to deactivate the glucosyltransferase to stop the reaction. Deactivated samples were then spun in a table centrifuge for 10 minutes at 12,000 RPM to pellet the water-insoluble polymer products. The supernatant was withdrawn and filtered through a 0.45-μm WHATMAN syringeless filter for HPLC analysis. After 24 hours, all the reactions were placed into an 80° C. water bath for ~30 minutes to deactivate the glucosyltransferase to stop the reaction. Polymer wet cakes were generated from each terminated reaction as described in Example 1. HPLC analysis of soluble sugars and analysis of insoluble polymer samples by NMR and SEC were carried out as described in Example 1 and the General Methods. The results of these analyses are provided in Tables 4 and 5.

TABLE 4

Structural Analysis of Alpha-1,3-Glucan Produced in Glucosyltransferase Reactions (24-hour) Containing P2 Primer

| Reaction | | Alpha-1,3-Glucan Product Profile | | | | | | |
|---|---|---|---|---|---|---|---|---|
| Sucrose | Primer | | | % | (% of total residues) | | | |
| (g/L) | (g/L) | DPw | PDI | primer | 1,3 | 1,2,6 | 1,2 | 1,6 |
| 53 | 0.0 | 841.0 | 1.7 | 0.0 | 100.0 | 0.0 | 0.0 | 0.0 |
|  | 1.2 | 3092.5 | 1.9 | 4.1 | 95.9 | 0.2 | 0.3 | 3.6 |
|  | 2.6 | 2615.3 | 1.7 | 6.9 | 93.1 | 0.4 | 0.5 | 6.1 |
|  | 9.8 | 2049.2 | 1.9 | 10.5 | 89.5 | 0.6 | 0.6 | 9.3 |
| 106 | 0.0 | 850 | 1.6 | 0.0 | 100.0 | 0.0 | 0.0 | 0.0 |
|  | 1.1 | 2459.3 | 2.8 | 2.1 | 97.9 | 0.1 | 0.1 | 1.9 |
|  | 2.6 | 2118.7 | 2.3 | 4.2 | 95.8 | 0.2 | 0.3 | 3.7 |
|  | 10.0 | 1769.8 | 2.0 | 8.2 | 91.8 | 0.5 | 0.5 | 7.2 |

TABLE 5

Profiles of Glucosyltransferase Reactions (24-hour) Containing P2 Primer

| Sucrose (g/L) | Primer (g/L) | Alpha-1,3-Glucan Yield (Glucosyl) | Sucrose Rate (g/L/h) | Glucan/Primer 3 hour (M ratio)$^a$ | Glucan/Primer 24 hour (M ratio)$^a$ |
|---|---|---|---|---|---|
| 53 | 0.0 | 81% | 7.7 | NA | NA |
|  | 1.2 | 80% | 9.9 | 1.9 | 2.3 |
|  | 2.6 | 84% | 11.9 | 1.5 | 1.4 |
|  | 9.8 | 88% | 14.2 | 1.3 | 1.2 |
| 106 | 0.0 | 81% | 10.0 | NA | NA |
|  | 1.0 | 81% | 13.2 | 2.3 | 4.3 |
|  | 2.6 | 83% | 16.0 | 1.6 | 2.3 |
|  | 10.0 | 87% | 17.9 | 1.5 | 1.6 |

$^a$Glucan/primer molar ratio was calculated using DPw (estimated) of glucan arm (841) for 53 g/L sucrose reactions, 850 for 106 g/L sucrose reactions) and DPw of primer (90).

As indicated in Tables 4 and 5, significantly improved priming was observed compared to reactions in Example 1 (Tables 2 and 3). In general, and as a trend, the P2 priming reactions exhibited higher reaction rates, higher yield, and likely most importantly, a higher percentage of primer incorporation. The glucan-to-primer ratios were also better at both the 3- and 24-hour time points, implying that there were more consistent priming reactions. Increases in alpha-1,3-glucan molecular weight were also observed for all the P2-primed reactions (especially at 1 g/L), and the values seemed higher than those from corresponding reactions using P1 primer. Similar to reactions using primer P1, the effect of priming with P2 on alpha-1,3-glucan DPw and primer consumption was less in reactions with 100 g/L sucrose than those with 50 g/L sucrose.

Thus, it is fair to conclude that the P2 primer, which had a lower branching frequency (9.2% alpha-1,2 branches compared to 18.6% in P1 primer), but the same dextran backbone as the P1 primer, allowed for more efficient alpha-1,3-glucan synthesis compared to the P1 primer. This conclusion suggests that the addition of alpha-1,2 branches to the dextran backbone of a primer downregulates its ability to prime glucan synthesis in a glucosyltransferase reaction. This observation was surprising because it had been expected that the addition of more non-reducing ends (more free hydroxyl groups) to a dextran primer by a branching enzyme would have allowed for better priming activity, and therefore better alpha-1,3-glucan synthesis. Alpha-1,2 branching technology can therefore be used as an input for regulating/controlling glucan synthesis in primed glucosyltransferase reactions.

Example 3

Producing Alpha-1,3-Glucan in Glucosyltransferase Reactions Containing Dextran with 9.2% Alpha-1,2 Branches (2-Liter Scale)

This Example describes scaling up the P2-primed reactions described in Example 2, which were done in shake flasks at a 100-mL scale, to 2-L reactor scale. Other than the reaction volumes, similar reaction conditions (as described in Example 2) were used in this Example to synthesize graft copolymers comprising a dextran backbone and alpha-1,3-glucan arms. Thus, in brief, this Example describes additional alpha-1,3-glucan synthesis reactions primed with dextran previously modified to have 9.2% alpha-1,2 branches.

Two glucosyltransferase reactions were prepared. Each was made by dissolving 200 grams of sucrose in ~1 L of water, with addition of 10 mL of 1 M sodium phosphate buffer (pH 5.5) and either 9.61 or 48.05 mL of a 208 g/L P2 primer stock. The final volumes of both preparations were adjusted to 2 L using a volumetric flask. The final primer concentrations were about 1 and 5 g/L, respectively. Each preparation was filtered through a 0.22-micron filter, and then charged into a 2-L glass-jacketed reactor fitted with overhead stirring. A 0.5-mL aliquot was withdrawn from each preparation for HPLC analysis prior to adding the glucosyltransferase enzyme (t=0). Each reaction was initiated by adding 4.535 mL of glucosyltransferase enzyme stock (for final enzyme concentration of 100 U/L) (same enzyme as used in above Examples). The reactions were carried out at 30° C.

At 1, 2, 3 and 24 hours after commencing the reactions, 1 mL of each reaction was withdrawn to a micro-centrifuge tube. Samples were heated to 80° C. for ~10 minutes in a dry heat block to deactivate the glucosyltransferase to stop the reaction. Deactivated samples were then spun in a table centrifuge for 10 minutes at 12,000 RPM to pellet the water-insoluble polymer products. The supernatant was withdrawn and filtered through a 0.45-μm WHATMAN syringeless filter for HPLC analysis. After 24 hours, both reactions were placed into an 80° C. water bath for ~30 minutes to deactivate the glucosyltransferase to stop the reaction. Both terminated reactions were loaded on a ~40-μm CHEMRUS disposable fritted filter, and fully suction-filtered. Retained material was then washed with ~3×1-L de-ionized (DI) water to remove any residual soluble components, leaving behind a clean glucan polymer wet cake. Approximately 300-500 mg of each wet cake was reserved for SEC analysis. Each remainder was dried in a vacuum oven at 40° C., −40 cmHg. HPLC analysis of soluble sugars and analysis of insoluble polymer samples by NMR and SEC were carried out as described in Example 1 and the General Methods. The results of these analyses are provided in Tables 6 and 7.

TABLE 6

Structural Analysis of Alpha-1,3-Glucan Produced in Glucosyltransferase Reactions (24-hour, 2-L) Containing P2 Primer

| Reaction | | Alpha-1,3-Glucan Product Profile | | | | | | |
|---|---|---|---|---|---|---|---|---|
| | | | | % | (% of total residues) | | | |
| Sucrose (g/L) | Primer (g/L) | DPw | PDI | primer | 1,3 | 1,2,6 | 1,2 | 1,6 |
| 104 | 1.1 | 2396.2 | 2.6 | 1.9 | 98.1 | 0.1 | 0.1 | 1.7 |
|  | 5.0 | 2232.9 | 2.0 | 5.7 | 94.3 | 0.4 | 0.4 | 5.0 |

TABLE 7

Profiles of Glucosyltransferase Reactions (24-hour, 2-L) Containing P2 Primer

| Sucrose (g/L) | Primer (g/L) | Alpha-1,3-Glucan Yield (Glucosyl) | Sucrose Rate (g/L/h) | Glucan/Primer 3 hour (M ratio)$^a$ | Glucan/Primer 24 hour (M ratio)$^a$ |
|---|---|---|---|---|---|
| 104 | 1.1 | 79% | 12.9 | 2.2 | 4.6 |
|  | 5.0 | 84% | 16.7 | 1.5 | 1.6 |

$^a$Glucan/primer molar ratio was calculated using DPw (estimated) of glucan arm (850) and DPw of primer (90).

By comparing the data in Tables 6 and 7 with Tables 4 and 5, respectively, it was observed that the scaled-up reactions (2-L) of this Example provided similar results (e.g., DPw of, and primer incorporation in, alpha-1,3-glucan product) with those of the reactions performed in Example 2 on a smaller scale (100-mL).

Example 4

Producing Alpha-1,3-Glucan in Glucosyltransferase Reactions Containing Dextran with 9.2% Alpha-1,2 Branches (50-Liter Scale)

This Example describes scaling up the P2-primed reactions described in Example 3, which were done at 2-L scale, to 50-L scale. Other than the reaction volumes and primer purity (discussed below), similar reaction conditions (as described in Example 2) were used in this Example to synthesize graft copolymers comprising a dextran backbone and alpha-1,3-glucan arms. Thus, in brief, this Example describes additional alpha-1,3-glucan synthesis reactions primed with dextran previously modified to have 9.2% alpha-1,2 branches.

The primers employed in Examples 1-3 had been purified prior to their use in alpha-1,3-glucan synthesis reactions. However, in this Example, the P2 primer was provided in alpha-1,3-glucan synthesis reactions in the form of a crude reaction mix resulting from the enzymatic 1,2-branching of dextran (as described in Example 2).

A glucosyltransferase reaction with the following conditions was prepared: roughly 100 g/L sucrose, 5 mM sodium phosphate (pH 5.5), roughly 10 g/L P2 primer. Briefly, a 50-L glass-jacketed reactor outfitted with overhead stirring was charged with ~20 L of DI water, after which 5 kg sucrose, 2.3 L of a 216.1 g/L crude P2 primer stock, and 250 mL of a 1 M sodium phosphate buffer (pH 5.5) were added. The solids were allowed to dissolve with stirring before the reactor was filled to 50 L by addition of DI water. A 1-mL aliquot was withdrawn (for t=0 HPLC analysis) before initiating the reaction by adding 113.38 mL of glucosyl-transferase enzyme stock (for final enzyme concentration of 100 U/L) (same enzyme as used in above Examples). The reaction was carried out at 30° C.

HPLC samples were taken at 2.5 and 24 hours after starting the reaction, and were processed and analyzed as described in Example 1. After 24 hours from starting the reaction, the entire reaction was heated to ~80° C. for ~30 minutes to deactivate the glucosyltransferase to stop the reaction. The terminated reaction was loaded onto a cloth filter and fully vacuum-filtered. Retained material was washed with 3×~20-L DI water to remove any residual soluble components, and then pressed overnight by suctioning on a latex rubber sheet to form a compact clean glucan polymer wet cake. A sample for SEC was taken as described in Example 1. The wet cake was then dried in a vacuum oven for ~3 days at 60° C., −40 cmHg. A dried polymer sample was submitted for NMR analysis as described in Example 1. The results of these analyses are provided in Tables 8 and 9.

TABLE 8

Structural Analysis of Alpha-1,3-Glucan Produced in Glucosyltransferase Reaction (24-hour, 50-L) Containing P2 Primer

| Reaction | | Alpha-1,3-Glucan Product Profile | | | | | | |
|---|---|---|---|---|---|---|---|---|
| | | | | % | (% of total residues) | | | |
| Sucrose (g/L) | Primer (g/L) | DPw | PDI | primer | 1,3 | 1,2,6 | 1,2 | 1,6 |
| 104 | 9.6 | 2224.7 | 2.1 | 8.7 | 91.3 | 0.7 | 0.6 | 7.4 |

TABLE 9

Profiles of Glucosyltransferase Reaction (24-hour, 50-L) Containing P2 Primer

| Sucrose (g/L) | Primer (g/L) | Alpha-1,3-Glucan Yield (Glucosyl) | Sucrose Rate (g/L/h) | Glucan/Primer 3 hour (M ratio)$^a$ | Glucan/Primer 24 hour (M ratio)$^a$ |
|---|---|---|---|---|---|
| 104 | 9.6 | 80% | 17.8 | 1.5 | 1.4 |

$^a$Glucan/primer molar ratio was calculated using DPw (estimated) of glucan arm (850) and DPw of primer (90).

These results indicate that further scaled-up reactions likely perform in a manner consistent with reactions run on a smaller scale.

Example 5

Producing Alpha-1,3-Glucan in Glucosyltransferase Reactions Containing Dextran Lacking Alpha-1,2 Branches This Example describes priming alpha-1,3-glucan synthesis reactions with dextran that was not previously modified to have alpha-1,2 branches (i.e., the dextran was unbranched). This Example allows comparing the use of alpha-1,2-branched dextran as primer for alpha-1,3-glucan synthesis (see results of Examples 1-4 and 6) versus using an unbranched dextran primer.

The procedure as described in Example 1 was followed to synthesize a series of four alpha-1,3-glucan polymers using an unbranched dextran as primer. The dextran used in this Example was the same one as used in Examples 1-4, but was not subjected to alpha-1,2 branching (i.e., the dextran primer in this Example has 0% alpha-1,2 branching). This linear dextran primer is referred to herein as P3 primer, and has a molecular weight of ~14 kDa (DPw of ~89). Thus, each of the P1-P3 primers share the same dextran backbone, but only the P1 and P2 primers have alpha-1,2 branches.

All the reactions were prepared to have roughly 100 g/L sucrose, 5 mM sodium phosphate (pH 5.5), and about 0, 1, 2.5, or 10 g/L of P3 primer. Four plastic 250-mL shake flasks were charged with 20 mL of a 500 g/L sterile-filtered sucrose solution, 5 mL of a 100 mM sterile-filtered sodium phosphate stock (pH 5.5), and 0, 1.045, 2.612, or 10.448 mL of a 95.7 g/L P3 primer stock. DI water was added to bring the final volume to 100 mL. A 0.5-mL t=0 hour HPLC aliquot was withdrawn from each preparation before adding 0.2256 mL of a glucosyltransferase enzyme stock (for final enzyme concentration of 100 U/L) (same enzyme as used in above Examples) to initiate each reaction. The reactions were carried out at 30° C.

At 1, 2, 3, 4 and 24 hours following reaction initiation, 1-mL samples were withdrawn for HPLC analysis. HPLC samples were processed and analyzed as described in Example 1. At 24 hours following reaction initiation, all reaction vessels were placed in an 80° C. water bath for ~30 minutes to deactivate the glucosyltransferase enzyme thereby stopping the reactions. The terminated reactions were then loaded onto a 0.45-micron NALGENE RAPID FLOW disposable PES filter and fully suction-filtered. Retained material was then washed with 3×100 mL of DI water to remove any residual soluble components, leaving behind a clean glucan polymer wet cake. Each wet cake was then dried in a vacuum oven at 40° C., −40 cmHg. HPLC analysis of soluble sugars and analysis of insoluble polymer samples by NMR and SEC were carried out as described in Example 1 and the General Methods. The results of these analyses are provided in Tables 10 and 11.

TABLE 10

Structural Analysis of Alpha-1,3-Glucan Produced in Glucosyltransferase Reactions (24-hour) Containing P3 Primer

| Reaction | | | | Alpha-1,3-Glucan Product Profile | | | | |
|---|---|---|---|---|---|---|---|---|
| Sucrose | Primer | | | % | Linkages (% of total residues) | | | |
| (g/L) | (g/L) | DPw | PDI | primer | 1,3 | 1,2,6 | 1,2 | 1,6 |
| 108 | 0.0 | 919.0 | 1.7 | 0.0 | 100.0 | 0.0 | 0.0 | 0.0 |
| | 1.0 | 3429.0 | 2.7 | 2.4 | 97.6 | 0.0 | 0.0 | 2.3 |
| | 2.5 | 2940.0 | 2.0 | 4.5 | 95.5 | 0.0 | 0.0 | 4.5 |
| | 10.2 | 2000.0 | 2.0 | 8.1 | 91.9 | 0.0 | 0.0 | 8.1 |

TABLE 11

Profiles of Glucosyltransferase Reactions (24-hour) Containing P3 Primer

| Sucrose (g/L) | Primer (g/L) | Alpha-1,3-Glucan Yield (Glucosyl) | Sucrose Rate (g/L/h) | Glucan/Primer 3 hour (M ratio)[a] | Glucan/Primer 24 hour (M ratio)[a] |
|---|---|---|---|---|---|
| 108 | 0.0 | 84% | 18.3 | NA | NA |
| | 1.0 | 80% | 13.4 | 2.4 | 4.5 |
| | 2.5 | 83% | 17.3 | 1.7 | 2.0 |
| | 10.2 | 86% | 20.5 | 2.0 | 1.4 |

[a]Glucan/primer molar ratio was calculated using DPw (estimated) of glucan arm (919) and DPw of primer (89).

As shown in Tables 10-11, a series of four alpha-1,3-glucan polymers was synthesized in glucosyltransferase reactions comprising an unbranched dextran primer. Some interesting differences were observed by comparing the results of this Example (using unbranched dextran primer P3) with those of Example 2 (using 9.2% alpha-1,2-branched primer P2), both of which Examples utilized the same reaction conditions except for different primers. For example, there appeared to be a more substantial increase in alpha-1,3-glucan yield when ~2.5 g/L or ~10 g/L of P2 primer was used (Table 5) as opposed to when ~2.5 g/L or ~10 g/L of P3 primer was used (Table 11). As another example, the molecular weights of alpha-1,3-glucan products produced using P2 primer (and P1 primer) were generally less than the molecular weights observed when using P3 primer. Alpha-1,2-branched dextran primers could therefore be useful for down-regulating alpha-1,3-glucan product molecular weight.

Example 6

Producing Alpha-1,3-Glucan in Glucosyltransferase Reactions Containing Dextran with ~29.2% Alpha-1,2 Branches This Example, in addition to Examples 1-4, describes how the efficacy of dextran priming of alpha-1,3-glucan synthesis can be controlled by varying the alpha-1,2 branching frequency on the dextran primer. In particular, this Example shows that a dextran primer with about 29.2% alpha-1,2-branches failed to prime alpha-1,3-glucan synthesis in a glucosyltransferase reaction. Alpha-1,3-glucan homopolymer was produced, whereas very little or no alpha-1,3-glucan was synthesized from dextran primer.

The procedure as described in Example 1 was followed to synthesize a series of four alpha-1,3-glucan graft copolymers using a dextran primer having ~29.2% alpha-1,2 branches. This dextran primer is referred to herein as P4 primer, and has a molecular weight of ~22 kDa (DPw of ~139). The P4 primer shares the same dextran backbone as primers P1-P3.

All the reactions were prepared to have roughly 100 g/L sucrose, 5 mM sodium phosphate (pH 5.5), and about 0, 1, 5, or 10 g/L of P4 primer. Four plastic 250-mL shake flasks were charged with 20 mL of a 500 g/L sterile-filtered sucrose solution, 5 mL of a 100 mM sterile-filtered sodium phosphate stock (pH 5.5), and 0, 0.504, 2.520 or 5.040 mL of a 198.4 g/L P4 primer stock. DI water was added to bring the final volume to 100 mL. A 0.5-mL t=0 hour HPLC aliquot was withdrawn from each preparation before adding 0.2256 mL of a glucosyltransferase enzyme stock (for final enzyme concentration of 100 U/L) (same enzyme as used in above Examples) to initiate each reaction. The reactions were carried out at 30° C.

At 1, 2, 3, 4 and 24 hours following reaction initiation, 1-mL samples were withdrawn for HPLC analysis. HPLC samples were processed and analyzed as described in Example 1. At 24 hours following reaction initiation, all reaction vessels were placed in an 80° C. water bath for ~30 minutes to deactivate the glucosyltransferase enzyme thereby stopping the reactions. A polymer wet cake was generated as described in Example 4. HPLC analysis of soluble sugars and analysis of insoluble polymer samples by NMR and SEC were carried out as described in Example 1 and the General Methods. The results of these analyses are provided in Tables 12 and 13.

TABLE 12

Structural Analysis of Alpha-1,3-Glucan Produced in Glucosyltransferase Reactions (24-hour) Containing P4 Primer

| Reaction | | | | Alpha-1,3-Glucan Product Profile | | | | |
|---|---|---|---|---|---|---|---|---|
| Sucrose | Primer | | | % | (% of total residues) | | | |
| (g/L) | (g/L) | DPw | PDI | primer | 1,3 | 1,2,6 | 1,2 | 1,6 |
| 109 | 0.0 | 919.0 | 1.7 | 0.0 | 100.0 | 0.0 | 0.0 | 0.0 |
|  | 0.9 | 1547.0 | 2.1 | 0.0 | 100.0 | 0.0 | 0.0 | 0.0 |
|  | 5.0 | 1494.0 | 2.0 | 0.0 | 100.0 | 0.0 | 0.0 | 0.0 |
|  | 9.9 | 1457.0 | 2.2 | 0.0 | 100.0 | 0.0 | 0.0 | 0.0 |

TABLE 13

Profiles of Glucosyltransferase Reactions (24-hour) Containing P4 Primer

| Sucrose (g/L) | Primer (g/L) | Alpha-1,3-Glucan Yield (Glucosyl) | Sucrose Rate (g/L/h) | Glucan/ Primer 3 hour (M ratio)$^a$ | Glucan/ Primer 24 hour (M ratio)$^a$ |
|---|---|---|---|---|---|
| 109 | 0.0 | 84% | 18.3 | NA | NA |
|  | 0.9 | 81% | 16.1 | 13.9 | 27.4 |
|  | 5.0 | 83% | 18.0 | 14.5 | 35.8 |
|  | 9.9 | 83% | 20.8 | 9.7 | 57.8 |

$^a$Glucan/primer molar ratio was calculated using DPw (estimated) of glucan arm (919) and DPw of primer (139).

As shown in Tables 12-13, a series of four alpha-1,3-glucan polymers was synthesized in glucosyltransferase reactions comprising a ~29.2% alpha-1,2-branched dextran primer. Based on SEC, NMR and HPLC results, minimal P4 primer was incorporated into the final insoluble alpha-1,3-glucan products. The linkage profile of the glucan products in reactions containing the P4 primer was nearly identical to that of the product of the reaction not containing the P4 primer. Only a tiny amount of alpha-1,6 linkages was observed by NMR, but were below quantifiable levels, for glucan products of P4-containing reactions. No significant changes in glucan product DPw were observed by SEC, and only trace amounts of primer were consumed based on HPLC results, for P4-containing reactions. Thus, it appears that nearly all of the insoluble glucan produced in P4-containing reactions was alpha-1,3-glucan homopolymer.

As noted in Example 5, the molecular weights of alpha-1,3-glucan products produced using P2 primer (9.2% alpha-1,2 branches) or P1 primer (18.6% alpha-1,2 branches) were generally less than the product molecular weights observed when using P3 primer (no alpha-1,2 branches). It is noted in this Example that the same phenomenon also occurred when using the P4 primer (29.2% alpha-1,2 branches). Further, by comparing Tables 2, 4, 10 and 12, it is apparent that, as the percent of primer alpha-1,2 branching increases, the molecular weight of alpha-1,3-glucan product (of a reaction comprising the primer) decreases. This is further evidence that alpha-1,2-branched dextran primers could be useful for down-regulating alpha-1,3-glucan product molecular weight in glucosyltransferase reactions.

Example 7

Preparation and Use of Film Comprising Dextran-Alpha-1,3-Glucan Graft Copolymer

This Example describes producing film comprising dextran-alpha-1,3-glucan graft copolymer as produced in alpha-1,3-glucan synthesis reactions primed with P2 primer (dextran with 9.2% alpha-1,2 branches). This film was compared to film comprising insoluble alpha-1,3-glucan homopolymer as produced in glucosyltransferase reactions lacking dextran primer. Film comprising the dextran-alpha-1,3-glucan graft copolymer exhibited enhanced performance characteristics compared to film comprising alpha-1,3-glucan homopolymer.

Materials

Sodium hydroxide was obtained from Fisher Scientific (Fair Lawn, NJ). Sulfuric acid and sodium sulfate were obtained from EMD Millipore (Darmstadt, Germany). Dextran-alpha-1,3-glucan graft copolymer preparations were as described in Example 3 (Tables 6-7, product of alpha-1,3-glucan synthesis reaction comprising 5.0 g/L of P2 primer and 104 g/L of sucrose, termed herein as "F-104-5"), Example 3 (Tables 6-7, product of alpha-1,3-glucan synthesis reaction comprising 1.1 g/L of P2 primer and 104 g/L of sucrose, termed herein as "F-104-1"), and Example 4 (Tables 8-9, product of alpha-1,3-glucan synthesis reaction comprising 9.6 g/L of P2 primer and 104 g/L of sucrose, termed herein as ""F-104-10"). Alpha-1,3-glucan homopolymer (DPw~800) was prepared in an unprimed glucosyltransferase reaction comprising about 100 g/L sucrose and the non-native glucosyltransferase used in the above Examples.

Solution and Film Preparation

Solutions of each alpha-1,3-glucan polymer were prepared using an IKA overhead stirrer with a PTFE oval paddle blade. Slurries of polymer and water (37.5 g total mass) were mixed by hand and then stir-added to 22.5 g of a 10 wt % solution of NaOH, after which the solutions were stirred for 3 hours. An appropriate amount of polymer was used to achieve a particular desired final polymer concentration (10-12 wt %, see Table 14). Each polymer's moisture content was measured and accounted for during solution preparation. Each solution was transferred to a FALCON tube and centrifuged to de-aerate the solution.

For film preparation, solutions were poured onto individuals glass plates with 5-mil tape on the sides (to control film thickness) and casted using a glass rod. Films were then coagulated in an acid bath (14 wt % sulfuric acid, 25 wt % sodium sulfate, 61 wt % DI water) for 3 minutes. Films were then washed in DI water to a neutral pH, transferred to a 5 wt % glycerol bath for 3 minutes, and then placed in an oven at 80° C. for 15 minutes.

Film Test Methods

Film thickness was determined using a FEDERAL 22P-10 micrometer. Tensile properties were measured on an INSTRON 5500R Model 1122 using 1-inch grips and a 2-inch gauge length, in accordance with ASTM D882-09 ("Standard Test Method for Tensile Properties of Thin Plastic Sheeting"), which is incorporated herein by reference. Films were cut into 3-inch dog bones for tensile strength measurements, which are represented in Table 14 below as an average of 4-5 breaks.

TABLE 14

Characteristics of Films Comprising Alpha-1,3-Glucan Polymers

| Property | Film Comprising: | | | | | |
|---|---|---|---|---|---|---|
| | Alpha-1,3-Glucan Homopolymer Only | F-104-5[a] | F104-10[b] | | | F104-1[c] |
| Solution solids (wt %) | 12 | 10 | 10 | 12 | 12 | 10 |
| Thickness (mil) | 0.89 | 0.92 | 0.95 | 1.36 | 0.98 | 0.89 |
| ± | 0.064 | 0.034 | 0.051 | 0.055 | 0.049 | 0.056 |
| Width (in.) | 0.5 | 0.5 | 0.5 | 0.5 | 0.5 | 0.5 |
| Initial Modulus (MPa) | 543.6 | 417.86 | 344.35 | 614.17 | 516.66 | 486.21 |
| ± | 45.385 | 52.545 | 63.135 | 122.286 | 123.832 | 74.08 |
| Stress @ Max (MPa) | 14.619 | 16.144 | 13.087 | 19.096 | 17.564 | 14.747 |
| ± | 1.542 | 2.141 | 0.565 | 1.974 | 1.868 | 2.12 |
| % Elongation at Break | 17.25 | 33.84 | 33.48 | 20.02 | 21.99 | 26.99 |
| ± | 4.44 | 7.997 | 4.342 | 1.969 | 6.562 | 7.401 |
| WTM[d] (in-lb./in) | 0.12 | 0.265 | 0.224 | 0.295 | 0.212 | 0.196 |
| ± | 0.043 | 0.092 | 0.042 | 0.027 | 0.055 | 0.073 |
| Toughness (in-lb./in³) | 269.066 | 579.656 | 469.127 | 435.411 | 429.626 | 441.463 |
| ± | 86.285 | 203.173 | 73.130 | 58.528 | 91.178 | 160.838 |

[a] Alpha-1,3-glucan product of glucan synthesis reaction comprising 5.0 g/L of P2 primer and 104 g/L of sucrose (Tables 6-7, Example 3).
[b] Alpha-1,3-glucan product of glucan synthesis reaction comprising 1.1 g/L of P2 primer and 104 g/L of sucrose (Tables 6-7, Example 3).
[c] Alpha-1,3-glucan product of glucan synthesis reaction comprising 9.6 g/L of P2 primer and 104 g/L of sucrose (Tables 8-9, Example 4).
[d] WTM, "work-to-max". WTM is dependent on the maximum load measurement, indicating the work necessary to break the film.

As shown in Table 14, film comprising alpha-1,3-glucan synthesized in a glucosyltransferase reaction primed with alpha-1,2-branched (9.2%) dextran exhibited, for example, an improvement in elongation (e.g., % elongation at break) and maintained strength (Stress @ Max), as compared to film comprising alpha-1,3-glucan homopolymer. Also, toughness and WTM were improved. Thus, film comprising a dextran-alpha-1,3-glucan graft copolymer can exhibit enhanced performance characteristics compared to film comprising alpha-1,3-glucan homopolymer.

Example 8

Reactions Containing Dextran with 18.6% Alpha-1,2 Branches and Glucosyltransferase That Produces Low Molecular Weight Alpha-1,3-Glucan This Example describes synthesis of alpha-1,3-glucan in glucosyltransferase reactions containing a dextran primer that was previously modified to have 18.6% alpha-1,2 branches. The glucosyltransferase enzyme used in these reactions was modified to produce alpha-1,3-glucan of lower molecular weight compared to glucan product made by the enzyme's unmodified counterpart. Graft copolymers were synthesized comprising a dextran backbone and alpha-1,3-glucan arms.

Alpha-1,2-branched dextran was produced to prime glucosyltransferase reactions for alpha-1,3-glucan synthesis. Preparation of this primer was performed as described in Example 1 (above) for the P1 primer The resulting dextran, which had a DPw of about 104 (~17 kDa) and 18.6% alpha-1,2-branches, is referred to herein as P5 primer.

P5 primer was then included in alpha-1,3-glucan synthesis reactions comprising a glucosyltransferase to produce graft copolymers comprising a dextran backbone and alpha-1,3-glucan arms. The glucosyltransferase used in these reactions, which produces alpha-1,3-glucan with about 100% alpha-1,3 linkages, was a Streptococcus salivarius glucosyltransferase modified in its catalytic domain such that the enzyme could produce alpha-glucan of lower molecular weight, as compared to the molecular weight of alpha-glucan produced by the enzyme's unmodified counterpart. The General Methods section describes assaying this non-native glucosyltransferase (Table D). Enzyme preparation in this Example was conducted as follows. Briefly, KOBW-3a cells heterologously expressing the glucosyltransferase were grown in LB medium containing 100 ng/mL ampicillin and 0.025% L-arabinose at 30° C. overnight. Cells were pelleted by centrifugation and then lysed with a 10% volume of BugBuster® Protein Extraction Reagent (EMD Millipore) at room temperature for at least 1 hour; cell debris was removed by centrifugation, after which clear cell lysate was collected for testing.

Thirteen separate 4.0-mL alpha-1,3-glucan synthesis reactions were performed in glass 50-mL indented flasks. Each reaction comprised water, sucrose (roughly 20, 50, or 200 g/L), phosphate buffer (5 mM, pH 5.7), optionally P5 primer (roughly 0.2, 1.0, or 5.0 g/L), and a glucosyltransferase (above). The reactions were prepared by mixing an appropriate amount of P5 primer (using 50 g/L stock solution), 0.2 mL of cell lysate (containing the glucosyltransferase) and corresponding buffer. Each of these preparations and a sucrose stock solution (400 g/L) was warmed at 35° C. for at least 30 minutes. An appropriate volume of sucrose solution was then added to each preparation to initiate alpha-1,3-glucan synthesis. The reactions were carried out at 35° C. with shaking (10 rpm) for about 60 hours. Following this incubation, the entire contents of the reactions were individually transferred to 15-mL centrifuge tubes, which were placed in an 85° C. oven for about 30 minutes to deactivate the glucosyltransferase thereby terminating the reactions. Approximately 300-500 mg of wet cake produced in each reaction was analyzed by SEC to determine the molecular weight and DP of the insoluble polymer products. Table 15 provides the results of these analyses.

TABLE 15

Analysis of Alpha-1,3-Glucan Produced in Glucosyltransferase Reactions Containing P5 Primer

| Reaction | | Alpha-1,3-Glucan Product Profile | | | | |
|---|---|---|---|---|---|---|
| Primer[a] (g/L) | Sucrose (g/L) | Polymer Type | DPw | Mw | Mp | Mw/Mn |
| 0.0 | 20 | non-grafted | 58 | 9439 | 9948 | 1.22 |
| 0.2 | | grafted | 625 | 101191 | 97726 | 1.33 |
| 1.0 | | grafted | 402 | 65163 | 62668 | 1.32 |
| 5.0 | | grafted | 245 | 39628 | 35874 | 1.21 |
| 0.0 | 50 | non-grafted | 52 | 8363 | 8117 | 1.25 |
| 0.2 | | grafted | 680 | 110189 | 95028 | 1.36 |
| 1.0 | | grafted | 425 | 68878 | 68877 | 1.28 |
| 5.0 | | grafted | 251 | 40718 | 36926 | 1.22 |
| 0.0 | 200 | non-grafted | 41 | 6690 | 5945 | 1.22 |
| 0.2 | | grafted | 517 | 83679 | 88410 | 1.3 |
| 1.0 | | grafted | 374 | 60530 | 59285 | 1.24 |
| 5.0 | | grafted | 236 | 38264 | 35119 | 1.2 |

[a]Primer P5 is DPw 104 (Mw = 16869 Da) (Mw/Mn = 1.48).

The size of individual alpha-1,3-glucan arms grafted onto primer in the glucan product of each primer-containing reaction is contemplated to be very similar to the size of alpha-1,3-glucan produced in control reactions that did not contain added primer; the control reaction products comprised alpha-1,3-glucan homopolymer. That said, it seems notable that, as the concentration of primer was increased in each set of reaction series (20, 50, or 200 g/L sucrose), graft copolymer product DPw decreased significantly.

Glucan-to-primer molar ratios (M ratios) were calculated based on the respective control DPw value (homopolymer DPw) under each tested condition and the DPw of the P5 primer (~104). The data from these analyses are provided in Table 16.

TABLE 16

Glucan-to-Primer Molar Ratio of Alpha-1,3-Glucan Graft Copolymer Produced in Glucosyltransferase Reactions Containing P5 Primer

| Primer | Sucrose | Alpha-1,3-Glucan Product Profile | |
|---|---|---|---|
| (g/L) | (g/L) | DPw | M Ratio |
| 0.2 | 20 | 625 | 9 |
| 1.0 | | 402 | 5 |
| 5.0 | | 245 | 2 |
| 0.2 | 50 | 680 | 11 |
| 1.0 | | 425 | 6 |
| 5.0 | | 251 | 3 |
| 0.2 | 200 | 517 | 10 |
| 1.0 | | 374 | 7 |
| 5.0 | | 236 | 3 |

Thus, by providing an alpha-1,2-branched dextran primer to alpha-1,3-glucan synthesis reactions, graft copolymers were synthesized comprising a dextran backbone and alpha-1,3-glucan arms. Primer was demonstrably consumed and incorporated into graft copolymer products.

Example 9

Reactions Containing Dextran with 9.7% Alpha-1,2 Branches and Glucosyltransferase That Produces Low Molecular Weight Alpha-1,3-Glucan This Example describes synthesis of alpha-1,3-glucan in glucosyltransferase reactions containing a dextran primer that was previously modified to have 9.7% alpha-1,2 branches. The glucosyltransferase enzyme used in these reactions was modified to produce alpha-1,3-glucan of lower molecular weight compared to glucan product made by the enzyme's unmodified counterpart. Graft copolymers were synthesized comprising a dextran backbone and alpha-1,3-glucan arms.

Alpha-1,2-branched dextran was produced to prime glucosyltransferase reactions for alpha-1,3-glucan synthesis. Preparation of this primer was performed essentially as described in International Patent. Appl. Publ. No. WO2017/091533, which is incorporated herein by reference. Briefly, linear dextran (i.e., polysaccharide with 100% alpha-1,6 glycosidic linkages) of molecular weight ~40 kDa (DPw of ~250) was produced using glucosyltransferase GTF6831 (SEQ ID NO:68). This dextran was then modified to have 9.7% alpha-1,2-branches using alpha-1,2-branching enzyme GTFJ18T1 (SEQ ID NO:70). The resulting alpha-1,2-branched dextran, which had a DPw of about 271 (~44 kDa), is referred to herein as P6 primer.

P6 primer was then included in alpha-1,3-glucan synthesis reactions comprising a glucosyltransferase to produce graft copolymers comprising a dextran backbone and alpha-1,3-glucan arms. The glucosyltransferase used in these reactions was the same as used and prepared in Example 8.

Thirteen separate 4.0-mL alpha-1,3-glucan synthesis reactions were performed in glass 50-mL indented flasks. Each reaction comprised water, sucrose (roughly 20, 50, or 200 g/L), phosphate buffer (5 mM, pH 5.7), optionally P6 primer (roughly 0.2, 1.0, or 5.0 g/L), and a glucosyltransferase (above). The reactions were prepared by mixing an appropriate amount of P6 primer (using 50 g/L stock solution), 0.2 mL of cell lysate (containing the glucosyltransferase) and corresponding buffer. Each of these preparations and a sucrose stock solution (400 g/L) was warmed at 35° C. for at least 30 minutes. An appropriate volume of sucrose solution was then added to each preparation to initiate alpha-1,3-glucan synthesis. The reactions were carried out at 35° C. with shaking (10 rpm) for about 60 hours. Following this incubation, the entire contents of the reactions were individually transferred to 15-mL centrifuge tubes, which were placed in an 85° C. oven for about 30 minutes to deactivate the glucosyltransferase thereby terminating the reactions. Approximately 300-500 mg of wet cake produced in each reaction was analyzed by SEC to determine the molecular weight and DP of the insoluble polymer products. Table 17 provides the results of these analyses.

TABLE 17

Analysis of Alpha-1,3-Glucan Produced in Glucosyltransferase Reactions Containing P6 Primer

| Reaction | | Alpha-1,3-Glucan Product Profile | | | | |
|---|---|---|---|---|---|---|
| Primer[a] (g/L) | Sucrose (g/L) | Polymer Type | DPw | Mw | Mp | Mw/Mn |
| 0.0 | 20 | non-grafted | 58 | 9439 | 9948 | 1.22 |
| 0.2 | | grafted | 1224 | 198295 | 222340 | 1.55 |

TABLE 17-continued

Analysis of Alpha-1,3-Glucan Produced in Glucosyltransferase Reactions Containing P6 Primer

| Reaction | | Alpha-1,3-Glucan Product Profile | | | | |
|---|---|---|---|---|---|---|
| Primer[a] (g/L) | Sucrose (g/L) | Polymer Type | DPw | Mw | Mp | Mw/Mn |
| 1.0 | | grafted | 1023 | 167308 | 177954 | 1.7 |
| 5.0 | | grafted | 769 | 124646 | 95437 | 1.6 |
| 0.0 | 50 | non-grafted | 52 | 8363 | 8117 | 1.25 |
| 0.2 | | grafted | 1211 | 196134 | 224349 | 1.59 |
| 1.0 | | grafted | 1085 | 175800 | 187403 | 1.58 |
| 5.0 | | grafted | 768 | 124454 | 112146 | 1.64 |
| 0.0 | 200 | non-grafted | 41 | 6690 | 5945 | 1.22 |
| 0.2 | | grafted | 993 | 160848 | 206992 | 1.58 |
| 1.0 | | grafted | 1060 | 171788 | 184475 | 1.45 |
| 5.0 | | grafted | 749 | 121391 | 114253 | 1.61 |

[a]Primer P6 is DPw 271 (Mw = 43958 Da) (Mw/Mn = 1.19).

The size of individual alpha-1,3-glucan arms grafted onto primer in the glucan product of each primer-containing reaction is contemplated to be very similar to the size of alpha-1,3-glucan produced in control reactions that did not contain added primer; the control reaction products comprised alpha-1,3-glucan homopolymer. That said, it seems notable that generally, as the concentration of primer was increased in each set of reaction series (20, 50, or 200 g/L sucrose), graft copolymer product DPw decreased significantly.

Glucan-to-primer molar ratios (M ratios) were calculated based on the respective control DPw value (homopolymer DPw) under each tested condition and the DPw of the P6 primer (271). The data from these analyses are provided in Table 18.

TABLE 18

Glucan-to-Primer Molar Ratio of Alpha-1,3-Glucan Graft Copolymer Produced in Glucosyltransferase Reactions Containing P5 Primer

| Primer (g/L) | Sucrose (g/L) | Alpha-1,3-Glucan Product Profile | |
|---|---|---|---|
| | | DPw | M Ratio |
| 0.2 | 20 | 1224 | 16 |
| 1.0 | | 1023 | 13 |
| 5.0 | | 769 | 9 |
| 0.2 | 50 | 1211 | 18 |
| 1.0 | | 1085 | 16 |
| 5.0 | | 768 | 10 |
| 0.2 | 200 | 993 | 18 |
| 1.0 | | 1060 | 19 |
| 5.0 | | 749 | 12 |

Thus, by providing an alpha-1,2-branched dextran primer to alpha-1,3-glucan synthesis reactions, graft copolymers were synthesized comprising a dextran backbone and alpha-1,3-glucan arms. Primer was demonstrably consumed and incorporated into graft copolymer products.

What is claimed is:

1. A composition comprising an ether- or ester-derivative of a graft copolymer, wherein said graft copolymer comprises:
   (i) a backbone comprising a dextran, wherein the weight-average degree of polymerization (DPw) of the backbone is 10 to 500, and
   (ii) one or more alpha-1,3-glucan side chains comprising at least about 50% alpha-1,3 glycosidic linkages.

2. The composition of claim 1, wherein the DPw of the backbone is about 10 to 200.

3. The composition of claim 1, wherein said one or more alpha-1,3-glucan side chains comprise at least about 90% alpha-1,3 glycosidic linkages.

4. The composition of claim 1, wherein the DP or DPw of said one or more alpha-1,3-glucan side chains is at least about 10.

5. The composition of claim 1, wherein said graft copolymer comprises one or two of said alpha-1,3-glucan side chains.

6. The composition of claim 1, wherein the composition comprises the ester-derivative of the graft copolymer.

7. The composition of claim 1, wherein the composition comprises the ether-derivative of the graft copolymer.

8. The composition of claim 7, wherein the composition is a household care product, personal care product, industrial product, pharmaceutical product, or food product.

9. The composition of claim 1, wherein the composition is a film or coating.

10. The composition of claim 6, wherein the composition is a detergent composition.

11. The composition of claim 7, wherein the composition is a detergent composition.

12. The composition of claim 6, wherein the composition is a household care product, personal care product, industrial product, pharmaceutical product, or food product.

13. The composition of claim 1, wherein the dextran comprises at least 97% alpha-1,6 glycosidic linkages.

14. The composition of claim 1, wherein the dextran comprises at least 98% alpha-1,6 glycosidic linkages.

15. The composition of claim 1, wherein the dextran comprises at least 99% alpha-1,6 glycosidic linkages.

16. The composition of claim 1, wherein the dextran comprises 100% alpha-1,6 glycosidic linkages.

* * * * *